(12) United States Patent
Koo et al.

(10) Patent No.: US 11,201,293 B2
(45) Date of Patent: Dec. 14, 2021

(54) HETEROCYCLIC COMPOUND AND ORGANIC LIGHT-EMITTING DEVICE COMPRISING SAME

(71) Applicant: LG CHEM, LTD., Seoul (KR)

(72) Inventors: Ki Dong Koo, Daejeon (KR); Kongkyeom Kim, Daejeon (KR); Dongheon Kim, Daejeon (KR); Sujeong Geum, Daejeon (KR)

(73) Assignee: LG CHEM, LTD., Seoul (KR)

( * ) Notice: Subject to any disclaimer, the term of this patent is extended or adjusted under 35 U.S.C. 154(b) by 485 days.

(21) Appl. No.: 16/342,171

(22) PCT Filed: Feb. 28, 2018

(86) PCT No.: PCT/KR2018/002464
§ 371 (c)(1),
(2) Date: Apr. 15, 2019

(87) PCT Pub. No.: WO2018/160003
PCT Pub. Date: Sep. 7, 2018

(65) Prior Publication Data
US 2019/0326517 A1    Oct. 24, 2019

(30) Foreign Application Priority Data
Feb. 28, 2017    (KR) .................. 10-2017-0026716

(51) Int. Cl.
*C07D 498/10*    (2006.01)
*H01L 51/00*    (2006.01)
(Continued)

(52) U.S. Cl.
CPC ........ *H01L 51/0061* (2013.01); *C07D 491/20* (2013.01); *C07D 491/22* (2013.01);
(Continued)

(58) Field of Classification Search
None
See application file for complete search history.

(56) References Cited

U.S. PATENT DOCUMENTS

| 2015/0263291 A1 | 9/2015 | Jung et al. |
| 2018/0130968 A1 | 5/2018 | Ikeda |

FOREIGN PATENT DOCUMENTS

| JP | 2015221780 A | 12/2015 |
| KR | 1020060051607 A | 5/2006 |

(Continued)

*Primary Examiner* — Robert S Loewe
(74) *Attorney, Agent, or Firm* — Denton US LLP

(57) ABSTRACT

The present specification relates to a heterocyclic compound of Chemical Formula 1, and an organic light emitting device including the same. The heterocyclic compound as a material of an organic material layer of the organic light emitting device provides enhanced efficiency, low driving voltage and enhanced lifetime properties.

(Continued)

[Chemical Formula 1]

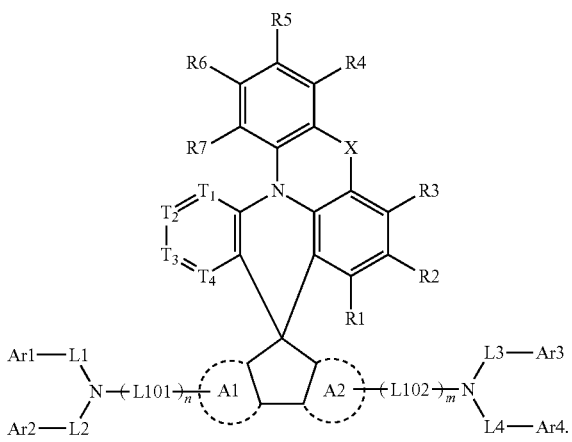

17 Claims, 3 Drawing Sheets

(51) Int. Cl.
C07D 491/20 (2006.01)
C07D 491/22 (2006.01)
C07D 498/22 (2006.01)
C07D 513/20 (2006.01)
C07F 7/08 (2006.01)
C09K 11/06 (2006.01)
H01L 51/50 (2006.01)

(52) U.S. Cl.
CPC ......... C07D 498/10 (2013.01); C07D 498/22 (2013.01); C07D 513/20 (2013.01); C07F 7/0812 (2013.01); C09K 11/06 (2013.01); H01L 51/006 (2013.01); H01L 51/0094 (2013.01); C09K 2211/1018 (2013.01); H01L 51/0054 (2013.01); H01L 51/0058 (2013.01); H01L 51/0071 (2013.01); H01L 51/0073 (2013.01); H01L 51/5012 (2013.01); H01L 51/5016 (2013.01); H01L 51/5056 (2013.01); H01L 51/5072 (2013.01); H01L 51/5088 (2013.01); H01L 51/5092 (2013.01)

(56) References Cited

FOREIGN PATENT DOCUMENTS

| | | |
|---|---|---|
| KR | 1020100119077 A | 11/2010 |
| KR | 1020110041730 A | 4/2011 |
| KR | 1020110106193 A | 9/2011 |
| KR | 1020130073853 A | 7/2013 |
| KR | 1020130078746 A | 7/2013 |
| KR | 1020150034612 A | 4/2015 |
| WO | 2013095039 A1 | 6/2013 |
| WO | 2017010438 A1 | 1/2017 |

【FIG. 1】
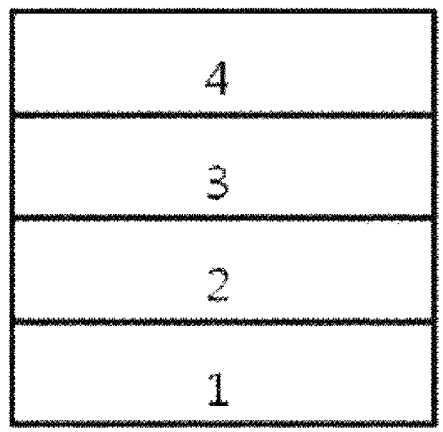
【FIG. 2】
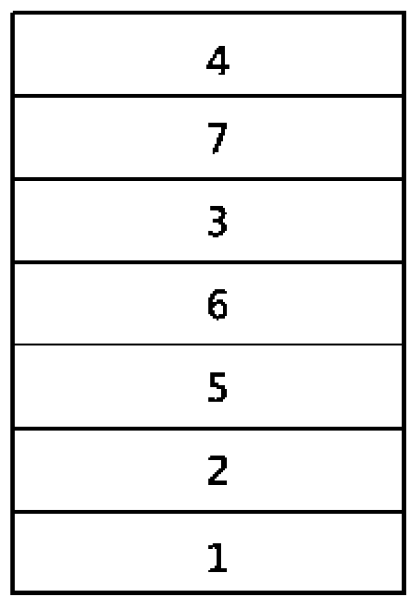

【FIG. 3】
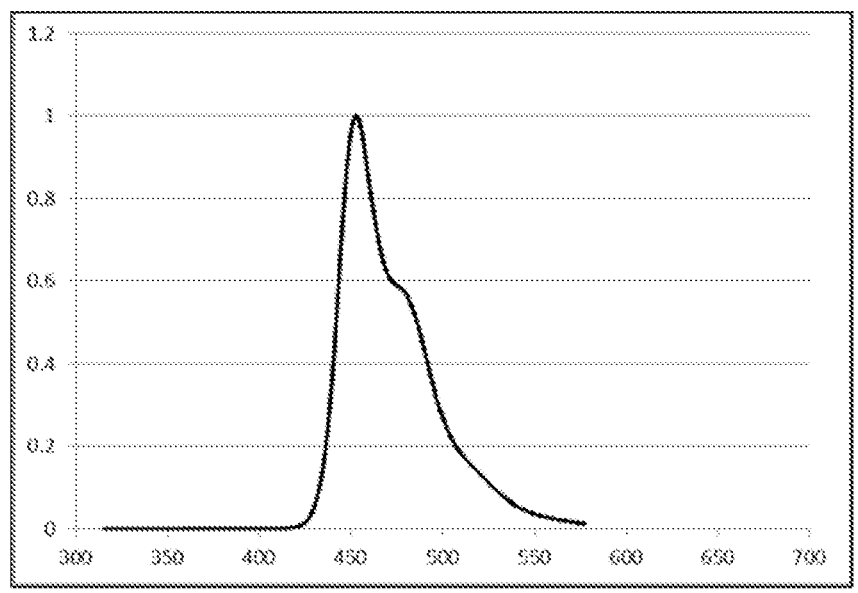
【FIG. 4】
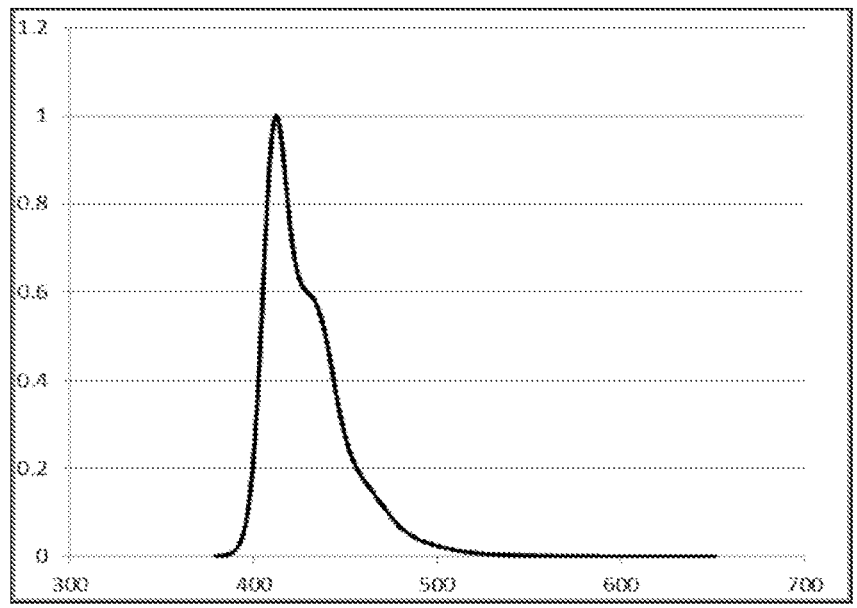

[FIG. 5]
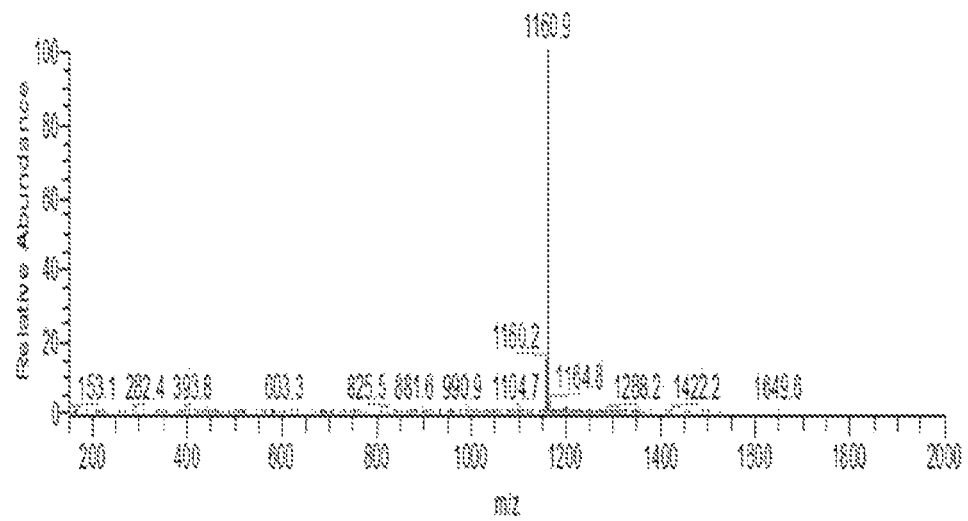

HETEROCYCLIC COMPOUND AND ORGANIC LIGHT-EMITTING DEVICE COMPRISING SAME

TECHNICAL FIELD

This application is a National Stage Application of International Application No. PCT/KR2018/002464, filed on Feb. 28, 2018, which claims priority to and the benefits of Korean Patent Application No. 10-2017-0026716, filed with the Korean Intellectual Property Office on Feb. 28, 2017, the entire contents of which are incorporated herein by reference.

The present specification relates to a heterocyclic compound and an organic light emitting device comprising the same.

BACKGROUND ART

An organic light emitting device has a structure disposing an organic thin film between two electrodes. When a voltage is applied to an organic light emitting device having such a structure, electrons and holes injected from the two electrodes bind in the organic thin film to form a pair, and light emits as they disappear. The organic thin film may be formed in a single layer or a multilayer as necessary.

Materials used in organic light emitting devices are mostly pure organic materials or complex compounds in which organic materials and metals form complexes, and may be divided into hole injection materials, hole transfer materials, light emitting materials, electron transfer materials, electron injection materials and the like depending on the application. Herein, as the hole injection material or the hole transfer material, organic materials having a p-type property, that is, organic materials readily oxidized and electrochemically stable when oxidized, are generally used. Meanwhile, as the electron injection material or the electron transfer material, organic materials having an n-type property, that is, organic materials readily reduced and electrochemically stable when reduced, are generally used. As the light emitting layer material, materials having both a p-type property and an n-type property, that is, materials having a stable form in both oxidized and reduced states, are preferred, and materials having high light emission efficiency converting, when excitons generated by the holes and the electrons recombining in the light emitting layer are formed, the excitons to light are preferred.

In order to enhance performance, lifetime or efficiency of an organic light emitting device, development of organic thin film materials has been consistently required.

DISCLOSURE

Technical Problem

The present specification is directed to providing a heterocyclic compound and an organic light emitting device comprising the same.

Technical Solution

One embodiment of the present specification provides a heterocyclic compound represented by the following Chemical Formula 1.

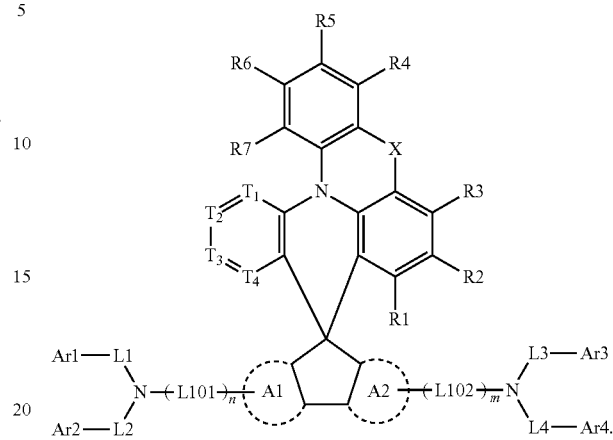

[Chemical Formula 1]

In Chemical Formula 1,

Ar1 to Ar4 are the same as or different from each other, and each independently hydrogen; deuterium; a halogen group; a nitrile group; a nitro group; a silyl group; a boron group; a substituted or unsubstituted amine group; a substituted or unsubstituted alkyl group; a substituted or unsubstituted cycloalkyl group; a substituted or unsubstituted aryl group; or a substituted or unsubstituted heteroaryl group, L1 to L4, L101 and L102 are the same as or different from each other, and each independently a direct bond; a substituted or unsubstituted arylene group; or a substituted or unsubstituted heteroarylene group, A1 and A2 are the same as or different from each other, and each independently a substituted or unsubstituted aromatic hydrocarbon ring; or a substituted or unsubstituted heteroring, provided that one of A1 and A2 is benzene, the other one is a substituted or unsubstituted polycyclic aromatic hydrocarbon ring; or a substituted or unsubstituted heteroring, X is NR, CR'R", O or S, $T_1$ to $T_4$ are the same as or different from each other, and each independently CRa or N, R, R', R", R1 to R7 and Ra are the same as or different from each other, and each independently hydrogen; deuterium; a halogen group; a nitrile group; a nitro group; a silyl group; a boron group; a substituted or unsubstituted amine group; a substituted or unsubstituted alkyl group; a substituted or unsubstituted cycloalkyl group; a substituted or unsubstituted aryl group; or a substituted or unsubstituted heteroaryl group, m and n are each 1 or 2, and provided that m or n is 2, substituents in the parentheses are the same as or different from each other.

Another embodiment of the present specification provides an organic light emitting device comprising an anode, a cathode and one or more organic material layers disposed between the anode and the cathode, wherein one or more layers of the organic material layers comprise the heterocyclic compound of Chemical Formula 1 described above.

Advantageous Effects

A compound described in the present specification can be used as a material of an organic material layer of an organic light emitting device. A compound according to at least one embodiment is capable of enhancing efficiency, obtaining a low driving voltage and/or enhancing lifetime properties in an organic light emitting device. A compound described in the present specification can be used as a material of a hole injection layer, a hole transfer layer, a hole injection layer and hole transfer layer, an electron blocking layer, a light emitting layer, a hole blocking layer, an electron transfer layer or an electron injection layer.

DESCRIPTION OF DRAWINGS

FIG. 1 illustrates an example of an organic light emitting device formed with a substrate (1), an anode (2), a light emitting layer (3) and a cathode (4).

FIG. 2 illustrates an example of an organic light emitting device formed with a substrate (1), an anode (2), a hole injection layer (5), a hole transfer layer (6), a light emitting layer (3), an electron transfer layer (7) and a cathode (4).

FIG. 3 is a diagram showing a fluorescent light emission spectrum of Compound 3.

FIG. 4 is a diagram showing a fluorescent light emission spectrum of BD-C.

FIG. 5 is a diagram showing mass data of Compound 3.

1: Substrate
2: Anode
3: Light Emitting Layer
4: Cathode
5: Hole Injection Layer
6: Hole Transfer Layer
7: Electron Transfer Layer

MODE FOR DISCLOSURE

Hereinafter, the present specification will be described in more detail.

Examples of the substituents in the present specification are described below, however, the substituents are not limited thereto.

The term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

The term "substituted or unsubstituted" in the present specification means being substituted with one, two or more substituents selected from the group consisting of deuterium; a halogen group; a cyano group; a silyl group; an alkyl group; a cycloalkyl group; an aryl group; and a heteroaryl group, or being substituted with a substituent linking two or more substituents among the substituents illustrated above, or having no substituents. For example, "a substituent linking two or more substituents" may comprise a biphenyl group. In other words, a biphenyl group may be an aryl group, or interpreted as a substituent linking two phenyl groups.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification, "⁃⁎⁃" and "⁃⁃⁃⁃⁃⁃" mean a site bonding to Chemical Formula 1.

In the present specification, examples of the halogen group may comprise fluorine (F), chlorine (Cl), bromine (Br) or iodine (I).

In the present specification, the silyl group may be represented by a chemical formula of —SiR$_a$R$_b$R$_c$, and R$_a$, R$_b$ and R$_c$ may each be hydrogen; a substituted or unsubstituted alkyl group; or a substituted or unsubstituted aryl group. Specific examples of the silyl group may comprise a trimethylsilyl group; a triethylsilyl group; a t-butyldimethylsilyl group; a vinyldimethylsilyl group; a propyldimethylsilyl group; a triphenylsilyl group; a diphenylsilyl group; a phenylsilyl group and the like, but are not limited thereto.

In the present specification, the boron group may be represented by a chemical formula of —BR$_a$R$_b$, and R$_a$ and R$_b$ may each be hydrogen; a substituted or unsubstituted alkyl group; or a substituted or unsubstituted aryl group. Specific examples of the boron group may comprise a trimethylboron group, a triethylboron group, a t-butyldimethylboron group, a triphenylboron group, a phenylboron group and the like, but are not limited thereto.

In the present specification, the amine group may be selected from the group consisting of —NH$_2$; an alkylamine group; an N-arylalkylamine group; an arylamine group; an N-arylheteroarylamine group; an N-alkylheteroarylamine group and a heteroarylamine group, and although not particularly limited thereto, the number of carbon atoms is preferably from 1 to 30. Specific examples of the amine group may comprise a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, an N-phenylnaphthylamine group, a ditolylamine group, an N-phenyltolylamine group, a triphenylamine group and the like, but are not limited thereto.

In the present specification, the alkyl group may be linear or branched, and although not particularly limited thereto, the number of carbon atoms is preferably from 1 to 60. According to one embodiment, the number of carbon atoms of the alkyl group is from 1 to 40. According to another embodiment, the number of carbon atoms of the alkyl group is from 1 to 20.

Specific examples thereof may comprise a methyl group, an ethyl group, a propyl group, an n-propyl group, an isopropyl group, a butyl group, an n-butyl group, an isobutyl group, a tert-butyl group, a sec-butyl group, a 1-methylbutyl group, a 1-ethylbutyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the cycloalkyl group is not particularly limited, but preferably has 3 to 60 carbon atoms. According to one embodiment, the number of carbon atoms of the cycloalkyl group is from 3 to 40. According to another embodiment, the number of carbon atoms of the cycloalkyl group is from 1 to 20. Specific examples thereof may comprise a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

When the aryl group is a monocyclic aryl group in the present specification, the number of carbon atoms is not particularly limited, but is preferably from 6 to 60. According to one embodiment, the number of carbon atoms of the aryl group is from 6 to 30. Specific examples of the monocyclic aryl group may comprise a phenyl group, a biphenyl group, a terphenyl group and the like, but are not limited thereto.

When the aryl group is a polycyclic aryl group, the number of carbon atoms is not particularly limited, but is preferably from 10 to 60. According to one embodiment, the number of carbon atoms of the aryl group is from 10 to 30. Specific examples of the polycyclic aryl group may comprise a naphthyl group, an anthracenyl group, a phenanthrenyl group, a pyrenyl group, a perylenyl group, a triphenylenyl group, a fluoranthenyl group, a pyrenyl group, a chrysenyl group, a fluorenyl group, an indenofluorenyl group and the like, but are not limited thereto.

In the present specification, the fluorenyl group may be substituted, and adjacent substituents may bond to each other to form a ring.

When the fluorenyl group is substituted,

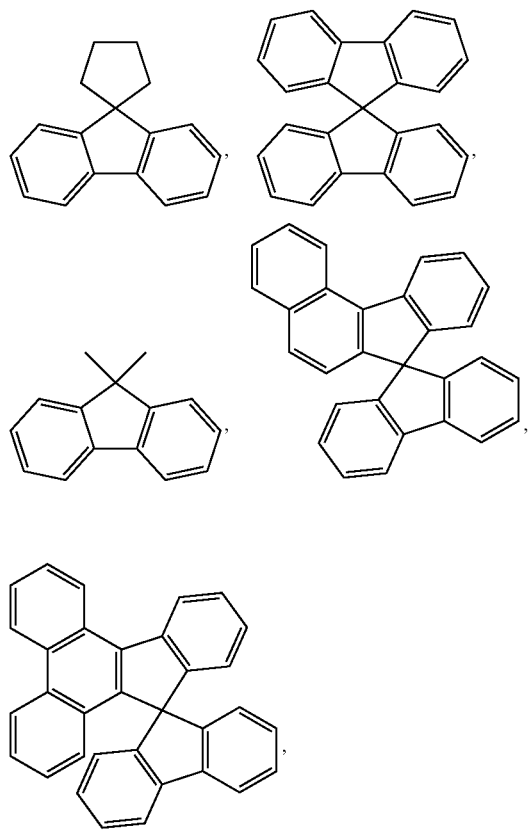

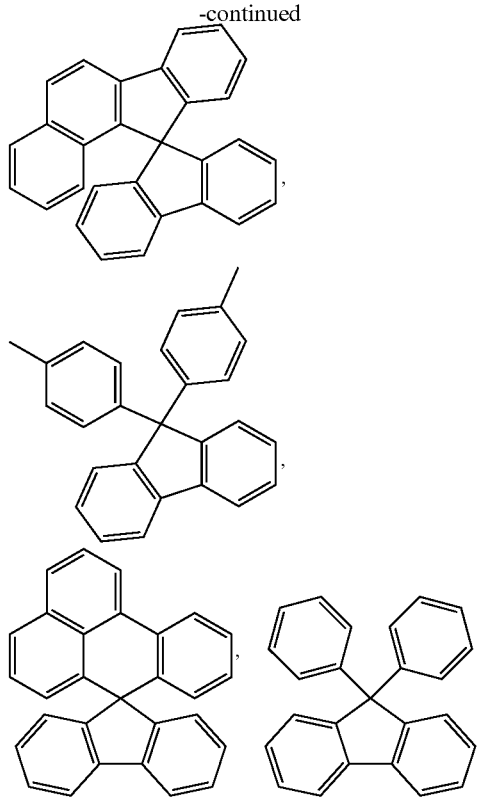

and the like may be included. However, the structure is not limited thereto.

In the present specification, the heterocyclic group comprises one or more atoms that are not carbon, that is, heteroatoms, and specifically, the heteroatom may comprise one or more atoms selected from the group consisting of O, N, Se, S and the like. The number of carbon atoms of the heterocyclic group is not particularly limited, but is preferably from 2 to 60. Examples of the heterocyclic group may comprise a thiophene group, a furan group, a pyrrole group, an imidazole group, a thiazole group, an oxazole group, an oxadiazole group, a pyridyl group, a bipyridyl group, a pyrimidyl group, a triazine group, a triazole group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group and the like, but are not limited thereto.

The heterocyclic group may be monocyclic or polycyclic, and may be aromatic, aliphatic, or a fused ring of aromatic and aliphatic.

In the present specification, the hydrocarbon ring may be selected from among examples of the cycloalkyl group or the aryl group except for those that are not monovalent. The heteroring may be aliphatic, aromatic, or a fused ring of aromatic and aliphatic, and may be selected from among examples of the heterocyclic group except for those that are not monovalent.

In the present specification, descriptions on the heterocyclic group may be applied to the heteroaryl group except for being aromatic.

In the present specification, the arylene group means an aryl group having two bonding sites, that is, a divalent group. Descriptions on the aryl group provided above may be applied thereto except for each being a divalent group.

In the present specification, the heteroarylene group means a heteroaryl group having two bonding sites, that is, a divalent group. Descriptions on the heteroaryl group provided above may be applied thereto except for each being a divalent group.

In one embodiment of the present specification, A1 and A2 are the same as or different from each other, and each independently a substituted or unsubstituted aromatic hydrocarbon ring; or a substituted or unsubstituted heteroring, provided that one of A1 and A2 is benzene, the other one is a substituted or unsubstituted polycyclic aromatic hydrocarbon ring; or a substituted or unsubstituted heteroring.

In one embodiment of the present specification, A1 and A2 are the same as or different from each other, and each independently a substituted or unsubstituted aromatic hydrocarbon ring having 6 to 60 carbon atoms; or a substituted or unsubstituted heteroring having 2 to 60 carbon atoms, provided that one of A1 and A2 is benzene, the other one is a substituted or unsubstituted polycyclic aromatic hydrocarbon ring having 12 to 60 carbon atoms; or a substituted or unsubstituted heteroring having 2 to 60 carbon atoms.

In another embodiment, A1 and A2 are the same as or different from each other, and each independently a substituted or unsubstituted aromatic hydrocarbon ring having 6 to 30 carbon atoms; or a substituted or unsubstituted heteroring having 2 to 60 carbon atoms, provided that one of A1 and A2 is benzene, the other one is a substituted or unsubstituted polycyclic aromatic hydrocarbon ring having 12 to 30 carbon atoms; or a substituted or unsubstituted heteroring having 2 to 30 carbon atoms.

In one embodiment of the present specification, A1 and A2 are the same as or different from each other, and each independently one of the following structures.

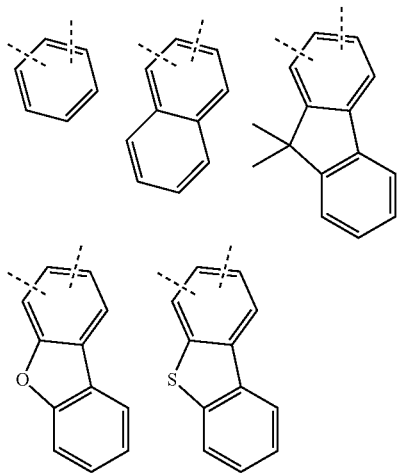

The structures may be further substituted, and "------" means a site bonding to Chemical Formula 1.

In one embodiment of the present specification, L101, L102, and L1 to L4 are the same as or different from each other, and each independently a direct bond; a substituted or unsubstituted arylene group; or a substituted or unsubstituted heteroarylene group.

In one embodiment of the present specification, L101, L102, and L1 to L4 are the same as or different from each other, and each independently a direct bond; or a substituted or unsubstituted arylene group having 6 to 60 carbon atoms. In another embodiment, L101, L102, and L1 to L4 are the same as or different from each other, and each independently a direct bond; or a substituted or unsubstituted arylene group having 6 to 30 carbon atoms.

In one embodiment of the present specification, L101, L102, and L1 to L4 are the same as or different from each other, and each independently a direct bond; a substituted or unsubstituted phenylene group; a substituted or unsubstituted biphenylene group; a substituted or unsubstituted terphenylene group; a substituted or unsubstituted anthracenylene group; a substituted or unsubstituted phenanthrenylene group; a substituted or unsubstituted naphthylene group; or a substituted or unsubstituted fluorenylene group.

In one embodiment of the present specification, L101, L102, and L1 to L4 are the same as or different from each other, and each independently a direct bond; or a substituted or unsubstituted heteroarylene group having 2 to 60 carbon atoms.

In another embodiment, L101, L102, and L1 to L4 are the same as or different from each other, and each independently a direct bond; or a substituted or unsubstituted heteroarylene group having 2 to 30 carbon atoms.

In one embodiment of the present specification, L101, L102, and L1 to L4 are the same as or different from each other, and each independently a direct bond; a substituted or unsubstituted divalent pyrrole group; a substituted or unsubstituted divalent thiophene group; or a substituted or unsubstituted divalent furan group.

In one embodiment of the present specification, L101, L102, and L1 to L4 may be a direct bond; or any one selected from among structures described below.

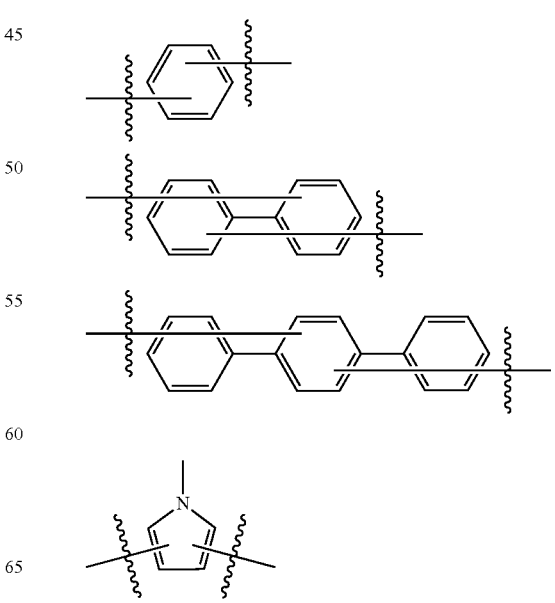

-continued

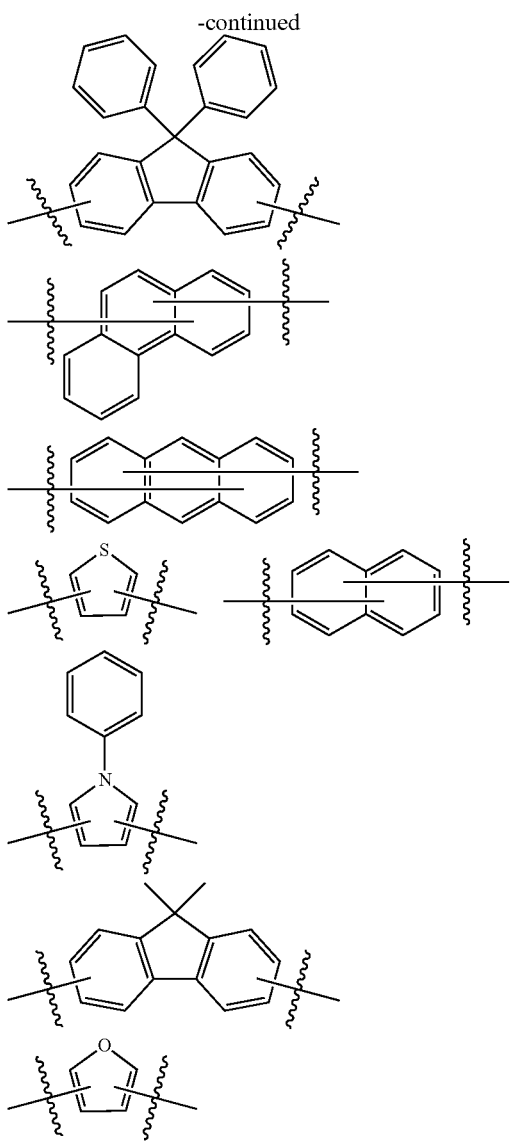

The structures may be further substituted.

In one embodiment of the present specification, An to Ar4 are the same as or different from each other, and each independently a substituted or unsubstituted alkyl group; a substituted or unsubstituted aryl group; or a substituted or unsubstituted heteroaryl group.

According to one embodiment of the present specification, An to Ar4 are the same as or different from each other, and each independently a substituted or unsubstituted alkyl group having 1 to 30 carbon atoms; a substituted or unsubstituted aryl group having 6 to 30 carbon atoms; or a substituted or unsubstituted heteroaryl group having 2 to 30 carbon atoms.

In another embodiment, An to Ar4 are the same as or different from each other, and each independently a substituted or unsubstituted aryl group having 6 to 30 carbon atoms; or a substituted or unsubstituted heteroaryl group having 2 to 30 carbon atoms.

According to another embodiment, An to Ar4 are the same as or different from each other, and each independently a substituted or unsubstituted aryl group having 6 to 20 carbon atoms; or a substituted or unsubstituted heteroaryl group having 2 to 20 carbon atoms.

According to another embodiment, An to Ar4 are the same as or different from each other, and each independently a substituted or unsubstituted phenyl group; a substituted or unsubstituted naphthyl group; a substituted or unsubstituted biphenyl group; a substituted or unsubstituted terphenyl group; a substituted or unsubstituted anthracenyl group; a substituted or unsubstituted phenanthryl group; a substituted or unsubstituted triphenylenyl group; a substituted or unsubstituted fluoranthenyl group; a substituted or unsubstituted chrysenyl group; a substituted or unsubstituted pyrenyl group; a substituted or unsubstituted fluorenyl group; a substituted or unsubstituted indenofluorenyl group; a substituted or unsubstituted benzofluorenyl group; a substituted or unsubstituted pyridyl group; a substituted or unsubstituted pyrazinyl group; a substituted or unsubstituted pyridazinyl group; a substituted or unsubstituted pyrimidinyl group; a substituted or unsubstituted quinolinyl group; a substituted or unsubstituted quinoxalinyl group; a substituted or unsubstituted furan group; a substituted or unsubstituted thiophene group; a substituted or unsubstituted dibenzofuran group; a substituted or unsubstituted dibenzothiophene group; a substituted or unsubstituted naphthobenzofuran group; a substituted or unsubstituted naphthobenzothiophene group; a substituted or unsubstituted benzofuran group; a substituted or unsubstituted benzothiophene group; a substituted or unsubstituted benzimidazole group; a substituted or unsubstituted benzoxazole group; a substituted or unsubstituted benzothiazole group; a substituted or unsubstituted fluorenobenzofuran group; or a substituted or unsubstituted benzofuranodibenzofuran group.

In one embodiment of the present specification, An to Ar4 may be any one selected from among structures described below.

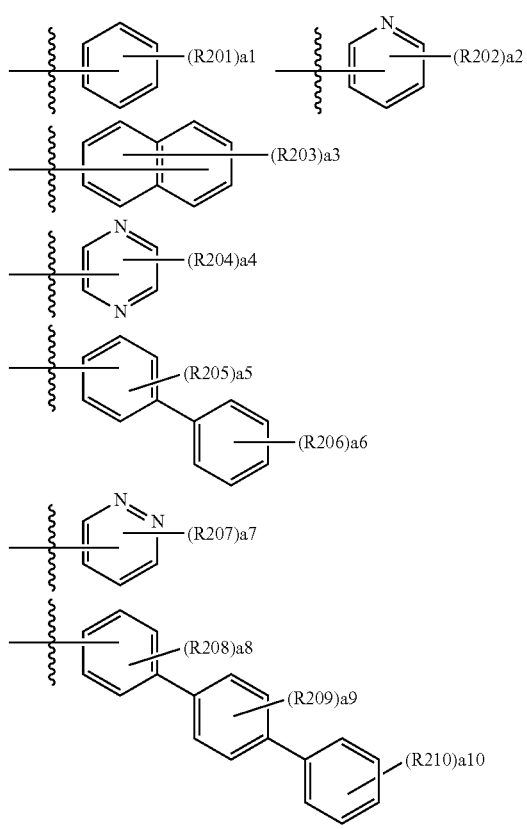

-continued
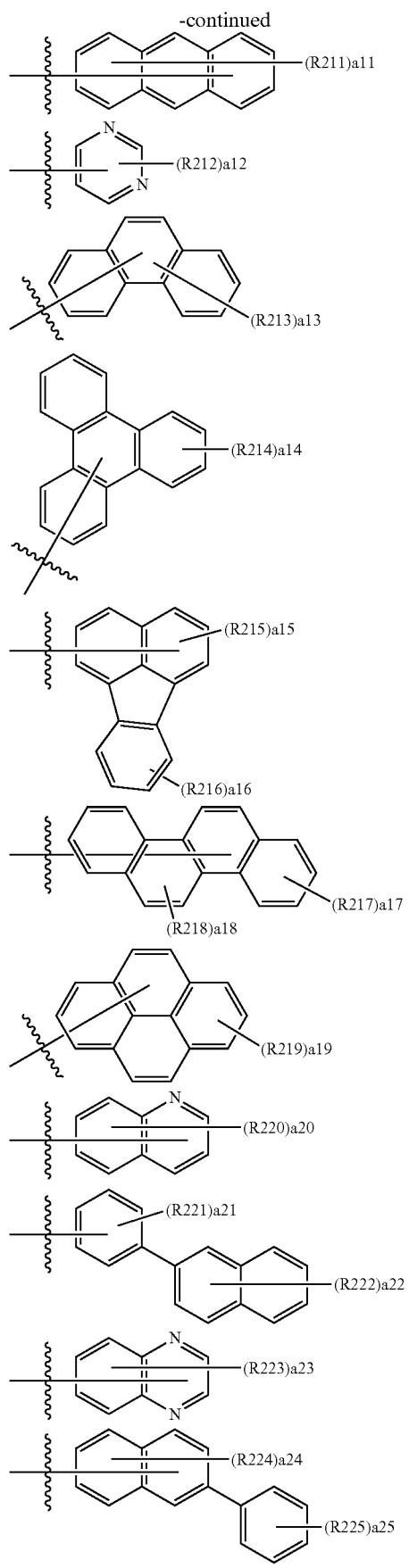
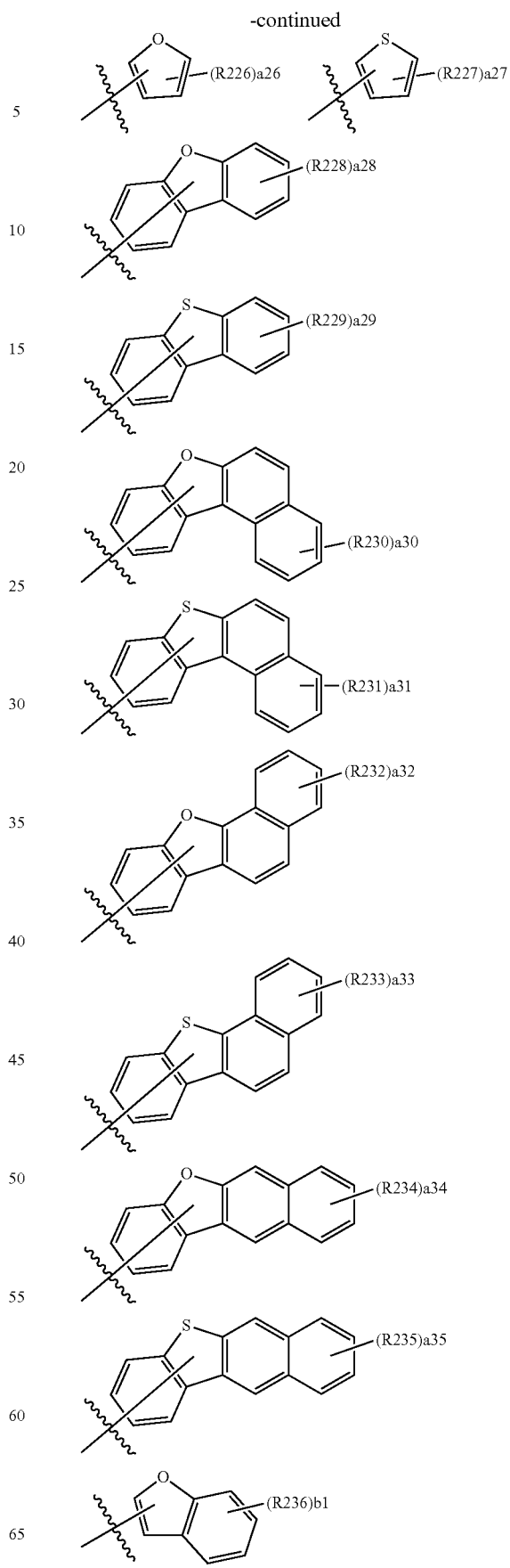

-continued
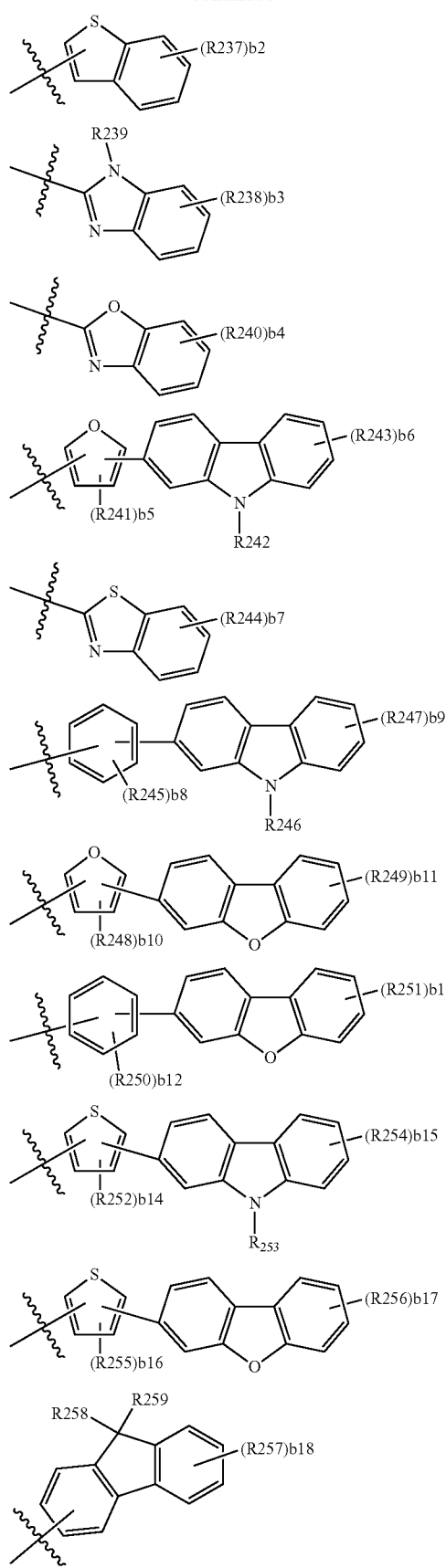
-continued
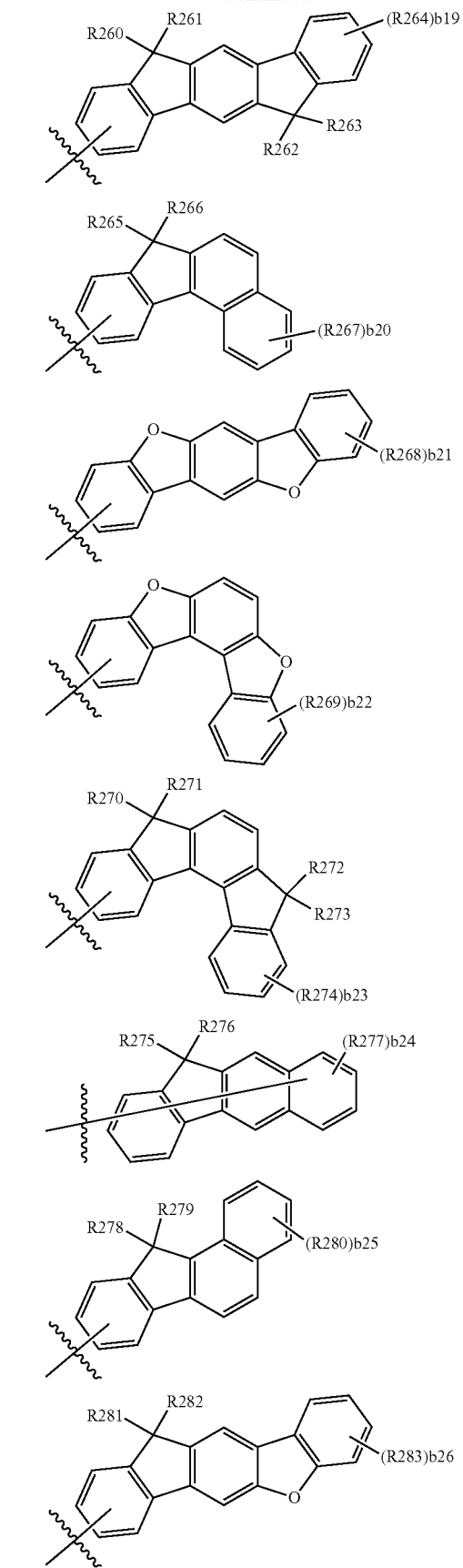

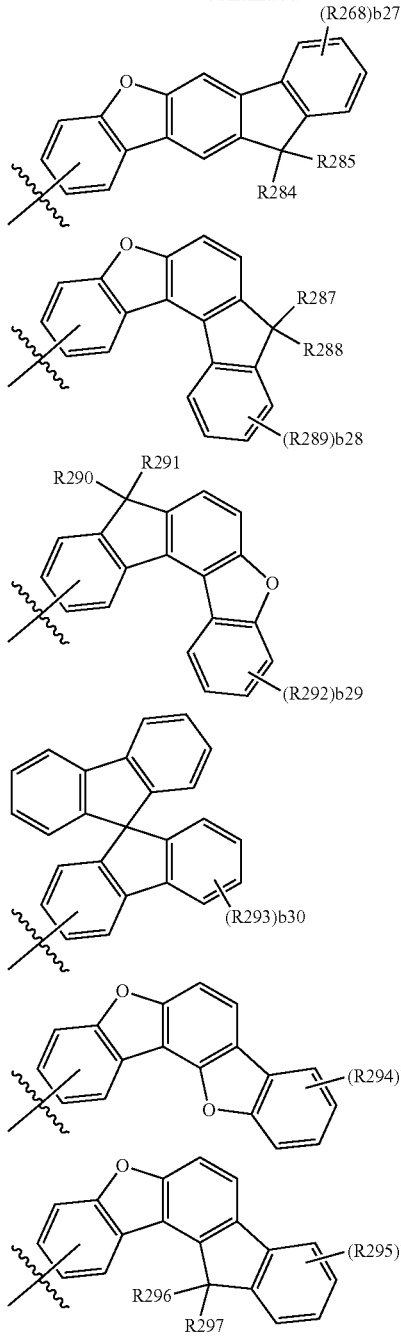

In the structures, R201 to R297 are the same as or different from each other, and each independently hydrogen; deuterium; a halogen group; a nitrile group; a nitro group; a silyl group; a boron group; a substituted or unsubstituted amine group; a substituted or unsubstituted alkyl group; a substituted or unsubstituted cycloalkyl group; a substituted or unsubstituted aryl group; or a substituted or unsubstituted heteroaryl group, a1, a6, a10, a23 and a25 are each an integer of 0 to 5, a2, a5, a8, a9, a14, a16, a17, a21, a28 to a35, b1 to b4, b6 to b9, b11 to b13, b15 and b17 to b32 are each an integer of 0 to 4, a3 and a22 are each an integer of 0 to 7, a4, a7, a12, a15. a19, a26 and a27 are each an integer of 0 to 3, a11 is an integer of 0 to 9, a13, a20 and a24 are each an integer of 0 to 6, a18, b5, b10, b14 and b16 are each an integer of 0 to 2, when a18, b5, b10, b14 and b16 are 2, substituents in the parentheses are different from each other, and when a1, a6, a10, a23, a25, a2, a5, a8, a9, a14, a16, a17, a21, a28 to a35, b1 to b4, b6 to b9, b11 to b13, b15, b17 to b32, a3, a22, a4, a7, a12, a15. a19, a26, a27, a11, a13, a20 and a24 are each 2 or greater, substituents in the parentheses are different from each other.

According to one embodiment of the present specification, Ar1 to Ar4 are the same as or different from each other, and each independently a phenyl group unsubstituted or substituted with a methyl group, a butyl group, a trimethylsilyl group or a naphthyl group; a biphenyl group unsubstituted or substituted with a methyl group; a dibenzofuranyl group; a naphthyl group; a phenanthrenyl group; a fluorenyl group substituted with a methyl group; a naphthobenzofuranyl group; an indenofluorenyl group substituted with a methyl group; or a benzofluorenyl group.

In one embodiment of the present specification, R201 to R297 are the same as or different from each other, and each independently hydrogen; deuterium; a silyl group; a substituted or unsubstituted alkyl group; a substituted or unsubstituted cycloalkyl group; or a substituted or unsubstituted aryl group.

In another embodiment, R201 to R297 are the same as or different from each other, and each independently hydrogen; deuterium; a silyl group; a substituted or unsubstituted alkyl group having 1 to 30 carbon atoms; a substituted or unsubstituted cycloalkyl group having 3 to 30 carbon atoms; or a substituted or unsubstituted aryl group having 6 to 30 carbon atoms.

In another embodiment, R201 to R297 are the same as or different from each other, and each independently hydrogen; deuterium; a silyl group; a substituted or unsubstituted alkyl group having 1 to 20 carbon atoms; a substituted or unsubstituted cycloalkyl group having 3 to 20 carbon atoms; or a substituted or unsubstituted aryl group having 6 to 20 carbon atoms.

In another embodiment, R201 to R297 are the same as or different from each other, and each independently hydrogen; deuterium; a silyl group unsubstituted or substituted with an alkyl group; a substituted or unsubstituted alkyl group having 1 to 20 carbon atoms; a substituted or unsubstituted cycloalkyl group having 3 to 20 carbon atoms; or a substituted or unsubstituted aryl group having 6 to 20 carbon atoms.

According to another embodiment, R201 to R297 are the same as or different from each other, and each independently hydrogen; deuterium; a silyl group substituted with a methyl group; a substituted or unsubstituted methyl group; a substituted or unsubstituted ethyl group; a substituted or unsubstituted propyl group; a substituted or unsubstituted t-butyl group; a substituted or unsubstituted phenyl group; a substituted or unsubstituted biphenyl group; a substituted or unsubstituted cyclopentyl group; or a substituted or unsubstituted cyclohexyl group.

In another embodiment, R201 to R297 are the same as or different from each other, and each independently hydrogen; deuterium; a trimethylsilyl group; a methyl group; a t-butyl group; a phenyl group; or a biphenyl group.

In one embodiment of the present specification, a1 to a35 and b1 to b32 are each an integer of 0 to 2.

In one embodiment of the present specification, R1 to R7 are the same as or different from each other, and each independently hydrogen; deuterium; a halogen group; a nitrile group; a nitro group; a silyl group; a boron group; a substituted or unsubstituted amine group; a substituted or unsubstituted alkyl group; a substituted or unsubstituted cycloalkyl group; a substituted or unsubstituted aryl group; or a substituted or unsubstituted heteroaryl group.

According to one embodiment of the present specification, R1 to R7 are the same as or different from each other, and each independently hydrogen; deuterium; a substituted or unsubstituted alkyl group having 1 to 30 carbon atoms; a substituted or unsubstituted aryl group having 6 to 30 carbon atoms; or a substituted or unsubstituted heteroaryl group having 2 to 30 carbon atoms.

In one embodiment of the present specification, R1 to R7 are the same as or different from each other, and each independently hydrogen; deuterium; an alkyl group having 1 to 30 carbon atoms; an aryl group having 6 to 30 carbon atoms; or an aryl group having 6 to 30 carbon atoms.

In another embodiment, R1 to R7 are hydrogen.

In one embodiment of the present specification, Chemical Formula 1 may be represented by any one of the following Chemical Formulae 2 to 5.

[Chemical Formula 3]

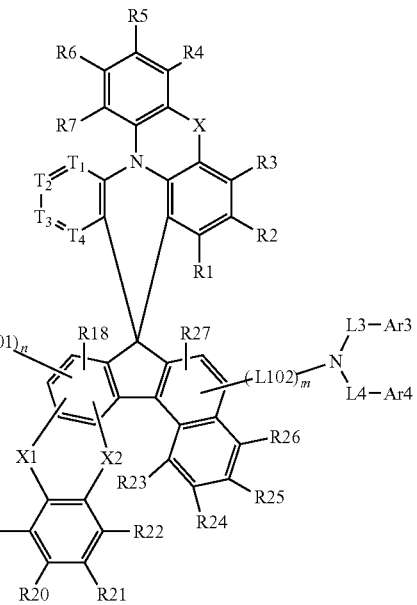

[Chemical Formula 2]

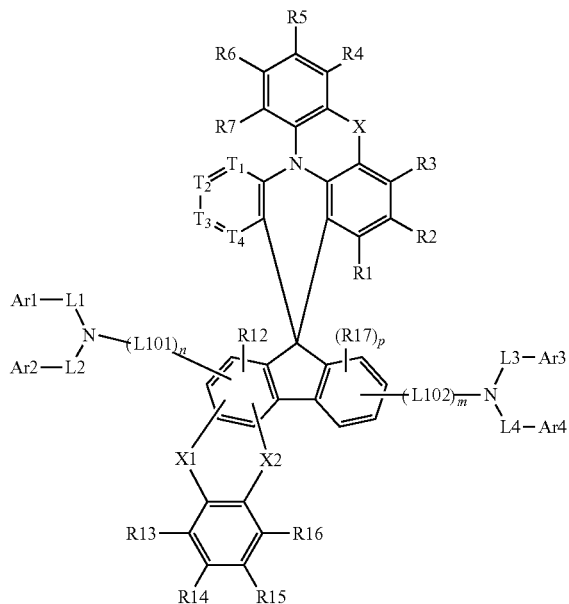

[Chemical Formula 4]

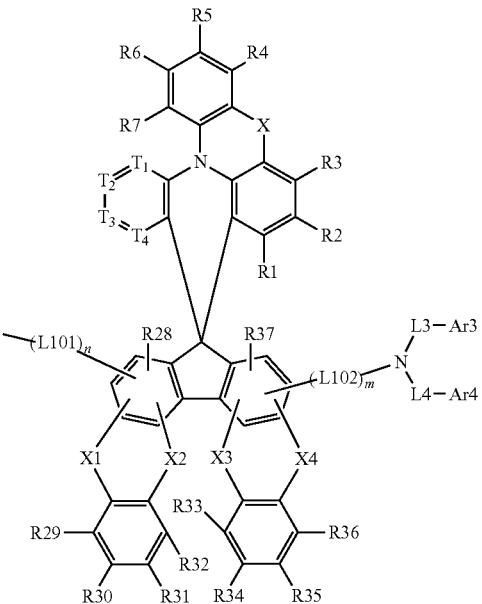

-continued

[Chemical Formula 5]

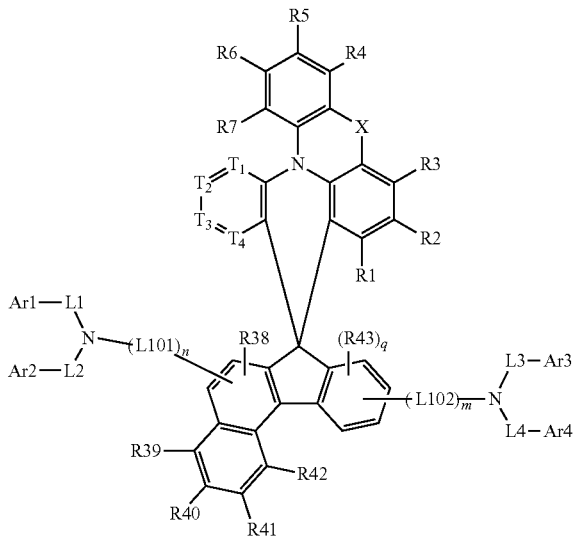

In Chemical Formulae 2 to 5,

L101, L102, L1 to L4, Ar1 to Ar4, R1 to R7, X, $T_1$ to $T_4$, m and n have the same definitions as in Chemical Formula 1, one of X1 and X2 is a direct bond, and the rest is O, S or CY1Y2, one of X3 and X4 is a direct bond, and the rest is O, S or CY3Y4, Y1 to Y4 and R12 to R43 are the same as or different from each other, and each independently hydrogen; deuterium; a halogen group; a nitrile group; a nitro group; a silyl group; a boron group; a substituted or unsubstituted amine group; a substituted or unsubstituted alkyl group; a substituted or unsubstituted cycloalkyl group; a substituted or unsubstituted aryl group; or a substituted or unsubstituted heteroaryl group, p and q are each an integer of 0 to 3, and when p and q are each 2 or greater, substituents in the parentheses are the same as or different from each other.

In one embodiment of the present specification, R12 to R43 are the same as or different from each other, and each independently hydrogen; deuterium; a substituted or unsubstituted alkyl group having 1 to 30 carbon atoms; a substituted or unsubstituted aryl group having 6 to 30 carbon atoms; or a substituted or unsubstituted heteroaryl group having 2 to 30 carbon atoms.

In another embodiment, R12 to R43 are hydrogen.

In one embodiment of the present specification, X is NR, CR'R", O or S.

In one embodiment of the present specification, R, R' and R" are the same as or different from each other, and each independently hydrogen; deuterium; a substituted or unsubstituted alkyl group having 1 to 30 carbon atoms; a substituted or unsubstituted cycloalkyl group having 3 to 30 carbon atoms; or a substituted or unsubstituted aryl group having 6 to 30 carbon atoms.

In one embodiment of the present specification, R, R' and R" are the same as or different from each other, and each independently hydrogen; deuterium; a substituted or unsubstituted alkyl group having 1 to 20 carbon atoms; a substituted or unsubstituted cycloalkyl group having 3 to 20 carbon atoms; or a substituted or unsubstituted aryl group having 6 to 20 carbon atoms.

In another embodiment, R, R' and R" are the same as or different from each other, and each independently hydrogen; deuterium; a substituted or unsubstituted methyl group; a substituted or unsubstituted ethyl group; a substituted or unsubstituted propyl group; a substituted or unsubstituted isopropyl group; a substituted or unsubstituted butyl group; a substituted or unsubstituted t-butyl group; a substituted or unsubstituted cyclopentyl group; a substituted or unsubstituted cyclohexyl group; a substituted or unsubstituted phenyl group; or a substituted or unsubstituted biphenyl group.

In one embodiment of the present specification, R, R' and R" are the same as or different from each other, and each independently a methyl group, an ethyl group, a propyl group, an isopropyl group, a butyl group, a t-butyl group, a cyclopentyl group, a cyclohexyl group, a phenyl group or a biphenyl group.

In one embodiment of the present specification, X1 to X4 are O, S or CY1Y2.

In one embodiment of the present specification, X1 is O, and X2 is a direct bond.

In one embodiment of the present specification, X1 is S, and X2 is a direct bond.

In one embodiment of the present specification, X1 is a direct bond, and X2 is O.

In one embodiment of the present specification, X1 is a direct bond, and X2 is S.

In one embodiment of the present specification, X1 is a direct bond, and X2 is CY1Y2.

In one embodiment of the present specification, X1 is CY1Y2, and X2 is a direct bond.

In one embodiment of the present specification, any one of X3 and X4 is a direct bond, and the rest is O, S or CY3Y4.

In one embodiment of the present specification, X3 is O, and X4 is a direct bond.

In one embodiment of the present specification, X3 is S, and X4 is a direct bond.

In one embodiment of the present specification, X3 is CY1Y2, and X4 is a direct bond.

In one embodiment of the present specification, X3 is a direct bond, and X4 is O.

In one embodiment of the present specification, X3 is a direct bond, and X4 is S.

In one embodiment of the present specification, X3 is a direct bond, and X4 is CY3Y4.

In one embodiment of the present specification, Y1 to Y4 are the same as or different from each other, and each independently hydrogen; deuterium; a substituted or unsubstituted alkyl group having 1 to 30 carbon atoms.

In another embodiment, Y1 to Y4 are the same as or different from each other, and each independently hydrogen; deuterium; an alkyl group having 1 to 30 carbon atoms.

In one embodiment of the present specification, Y1 to Y4 are the same as or different from each other, and each independently a methyl group, an ethyl group, a propyl group, an isopropyl group, a butyl group or a t-butyl group.

In one embodiment of the present specification, $T_1$ to $T_4$ are the same as or different from each other, and each independently CRa or N.

In another embodiment, $T_1$ to $T_4$ are the same as or different from each other, and each independently CRa or N.

In another embodiment, $T_1$ is N, and the rest are CRa.

In another embodiment, $T_2$ is N, and the rest are CRa.

In another embodiment, $T_3$ is N, and the rest are CRa.

In another embodiment, $T_4$ is N, and the rest are CRa.

In another embodiment, Ra is hydrogen; deuterium; or a substituted or unsubstituted alkyl group.

In another embodiment, Ra is hydrogen; deuterium; or a substituted or unsubstituted alkyl group having 1 to 30 carbon atoms.

In another embodiment, Ra is hydrogen; deuterium; or a substituted or unsubstituted alkyl group having 1 to 20 carbon atoms.

In another embodiment, Ra is hydrogen; deuterium; or a substituted or unsubstituted alkyl group having 1 to 12 carbon atoms.

In another embodiment, Ra is hydrogen; deuterium; a substituted or unsubstituted methyl group; a substituted or unsubstituted ethyl group; or a substituted or unsubstituted t-butyl group.

According to another embodiment, Ra is hydrogen; deuterium; a methyl group; an ethyl group; or a t-butyl group.

In one embodiment of the present specification, Chemical Formula 1 may be any one selected from among the following compounds.

Compound 1

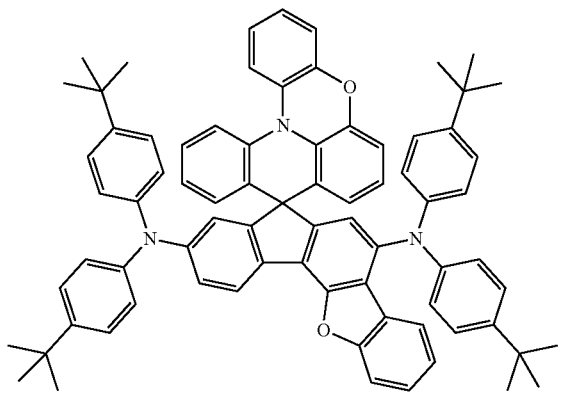

Compound 2

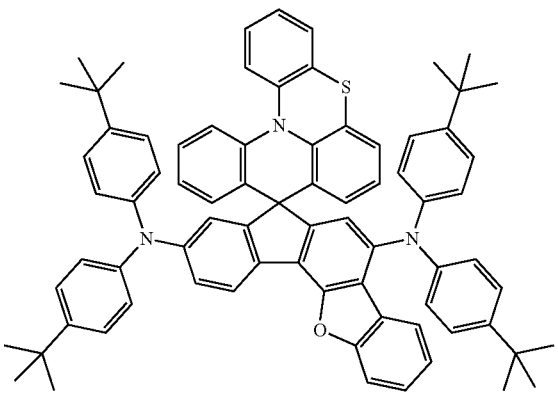

Compound 3

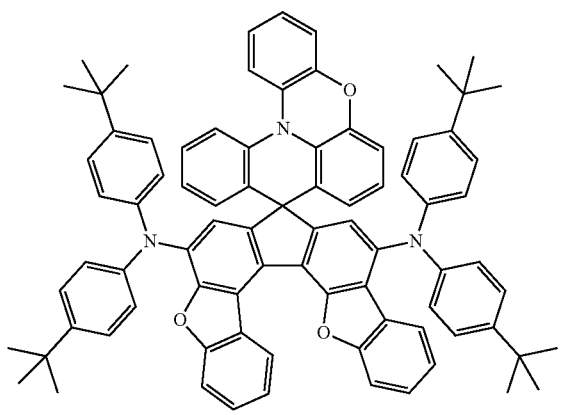

Compound 4

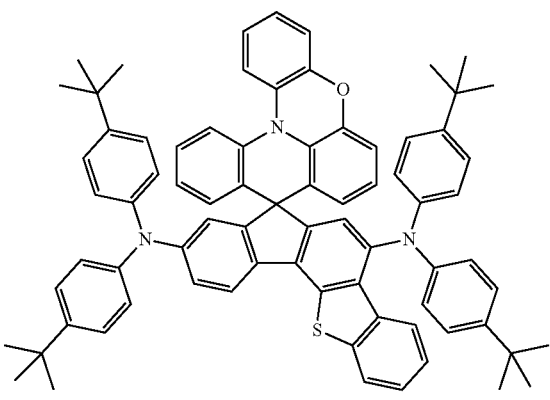

Compound 5

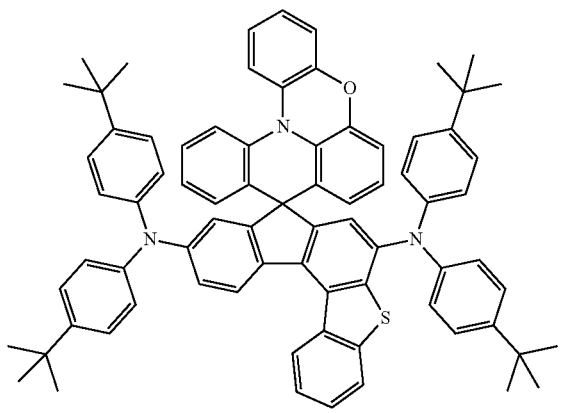

Compound 6

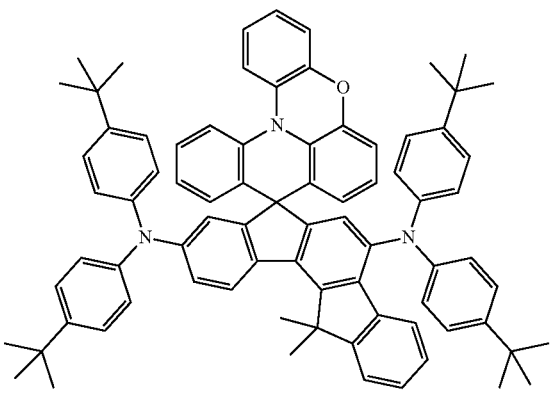

Compound 7
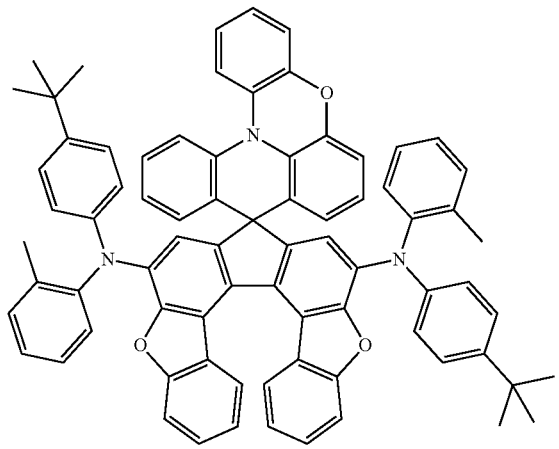
Compound 8
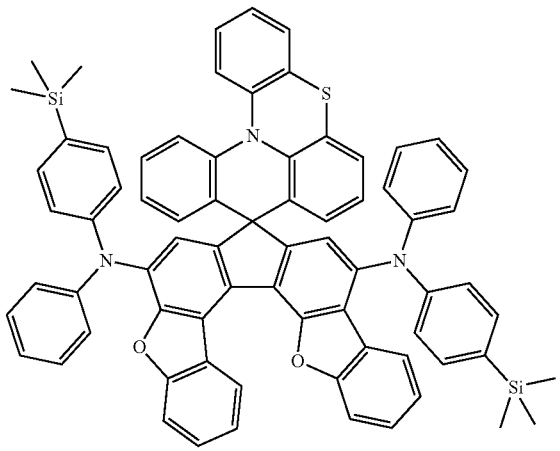
Compound 9
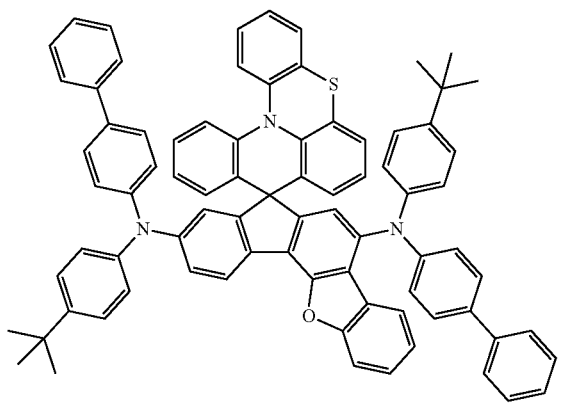
Compound 10
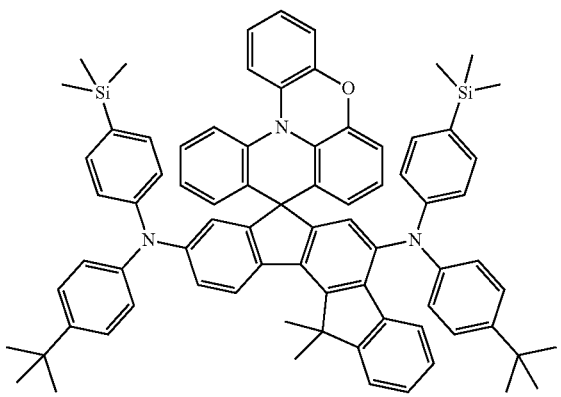
Compound 11
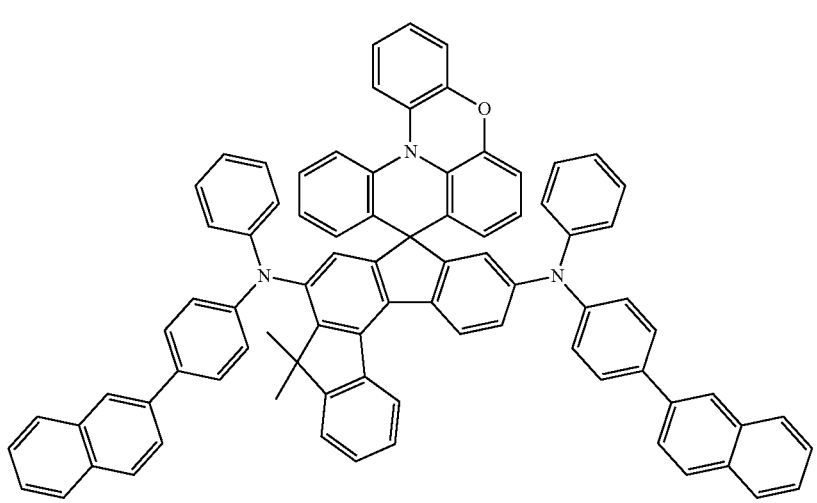

-continued
Compound 12
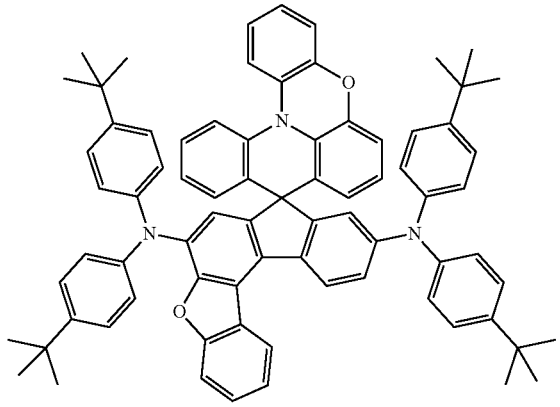
Compound 13
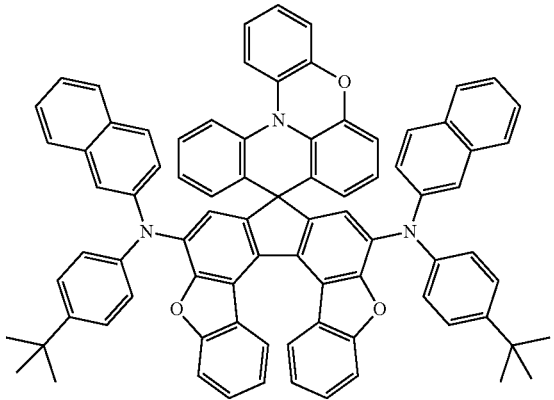
Compound 14
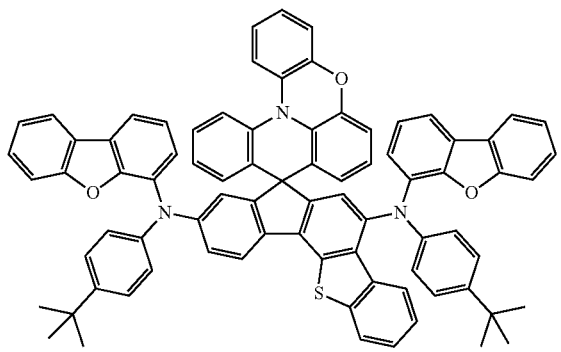
Compound 15
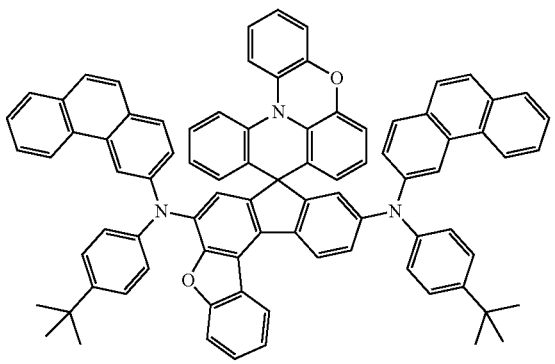
Compound 16
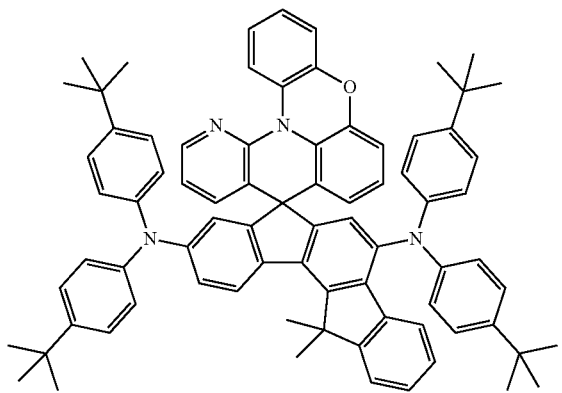
Compound 17
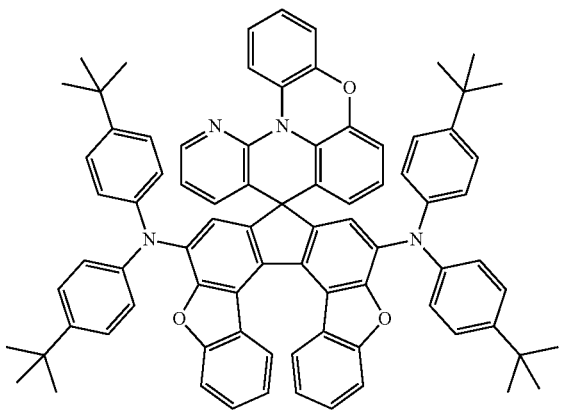

-continued
Compound 18
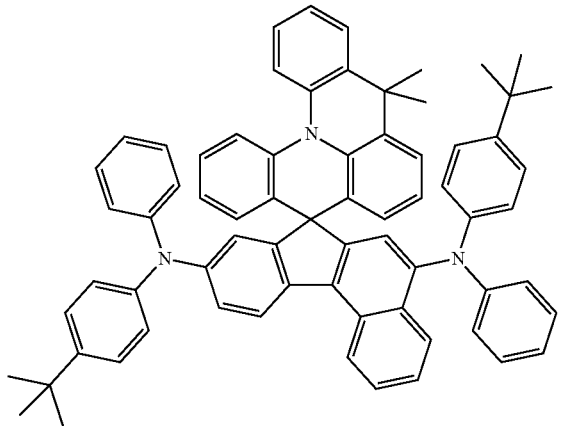
Compound 19
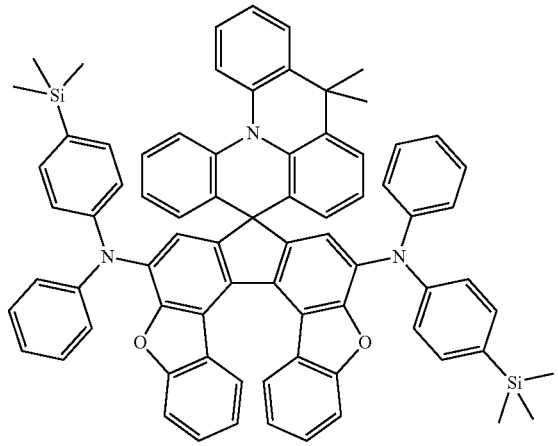
Compound 20
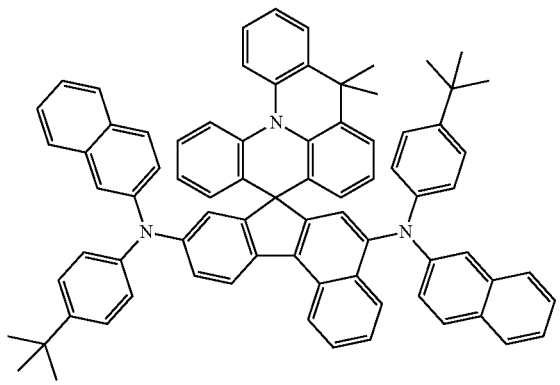
Compound 21
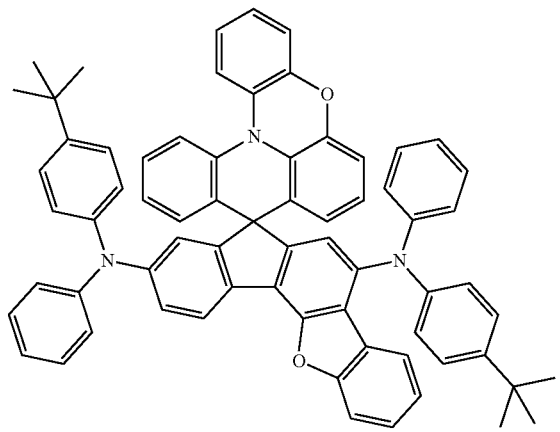
Compound 22
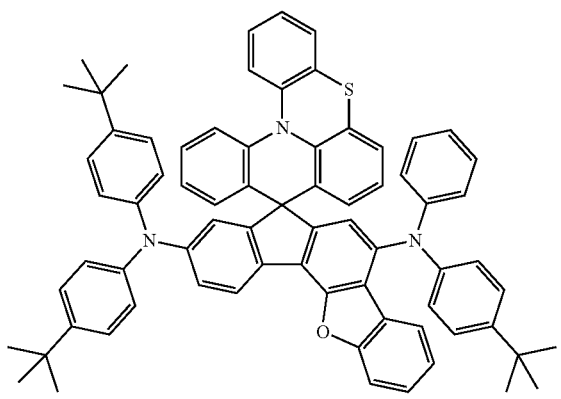
Compound 23
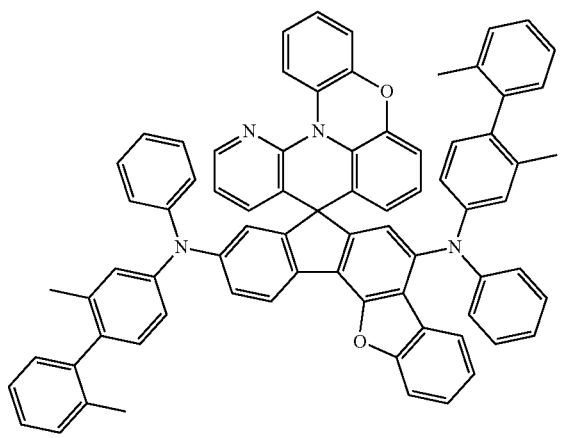

Compound 24
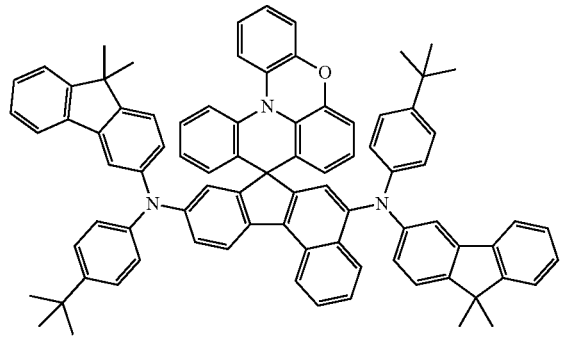
Compound 25
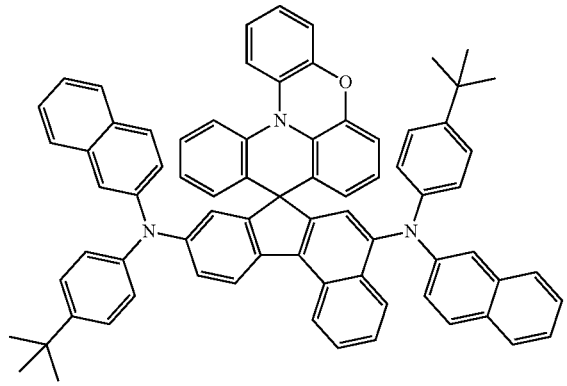
Compound 26
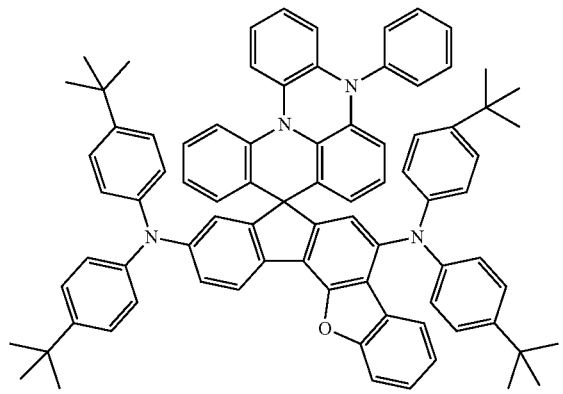
Compound 27
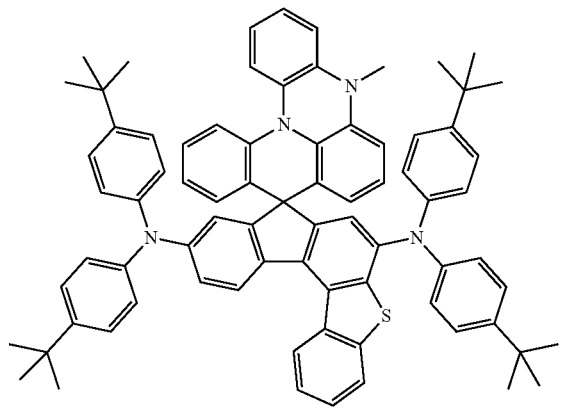
Compound 28
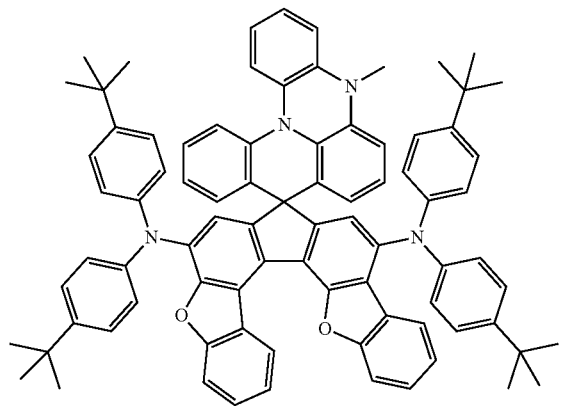
Compound 29
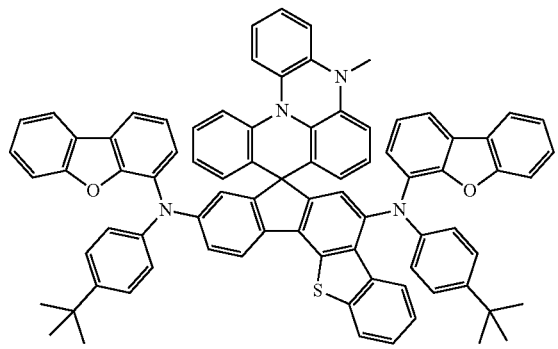

-continued
Compound 30
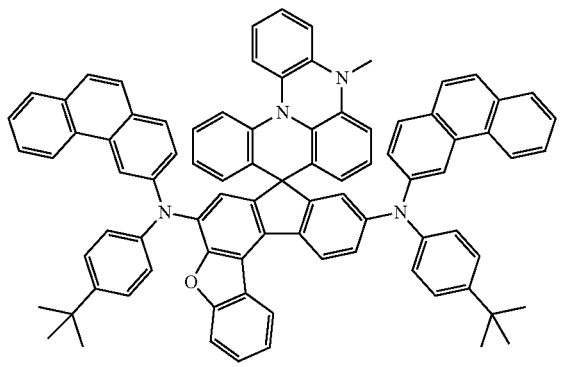
Compound 31
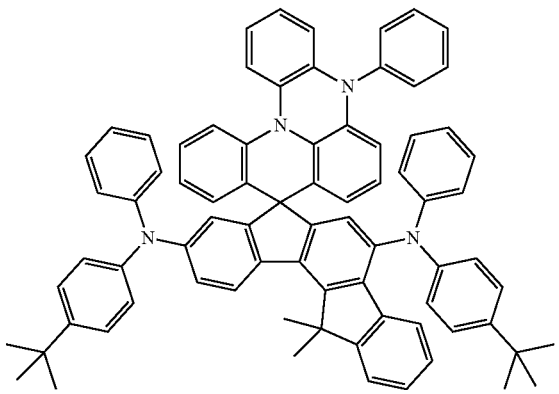
Compound 32
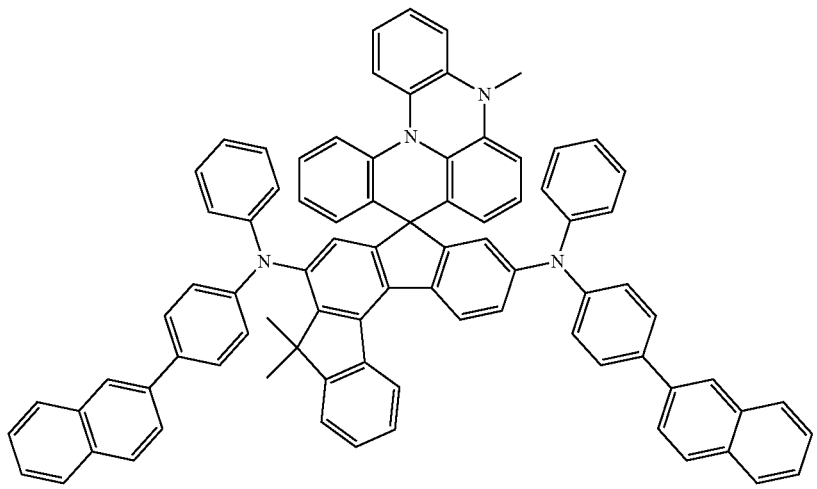
Compound 33
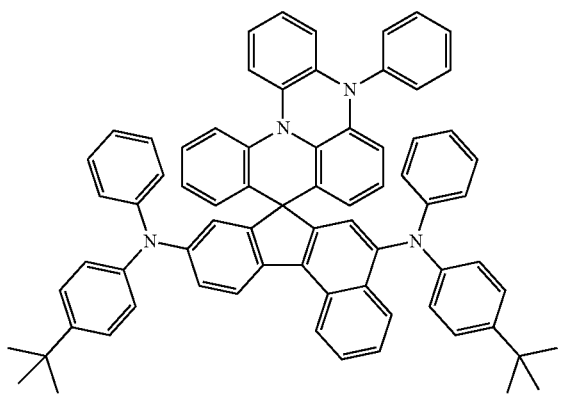
Compound 34
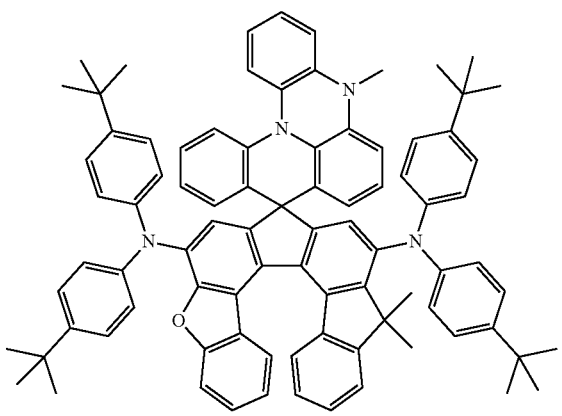

-continued
Compound 35
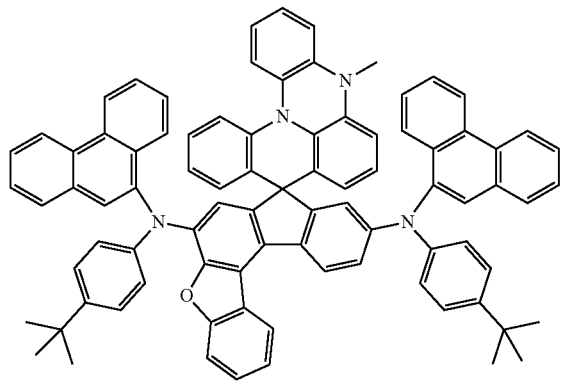
Compound 36
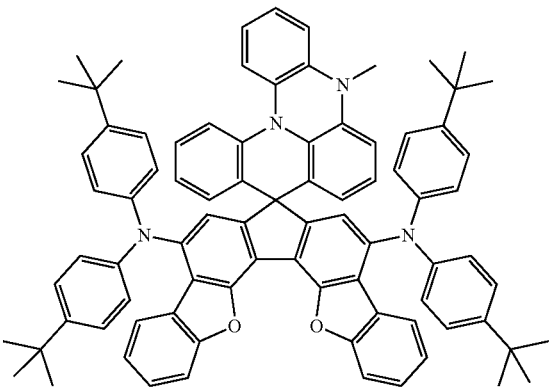
Compound 37
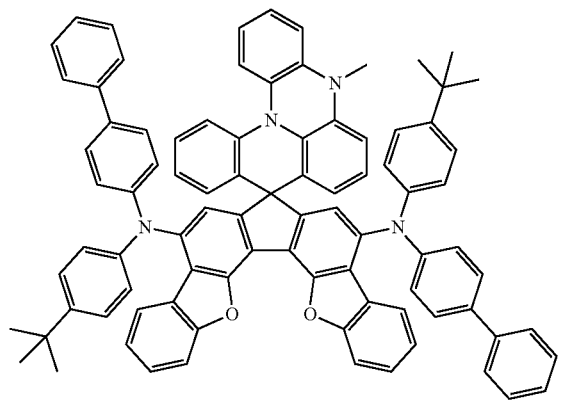
Compound 38
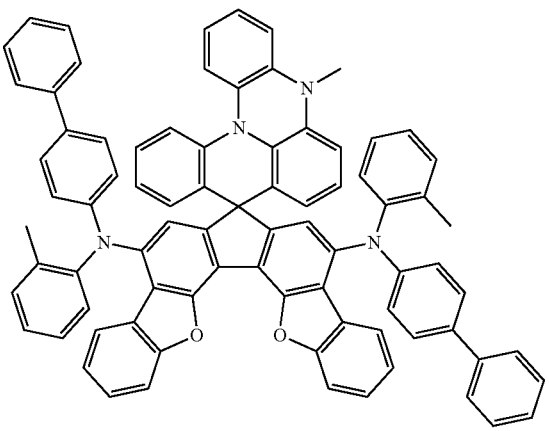
Compound 39
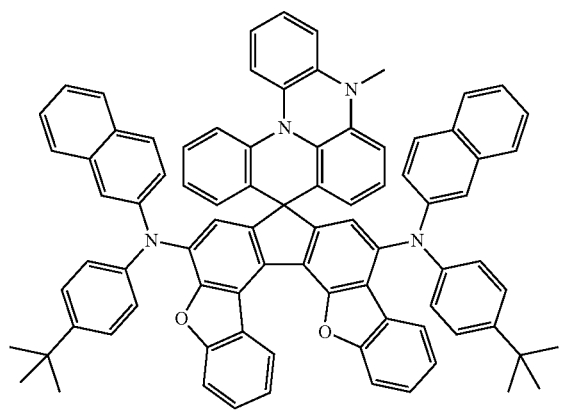
Compound 40
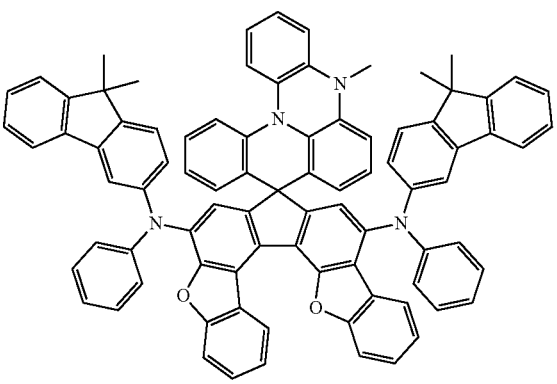

-continued
Compound 41
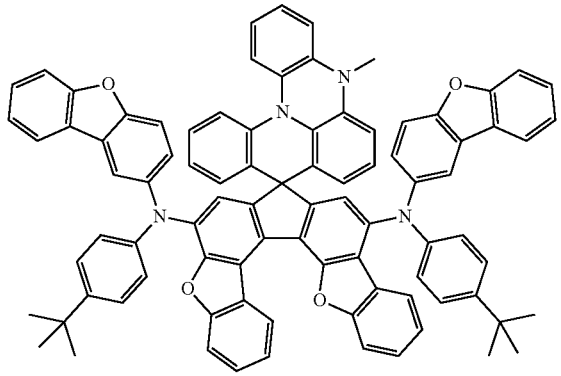
Compound 42
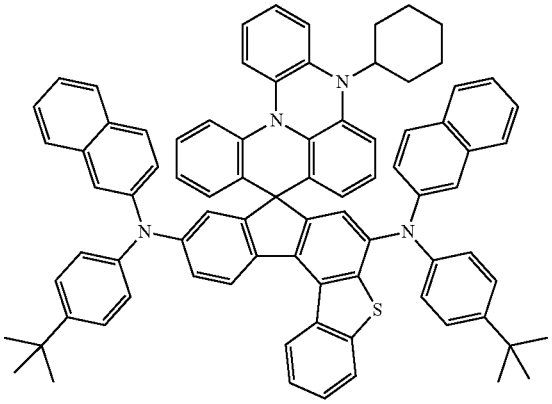
Compound 43
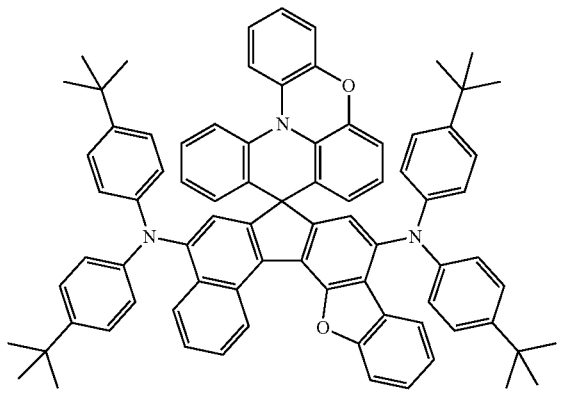
Compound 44
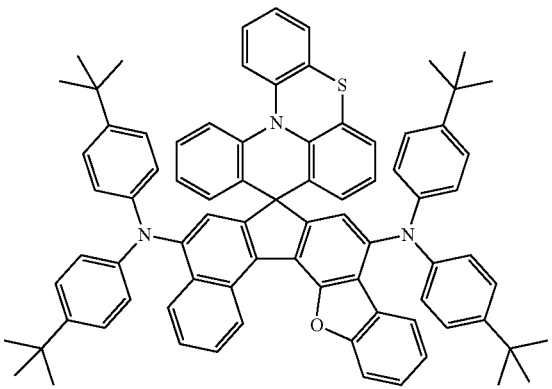
Compound 45
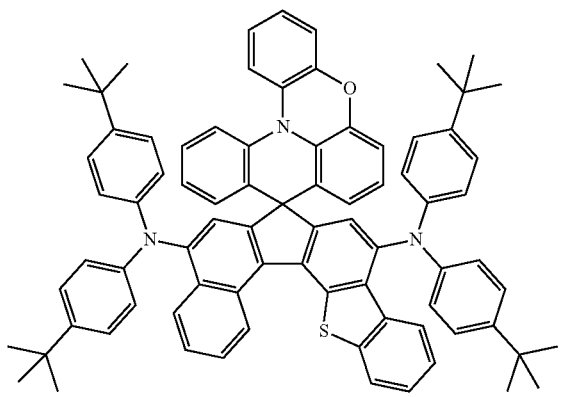
Compound 46
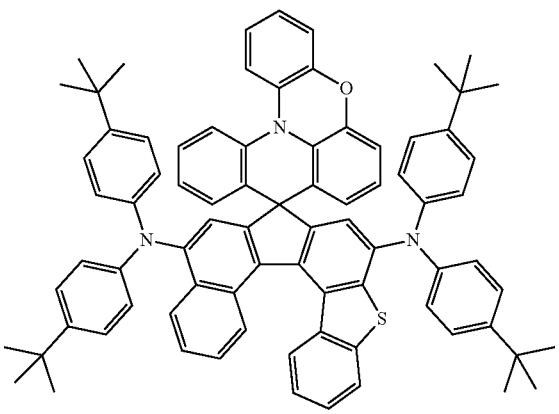

-continued
Compound 47
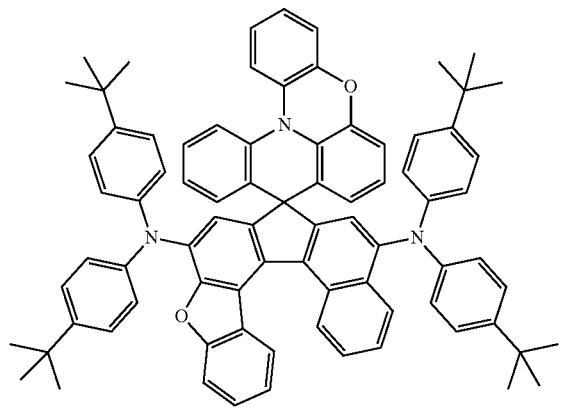
Compound 48
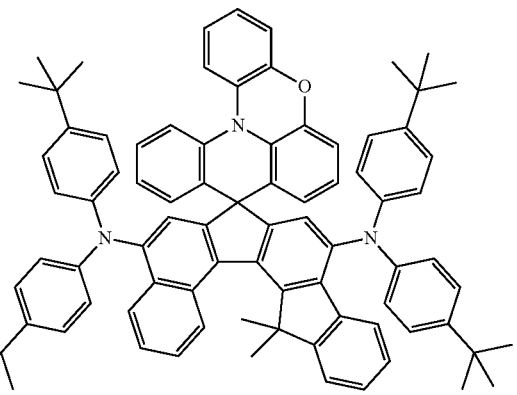
Compound 49
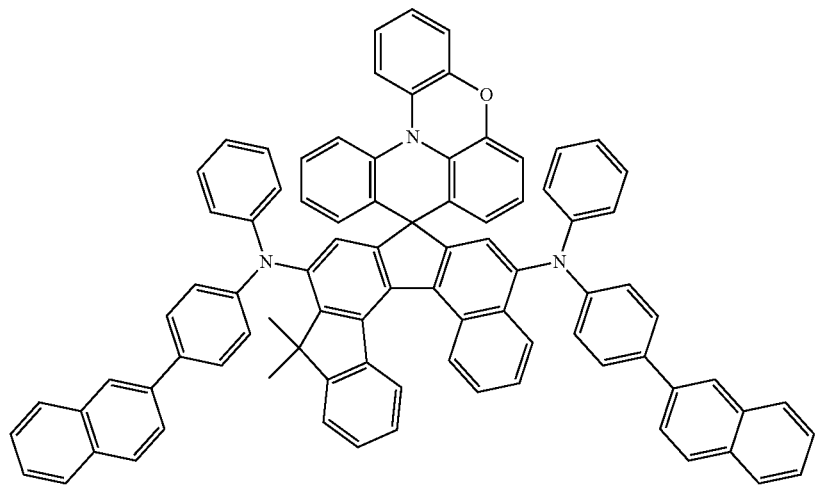
Compound 50
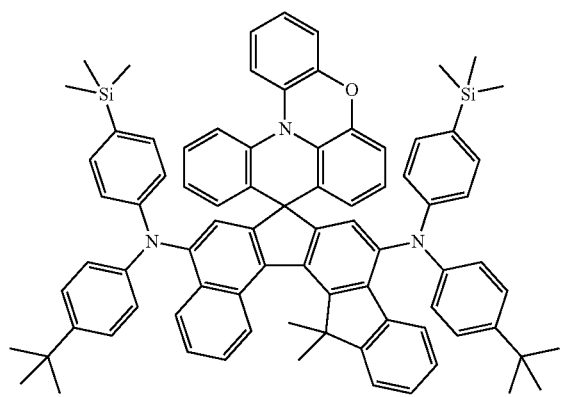
Compound 51
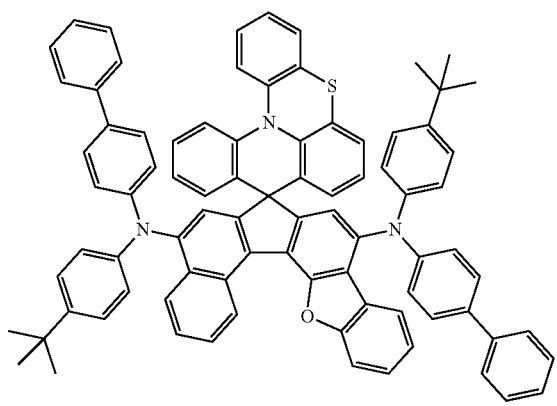

-continued
Compound 52
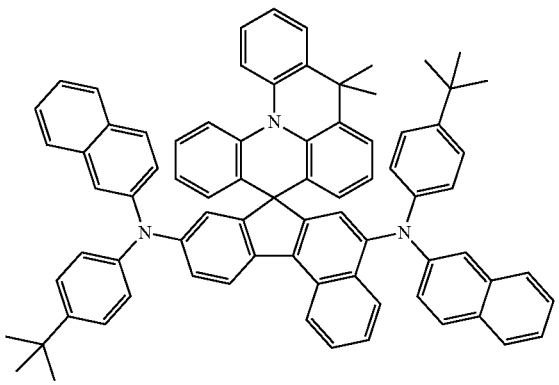
Compound 53
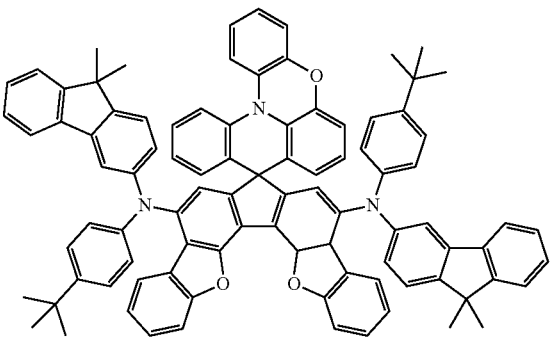
Compound 54
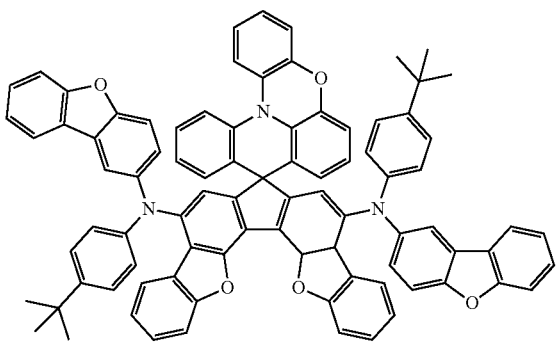
Compound 55
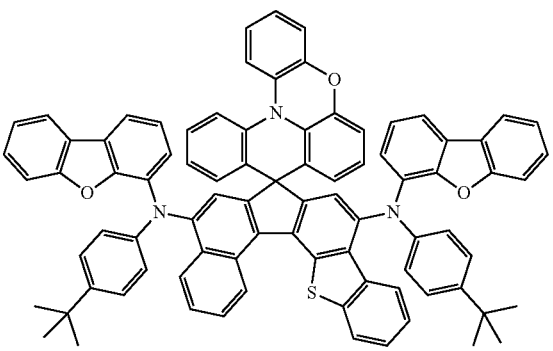
Compound 56
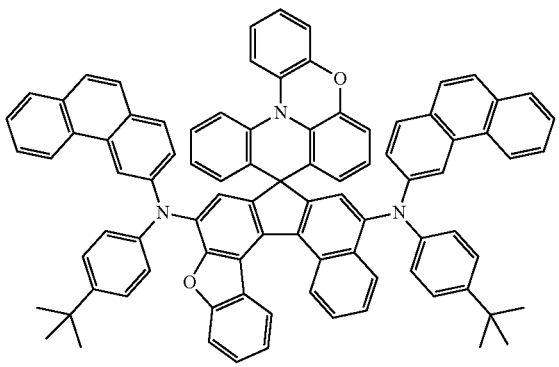
Compound 57
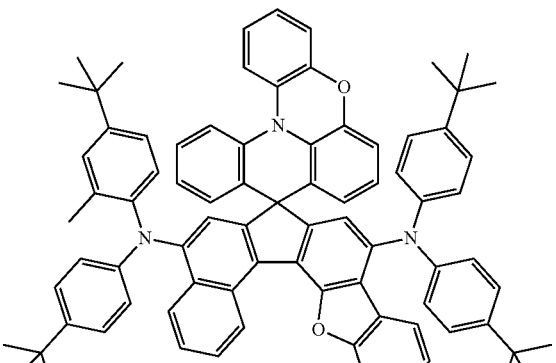
Compound 59
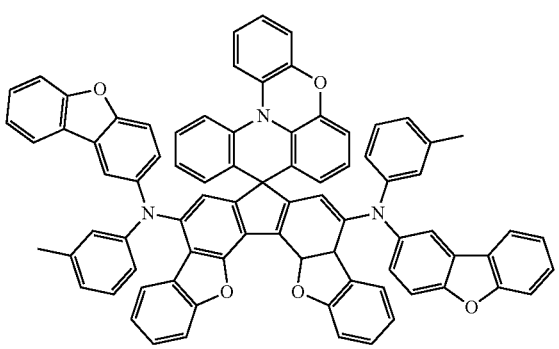
Compound 60
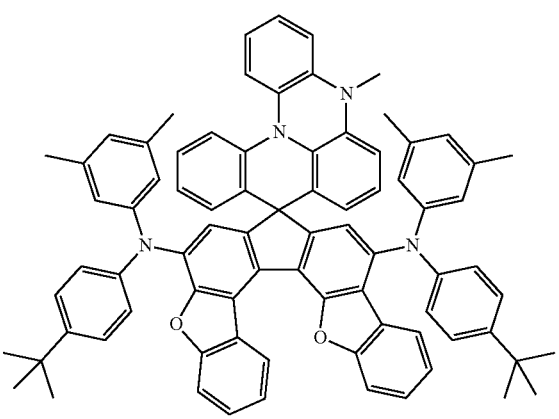

Compound 61
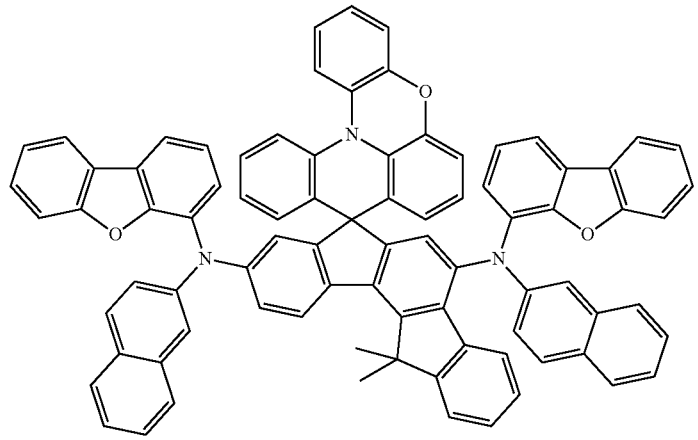
Compound 62
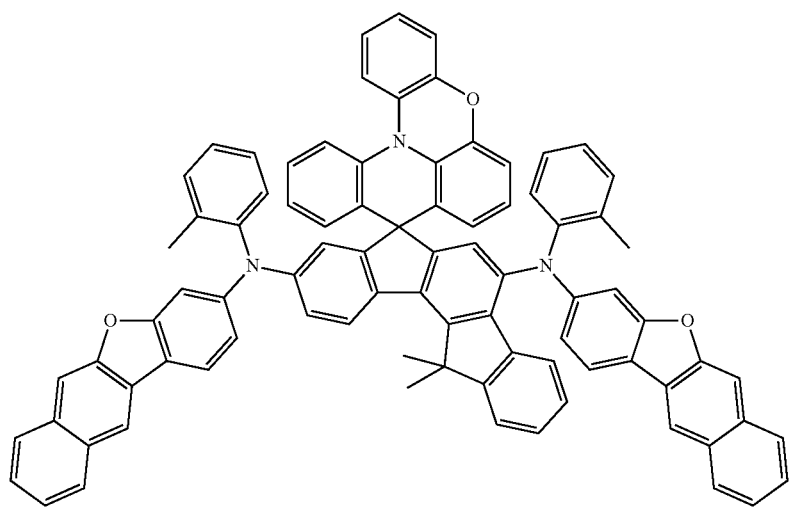
Compound 63
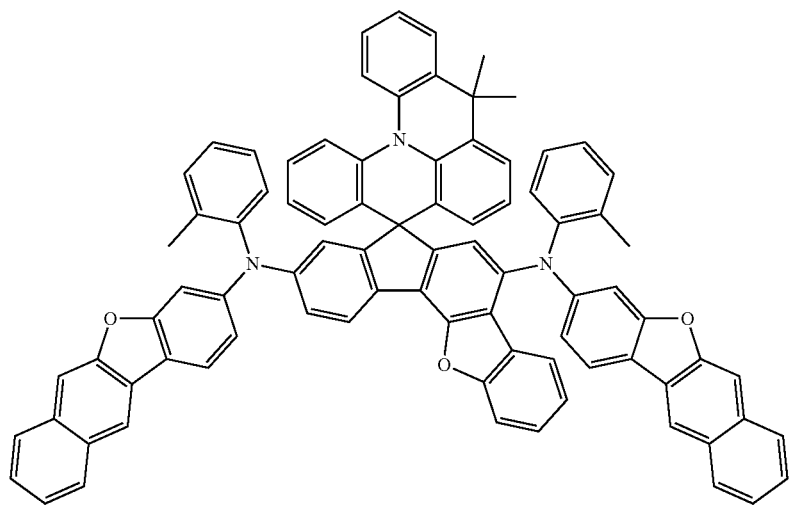

Compound 64
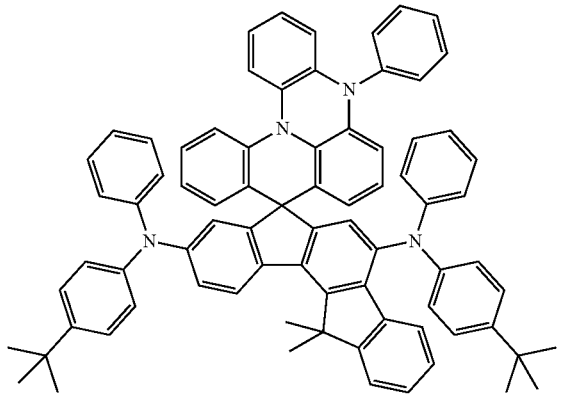
Compound 65
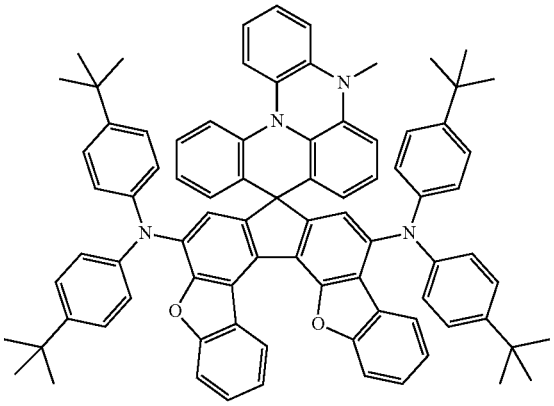
Compound 66
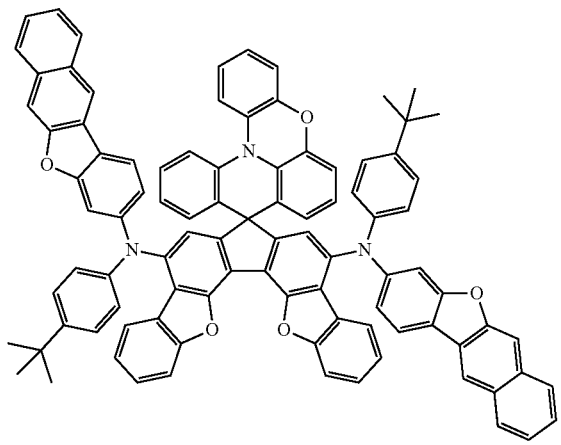
Compound 67
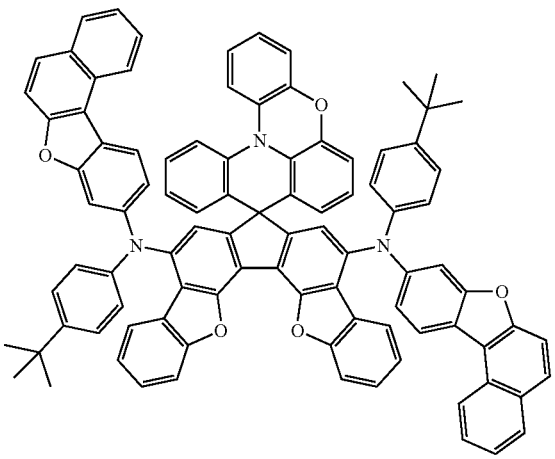
Compound 68
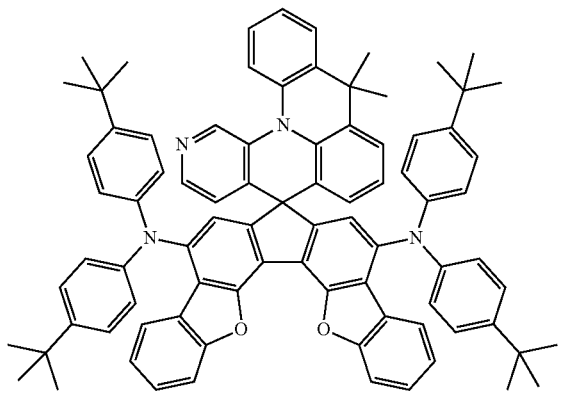
Compound 59
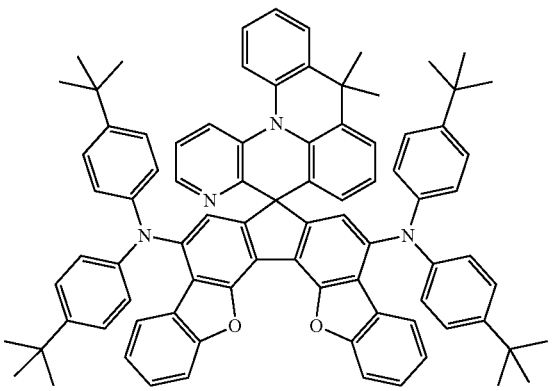

-continued
Compound 70
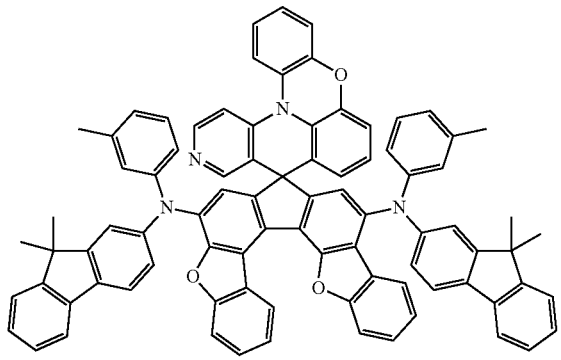
Compound 71
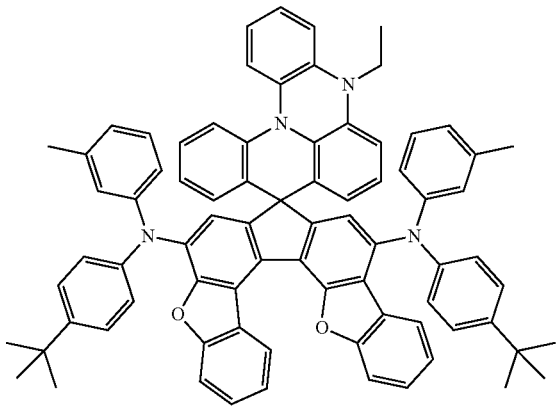
Compound 72
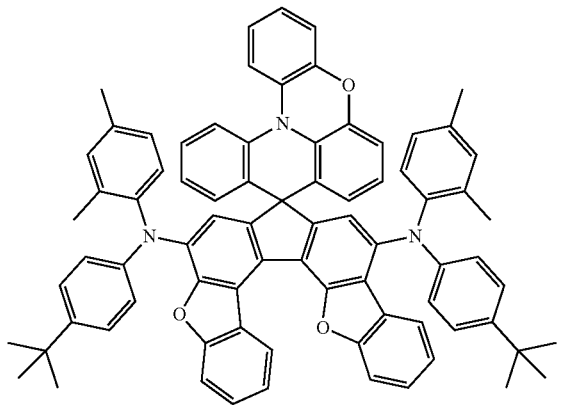
Compound 73
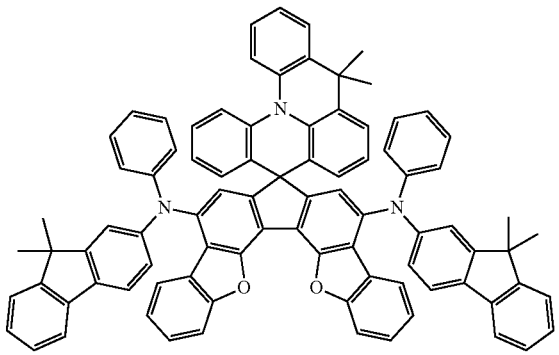
Compound 74
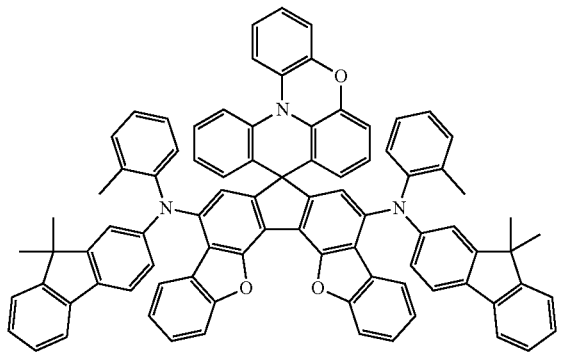
Compound 75
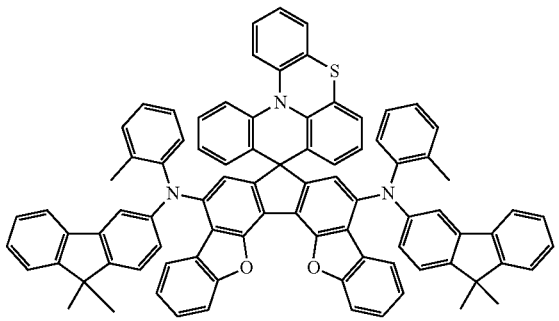

-continued
Compound 76
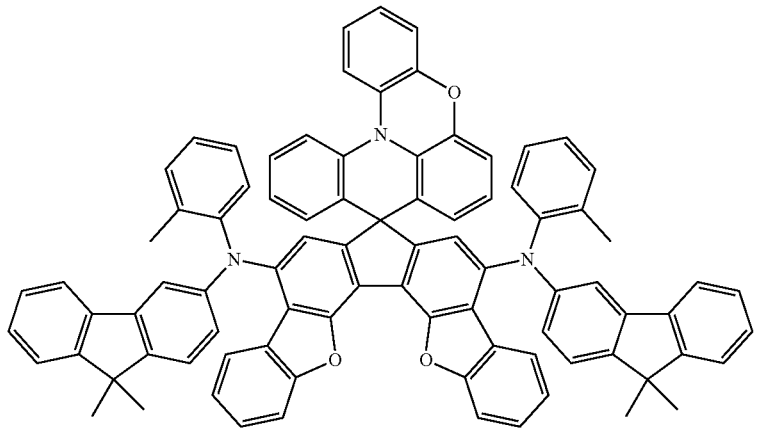
Compound 77
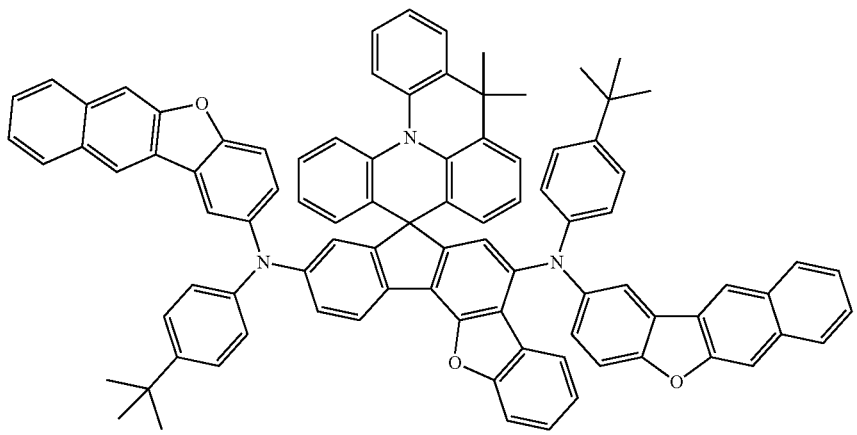
Compound 78
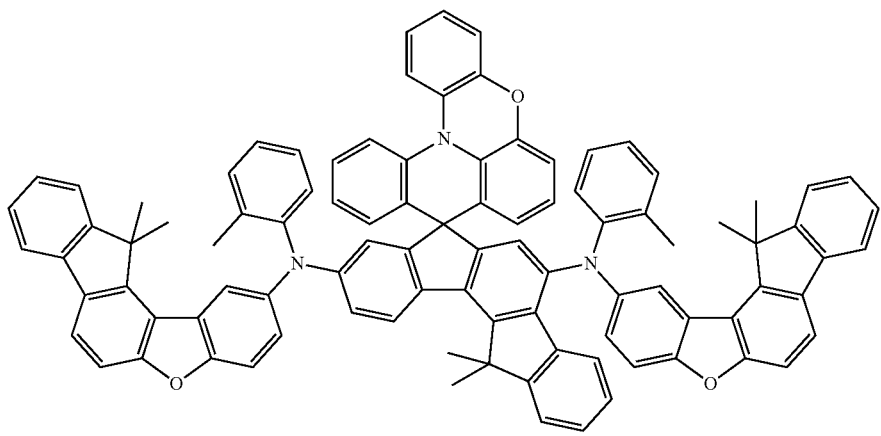

Compound 79
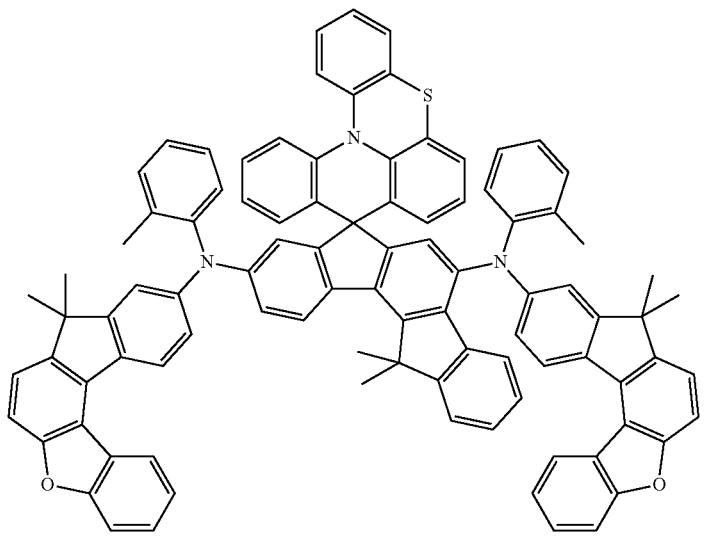
Compound 80
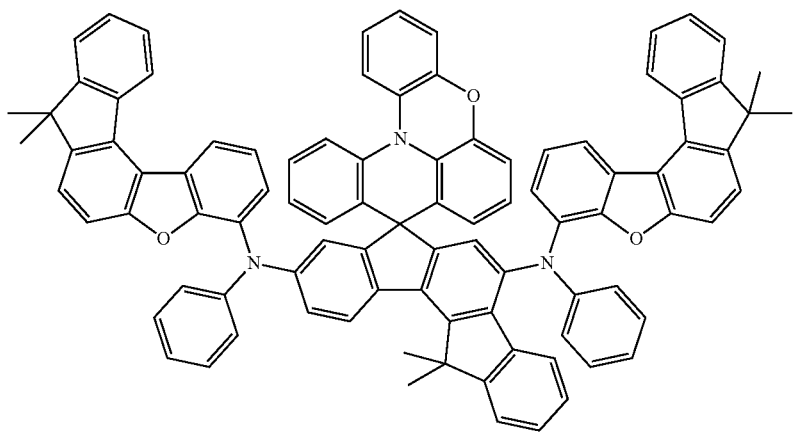
Compound 81
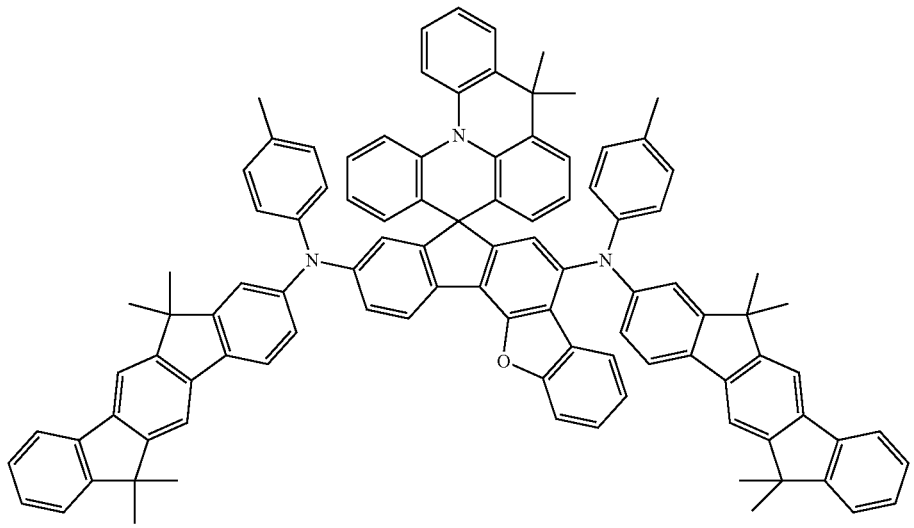

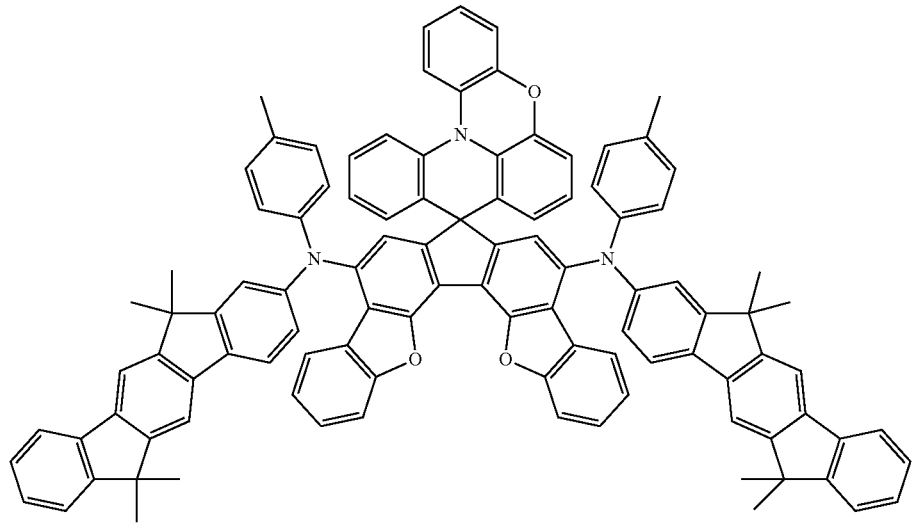
Compound 82
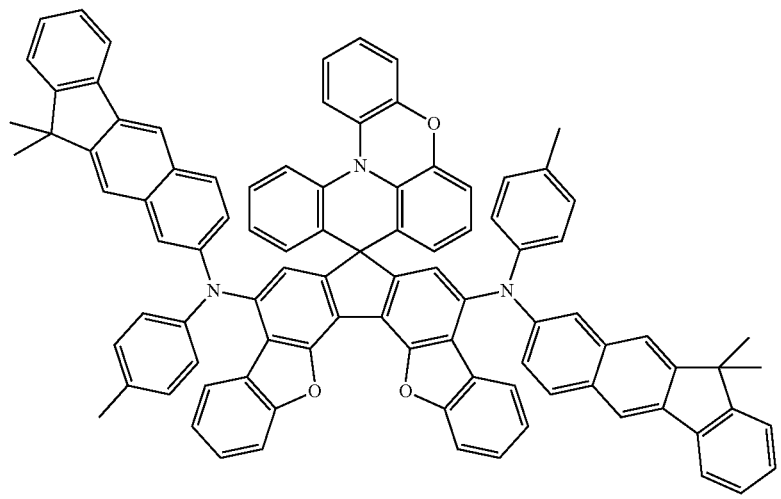
Compound 83

Compound 84

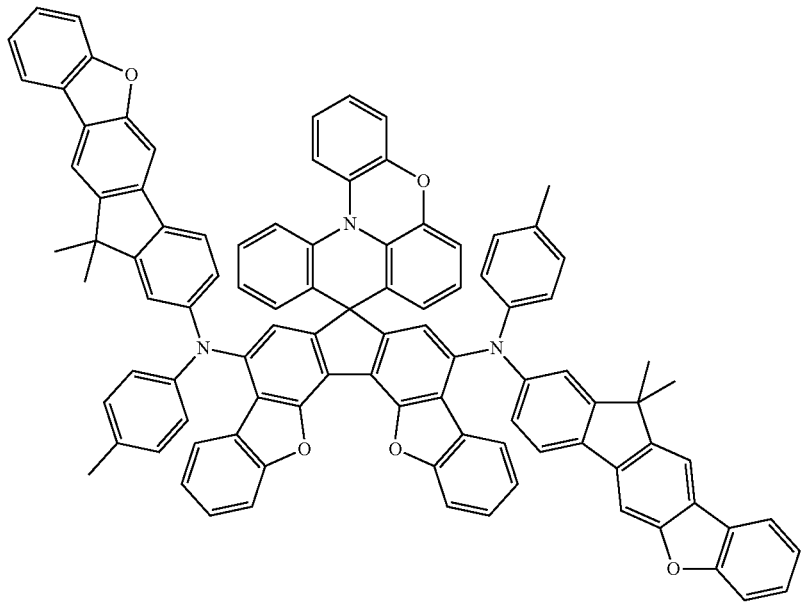

Compound 85

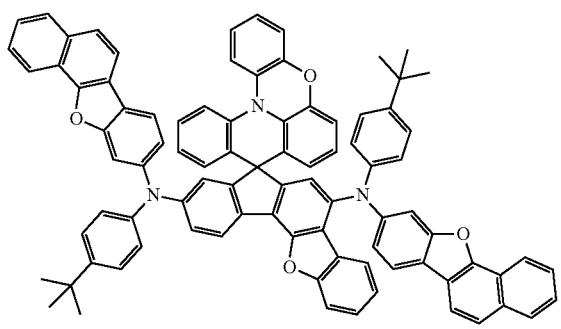

Compound 86

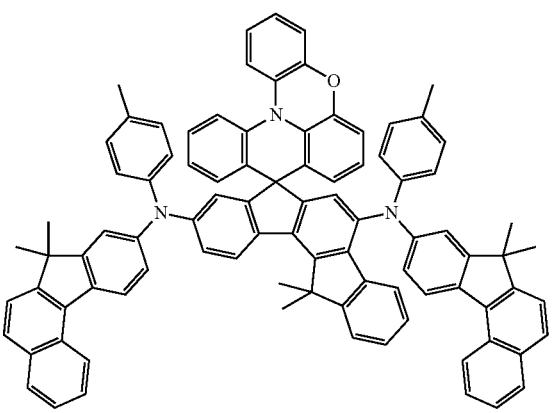

Compound 87

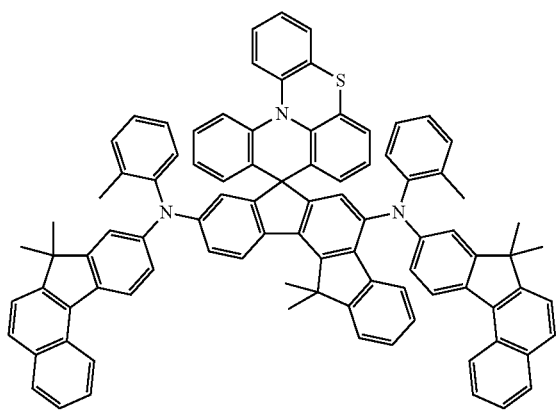

Compound 88

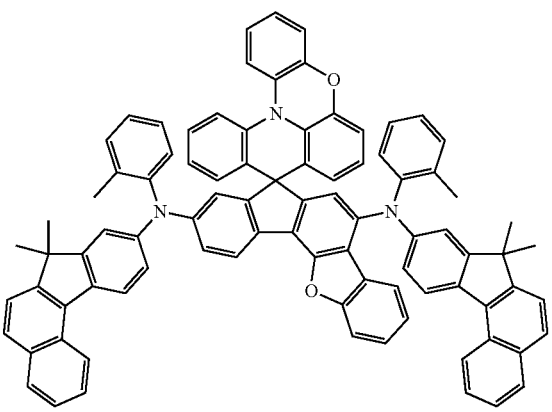

The heterocyclic compound of Chemical Formula 1 according to one embodiment of the present specification may have its core structure prepared using the following general preparation method.

In the general preparation method of the heterocyclic compound of Chemical Formula 1 to describe below, typical examples are described, however, substituents may be added or excluded as necessary, and positions of the substituents may change.

In addition, starting materials, reaction materials, reaction conditions and the like may vary based on technologies known in the art.

[General Preparation Method 1]

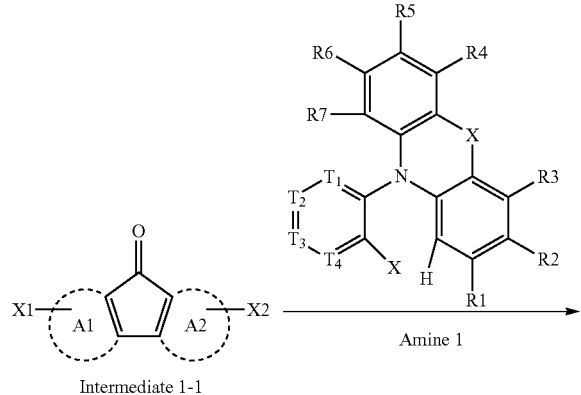

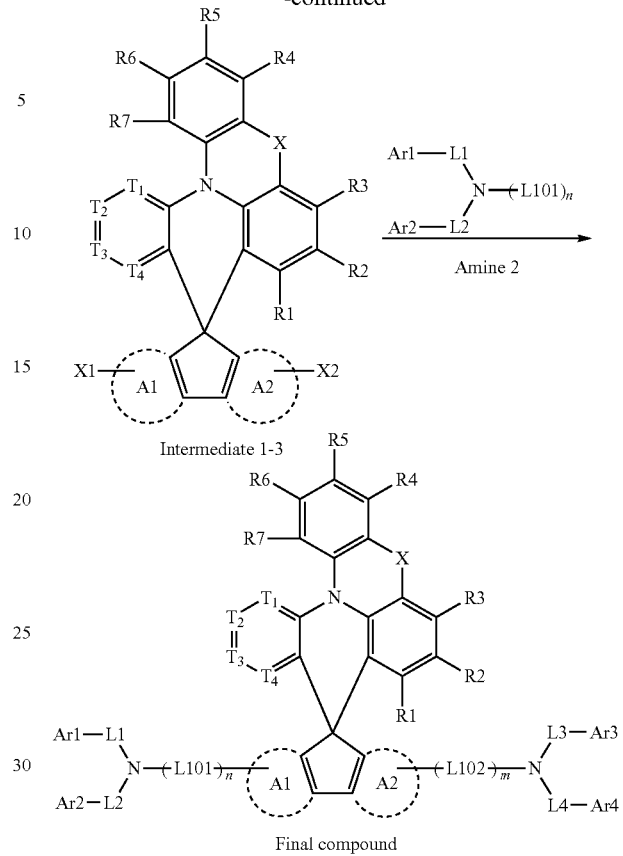

Using [Intermediate 1-1], [Intermediate 1-2] is synthesized through coupling using [Amine 1] and a base such as butyllithium. [Intermediate 1-3] may be obtained through a spiro cyclization reaction on the obtained [Intermediate 1-2] under an acidic condition, and this goes through a coupling reaction using proper [Amine 2] and a palladium catalyst to synthesize a final compound. (Among the substituents in the formulae, X1 and X2 are a halogen element such as Br, Cl, F or I, and the rest of the substituents have the same definitions as in Chemical Formula 1.)

[General Preparation Method 2]

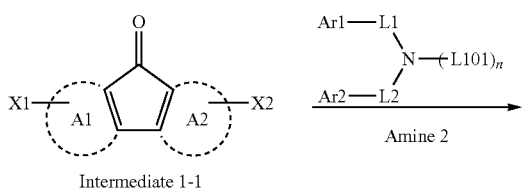

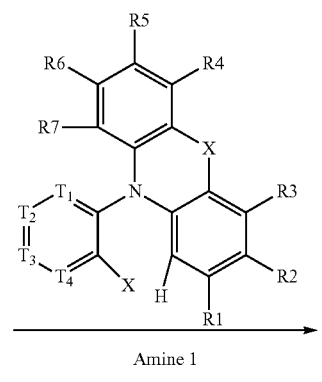

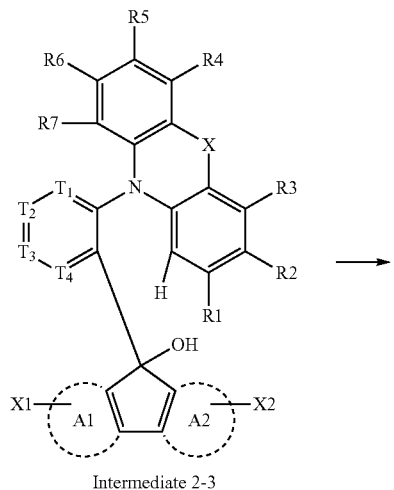

Intermediate 2-3

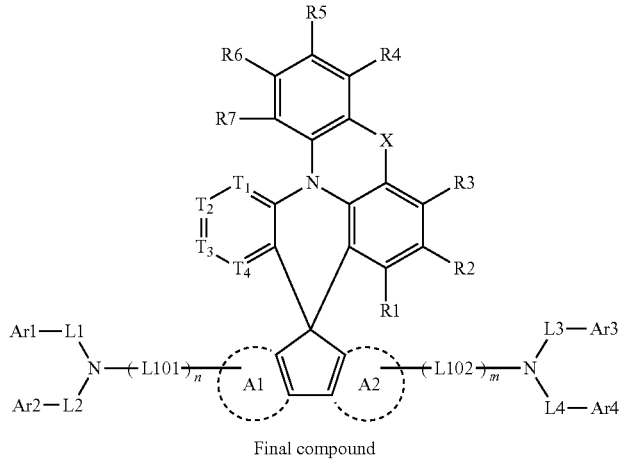

Final compound

Using [Intermediate 1-1], [Intermediate 2-2] is synthesized through a coupling reaction using proper [Amine 2] and a palladium catalyst, and this goes through coupling using [Amine 1] and a base such as butyllithium to synthesize [Intermediate 2-3]. The obtained [Intermediate 2-3] goes through a spiro cyclization reaction under an acidic condition to synthesize a final compound. (Among the substituents in the formulae, X1 and X2 are a halogen element such as Br, Cl, F or I, and the rest of the substituents have the same definitions as in Chemical Formula 1.)

General Preparation Method 2 is an improved preparation method of General Preparation Method 1, and may be used to improve a low synthesis yield of General Preparation Method 1, or to synthesize compounds having substituents that may not be synthesized using General Preparation Method 1.

A conjugation length of a compound and an energy band gap thereof are closely related. Specifically, as a conjugation length of a compound increases, an energy band gap thereof decreases.

By introducing various substituents to the core structure as above, compounds having various energy band gaps may be synthesized in the present disclosure. In addition, by introducing various substituents to the core structure having structures as above, HOMO and LUMO energy levels of the compound may also be controlled in the present disclosure.

In addition, by introducing various substituents to the core structure having structures as above, compounds having unique properties of the introduced substituents may be synthesized. For example, by introducing substituents normally used as a hole injection layer material, a material for hole transfer, a light emitting layer material and an electron transfer layer material used for manufacturing an organic light emitting device to the core structure, materials satisfying needs required from each organic material layer may be synthesized.

In addition, an organic light emitting device according to the present disclosure comprises an anode, a cathode, and one or more organic material layers disposed between the anode and the cathode, wherein one or more layers of the organic material layers comprise the heterocyclic compound.

The organic light emitting device of the present disclosure may be prepared using common methods and materials for preparing an organic light emitting device except that one or more organic material layers are formed using the compound described above.

The compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present disclosure may be formed in a single layer structure, but may be formed in a multilayer structure in which two or more organic material layers are laminated. For example, the organic light emitting device of the present disclosure may have a structure comprising a hole injection layer, a hole transfer layer, a light emitting layer, an electron transfer layer, an electron injection layer and the like as the organic material layer. However, the structure of the organic light emitting device is not limited thereto, and may comprise less numbers of organic material layers.

In the organic light emitting device of the present disclosure, the organic material layer may comprise one or more layers of an electron transfer layer, an electron injection layer and a layer carrying out electron injection and electron transfer at the same time, and one or more layers of the above-mentioned layers may comprise the heterocyclic compound represented by Chemical Formula 1.

In the organic light emitting device of the present disclosure, the organic material layer may comprise one or more layers of a hole injection layer, a hole transfer layer, and a layer carrying out hole injection and hole transfer at the same time, and one or more layers of the above-mentioned layers may comprise the heterocyclic compound represented by Chemical Formula 1.

In another embodiment, the organic material layer comprises a light emitting layer, and the light emitting layer comprises the heterocyclic compound represented by Chemical Formula 1. As one example, the heterocyclic compound represented by Chemical Formula 1 may be included as a dopant of the light emitting layer.

The organic material layer comprises the heterocyclic compound described above as a dopant of the light emitting layer, and may further comprise a host. The dopant may be included in 0.01 parts by weight to 10 parts by weight, preferably in 0.01 parts by weight to 7 parts by weight and more preferably in 0.1 parts by weight to 5 parts by weight with respect to 100 parts by weight of the host.

As another example, the organic material layer comprising the heterocyclic compound represented by Chemical Formula 1 comprises the heterocyclic compound represented by Chemical Formula 1 as a dopant, and may comprise a fluorescent host or a phosphorescent host.

In another embodiment, the organic material layer comprising the heterocyclic compound represented by Chemical Formula 1 comprises the heterocyclic compound represented by Chemical Formula 1 as a dopant, comprises a fluorescent host or a phosphorescent host, and may comprise other organic compounds, metals or metal compounds as a dopant.

As another embodiment, the organic material layer comprising the heterocyclic compound represented by Chemical Formula 1 comprises the compound represented by Chemical Formula 1 as a heterocyclic dopant, comprises a fluorescent host or a phosphorescent host, and may be used together with an iridium (Ir)-based dopant.

According to one embodiment of the present specification, the organic material layer comprises a light emitting layer, one or more layers of the organic material layers comprise the compound described above, and the light emitting layer may comprise a compound represented by the following Chemical Formula 1A.

As a material of the host of the light emitting layer of the organic material layer of the organic light emitting device of the present specification, a structure of the following Chemical Formula 1A may be included.

[Chemical Formula 1A]

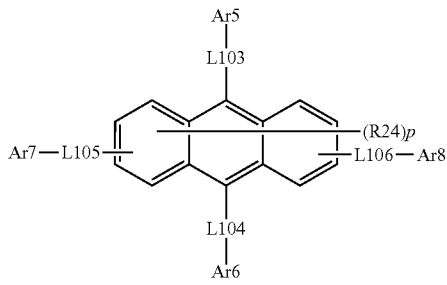

In Chemical Formula 1A, L103 to L106 are the same as or different from each other, and each independently a direct bond; a substituted or unsubstituted arylene group; or a substituted or unsubstituted heteroarylene group, Ar5 to Ar8 are the same as or different from each other, and each independently hydrogen; a substituted or unsubstituted aryl group; or a substituted or unsubstituted heteroaryl group, R24s are the same as or different from each other, and each independently hydrogen; deuterium; a halogen group; a nitrile group; a nitro group; a substituted or unsubstituted alkyl group; a substituted or unsubstituted cycloalkyl group; a substituted or unsubstituted silyl group; a substituted or unsubstituted phosphine oxide group; a substituted or unsubstituted aryl group; or a substituted or unsubstituted heteroaryl group, p is an integer of 0 to 6, and when p is 2 or greater, R24s are the same as or different from each other.

In one embodiment of the present specification, L103 to L106 are the same as or different from each other, and each independently a direct bond; a substituted or unsubstituted arylene group having 6 to 60 carbon atoms; or a substituted or unsubstituted heteroarylene group having 2 to 60 carbon atoms.

In one embodiment of the present specification, L103 to L106 are the same as or different from each other, and each independently a direct bond; a substituted or unsubstituted arylene group having 6 to 40 carbon atoms; or a substituted or unsubstituted heteroarylene group having 2 to 40 carbon atoms.

According to another embodiment, L103 to L106 are the same as or different from each other, and each independently a direct bond; a substituted or unsubstituted phenylene group; a substituted or unsubstituted biphenylylene group; a substituted or unsubstituted terphenylene group; a substituted or unsubstituted naphthylene group; a substituted or unsubstituted anthracenylene group; a substituted or unsubstituted phenanthrenylene group; a substituted or unsubstituted triphenylene group; a substituted or unsubstituted fluorenyl group; a substituted or unsubstituted thiophenylene group; a substituted or unsubstituted furanylene group; a substituted or unsubstituted dibenzothiophenylene group; a substituted or unsubstituted dibenzofuranylene group; or a substituted or unsubstituted carbazolylene group.

In another embodiment, L103 to L106 are the same as or different from each other, and each independently a direct bond; a phenylene group; a biphenylylene group; a terphenylene group; a naphthylene group; an anthracenylene group; a phenanthrenylene group; a triphenylene group; a fluorenyl group unsubstituted or substituted with a methyl group or a phenyl group; a thiophenylene group; a furanylene group; a dibenzothiophenylene group; a dibenzofuranylene group; or a carbazolylene group unsubstituted or substituted with an ethyl group or a phenyl group.

According to another embodiment, L103 to L106 are the same as or different from each other, and may be each independently selected from among a direct bond; or the following structures.

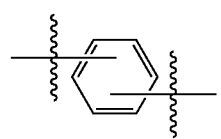
LB1

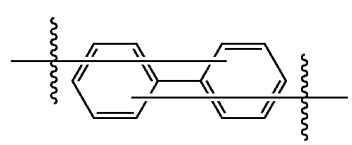
LB2

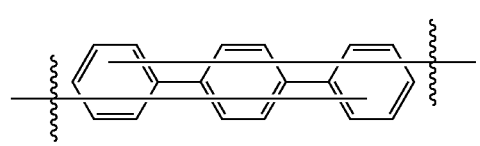
LB3

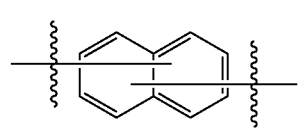
LB4

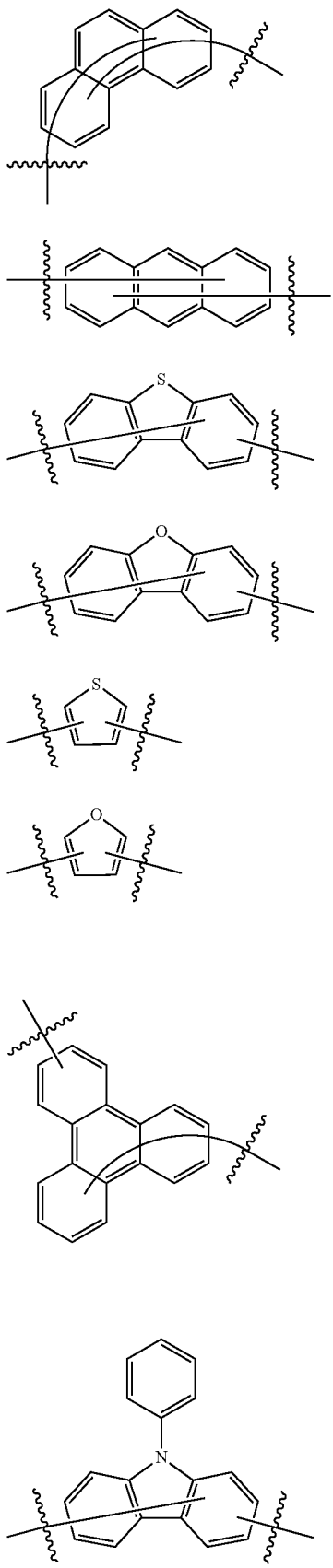

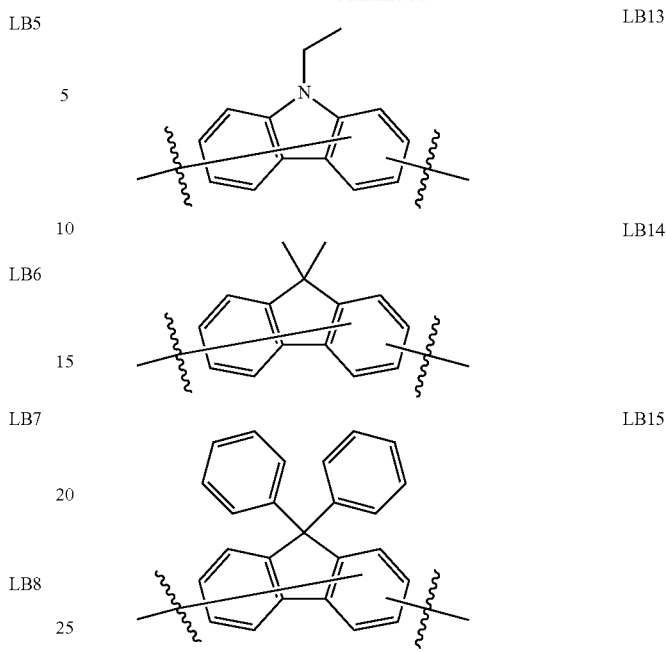

According to one embodiment of the present specification, L103 is a direct bond.

According to one embodiment of the present specification, L104 is a phenylene group.

According to one embodiment of the present specification, L105 and L106 are a direct bond.

In one embodiment of the present specification, R24 is hydrogen; deuterium; a halogen group; a silyl group; a boron group; a substituted or unsubstituted alkyl group; a substituted or unsubstituted cycloalkyl group; a substituted or unsubstituted aryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; or a substituted or unsubstituted heterocyclic group.

In one embodiment of the present specification, R24s are the same as or different from each other, and each independently hydrogen; deuterium; a substituted or unsubstituted alkyl group; a substituted or unsubstituted cycloalkyl group; a substituted or unsubstituted aryl group; or a substituted or unsubstituted heterocyclic group.

In one embodiment of the present specification, R24s are the same as or different from each other, and each independently hydrogen; deuterium; a substituted or unsubstituted alkyl group having 1 to 50 carbon atoms; a substituted or unsubstituted cycloalkyl group having 3 to 60 carbon atoms; a substituted or unsubstituted aryl group having to 60 carbon atoms; or a substituted or unsubstituted heterocyclic group having 2 to 40 carbon atoms.

In one embodiment of the present specification, R24s are the same as or different from each other, and each independently hydrogen; deuterium; a substituted or unsubstituted alkyl group having 1 to 30 carbon atoms; a substituted or unsubstituted cycloalkyl group having 3 to 30 carbon atoms; a substituted or unsubstituted aryl group having 6 to 30 carbon atoms; or a substituted or unsubstituted heterocyclic group having 2 to 25 carbon atoms.

In another embodiment, R24 is hydrogen.

According to one embodiment of the present specification, p is 0 or 1.

In one embodiment of the present specification, Ar5 to Ar8 are the same as or different from each other, and each independently hydrogen; a substituted or unsubstituted aryl group having 6 to 60 carbon atoms; or a substituted or unsubstituted heteroaryl group having 2 to 60 carbon atoms.

According to another embodiment, Ar5 to Ar8 are the same as or different from each other, and each independently hydrogen; an aryl group having 6 to 60 carbon atoms unsubstituted or substituted with an aryl group having 6 to 60 carbon atoms or a heteroaryl group having 2 to 60 carbon atoms; or a heteroaryl group having 2 to 60 carbon atoms unsubstituted or substituted with an aryl group having 6 to 60 carbon atoms or a heteroaryl group having 2 to 60 carbon atoms.

In another embodiment, Ar5 to Ar8 are the same as or different from each other, and each independently hydrogen; a substituted or unsubstituted phenyl group; a substituted or unsubstituted biphenyl group; a substituted or unsubstituted naphthyl group; a substituted or unsubstituted phenanthrene group; a substituted or unsubstituted anthracene group; a substituted or unsubstituted triphenylene group; a substituted or unsubstituted dibenzofuran group; a substituted or unsubstituted naphthobenzofuran group; a substituted or unsubstituted dibenzothiophene group; a substituted or unsubstituted carbazole group; a substituted or unsubstituted fluorene group; a substituted or unsubstituted thiophene group; a substituted or unsubstituted furan group; a substituted or unsubstituted benzothiophene group; a substituted or unsubstituted benzofuran group; a substituted or unsubstituted benzocarbazole group; a substituted or unsubstituted benzofluorene group; a substituted or unsubstituted indolocarbazole group; a substituted or unsubstituted pyridyl group; a substituted or unsubstituted isoquinolyl group; a substituted or unsubstituted quinolyl group; a substituted or unsubstituted quinazolyl group; a substituted or unsubstituted triazine group; a substituted or unsubstituted benzimidazole group; a substituted or unsubstituted benzoxazole group; a substituted or unsubstituted benzothiazole group; a substituted or unsubstituted dihydroacridine group; a substituted or unsubstituted xanthene group; or a substituted or unsubstituted dibenzosilole group.

According to another embodiment, Ar5 to Ar8 are the same as or different from each other, and each independently hydrogen; a phenyl group; a biphenyl group; a naphthyl group unsubstituted or substituted with an aryl group; a phenanthrene group; an anthracene group; a triphenylene group; a dibenzofuran group unsubstituted or substituted with an aryl group; a naphthobenzofuran group; a dibenzothiophene group unsubstituted or substituted with an aryl group; a carbazole group unsubstituted or substituted with an alkyl group or an aryl group; a fluorene group unsubstituted or substituted with an alkyl group or an aryl group; a thiophene group unsubstituted or substituted with an aryl group; a furan group unsubstituted or substituted with an aryl group; a benzothiophene group; a benzofuran group; a benzocarbazole group unsubstituted or substituted with an alkyl group or aryl group; a benzofluorene group unsubstituted or substituted with an alkyl group or an aryl group; an indolocarbazole group; a pyridyl group; an isoquinolyl group unsubstituted or substituted with an aryl group; a quinolyl group; a quinazolyl group unsubstituted or substituted with an aryl group; a triazine group unsubstituted or substituted with an aryl group; a benzimidazole group unsubstituted or substituted with an aryl group; a benzoxazole group unsubstituted or substituted with an aryl group; a benzothiazole group unsubstituted or substituted with an aryl group; a dihydroacridine group unsubstituted or substituted with an alkyl group or an aryl group; a xanthene group unsubstituted or substituted with an alkyl group or an aryl group; or a dibenzosilole group unsubstituted or substituted with an alkyl group or an aryl group.

In another embodiment, Ar5 to Ar8 are the same as or different from each other, and each independently hydrogen; a phenyl group; a biphenyl group; a naphthyl group unsubstituted or substituted with a phenyl group; a phenanthrene group; an anthracene group; a triphenylene group; a dibenzofuran group unsubstituted or substituted with a phenyl group; a naphthobenzofuran group; a dibenzothiophene group unsubstituted or substituted with a phenyl group; a carbazole group unsubstituted or substituted with a methyl group, an ethyl group or a phenyl group; a fluorene group unsubstituted or substituted with a methyl group or a phenyl group; a thiophene group unsubstituted or substituted with a phenyl group; a furan group unsubstituted or substituted with a phenyl group; a benzothiophene group; a benzofuran group; a benzocarbazole group unsubstituted or substituted with a methyl group or a phenyl group; a benzofluorene group unsubstituted or substituted with a methyl group or a phenyl group; an indolocarbazole group; a pyridyl group unsubstituted or substituted with a phenyl group or a naphthyl group; an isoquinolyl group unsubstituted or substituted with a phenyl group; a quinolyl group; a quinazolyl group unsubstituted or substituted with a phenyl group; a triazine group unsubstituted or substituted with a phenyl group; a benzimidazole group unsubstituted or substituted with a phenyl group; a benzoxazole group unsubstituted or substituted with a phenyl group; a benzothiazole group unsubstituted or substituted with a phenyl group; a dihydroacridine group unsubstituted or substituted with a methyl group or a phenyl group; a xanthene group unsubstituted or substituted with a methyl group or a phenyl group; or a dibenzosilole group unsubstituted or substituted with a methyl group or a phenyl group.

In one embodiment of the present specification, Ar5 to Ar8 are the same as or different from each other, and may be each independently selected from among hydrogen; or the following structures.

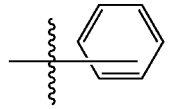

RA1

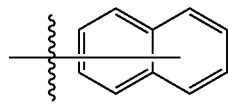

RA2

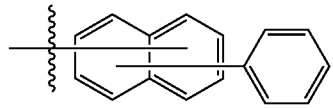

RA3

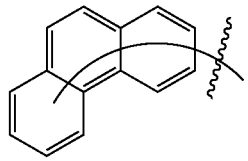

RA4

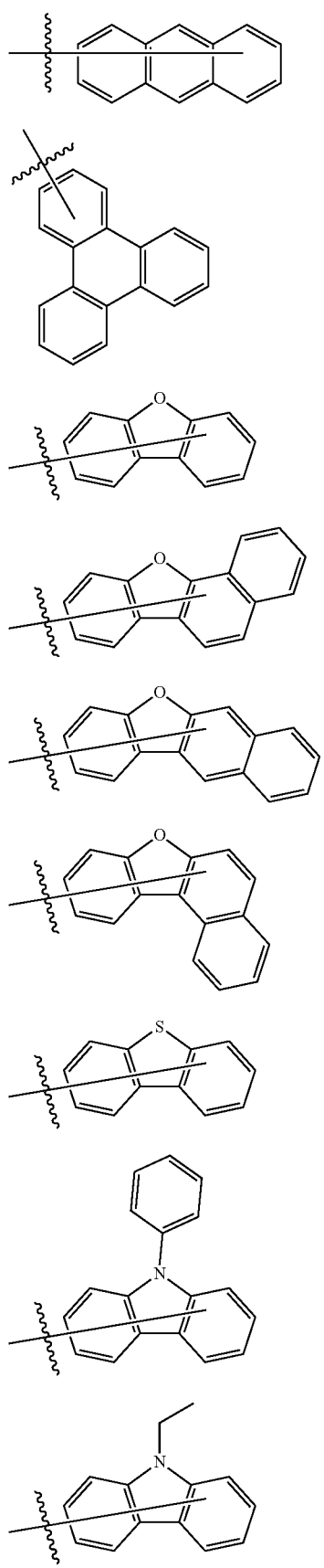
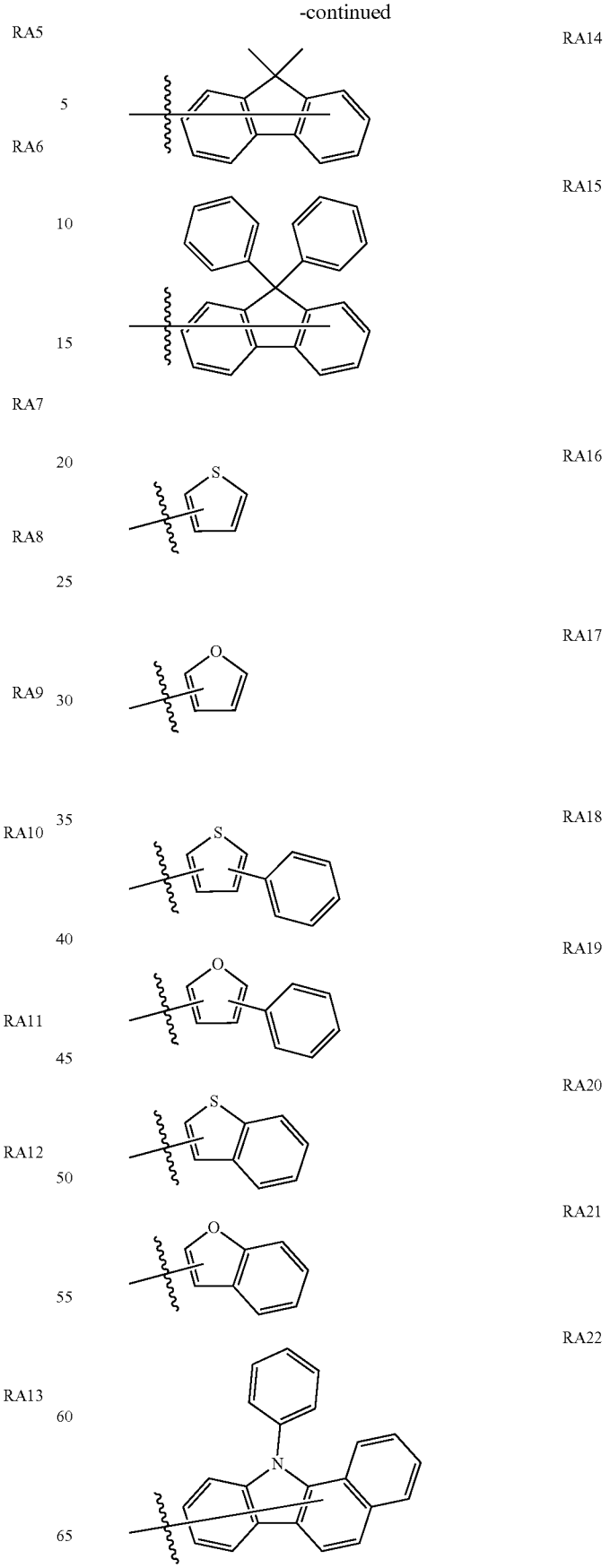

RA23 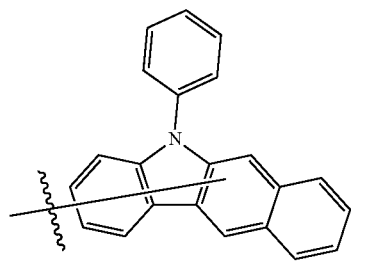
RA24 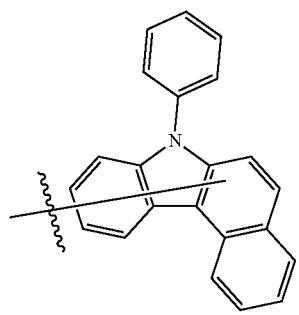
RA25 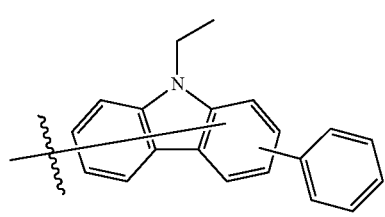
RA26 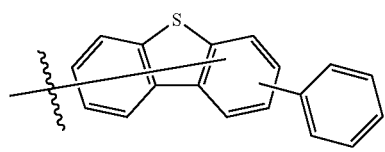
RA27 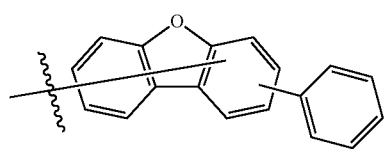
RA28 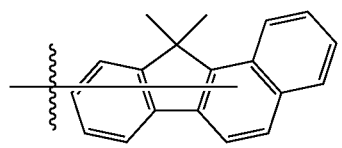
RA29 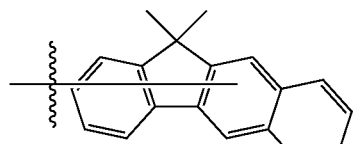
RA30 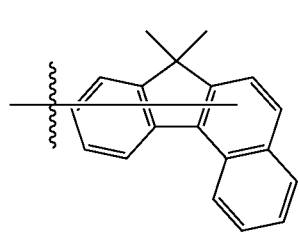
RA31 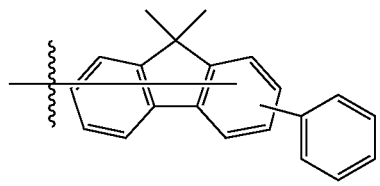
RA32 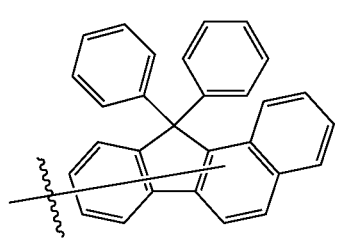
RA33 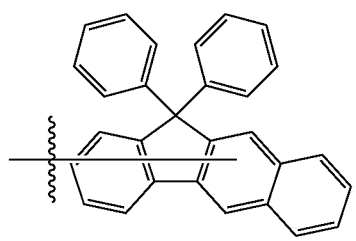
RA34 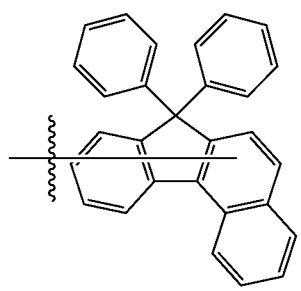
RA35 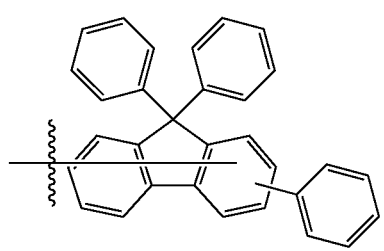
RA36 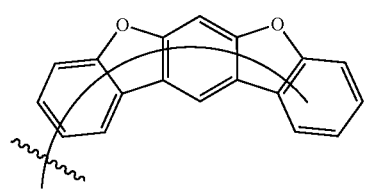

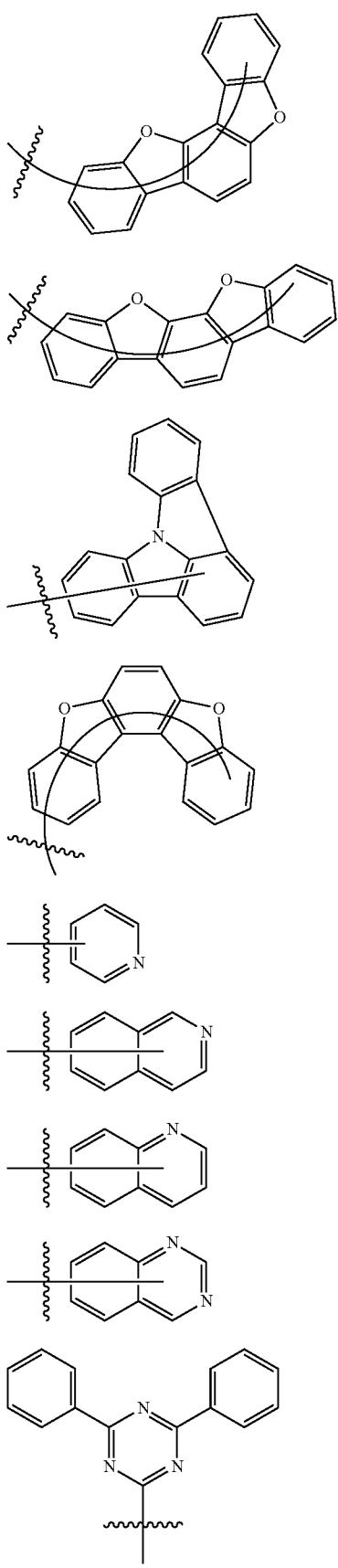
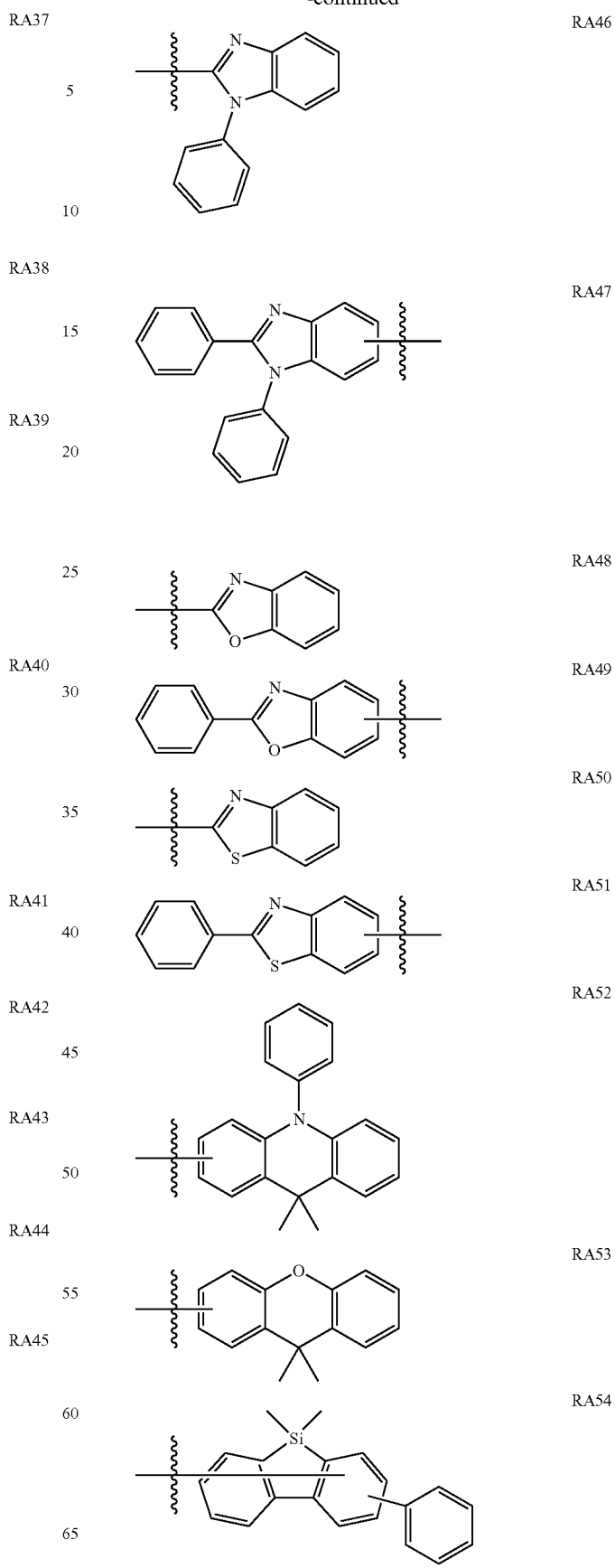

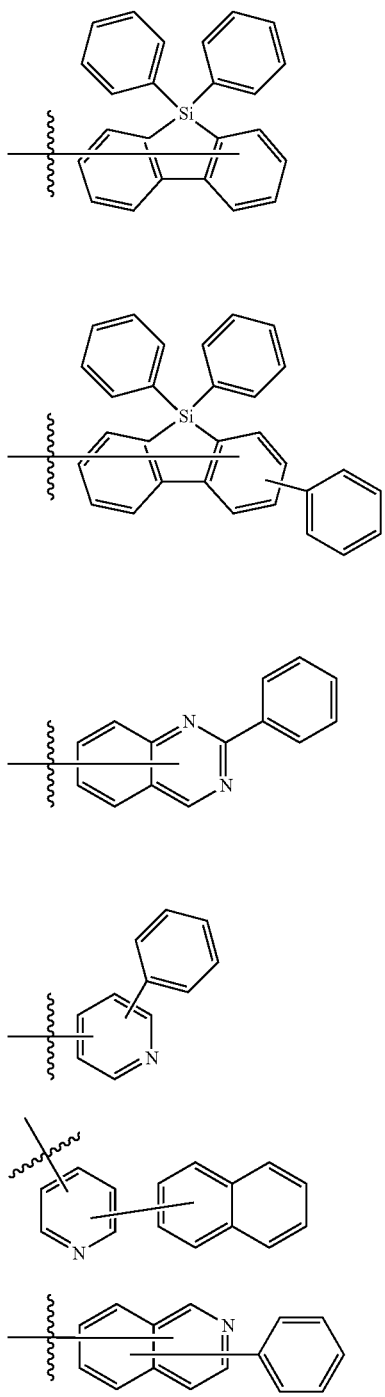

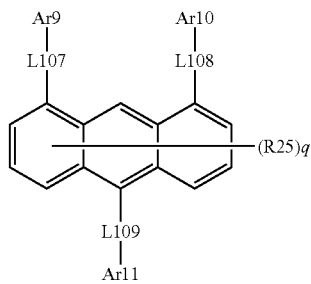

[Chemical Formula 1B]

In Chemical Formula 1B,

L107 to L109 are the same as or different from each other, and each independently a direct bond; a substituted or unsubstituted arylene group; or a substituted or unsubstituted heteroarylene group, Ar9 to Ar11 are the same as or different from each other, and each independently hydrogen; a substituted or unsubstituted aryl group; or a substituted or unsubstituted heteroaryl group, R25s are the same as or different from each other, and each independently hydrogen; deuterium; a halogen group; a nitrile group; a nitro group; a substituted or unsubstituted alkyl group; a substituted or unsubstituted cycloalkyl group; a substituted or unsubstituted silyl group; a substituted or unsubstituted phosphine oxide group; a substituted or unsubstituted aryl group; or a substituted or unsubstituted heteroaryl group, q is an integer of 0 to 7, and when q is 2 or greater, R25s are the same as or different from each other.

In one embodiment of the present specification, R25 is hydrogen; deuterium; a halogen group; a silyl group; a boron group; a substituted or unsubstituted alkyl group; a substituted or unsubstituted cycloalkyl group; a substituted or unsubstituted aryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; or a substituted or unsubstituted heterocyclic group.

In one embodiment of the present specification, R25s are the same as or different from each other, and each independently hydrogen; deuterium; a substituted or unsubstituted alkyl group; a substituted or unsubstituted cycloalkyl group; a substituted or unsubstituted aryl group; or a substituted or unsubstituted heterocyclic group.

In one embodiment of the present specification, R25s are the same as or different from each other, and each independently hydrogen; deuterium; a substituted or unsubstituted alkyl group having 1 to 50 carbon atoms; a substituted or unsubstituted cycloalkyl group having 3 to 60 carbon atoms; a substituted or unsubstituted aryl group having 6 to 60 carbon atoms; or a substituted or unsubstituted heterocyclic group having 2 to 40 carbon atoms.

In one embodiment of the present specification, R25s are the same as or different from each other, and each independently hydrogen; deuterium; a substituted or unsubstituted alkyl group having 1 to 30 carbon atoms; a substituted or unsubstituted cycloalkyl group having 3 to 30 carbon atoms; a substituted or unsubstituted aryl group having to 30 carbon atoms; or a substituted or unsubstituted heterocyclic group having 2 to 25 carbon atoms.

In another embodiment, R25 is hydrogen.

According to one embodiment of the present specification, q is 0 or 1.

According to one embodiment of the present specification, the organic material layer comprises a light emitting layer, one or more layers of the organic material layers comprise the compound described above, and the light emitting layer may comprise a compound represented by the following Chemical Formula 1B.

As a material of the host of the light emitting layer of the organic material layer of the organic light emitting device of the present specification, a structure of the following Chemical Formula 1B may be included.

In one embodiment of the present specification, L107 to L109 are the same as or different from each other, and each independently a direct bond; a substituted or unsubstituted arylene group having 6 to 60 carbon atoms; or a substituted or unsubstituted heteroarylene group having 2 to 60 carbon atoms.

In one embodiment of the present specification, L107 to L109 are the same as or different from each other, and each independently a direct bond; a substituted or unsubstituted arylene group having 6 to 40 carbon atoms; or a substituted or unsubstituted heteroarylene group having 2 to 40 carbon atoms.

According to another embodiment, L107 to L109 are the same as or different from each other, and each independently a direct bond; a substituted or unsubstituted phenylene group; a substituted or unsubstituted biphenylylene group; a substituted or unsubstituted terphenylene group; a substituted or unsubstituted naphthylene group; a substituted or unsubstituted anthracenylene group; a substituted or unsubstituted phenanthrenylene group; a substituted or unsubstituted triphenylene group; a substituted or unsubstituted fluorenyl group; a substituted or unsubstituted thiophenylene group; a substituted or unsubstituted furanylene group; a substituted or unsubstituted dibenzothiophenylene group; a substituted or unsubstituted dibenzofuranylene group; or a substituted or unsubstituted carbazolylene group.

In another embodiment, L107 to L109 are the same as or different from each other, and each independently a direct bond; a phenylene group; a biphenylylene group; a terphenylene group; a naphthylene group; an anthracenylene group; a phenanthrenylene group; a triphenylene group; a fluorenyl group unsubstituted or substituted with a methyl group or a phenyl group; a thiophenylene group; a furanylene group; a dibenzothiophenylene group; a dibenzofuranylene group; or a carbazolylene group unsubstituted or substituted with an ethyl group or a phenyl group.

According to another embodiment, L107 to L109 are the same as or different from each other, and may be each independently selected from among a direct bond; or the following structures.

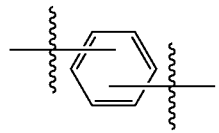
LC1

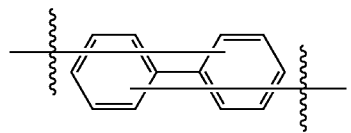
LC2

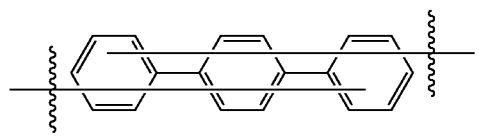
LC3

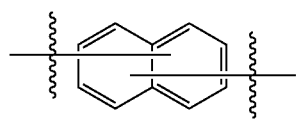
LC4

-continued

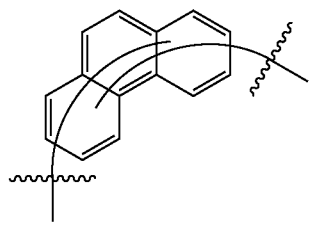
LC5

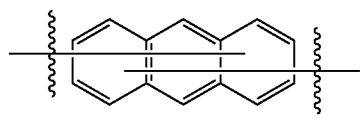
LC6

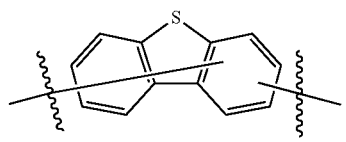
LC7

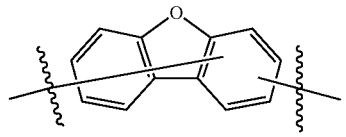
LC8

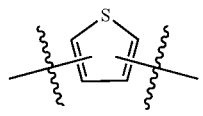
LC9

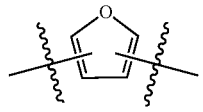
LC10

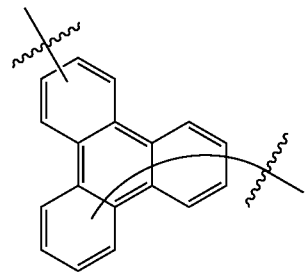
LC11

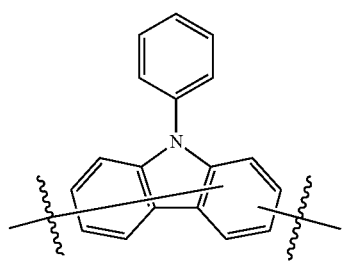
LC12

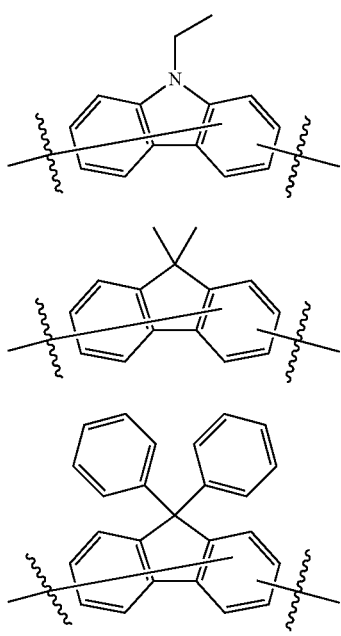

LC13

LC14

LC15

In one embodiment of the present specification, L107 to L109 are a direct bond.

In one embodiment of the present specification, Ar9 to Ar11 are the same as or different from each other, and each independently hydrogen; a substituted or unsubstituted aryl group having 6 to 60 carbon atoms; or a substituted or unsubstituted heteroaryl group having 2 to 60 carbon atoms.

According to another embodiment, Ar9 to Ar11 are the same as or different from each other, and each independently hydrogen; an aryl group having 6 to 60 carbon atoms unsubstituted or substituted with an aryl group having 6 to 60 carbon atoms or a heteroaryl group having 2 to 60 carbon atoms; or a heteroaryl group having 2 to 60 carbon atoms unsubstituted or substituted with an aryl group having 6 to 60 carbon atoms or a heteroaryl group having 2 to 60 carbon atoms.

In another embodiment, Ar9 to Ar11 are the same as or different from each other, and each independently hydrogen; a substituted or unsubstituted phenyl group; a substituted or unsubstituted biphenyl group; a substituted or unsubstituted naphthyl group; a substituted or unsubstituted phenanthrene group; a substituted or unsubstituted anthracene group; a substituted or unsubstituted triphenylene group; a substituted or unsubstituted dibenzofuran group; a substituted or unsubstituted naphthobenzofuran group; a substituted or unsubstituted dibenzothiophene group; a substituted or unsubstituted carbazole group; a substituted or unsubstituted fluorene group; a substituted or unsubstituted thiophene group; a substituted or unsubstituted furan group; a substituted or unsubstituted benzothiophene group; a substituted or unsubstituted benzofuran group; a substituted or unsubstituted benzocarbazole group; a substituted or unsubstituted benzofluorene group; a substituted or unsubstituted indolocarbazole group; a substituted or unsubstituted pyridyl group; a substituted or unsubstituted isoquinolyl group; a substituted or unsubstituted quinolyl group; a substituted or unsubstituted quinazolyl group; a substituted or unsubstituted triazine group; a substituted or unsubstituted benzimidazole group; a substituted or unsubstituted benzoxazole group; a substituted or unsubstituted benzothiazole group; a substituted or unsubstituted dihydroacridine group; a substituted or unsubstituted xanthene group; or a substituted or unsubstituted dibenzosilole group.

According to another embodiment, Ar9 to Ar11 are the same as or different from each other, and each independently hydrogen; a phenyl group; a biphenyl group; a naphthyl group unsubstituted or substituted with an aryl group; a phenanthrene group; an anthracene group; a triphenylene group; a dibenzofuran group unsubstituted or substituted with an aryl group; a naphthobenzofuran group; a dibenzothiophene group unsubstituted or substituted with an aryl group; a carbazole group unsubstituted or substituted with an alkyl group or an aryl group; a fluorene group unsubstituted or substituted with an alkyl group or an aryl group; a thiophene group unsubstituted or substituted with an aryl group; a furan group unsubstituted or substituted with an aryl group; a benzothiophene group; a benzofuran group; a benzocarbazole group unsubstituted or substituted with an alkyl group or an aryl group; a benzofluorene group unsubstituted or substituted with an alkyl group or an aryl group; an indolocarbazole group; a pyridyl group; an isoquinolyl group unsubstituted or substituted with an aryl group; a quinolyl group; a quinazolyl group unsubstituted or substituted with an aryl group; a triazine group unsubstituted or substituted with an aryl group; a benzimidazole group unsubstituted or substituted with an aryl group; a benzoxazole group unsubstituted or substituted with an aryl group; a benzothiazole group unsubstituted or substituted with an aryl group; a dihydroacridine group unsubstituted or substituted with an alkyl group or an aryl group; a xanthene group unsubstituted or substituted with an alkyl group or an aryl group; or a dibenzosilole group unsubstituted or substituted with an alkyl group or an aryl group.

In another embodiment, Ar9 to Ar11 are the same as or different from each other, and each independently hydrogen; a phenyl group; a biphenyl group; a naphthyl group unsubstituted or substituted with a phenyl group; a phenanthrene group; an anthracene group; a triphenylene group; a dibenzofuran group unsubstituted or substituted with a phenyl group; a naphthobenzofuran group; a dibenzothiophene group unsubstituted or substituted with a phenyl group; a carbazole group unsubstituted or substituted with a methyl group, an ethyl group or a phenyl group; a fluorene group unsubstituted or substituted with a methyl group or a phenyl group; a thiophene group unsubstituted or substituted with a phenyl group; a furan group unsubstituted or substituted with a phenyl group; a benzothiophene group; a benzofuran group; a benzocarbazole group unsubstituted or substituted with a methyl group or a phenyl group; a benzofluorene group unsubstituted or substituted with a methyl group or a phenyl group; an indolocarbazole group; a pyridyl group unsubstituted or substituted with a phenyl group or a naphthyl group; an isoquinolyl group unsubstituted or substituted with a phenyl group; a quinolyl group; a quinazolyl group unsubstituted or substituted with a phenyl group; a triazine group unsubstituted or substituted with a phenyl group; a benzimidazole group unsubstituted or substituted with a phenyl group; a benzoxazole group unsubstituted or substituted with a phenyl group; a benzothiazole group unsubstituted or substituted with a phenyl group; a dihydroacridine group unsubstituted or substituted with a methyl group or a phenyl group; a xanthene group unsubstituted or substituted with a methyl group or a phenyl group; or a dibenzosilole group unsubstituted or substituted with a methyl group or a phenyl group.

In one embodiment of the present specification, Ar9 to Ar11 are the same as or different from each other, and may be each independently selected from among hydrogen; or the following structures.
RB1
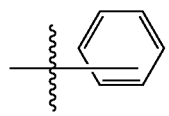
RB2
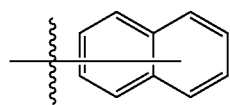
RB3
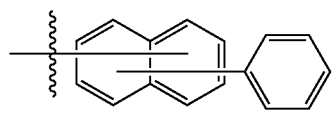
RB4
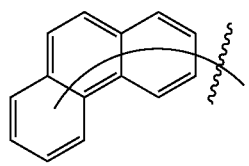
RB5
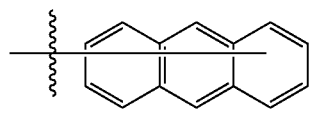
RB6
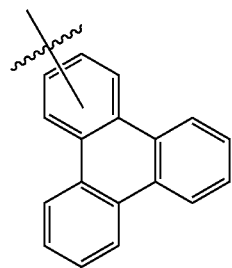
RB7
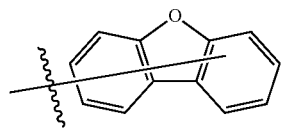
RB8
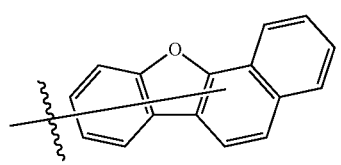
RB9
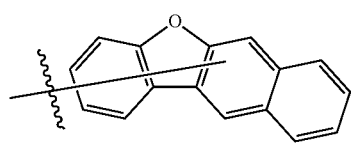
-continued
RB10
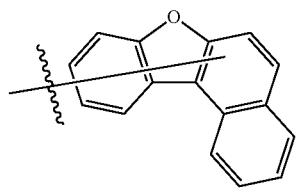
RB11
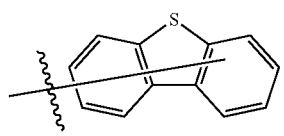
RB12
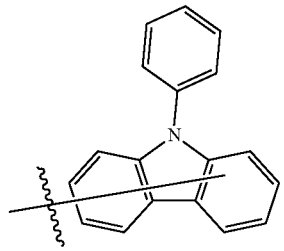
RB13
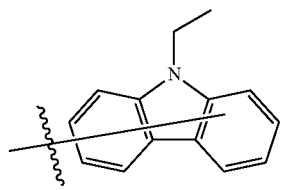
RB14
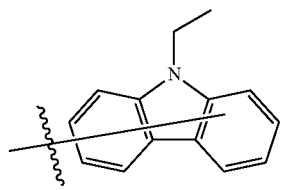
RB15
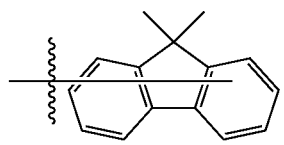
RB16
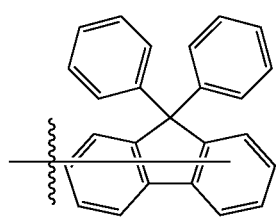
RB17
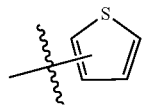
RB18
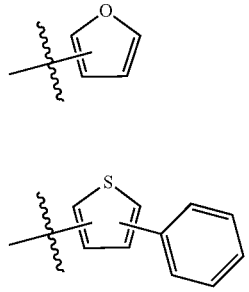

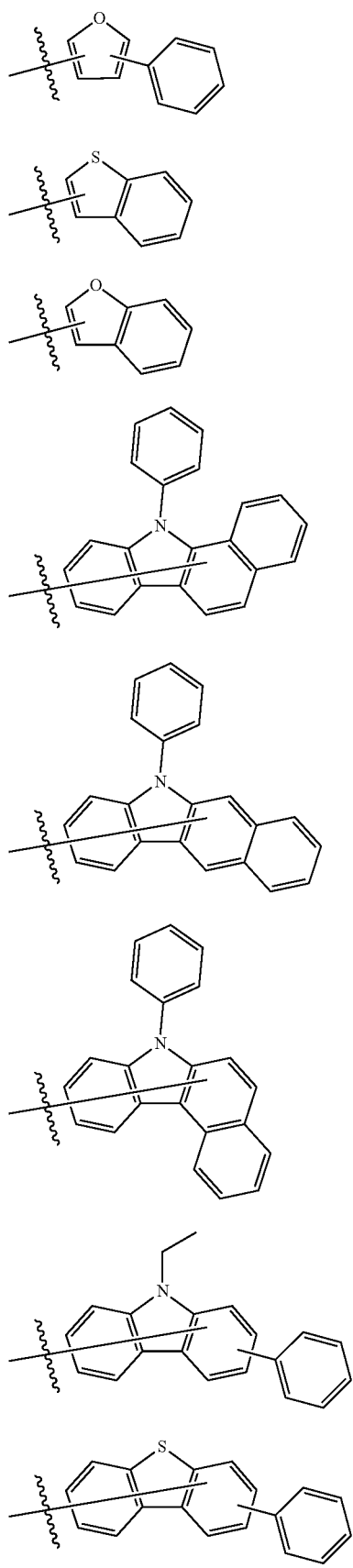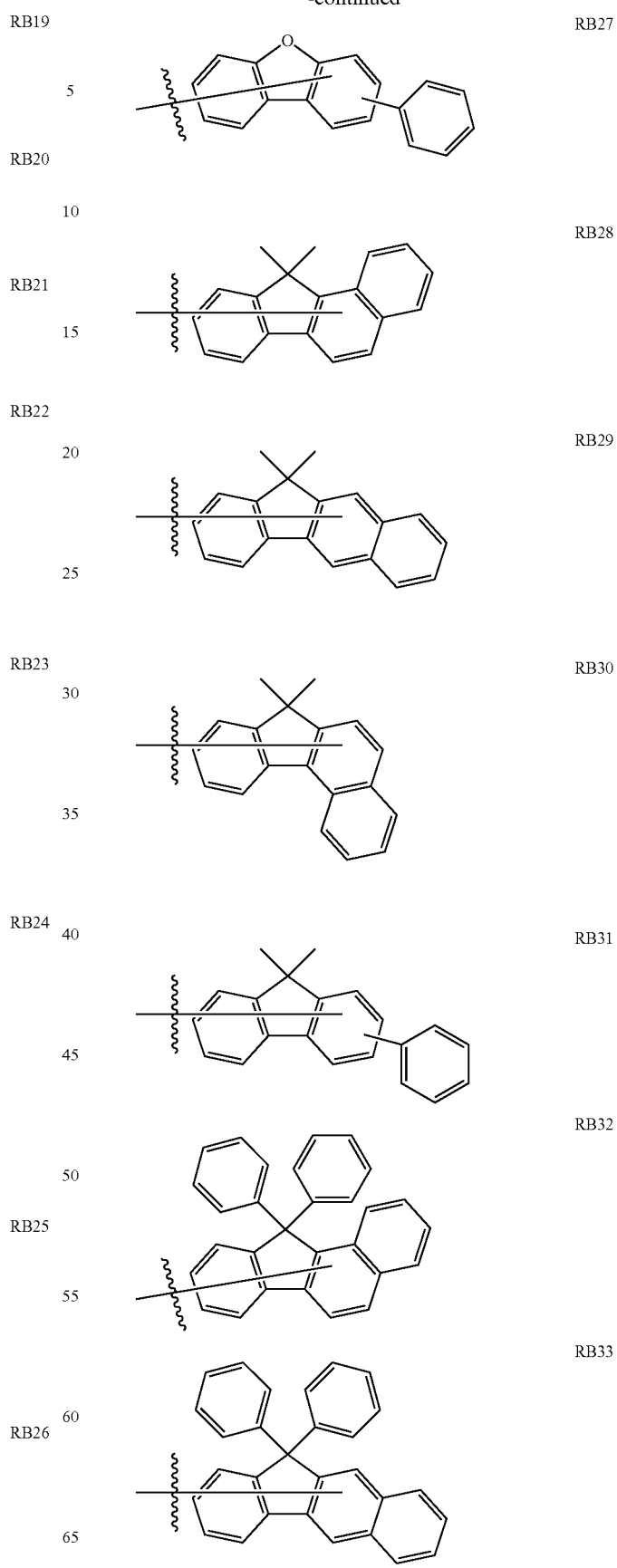

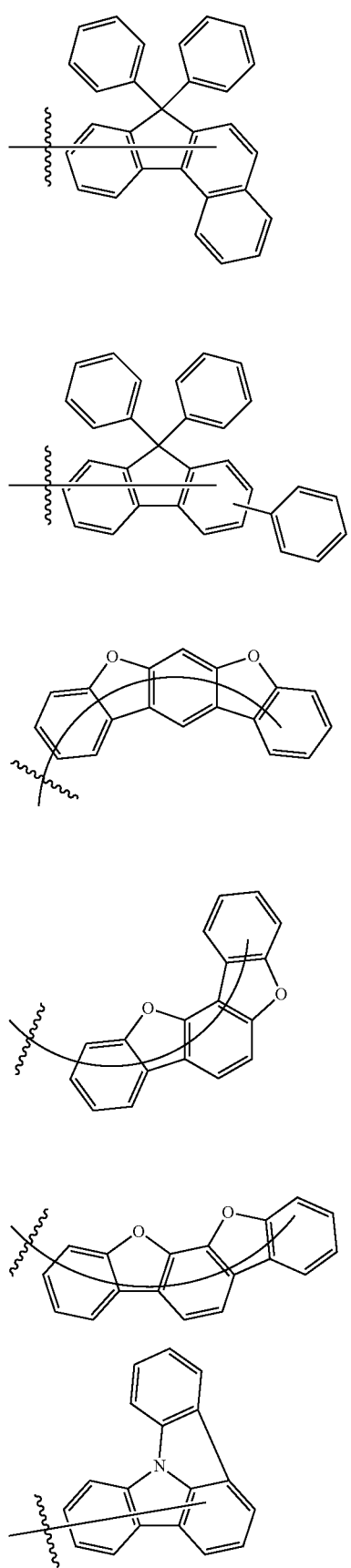
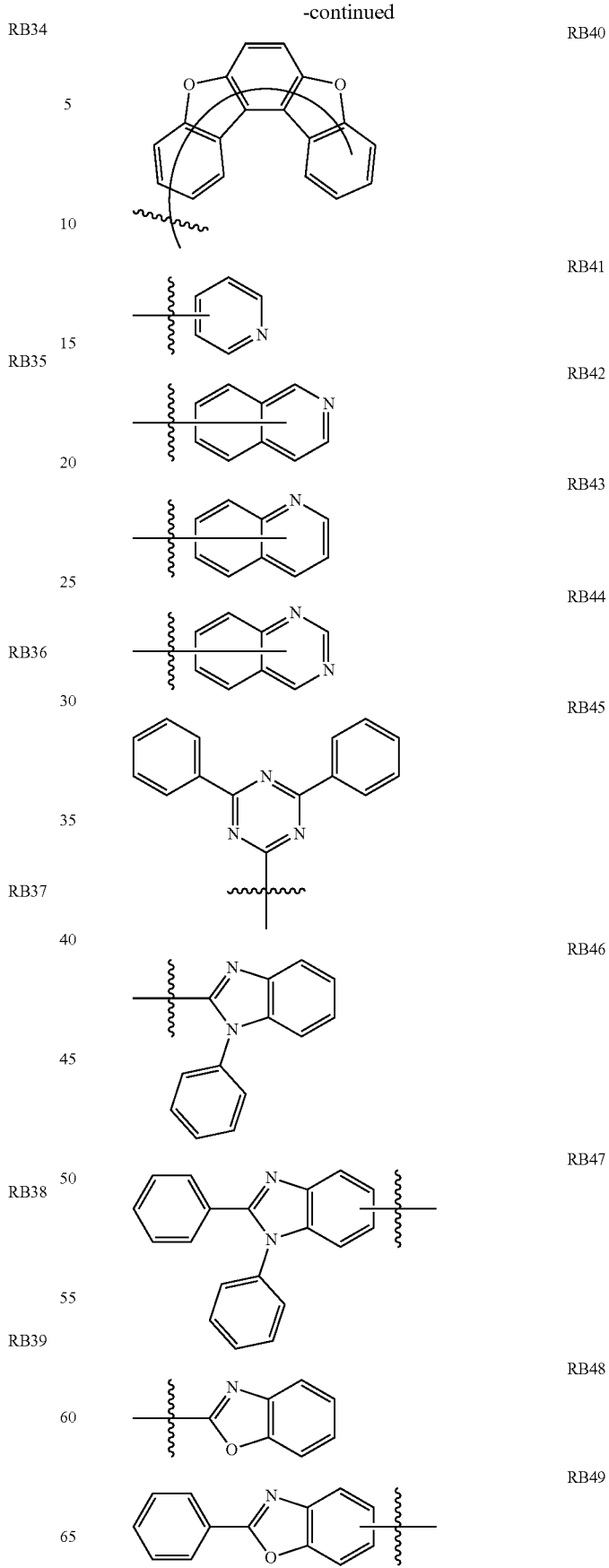

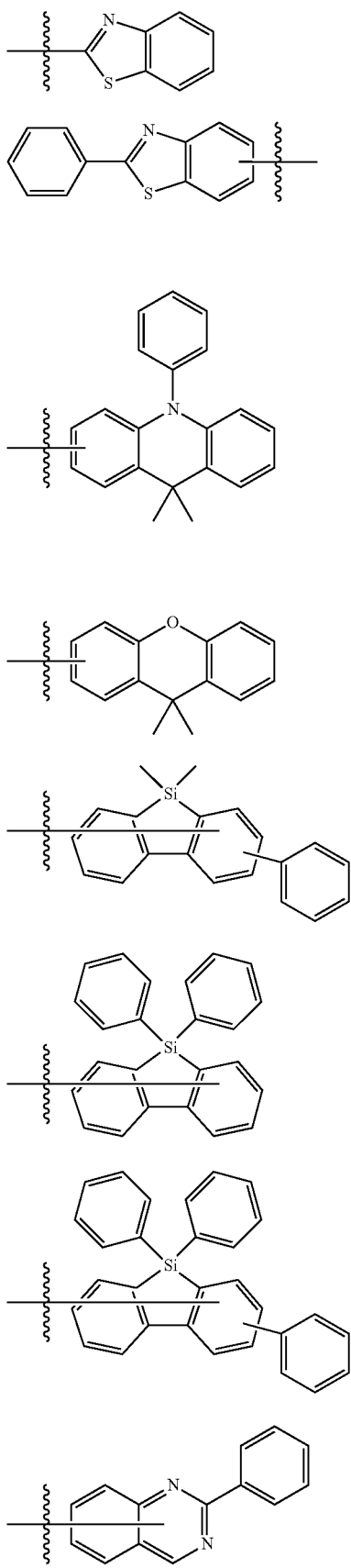

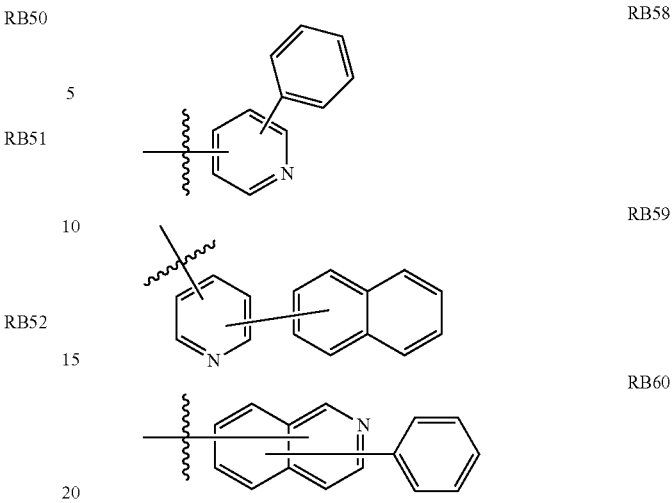

The organic light emitting device of the present disclosure may have a structure as illustrated in FIG. 1 and FIG. 2, however, the structure is not limited thereto.

FIG. 1 illustrates a structure of the organic light emitting device in which an anode (2), a light emitting layer (3) and a cathode (4) are consecutively laminated on a substrate (1). In such a structure, the compound may be included in the light emitting layer (3).

FIG. 2 illustrates a structure of the organic light emitting device in which an anode (2), a hole injection layer (5), a hole transfer layer (6), a light emitting layer (3), an electron transfer layer (7) and a cathode (4) are consecutively laminated on a substrate (1). In such a structure, the compound may be included in the hole injection layer (5), the hole transfer layer (6), the light emitting layer (3) or the electron transfer layer (7).

For example, the organic light emitting device according to the present disclosure may be manufactured by forming an anode on a substrate by depositing a metal, a metal oxide having conductivity, or an alloy thereof using a physical vapor deposition (PVD) method such as sputtering or e-beam evaporation, forming an organic material layer comprising a hole injection layer, a hole transfer layer, a light emitting layer and an electron transfer layer thereon, and then depositing a material capable of being used as a cathode thereon. In addition to such a method, the organic light emitting device may also be manufactured by consecutively depositing a cathode material, an organic material layer and an anode material on a substrate.

The organic material layer may have a multilayer structure comprising a hole injection layer, a hole transfer layer, a light emitting layer, an electron transfer layer and the like, however, the structure is not limited thereto, and the organic material layer may have a single layer structure. In addition, the organic material layer may be prepared to have less numbers of layers through a solvent process such as spin coating, dip coating, doctor blading, screen printing, inkjet printing or a thermal transfer method instead of a deposition method using various polymer materials.

As the anode material, materials having large work function are normally preferred so that hole injection to an organic material layer is smooth. Specific examples of the anode material capable of being used in the present disclosure comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, but are not limited thereto.

As the cathode material, materials having small work function are normally preferred so that electron injection to an organic material layer is smooth. Specific examples of the cathode material comprise metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

The hole injection material is a material favorably receiving holes from an anode at a low voltage, and the highest occupied molecular orbital (HOMO) of the hole injection material is preferably in between the work function of an anode material and the HOMO of surrounding organic material layers. Specific examples of the hole injection material comprise metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer material is a material capable of receiving holes from an anode or a hole injection layer and transferring the holes to a light emitting layer, and materials having high mobility for the holes are suited. Specific examples thereof comprise arylamine-based organic materials, conductive polymers, block copolymers having conjugated parts and non-conjugated parts together, and the like, but are not limited thereto.

The light emitting layer may emit light of red, green or blue, and may be formed with phosphorescent materials or fluorescent materials. The light emitting material is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof comprise 8-hydroxyquinoline aluminum complexes ($Alq_3$); carbazole-based compounds; dimerized styryl compounds; BAlq; 10-hydroxybenzo quinoline-metal compounds; benzoxazole-, benzothiazole- and benzimidazole-based compounds; poly(p-phenylenevinylene) (PPV)-based polymers; spiro compounds; polyfluorene, rubrene, and the like, but are not limited thereto.

The host material of the light emitting layer comprises fused aromatic ring derivatives, heteroring-containing compounds or the like. Specifically, the fused aromatic ring derivative comprises anthracene derivatives, pyrene derivatives, naphthalene derivatives, pentacene derivatives, phenanthrene compounds, fluoranthene compounds and the like, and the heteroring-containing compound comprises carbazole derivatives, dibenzofuran derivatives, ladder-type furan compounds, pyrimidine derivatives and the like, however, the material is not limited thereto.

As the dopant material of the light emitting layer, aromatic amine derivatives, styrylamine compounds, boron complexes, fluoranthene compounds, metal complexes and the like may be included. Specifically, the aromatic amine derivative is a fused aromatic ring derivative having a substituted or unsubstituted arylamino group, and arylamino group—comprising pyrene, anthracene, chrysene, peryflan-thene and the like may be used. As the styrylamine compound, a compound in which substituted or unsubstituted arylamine is substituted with at least one arylvinyl group may be used, and one, two or more substituents selected from the group consisting of an aryl group, a silyl group, an alkyl group, a cycloalkyl group and an arylamino group may substitute or unsubstitute. Specific examples thereof may comprise styrylamine, styryldiamine, styryltriamine, styryltetramine and the like, but are not limited thereto. In addition, the metal complex comprises iridium complexes, platinum complexes or the like, but is not limited thereto.

The electron transfer layer is a layer that receives electrons from an electron injection layer and transfers the electrons to a light emitting layer. As the electron transfer material, materials capable of favorably receiving electrons from a cathode, moving the electrons to a light emitting layer, and having high mobility for the electrons are suited. Examples of the electron transfer material comprise Al complexes of 8-hydroxyquinoline; complexes comprising $Alq_3$; organic radical compounds; hydroxyflavon-metal complexes, and the like, but are not limited thereto. The electron transfer layer may be used together with any desired cathode material as used in the art. Particularly, examples of the suitable cathode material comprise common materials that have small work function, and in which an aluminum layer or a silver layer follows. Specifically, the cathode material comprises cesium, barium, calcium, ytterbium and samarium, and in each case, an aluminum layer or a silver layer follows.

The electron injection layer is a layer injecting electrons from an electrode, and as the electron injection material, compounds having an electron transferring ability, having an electron injection effect from a cathode, having an excellent electron injection effect for a light emitting layer or light emitting material, and preventing excitons generated in the light emitting layer from moving to a hole injection layer, and in addition thereto, having an excellent thin film forming ability are preferred. Specific examples thereof comprise fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited thereto.

The metal complex compound comprises 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)berylium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato) (1-naphtholato)aluminum, bis(2-methyl-8-quinolinato) (2-naphtholato)gallium and the like, but is not limited thereto.

The hole blocking layer is a layer preventing holes from reaching a cathode, and may be generally formed under the same condition as the hole injection layer. Specifically, oxadiazole derivatives, triazole derivatives, phenanthroline derivatives, BCP, aluminum complexes or the like may be included, however, the hole blocking layer is not limited thereto.

The organic light emitting device according to the present specification may be a top-emission type, a bottom-emission type or a dual-emission type depending on the materials used.

Hereinafter, the present specification will be described in detail with reference to examples. However, the examples according to the present specification may be modified to various other forms, and the scope of the present application is not to be construed as being limited to the examples described below. Examples of the present application are provided in order to more fully describe the present specification to those having average knowledge in the art.

SYNTHESIS EXAMPLE

Synthesis Example 1: Synthesis of Intermediate 1-1

Intermediate 1-1 was synthesized according to the following reaction formula.

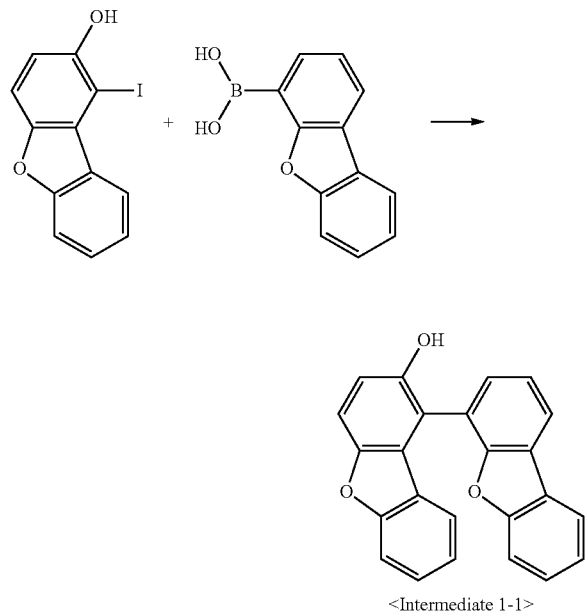

<Intermediate 1-1>

In a 1 L flask, 1-iododibenzo[b,d]furan-2-ol (80.0 g, 0.258 mol) and dibenzo[b,d]furan-4-yl boronic acid (60.2 g, 0.284 mol) were placed, and potassium carbonate (107.0 g, 0.774 mol) dissolved in tetrahydrofuran (500 mL) and water (340 mL) was introduced thereto. A tetrakis triphenylphosphine palladium catalyst (1.34 g, 1.16 mmol) was diluted with a small amount of tetrahydrofuran and then introduced thereto while raising the temperature of the reactor until reflux. After the reflux, termination of the reaction was checked, and the result was cooled again. This was extracted using water and ethyl acetate solvents to remove the water layer, and the result was treated with anhydrous magnesium sulfate, then filtered and concentrated to obtain a target material. <Intermediate 1-1> (65 g, yield 72%) was obtained through recrystallization purification using ethyl acetate and hexane.

Mass [M+1]=351

Synthesis Example 2: Synthesis of Intermediate 1-2

Intermediate 1-2 was synthesized according to the following reaction formula.

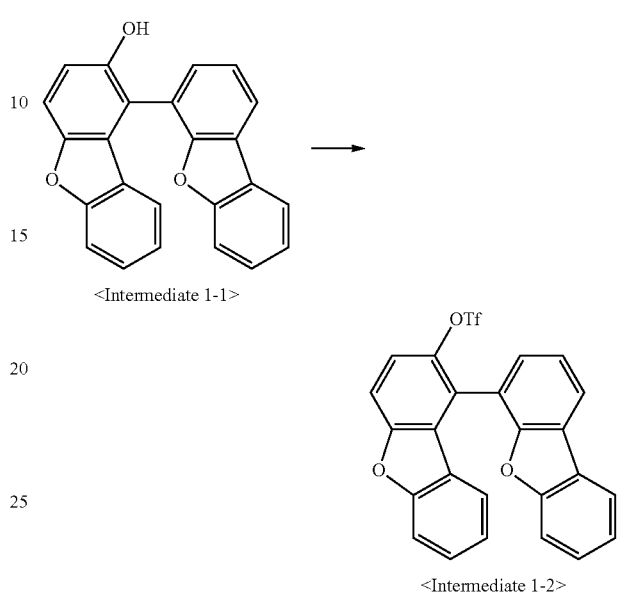

<Intermediate 1-1>

<Intermediate 1-2>

In a 1 L flask, <Intermediate 1-1> (65.0 g, 0.186 mol) was placed under nitrogen atmosphere, and diluted with dichloromethane (600 mL). After transferring the result to an ice bath, pyridine (22.0 g, 0.214 mol) was introduced thereto, and subsequently, trifluoromethanesulfonic anhydride (68.1 g, 0.1867 mmol) was dropped thereto. After the dropping, the ice bath was removed, the temperature was raised to room temperature, and the result was stirred for 2 hours. After the reaction was completed, the result was extracted with ethyl acetate and water. The organic layer was treated with anhydrous magnesium sulfate, then filtered and concentrated to obtain <Intermediate 1-2> (58.0 g, yield 65%) using a column chromatography method.

The reaction was checked with thin layer chromatography (TLC) and high performance liquid chromatography (HPLC).

Synthesis Example 3: Synthesis of Intermediate 1-3

Intermediate 1-3 was synthesized according to the following reaction formula.

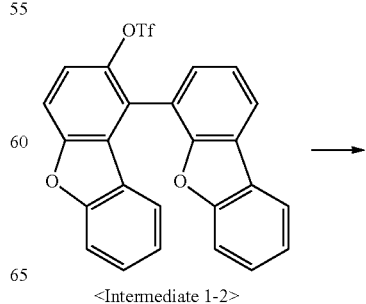

<Intermediate 1-2>

-continued

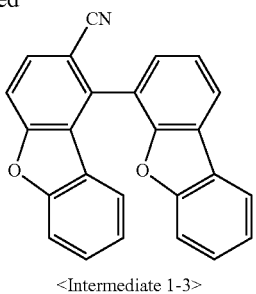

<Intermediate 1-3>

In a 0.5 L flask, <Intermediate 1-2> (55.0 g, 0.114 mol), potassium cyanide (14.8 g, 0.228 mol) and tetrakis triphenylphosphine palladium (0.59 g, 0.51 mmol) were placed, and N,N-dimethylformamide (300 mL) was introduced thereto. The result was stirred for 18 hours after raising the inner temperature to 130° C., and then the reaction was terminated. The reaction solvent was vacuum distilled to remove the solvent, and the result was extracted with ethyl acetate and water. The organic layer was treated with anhydrous magnesium sulfate, then filtered and concentrated to obtain <Intermediate 1-3> (29.0 g, yield 71%) using a column chromatography method.

Mass [M+1]=360

Synthesis Example 4: Synthesis of Intermediate 1-4

Intermediate 1-4 was synthesized according to the following reaction formula.

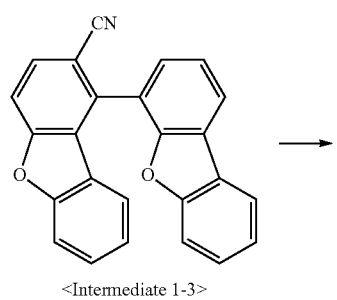

<Intermediate 1-3>

In a 0.5 L flask, <Intermediate 1-3> (29.0 g, 0.081 mol) and potassium hydroxide (9.1 g, 0.161 mol) were placed, and ethanol (300 mL) and water (100 mL) were introduced thereto. After reacting the result for approximately 30 hours through stirring under reflux, the result was cooled to room temperature, and then acidified using dilute hydrochloric acid. Dropped solids were filtered, washed with normal hexane, and then dried under nitrogen to obtain <Intermediate 1-4> (25.0 g, yield 82%).

The reaction was checked with TLC and HPLC.

Synthesis Example 5: Synthesis of Intermediate 1-5

Intermediate 1-5 was synthesized according to the following reaction formula.

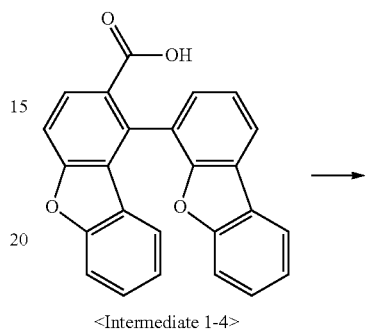

<Intermediate 1-4>

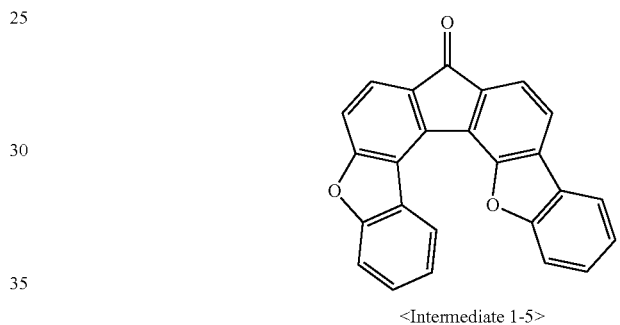

<Intermediate 1-5>

In a 0.5 L flask, <Intermediate 1-4> (25.0 g, 0.066 mol) and methanesulfonic acid (200 mL) were placed, and the result was stirred for 4 hours after raising the temperature to 120° C. After cooling the result, the reaction solution was dropped to excess water to solidify, and the solids obtained by filtering the result were purified again with toluene to obtain <Intermediate 1-5> (15.0 g, yield 63%).

Mass [M+1]=361

Synthesis Example 6: Synthesis of Intermediate 1-6

Intermediate 1-6 was synthesized according to the following reaction formula.

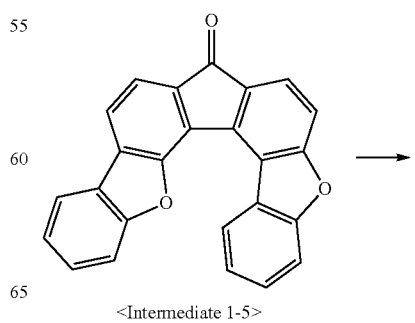

<Intermediate 1-5>

-continued

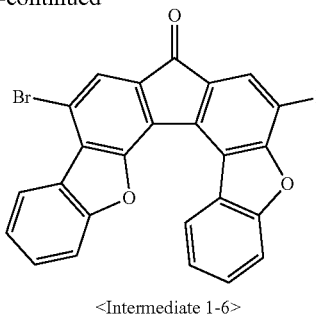

<Intermediate 1-6>

In a 0.5 L flask, <Intermediate 1-5> (10.0 g, 27.7 mmol) was introduced to dichloromethane (300 mL), the result was stirred, then bromine (13.3 g, 83.2 mmol) diluted in dichloromethane (50 mL) was slowly added dropwise thereto, and the result was stirred for 60 hours at room temperature. After that, the produced solids were filtered and then washed with dichloromethane and hexane. The solids were recrystallized with toluene and N-methylpyrrolidone to obtain <Intermediate 1-6> (3.5 g, yield 24%).

Synthesis Example 7: Synthesis of Intermediate 1-7

Intermediate 1-7 was synthesized according to the following reaction formula.

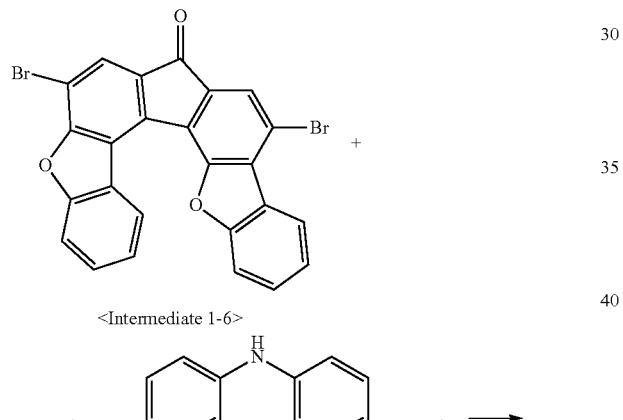

<Intermediate 1-7>

In a 0.25 L flask, <Intermediate 1-6> (35.0 g, 67.6 mmol), bis(4-t-butylphenyl)amine (41.8 g, 0.149 mol), sodium-t-butoxide (32.5 g, 0.338 mol) and bis(tri-t-butylphosphine)palladium(0) (2.1 g, 6.0 mmol) were introduced to toluene (1800 mL) under nitrogen atmosphere, and the result was stirred under reflux. After the reaction was terminated, the result was cooled to room temperature, then extracted with toluene and water, and the water layer was removed. The result was treated with anhydrous magnesium sulfate, then filtered and vacuum concentrated. After separation purifying the product using a column chromatography method, the result was recrystallized with toluene and normal hexane to obtain Intermediate 1-7 (43 g, yield 69%).

Synthesis Example 8: Synthesis of Intermediate 1-8

Intermediate 1-8 was synthesized according to the following reaction formula.

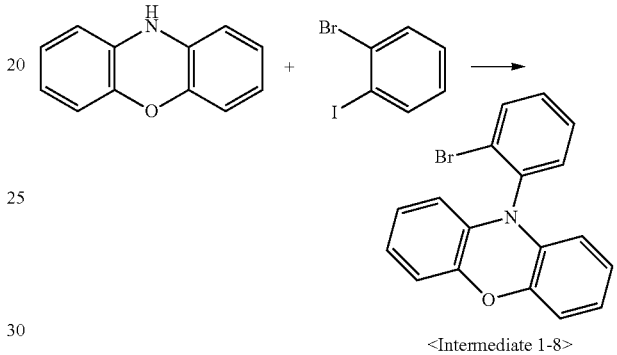

<Intermediate 1-8>

In a 0.5 L flask, phenoxazine (20 g, 0.145 mol), potassium hydroxide (60 g, 0.434 mol), copper (9.2 g, 0.22 mol) and 1-bromo-2-iodobenzene (160 g, 0.56 mol) were placed, and the result was refluxed at 200° C. After approximately 3 hours, the result was cooled to room temperature, filtered to remove copper, and then the filtrate was extracted with ammonia water and ethyl acetate. The obtained organic layer was filtered by being treated with anhydrous magnesium sulfate and activated carbon, and then concentrated. The result was recrystallized with ethyl acetate and normal hexane to obtain <Intermediate 1-8> (35.2 g, yield 72%).

Synthesis Example 9: Synthesis of Intermediate 1-9

Intermediate 1-9 was synthesized according to the following reaction formula.

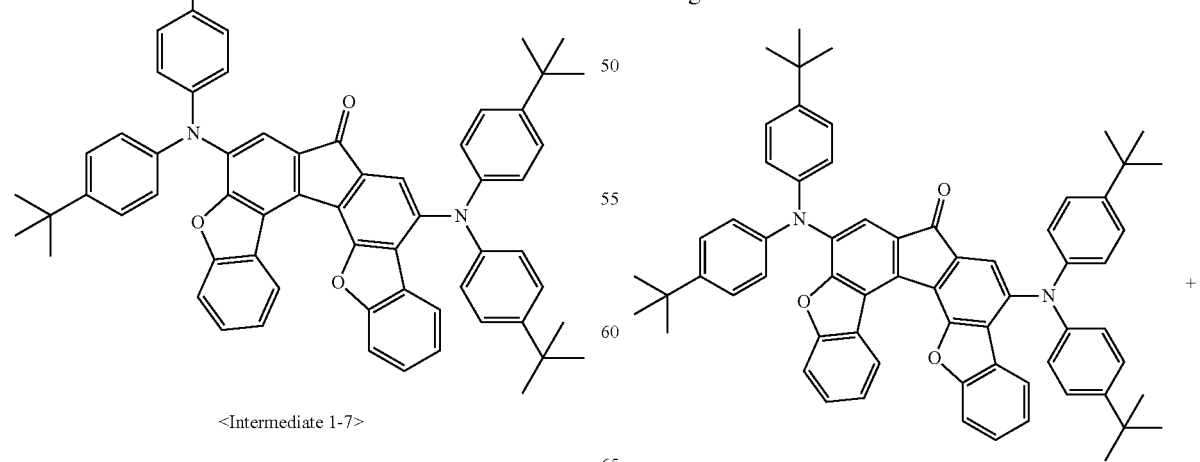

<Intermediate 1-7>

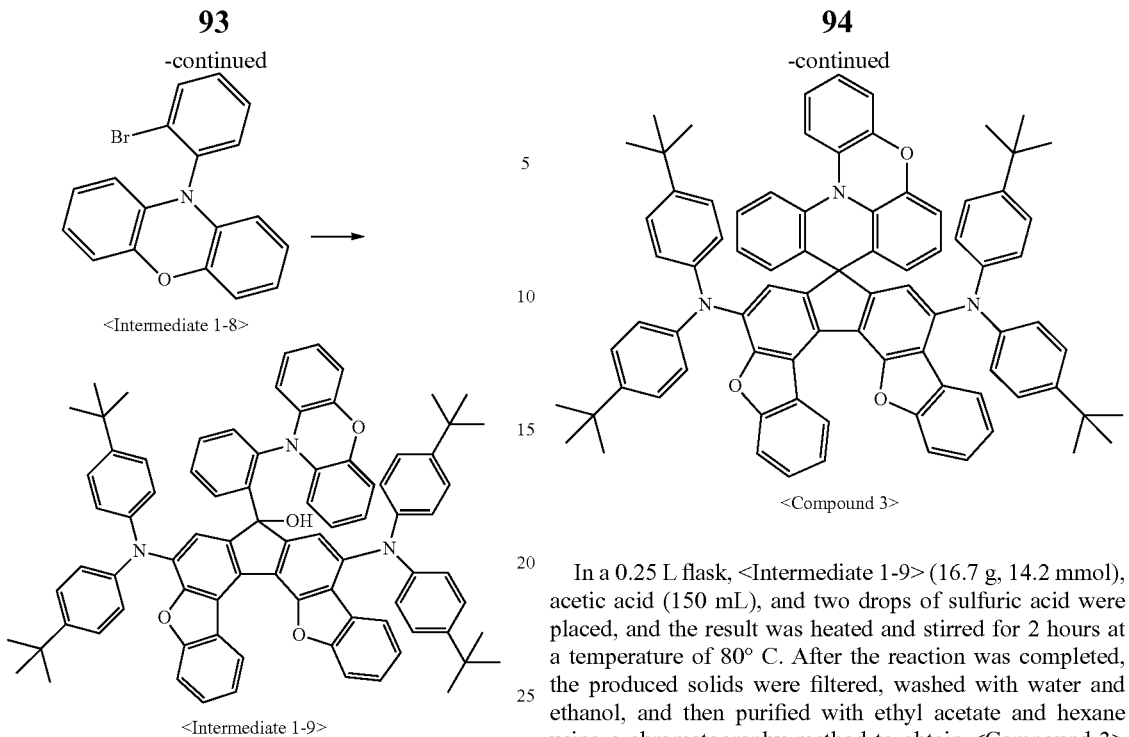

<Intermediate 1-8>

<Intermediate 1-9>

In a 0.25 L flask, <Intermediate 1-8> (6.7 g, 20 mmol) was placed under nitrogen atmosphere, and completely dissolved by introducing anhydrous tetrahydrofuran (THF) (200 mL) thereto. 1 M normal butyllithium (20 mL) was slowly dropped to the reaction solution at −78° C. After checking that the reaction was completed through TLC, <Intermediate 1-7> (18.4 g, 20 mmol) was introduced thereto, and the result was stirred. After the reaction was finished after reacting for 12 hours, the result was extracted with ethyl acetate together with an aqueous ammonium chloride solution. The obtained organic layer was dried using anhydrous magnesium sulfate-filtered, then concentrated and recrystallized with ethanol (EtOH) to obtain <Intermediate 1-9> (16.7 g, yield 71%).

Mass [M+1]=1179

Preparation Example 1; Synthesis of Compound 3

Compound 3 was synthesized according to the following reaction formula.

<Intermediate 1-9>

<Compound 3>

In a 0.25 L flask, <Intermediate 1-9> (16.7 g, 14.2 mmol), acetic acid (150 mL), and two drops of sulfuric acid were placed, and the result was heated and stirred for 2 hours at a temperature of 80° C. After the reaction was completed, the produced solids were filtered, washed with water and ethanol, and then purified with ethyl acetate and hexane using a chromatography method to obtain <Compound 3> (6.8 g, yield 48%). A diagram measuring mass data of Chemical Formula 3 is shown in FIG. 5.

Mass [M+1]=1161

Synthesis Example 10: Synthesis of Intermediate 2-1

Intermediate 2-1 was synthesized according to the following reaction formula.

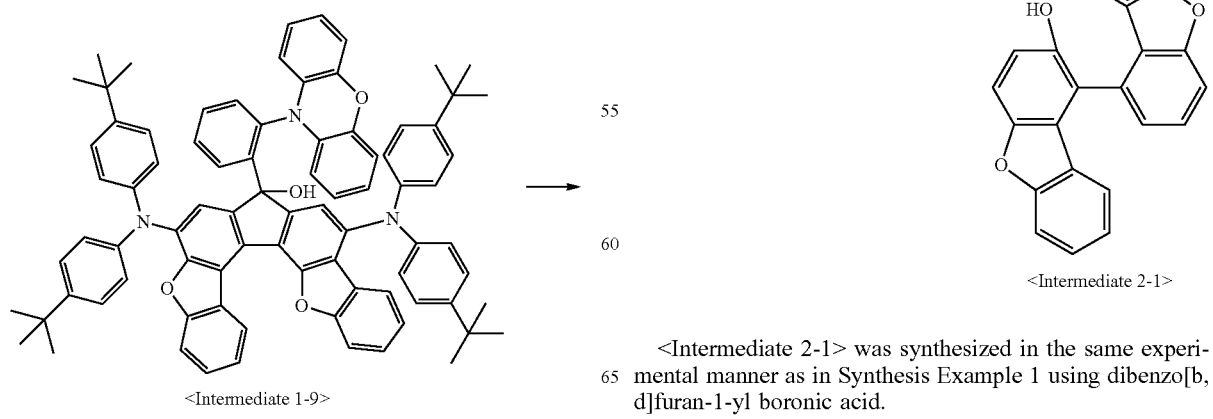

<Intermediate 2-1>

<Intermediate 2-1> was synthesized in the same experimental manner as in Synthesis Example 1 using dibenzo[b,d]furan-1-yl boronic acid.

Mass [M+1]=351

Synthesis Example 11: Synthesis of Intermediate 2-2

Intermediate 2-2 was synthesized according to the following reaction formula.

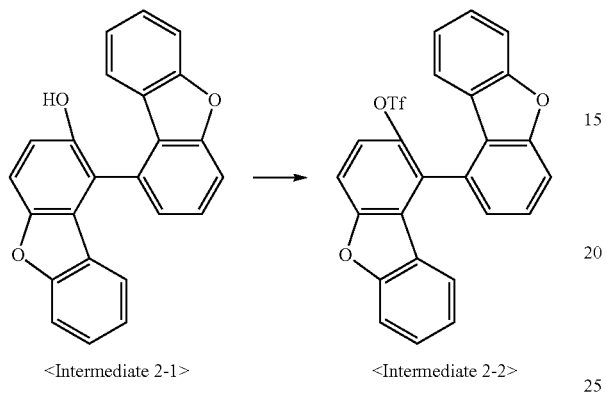

<Intermediate 2-1>    <Intermediate 2-2>

<Intermediate 2-2> was synthesized in the same experimental manner as in Synthesis Example 2 using <Intermediate 2-1>.

The reaction was checked by TLC and HPLC.

Synthesis Example 12: Synthesis of Intermediate 2-3

Intermediate 2-3 was synthesized according to the following reaction formula.

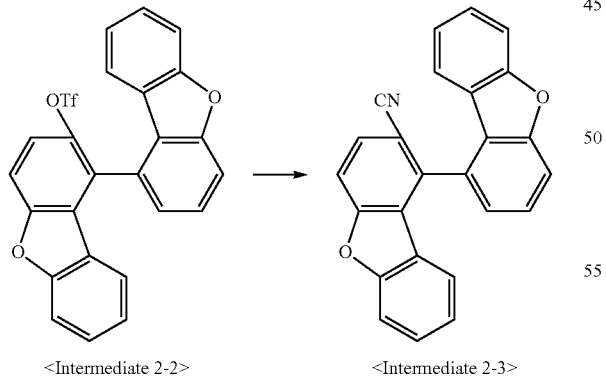

<Intermediate 2-2>    <Intermediate 2-3>

<Intermediate 2-3> was synthesized in the same experimental manner as in Synthesis Example 3 using <Intermediate 2-2>.

Mass [M+1]=360

Synthesis Example 13: Synthesis of Intermediate 2-4

Intermediate 2-4 was synthesized according to the following reaction formula.

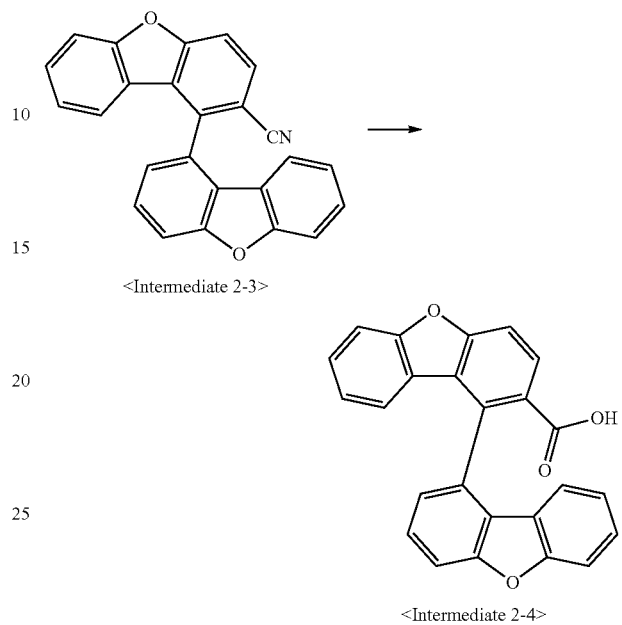

<Intermediate 2-3>

<Intermediate 2-4>

<Intermediate 2-4> was synthesized in the same experimental manner as in Synthesis Example 4 using <Intermediate 2-3>.

The reaction was checked by TLC and HPLC.

Synthesis Example 14: Synthesis of Intermediate 2-5

Intermediate 2-5 was synthesized according to the following reaction formula.

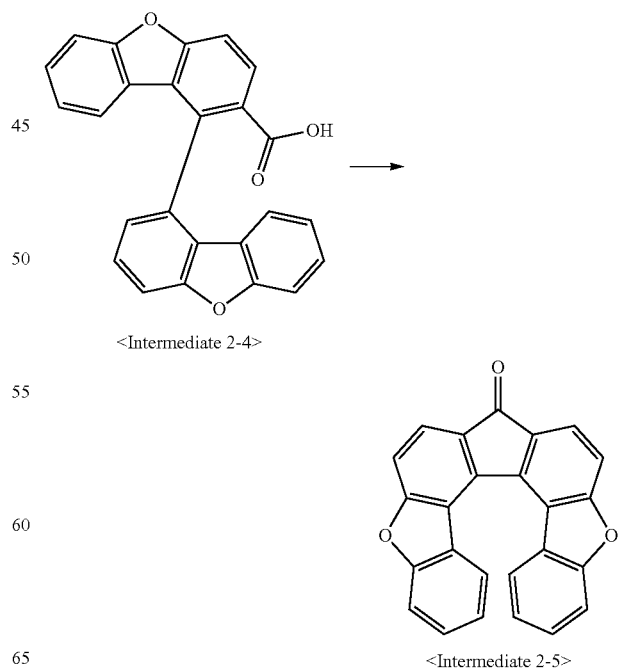

<Intermediate 2-4>

<Intermediate 2-5>

<Intermediate 2-5> was synthesized in the same experimental manner as in Synthesis Example 5 using <Intermediate 2-4>.

Mass [M+1]=361

Synthesis Example 15: Synthesis of Intermediate 2-6

Intermediate 2-6 was synthesized according to the following reaction formula.

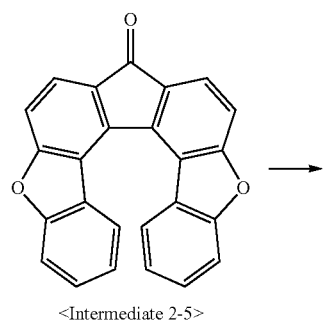

<Intermediate 2-5>

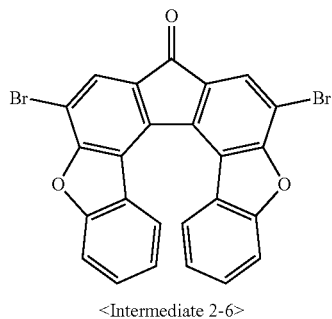

<Intermediate 2-6>

<Intermediate 2-6> was synthesized in the same experimental manner as in Synthesis Example 6 using <Intermediate 2-5>.

Mass [M+1]=517

Synthesis Example 16: Synthesis of Intermediate 2-7

Intermediate 2-7 was synthesized according to the following reaction formula.

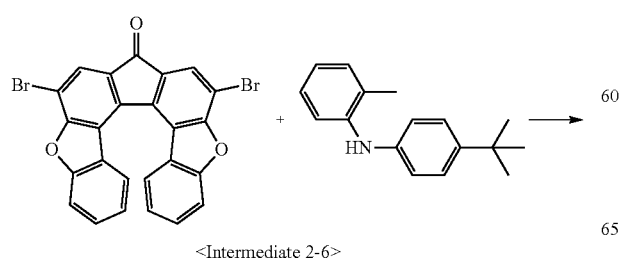

<Intermediate 2-6>

-continued

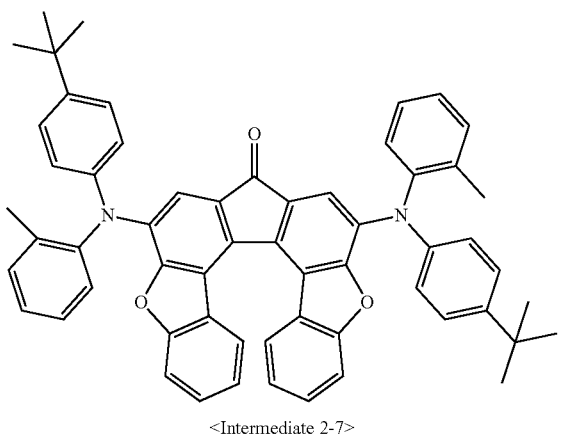

<Intermediate 2-7>

<Intermediate 2-7> was synthesized in the same experimental manner as in Synthesis Example 7 using <Intermediate 2-6> and N-(4-t-butylphenyl)-2-methylaniline.

Mass [M+1]=835

Synthesis Example 17: Synthesis of Intermediate 2-8

Intermediate 2-8 was synthesized according to the following reaction formula.

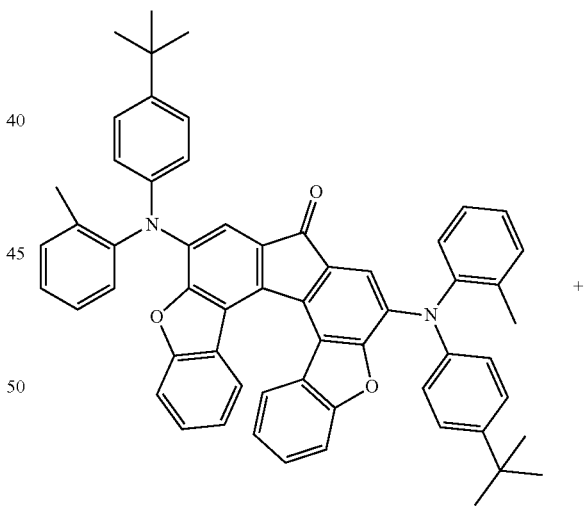

<Intermediate 2-7>

+

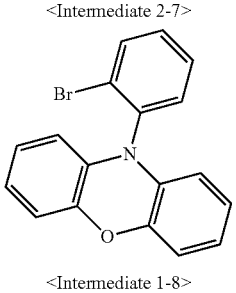

<Intermediate 1-8>

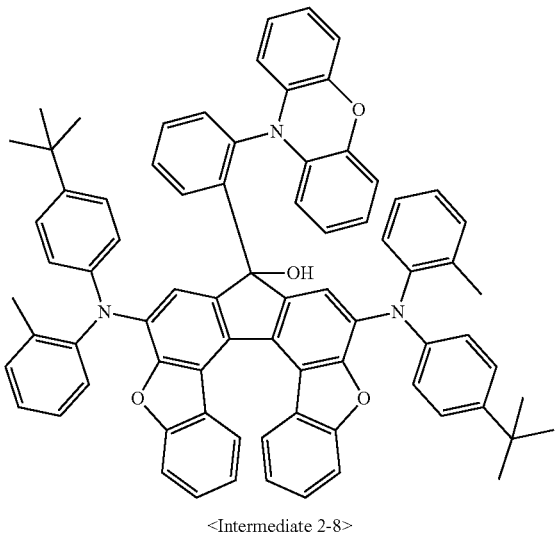

<Intermediate 2-8>

<Intermediate 2-8> was synthesized in the same experimental manner as in Synthesis Example 9 using <Intermediate 2-7> and <Intermediate 1-8>.

Mass [M+1]=1094

Preparation Example 2; Synthesis of Compound 7

Compound 7 was synthesized according to the following reaction formula.

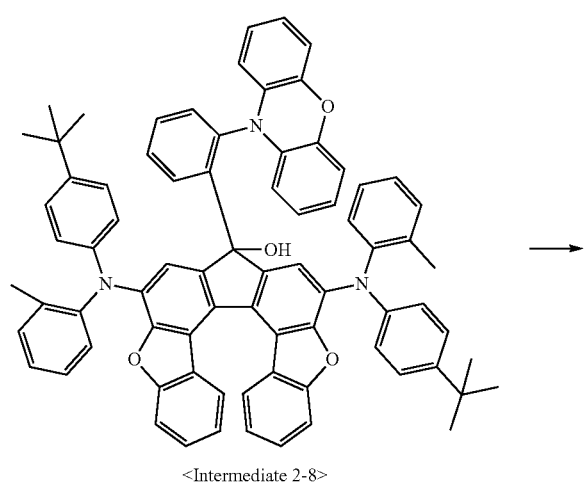

<Intermediate 2-8>

↓

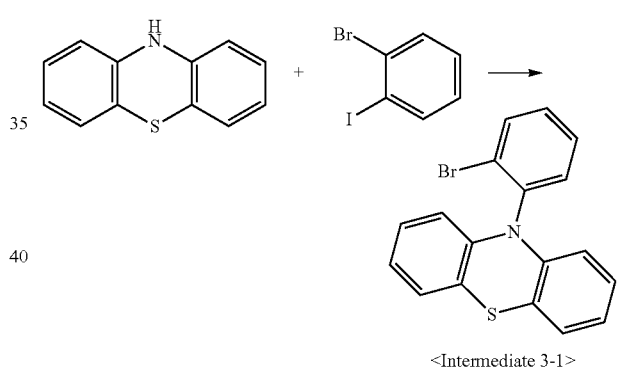

<Compound 7>

Compound 7 was synthesized in the same experimental manner as in Preparation Example 1 using <Intermediate 2-7>.

Mass [M+1]=1076

Synthesis Example 18: Synthesis of Intermediate 3-1

Intermediate 3-1 was synthesized according to the following reaction formula.

<Intermediate 3-1>

<Intermediate 3-1> was synthesized in the same experimental manner as in Synthesis Example 8 using phenothiazine.

Mass [M+1]=354

Synthesis Example 19: Synthesis of Intermediate 3-2

Intermediate 3-2 was synthesized according to the following reaction formula.

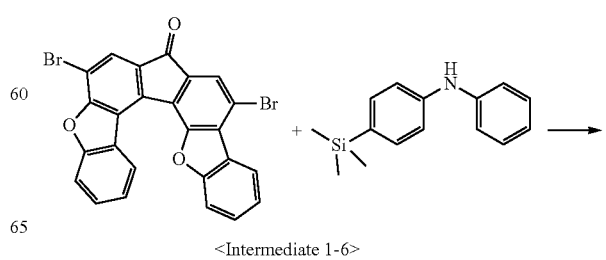

<Intermediate 1-6>

-continued

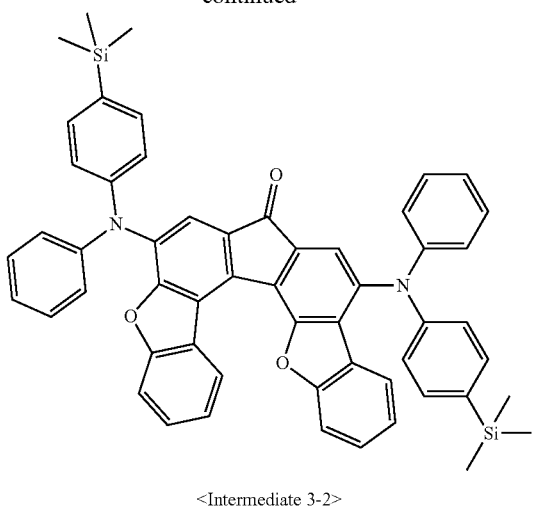

<Intermediate 3-2>

<Intermediate 3-2> was synthesized in the same experimental manner as in Synthesis Example 7 using <Intermediate 1-6> and N-phenyl-4-(t-butylsilyl)aniline.

Mass [M+1]=839

Synthesis Example 20: Synthesis of Intermediate 3-3

Intermediate 3-3 was synthesized according to the following reaction formula.

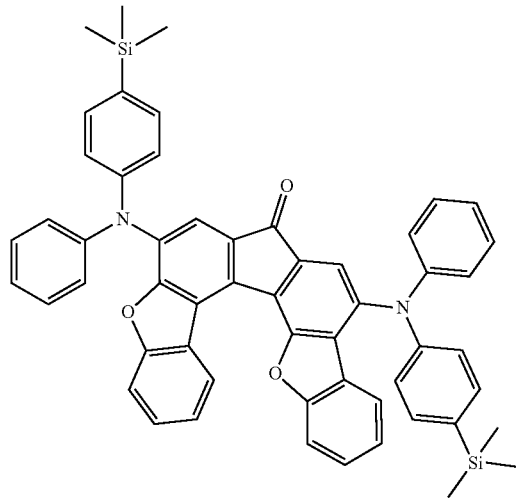

<Intermediate 3-2>

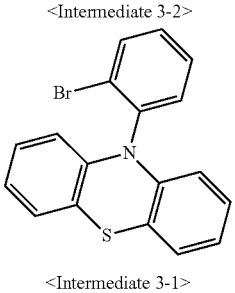

<Intermediate 3-1>

-continued

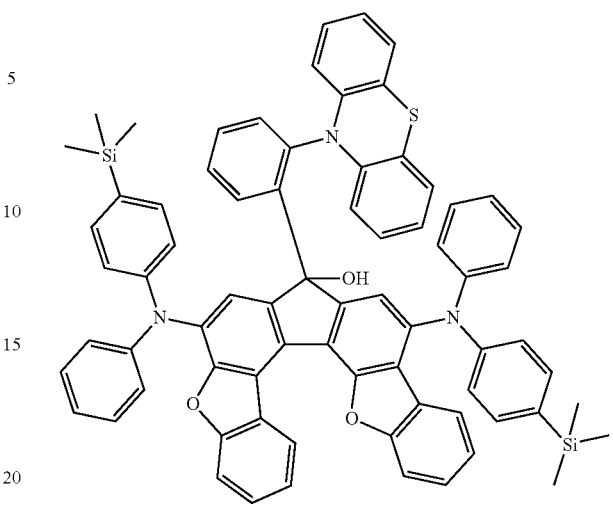

<Intermediate 3-3>

<Intermediate 3-3> was synthesized in the same experimental manner as in Synthesis Example 9 using <Intermediate 3-2> and <Intermediate 3-1>.

Mass [M+1]=1114

Preparation Example 3; Synthesis of Compound 8

Compound 8 was synthesized according to the following reaction formula.

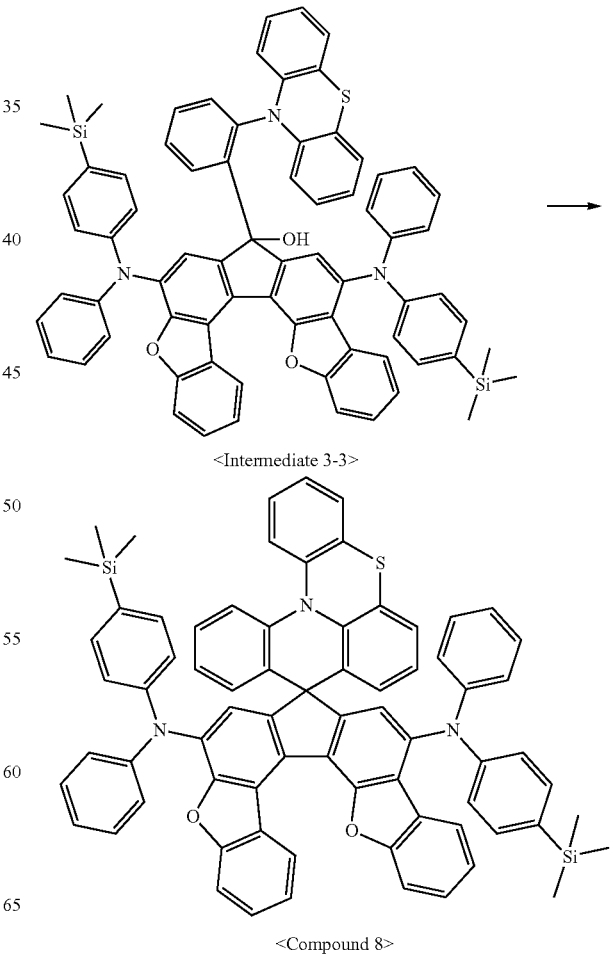

<Intermediate 3-3>

<Compound 8>

Compound 8 was synthesized in the same experimental manner as in Preparation Example 1 using <Intermediate 3-3>.

Mass [M+1]=1096

Synthesis Example 21: Synthesis of Intermediate 4-1

Intermediate 4-1 was synthesized according to the following reaction formula.

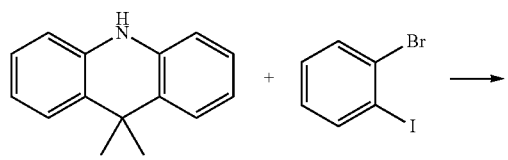

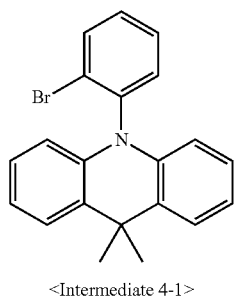

<Intermediate 4-1>

<Intermediate 4-1> was synthesized in the same experimental manner as in Synthesis Example 8 using 9,9-dimethyl-9,10-dihydroacridine.

Mass [M+1]=364

Synthesis Example 22: Synthesis of Intermediate 4-2

Intermediate 4-2 was synthesized according to the following reaction formula.

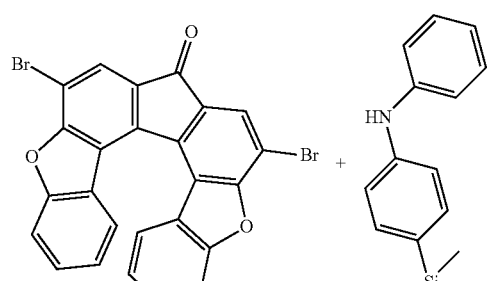

<Intermediate 2-6>

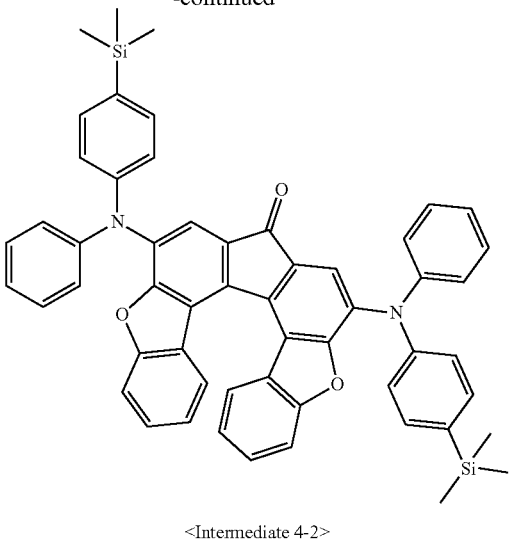

<Intermediate 4-2>

<Intermediate 4-2> was synthesized in the same experimental manner as in Synthesis Example 16 using <Intermediate 2-6> and N-phenyl-4-(t-butylsilyl)aniline.

Mass [M+1]=839

Synthesis Example 23: Synthesis of Intermediate 4-3

Intermediate 4-3 was synthesized according to the following reaction formula.

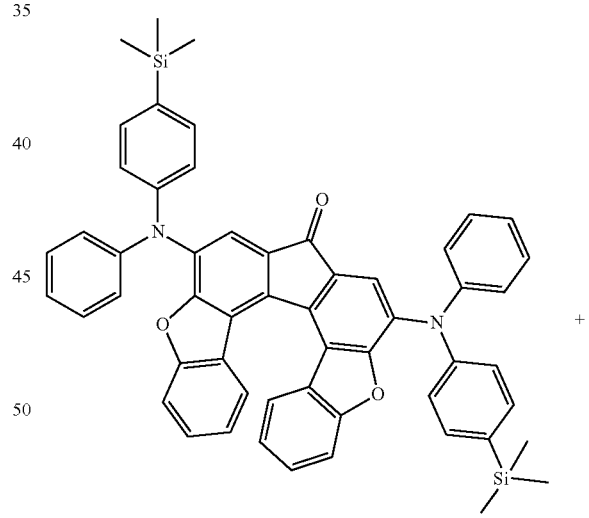

<Intermediate 4-2>

<Intermediate 4-1>

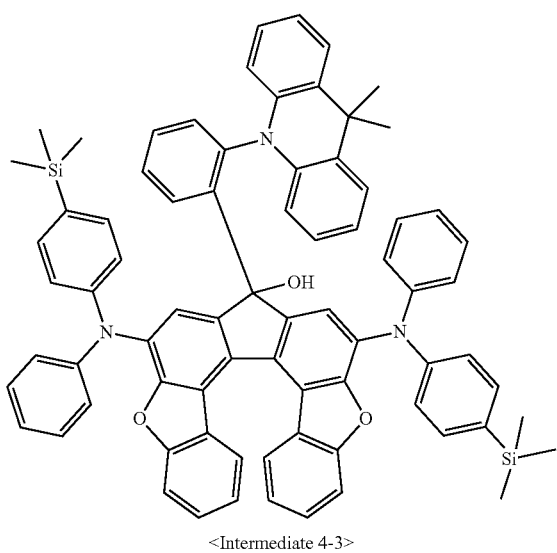

<Intermediate 4-3>

<Intermediate 4-3> was synthesized in the same experimental manner as in Synthesis Example 9 using <Intermediate 4-2> and <Intermediate 4-1>.

Mass [M+1]=1124

Preparation Example 4; Synthesis of Compound 19

Compound 19 was synthesized according to the following reaction formula.

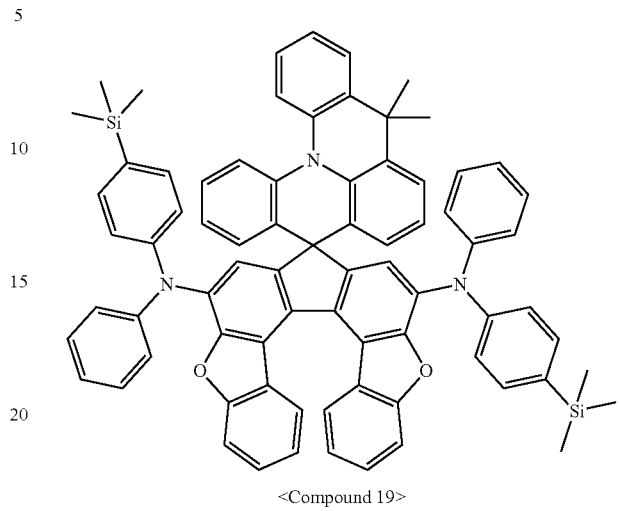

<Compound 19>

Compound 19 was synthesized in the same experimental manner as in Preparation Example 1 using <Intermediate 4-3>.

Mass [M+1]=1106

Synthesis Example 24: Synthesis of Intermediate 5-1

Intermediate 5-1 was synthesized according to the following reaction formula.

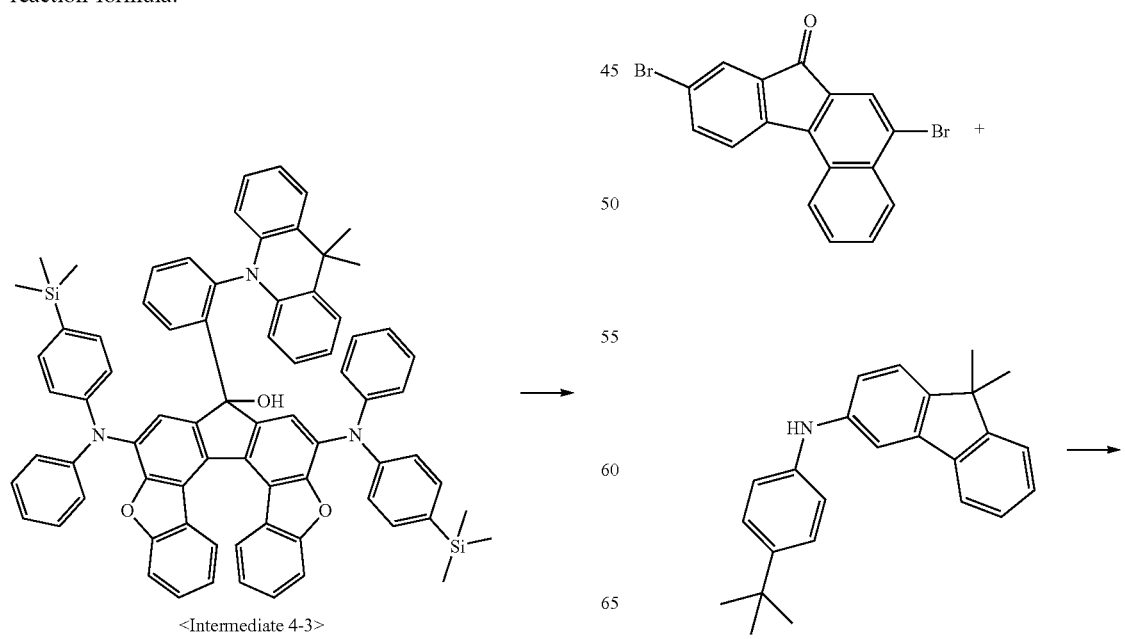

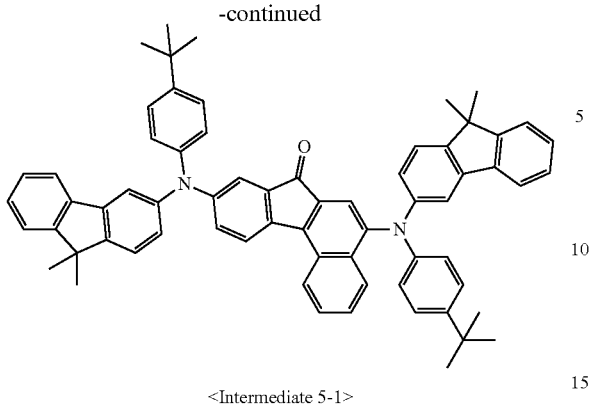

<Intermediate 5-1>

<Intermediate 5-1> was synthesized in the same experimental manner as in Synthesis Example 7 using 5,9-dibromo-7H-benzo[c]fluoren-7-one and N-(4-t-butylphenyl)-9,9-dimethyl-9H-fluorene-3-amine.

Mass [M+1]=909

Synthesis Example 25: Synthesis of Intermediate 5-2

Intermediate 5-2 was synthesized according to the following reaction formula.

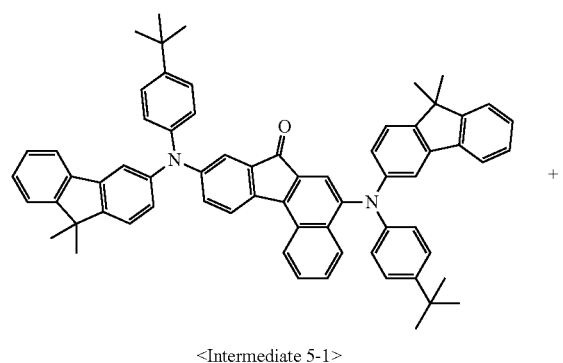

<Intermediate 5-1>

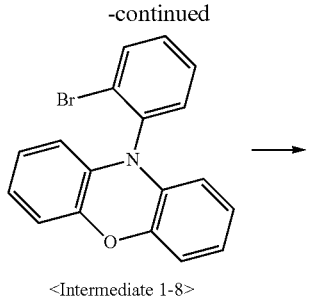

<Intermediate 1-8>

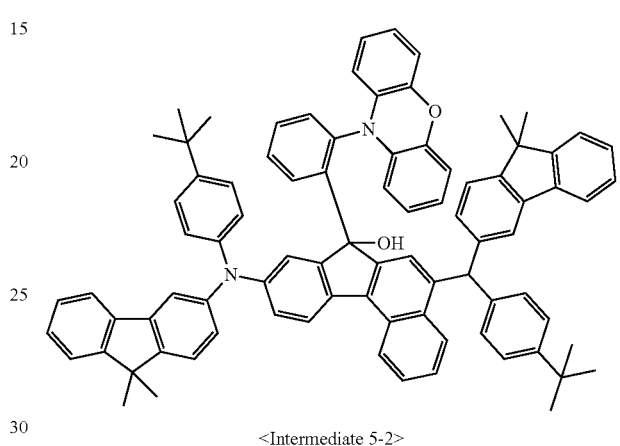

<Intermediate 5-2>

<Intermediate 5-2> was synthesized in the same experimental manner as in Synthesis Example 9 using <Intermediate 5-1> and <Intermediate 1-8>.

Mass [M+1]=1168

Preparation Example 5; Synthesis of Compound 24

Compound 24 was synthesized according to the following reaction formula.

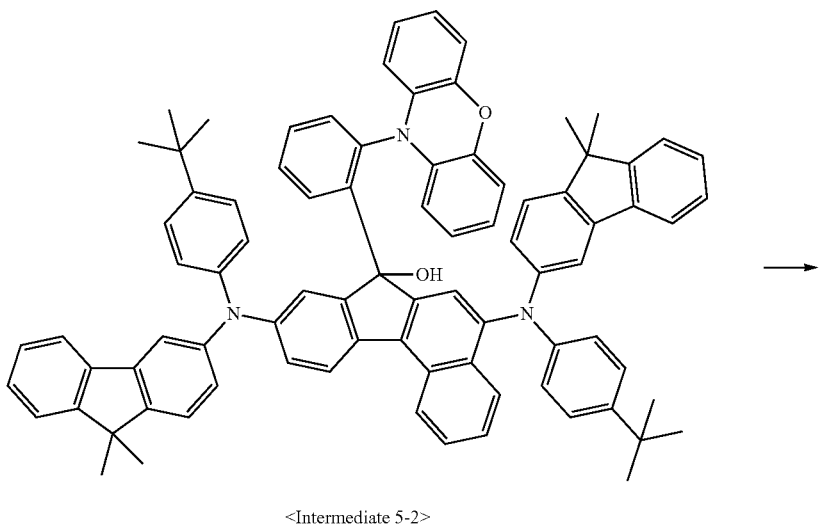

<Intermediate 5-2>

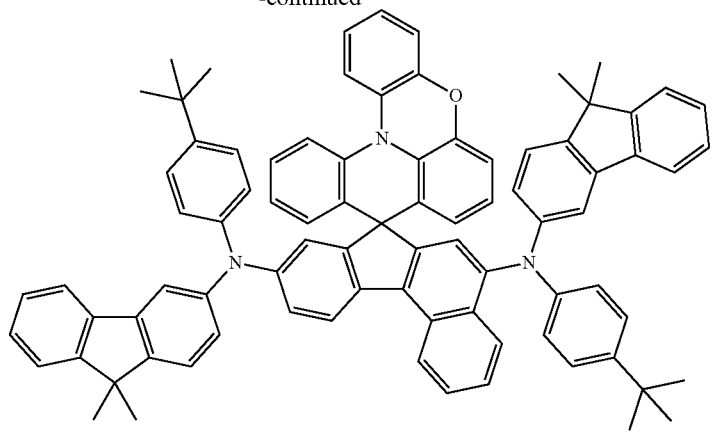

<Compound 24>

Compound 24 was synthesized in the same experimental manner as in Preparation Example 1 using <Intermediate 5-2>.

Mass [M+1]=1151

Synthesis Example 26. Synthesis of Intermediate 6-1

Intermediate 6-1 was synthesized according to the following reaction formula.

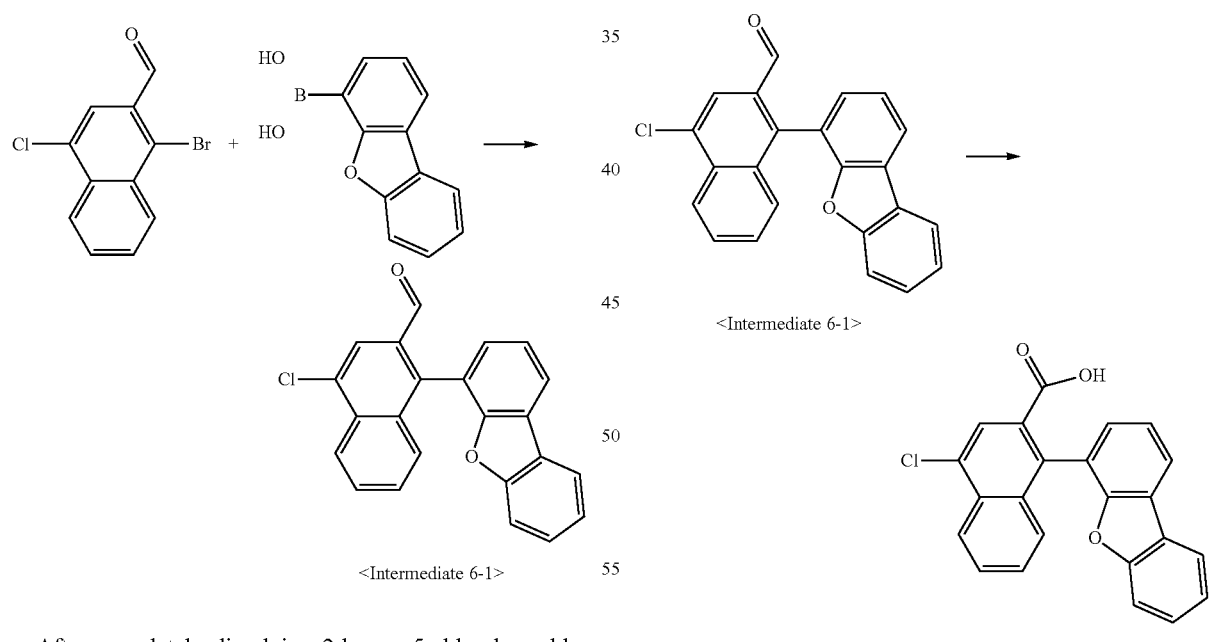

<Intermediate 6-1>

<Intermediate 6-1>

<Intermediate 6-2>

After completely dissolving 2-bromo-5-chlorobenzaldehyde (20.0 g, 74 mmol) and 4-dibenzofuranylboronic acid (17.3 g, 82 mmol) in tetrahydrofuran (300 mL), an aqueous potassium carbonate (30.7 g, 222 mmol) solution (100 mL) and then tetrakis-(triphenylphosphine)palladium (0.86 g, 0.74 mmol) were added thereto, and the result was stirred under reflux for 24 hours. After the reaction was completed, the result was cooled to room temperature, and then extracted with water and ethyl acetate to separate the organic layer. The organic layer was treated with anhydrous magnesium sulfate, then filtered and vacuum concentrated. The solids were recrystallized with ethyl acetate to obtain <Intermediate 6-1> (21.7 g, 82%).

MS [M+1]=357

Synthesis Example 27. Synthesis of Intermediate 6-2

Intermediate 6-2 was synthesized according to the following reaction formula.

After dissolving <Intermediate 6-1> (20.0 g, 56 mmol) in tetrahydrofuran (300 mL), sodium chlorite (5.6 g, 62 mmol) and sulfamic acid (8.2 g, 84 mmol) diluted in water (each 50 mL) were added thereto, and the result was stirred for 4 hours. After the reaction was completed, the result was cooled to room temperature, and then extracted with water and ethyl acetate to separate the organic layer.

The organic layer was treated with anhydrous magnesium sulfate, then filtered and vacuum concentrated. The solids were recrystallized with ethyl acetate and hexane to obtain Intermediate <6-2> (18.8 g, 90%).

MS [M+1]=374

Synthesis Example 28. Synthesis of Intermediate 6-3

Intermediate 6-3 was synthesized according to the following reaction formula.

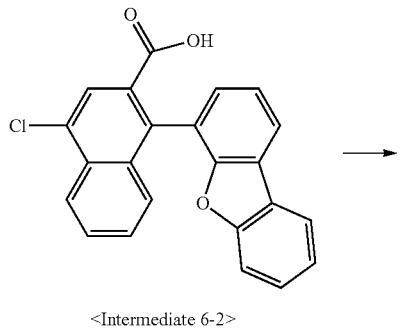

<Intermediate 6-2>

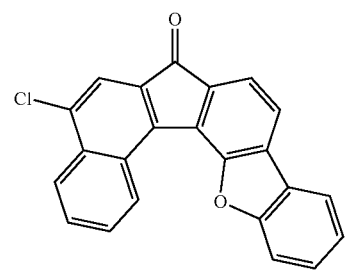

<Intermediate 6-3>

<Intermediate 6-2> (18.0 g, 48 mmol) and methanesulfonic acid (250 mL) were placed, and the result was heated and stirred for 9 hours at 80° C. After the reaction was completed, the result was cooled to room temperature, and slowly added dropwise to water to produce solids. The produced solids were washed with water and ethanol to obtain <Intermediate 6-3> (16.2 g, 95%).

MS [M+1]=356

Synthesis Example 29. Synthesis of Intermediate 6-4

Intermediate 6-4 was synthesized according to the following reaction formula.

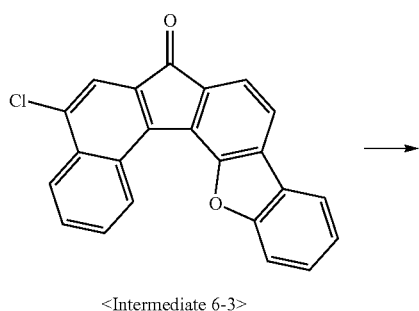

<Intermediate 6-3>

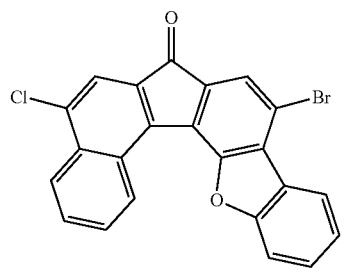

<Intermediate 6-4>

<Intermediate 6-3> (10.0 g, 28.1 mmol) was introduced to dichloromethane (300 mL), the result was stirred, then bromine (6.76 g, 42.3 mmol) diluted in dichloromethane (50 mL) was slowly added dropwise thereto, and the result was stirred for 48 hours at room temperature. After that, the produced solids were filtered and then washed with dichloromethane and hexane.

The solids were recrystallized with toluene and normal hexane to obtain <Intermediate 6-4> (7.92 g, 65%).

MS [M+1]=435

Synthesis Example 30: Synthesis of Intermediate 6-5

Intermediate 6-5 was synthesized according to the following reaction formula.

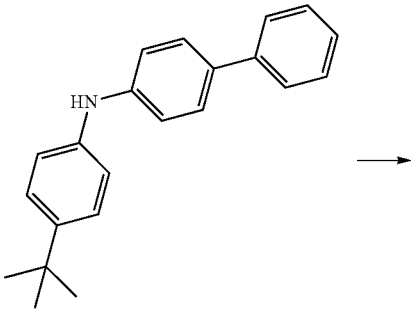

<Intermediate 6-4>

+

113

-continued

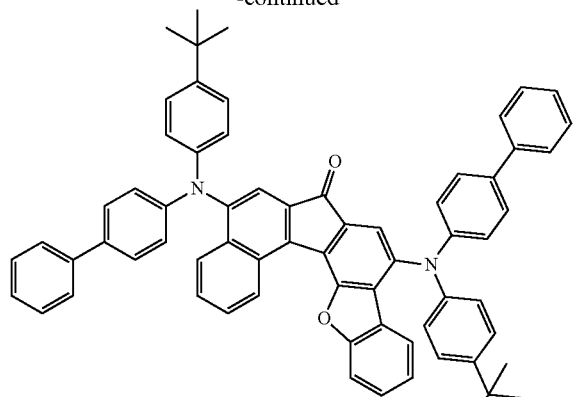

<Intermediate 6-5>

<Intermediate 6-5> was synthesized in the same experimental manner as in Synthesis Example 7 using <Intermediate 6-4> and N-(4-t-butylphenyl)-(1,1'-biphenyl)-4-amine.

Mass [M+1]=919

Synthesis Example 31: Synthesis of Intermediate 6-6

Intermediate 6-6 was synthesized according to the following reaction formula.

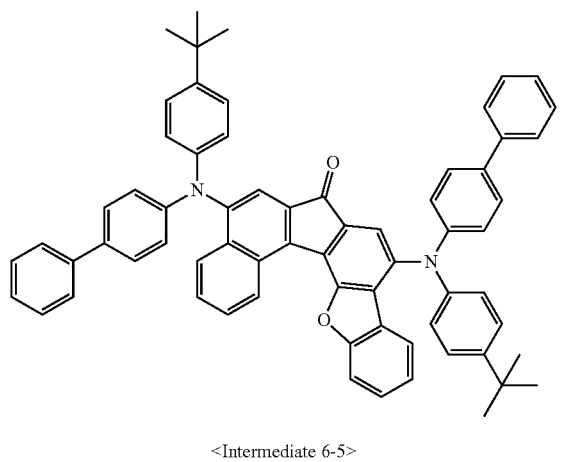

<Intermediate 6-5>

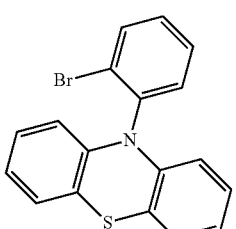

<Intermediate 3-1>

114

-continued

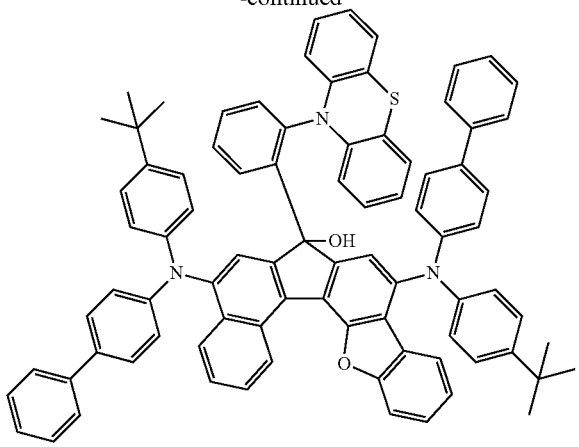

<Intermediate 6-6>

<Intermediate 6-6> was synthesized in the same experimental manner as in Synthesis Example 9 using <Intermediate 6-5> and <Intermediate 3-1>.

Mass [M+1]=1194

Preparation Example 6; Synthesis of Compound 51

Compound 51 was synthesized according to the following reaction formula.

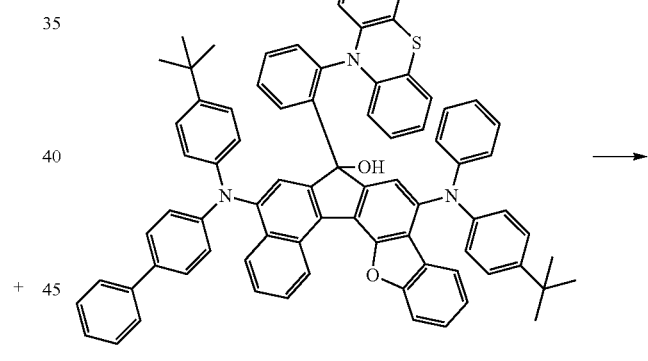

<Intermediate 6-6>

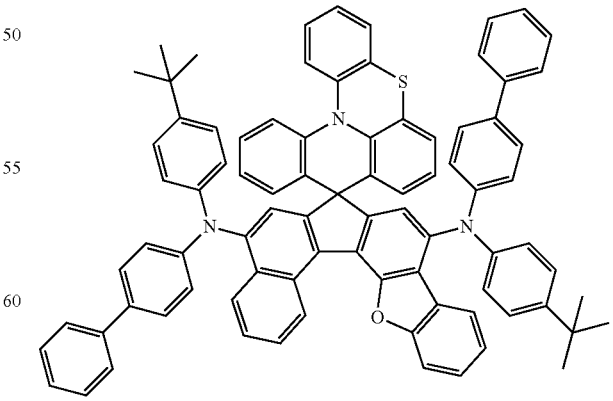

<Compound 51>

Compound 51 was synthesized in the same experimental manner as in Preparation Example 1 using <Intermediate 6-6>. Mass [M+1]=1176

Synthesis Example 32: Synthesis of Intermediate 7-1

Intermediate 7-1 was synthesized according to the following reaction formula.

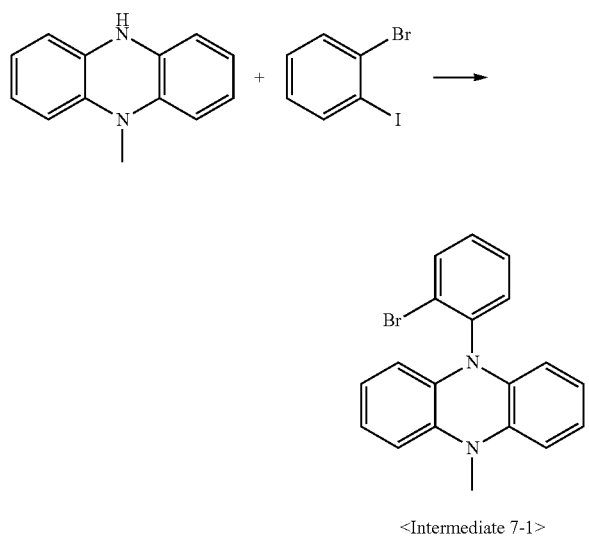

<Intermediate 7-1>

<Intermediate 7-1> was synthesized in the same experimental manner as in Synthesis Example 8 using 5-dimethyl-5,10-dihydrophenazine.
Mass [M+1]=364

Synthesis Example 33: Synthesis of Intermediate 7-2

Intermediate 7-2 was synthesized according to the following reaction formula.

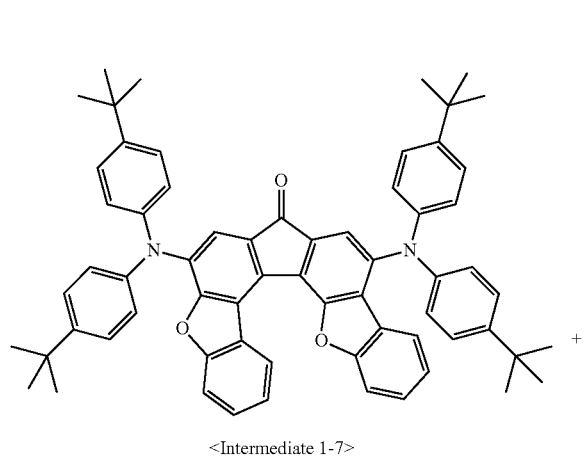

<Intermediate 7-2> was synthesized in the same experimental manner as in Synthesis Example 9 using <Intermediate 1-7> and <Intermediate 7-1>.
Mass [M+1]=1191

Preparation Example 7; Synthesis of Compound 65

Compound 65 was synthesized according to the following reaction formula.

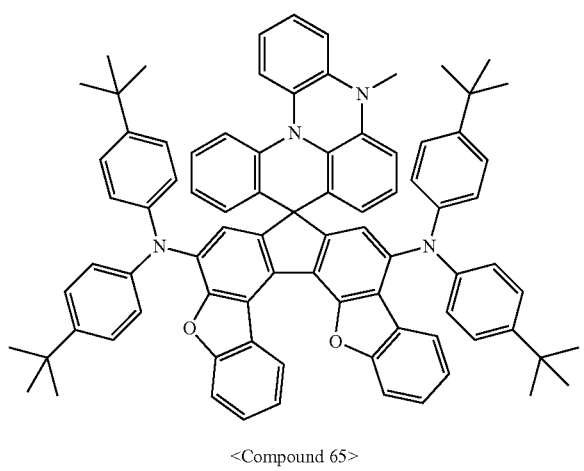

<Compound 65>

Compound 65 was synthesized in the same experimental manner as in Preparation Example 1 using <Intermediate 7-2>.

Mass [M+1]=1173

Synthesis Example 34: Synthesis of Intermediate 8-1

Intermediate 8-1 was synthesized according to the following reaction formula.

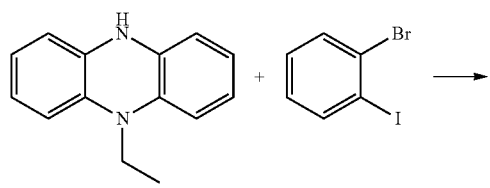

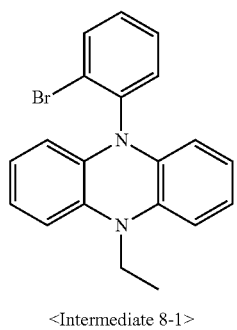

<Intermediate 8-1>

<Intermediate 8-1> was synthesized in the same experimental manner as in Synthesis Example 8 using 5-ethyl-5,10-dihydrophenazine.

Mass [M+1]=365

Synthesis Example 35: Synthesis of Intermediate 8-2

Intermediate 8-2 was synthesized according to the following reaction formula.

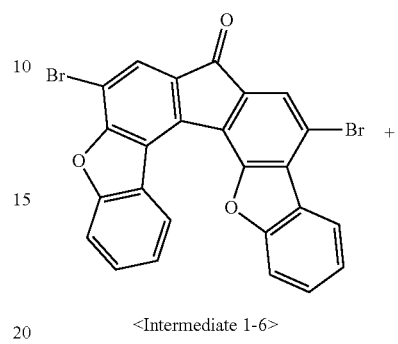

<Intermediate 1-6>

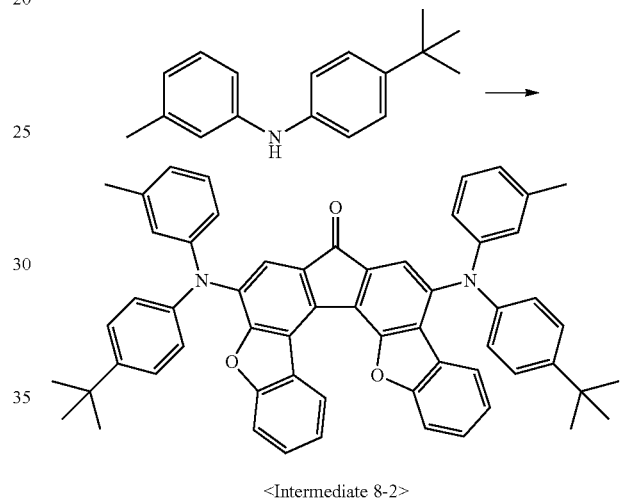

<Intermediate 8-2>

<Intermediate 8-2> was synthesized in the same experimental manner as in Synthesis Example 7 using <Intermediate 1-6> and N-(4-t-butylphenyl)-3-methylaniline.

Mass [M+1]=835

Synthesis Example 36: Synthesis of Intermediate 8-3

Intermediate 8-3 was synthesized according to the following reaction formula.

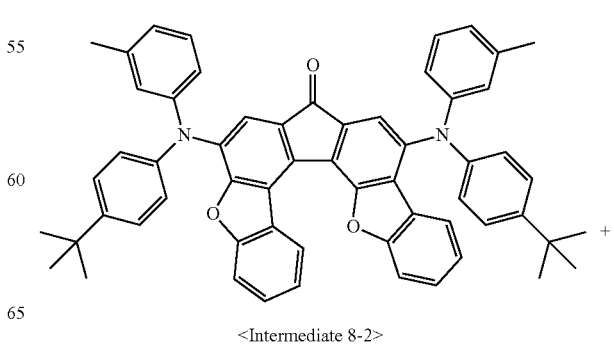

<Intermediate 8-2>

-continued

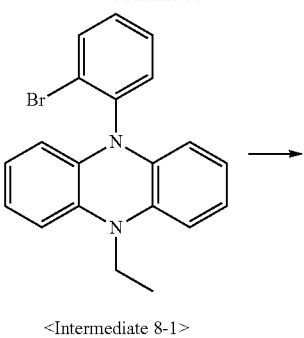

<Intermediate 8-1>

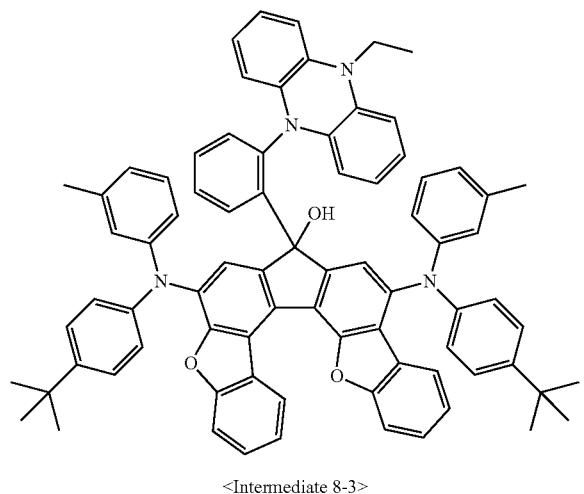

<Intermediate 8-3>

<Intermediate 8-3> was synthesized in the same experimental manner as in Synthesis Example 9 using <Intermediate 8-2> and <Intermediate 8-1>.

Mass [M+1]=1121

Preparation Example 8; Synthesis of Compound 71

Compound 71 was synthesized according to the following reaction formula.

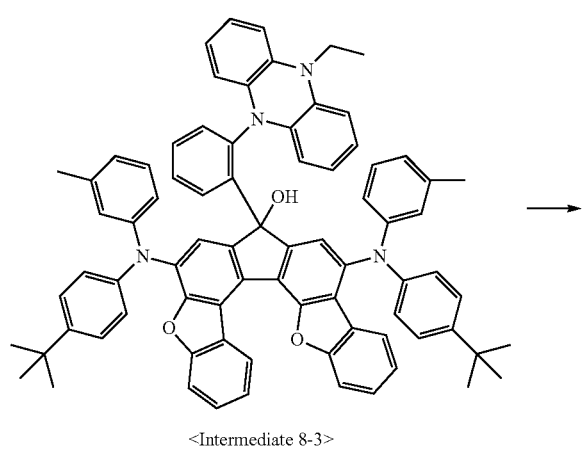

<Intermediate 8-3>

-continued

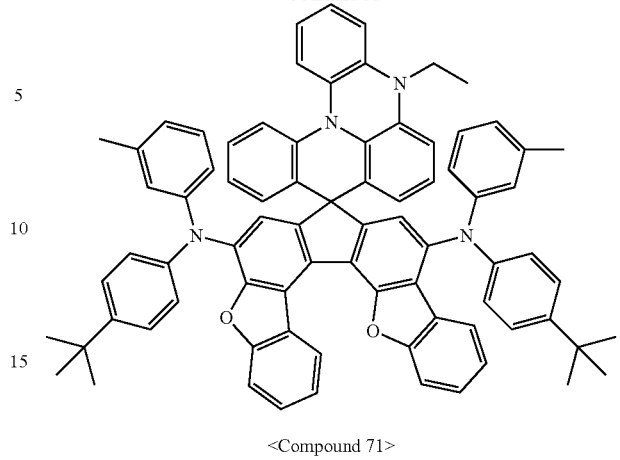

<Compound 71>

Compound 71 was synthesized in the same experimental manner as in Preparation Example 1 using <Intermediate 8-3>.

Mass [M+1]=1103

Synthesis Example 37. Synthesis of Intermediate 9-1

Intermediate 9-1 was synthesized according to the following reaction formula.

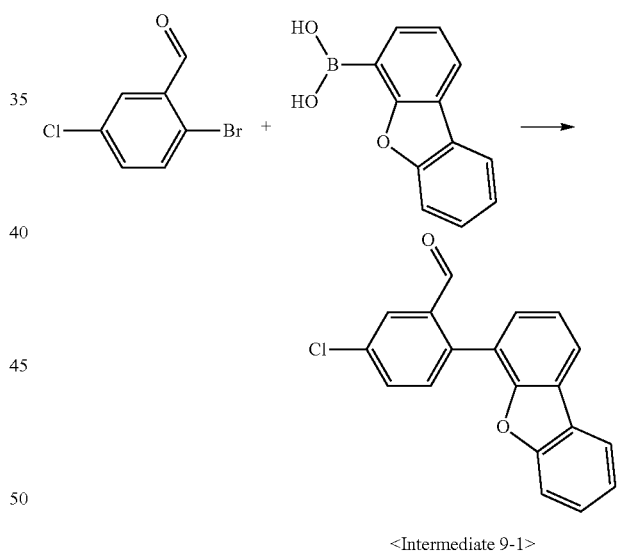

<Intermediate 9-1>

After completely dissolving 2-bromo-5-chlorobenzaldehyde (30.0 g, 137 mmol) and 4-dibenzofuranylboronic acid (31.9 g, 150 mmol) in tetrahydrofuran (375 mL) in a 1 L flask under nitrogen atmosphere, an aqueous potassium carbonate (56.7 g, 410 mmol) solution (125 mL) and then tetrakis-(triphenylphosphine)palladium (3.16 g, 2.73 mmol) were added thereto, and the result was stirred under reflux for 24 hours. After the reaction was completed, the result was cooled to room temperature, and then extracted with water and ethyl acetate to separate the organic layer. The organic layer was treated with anhydrous magnesium sulfate, then filtered and vacuum concentrated. The solids were recrystallized with ethyl acetate to obtain <Intermediate 9-1> (32.3 g, yield 77%).

Mass [M+1]=307

Synthesis Example 38. Synthesis of Intermediate 9-2

Intermediate 9-2 was synthesized according to the following reaction formula.

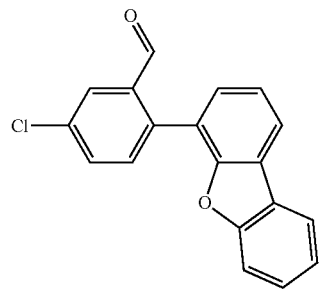

<Intermediate 9-1>

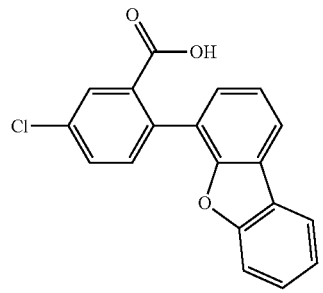

<Intermediate 9-2>

After dissolving <Intermediate 9-1> (32.0 g, 104 mmol) in tetrahydrofuran (450 mL) in a 1 L flask, sodium chlorite (14.2 g, 115 mmol) and sulfamic acid (20.3 g, 209 mmol) diluted in water (each 75 mL) were added thereto, and the result was heated and stirred for 4 hours. After the reaction was completed, the result was cooled to room temperature, and then extracted with water and ethyl acetate to separate the organic layer. The organic layer was treated with anhydrous magnesium sulfate, then filtered and vacuum concentrated. The solids were recrystallized with ethyl acetate and normal hexane to obtain <Intermediate 9-2> (28.3 g, yield 84%).

The reaction was checked by TLC.

Synthesis Example 39. Synthesis of Intermediate 9-3

Intermediate 9-3 was synthesized according to the following reaction formula.

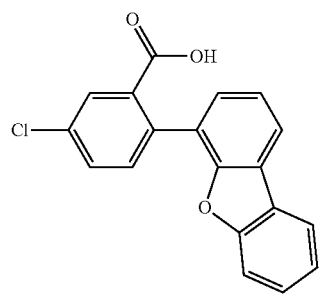

<Intermediate 9-2>

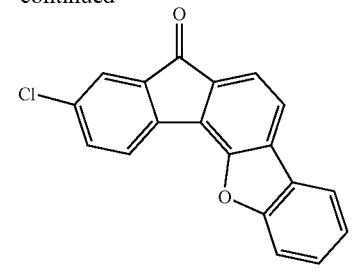

<Intermediate 9-3>

In a 0.5 L flask, <Intermediate 9-2> (28 g, 86.8 mmol) and methanesulfonic acid (350 mL) were placed, and the result was heated and stirred for 9 hours at 80° C. After the reaction was completed, the result was cooled to room temperature, and slowly added dropwise to water to produce solids. The produced solids were washed with water and ethanol to obtain <Intermediate 9-3> (24.3 g, yield 92%).

Mass [M+1]=305

Synthesis Example 40. Synthesis of Intermediate 9-4

Intermediate 9-4 was synthesized according to the following reaction formula.

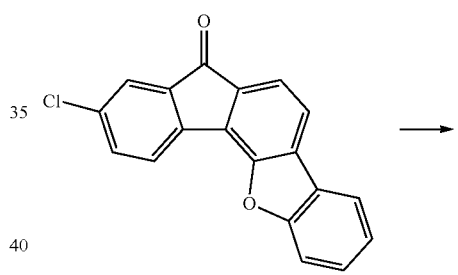

<Intermediate 9-3>

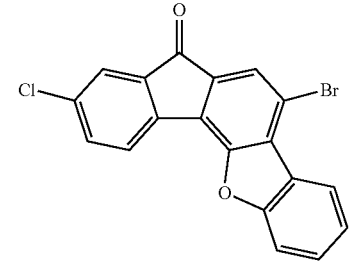

<Intermediate 9-4>

In a 0.5 L flask, <Intermediate 9-3> (9.50 g, 31.2 mmol) was introduced to dichloromethane (300 mL) under nitrogen atmosphere, the result was stirred, then bromine (9.97 g, 62.3 mmol) diluted in dichloromethane (50 mL) was slowly added dropwise thereto, and the result was stirred for 48 hours at room temperature. After that, the produced solids were filtered and then washed with dichloromethane and normal hexane. The solids were recrystallized with toluene and normal hexane to obtain <Intermediate 9-4> (7.0 g, yield 59%).

Mass [M+1]=383

Synthesis Example 41: Synthesis of Intermediate 9-5

Intermediate 9-5 was synthesized according to the following reaction formula.

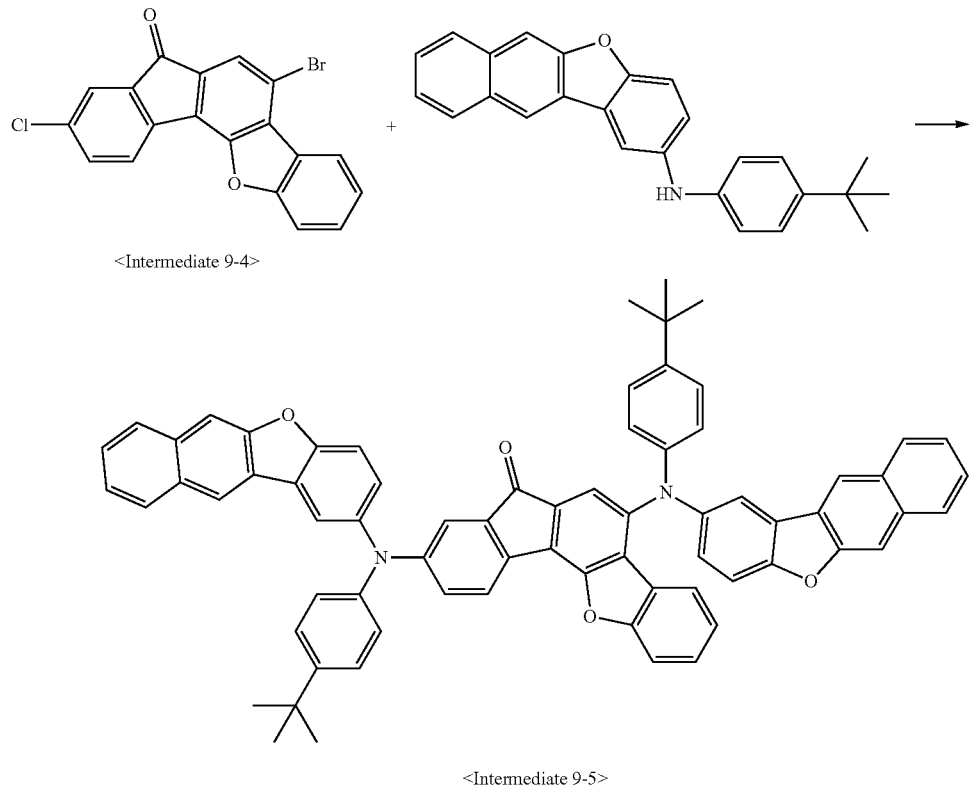

<Intermediate 9-5> was synthesized in the same experimental manner as in Synthesis Example 7 using <Intermediate 6-4> and N-(4-t-butylphenyl)naphtho[2,3-b]benzofuran-2-amine.

Mass [M+1]=997

Synthesis Example 42: Synthesis of Intermediate 9-6

Intermediate 9-6 was synthesized according to the following reaction formula.

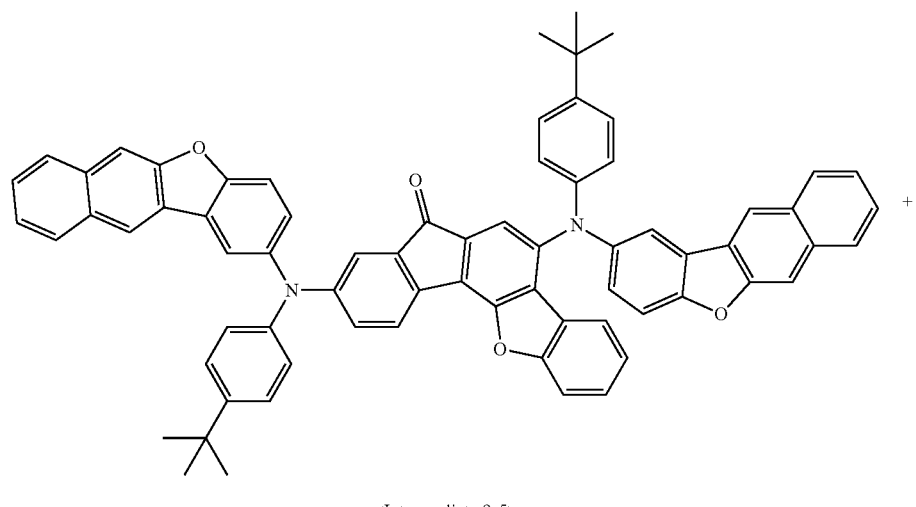

<Intermediate 9-5>

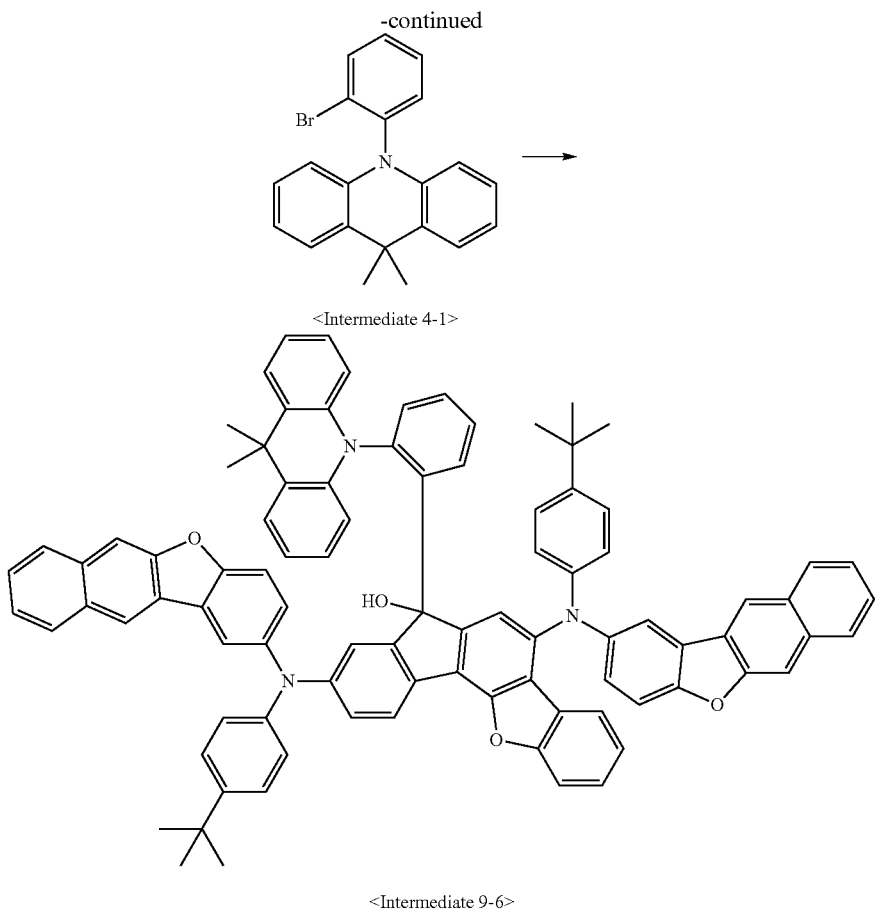
<Intermediate 4-1>
<Intermediate 9-6>
<Intermediate 9-6> was synthesized in the same experimental manner as in Synthesis Example 9 using <Intermediate 9-5> and <Intermediate 4-1>.
Mass [M+1]=1283
Preparation Example 9; Synthesis of Compound 77
Compound 77 was synthesized according to the following reaction formula.
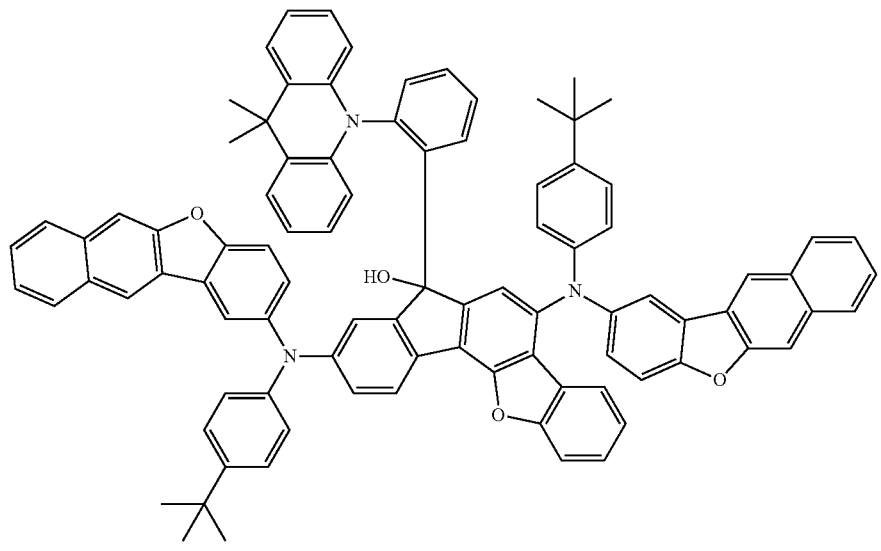
<Intermediate 9-6>

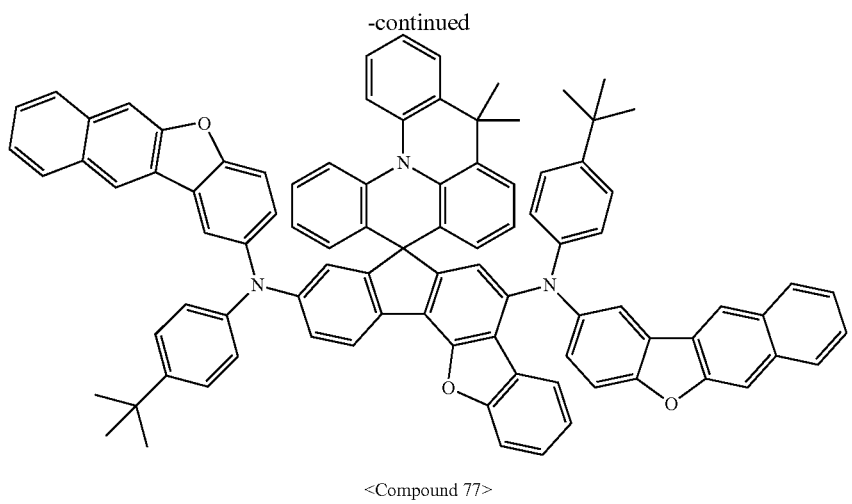

<Compound 77>

Compound 77 was synthesized in the same experimental manner as in Preparation Example 1 using <Intermediate 9-6>.

Mass [M+1]=1264

Synthesis Example 43: Synthesis of Intermediate 10-1

Intermediate 10-1 was synthesized according to the following reaction formula.

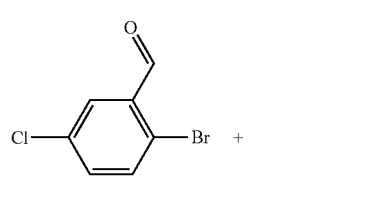

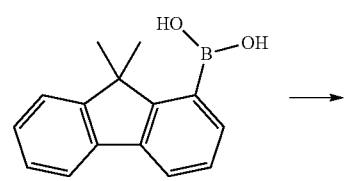

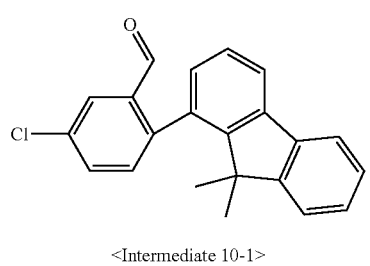

<Intermediate 10-1>

<Intermediate 10-1> was synthesized in the same experimental manner as in Synthesis Example 37 using (9,9-dimethyl-9H-fluoren-1-yl)boronic acid.

Mass [M+1]=333

Synthesis Example 44: Synthesis of Intermediate 10-2

Intermediate 10-2 was synthesized according to the following reaction formula.

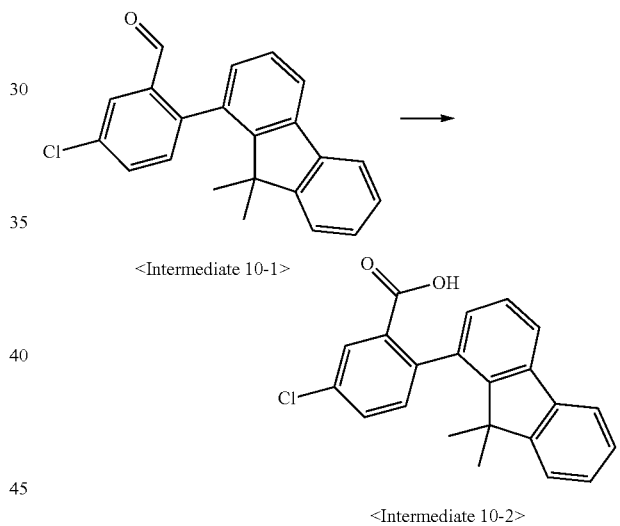

<Intermediate 10-2> was synthesized in the same experimental manner as in Synthesis Example 38 using <Intermediate 10-1>.

Synthesis Example 45: Synthesis of Intermediate 10-3

Intermediate 10-3 was synthesized according to the following reaction formula.

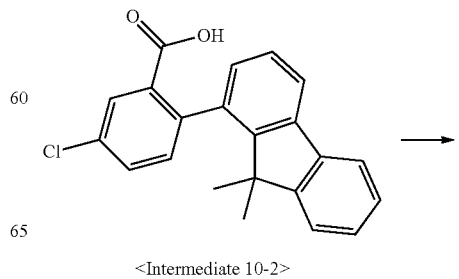

<Intermediate 10-2>

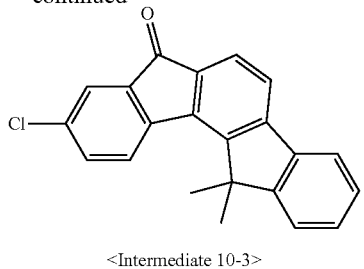

<Intermediate 10-3>

<Intermediate 10-3> was synthesized in the same experimental manner as in Synthesis Example 39 using (9,9-dimethyl-9H-fluoren-1-yl)boronic acid.
Mass [M+1]=333

Synthesis Example 46: Synthesis of Intermediate 10-4

Intermediate 10-4 was synthesized according to the following reaction formula.

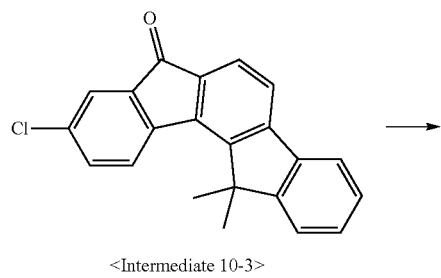

<Intermediate 10-4>

<Intermediate 10-4> was synthesized in the same experimental manner as in Synthesis Example 40 using <Intermediate 10-3>.
Mass [M+1]=333

Synthesis Example 47: Synthesis of Intermediate 10-5

Intermediate 10-5 was synthesized according to the following reaction formula.

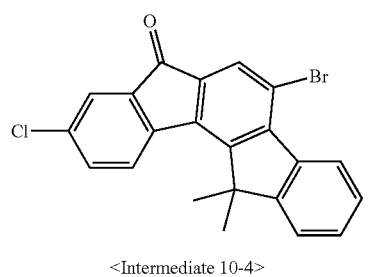

<Intermediate 10-4>

+

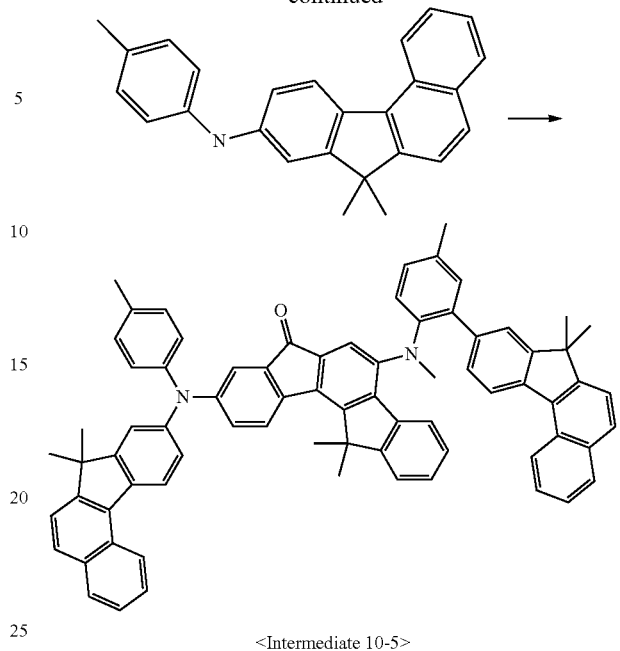

<Intermediate 10-5>

<Intermediate 10-5> was synthesized in the same experimental manner as in Synthesis Example 7 using <Intermediate 10-4> and 7,7-dimethyl-N-(p-tolyl)-7H-benzo[C]fluorene-9-amine.
Mass [M+1]=991

Synthesis Example 48: Synthesis of Intermediate 10-6

Intermediate 9-6 was synthesized according to the following reaction formula.

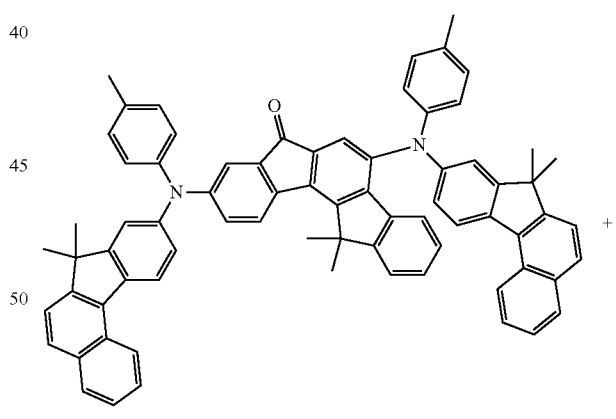

<Intermediate 10-5>

+

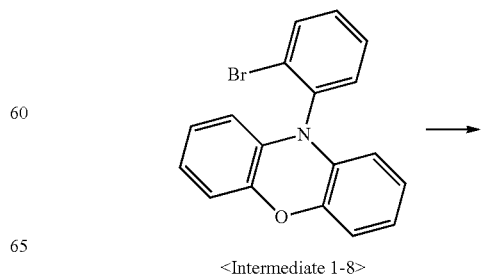

<Intermediate 1-8>

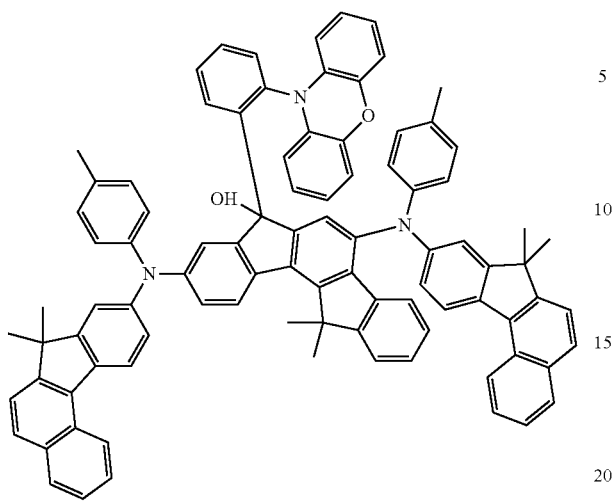
<Intermediate 10-6>
<Intermediate 10-6> was synthesized in the same experimental manner as in Synthesis Example 9 using <Intermediate 10-5> and <Intermediate 1-8>.
Mass [M+1]=1251
Preparation Example 10; Synthesis of Compound 86
Compound 86 was synthesized according to the following reaction formula.
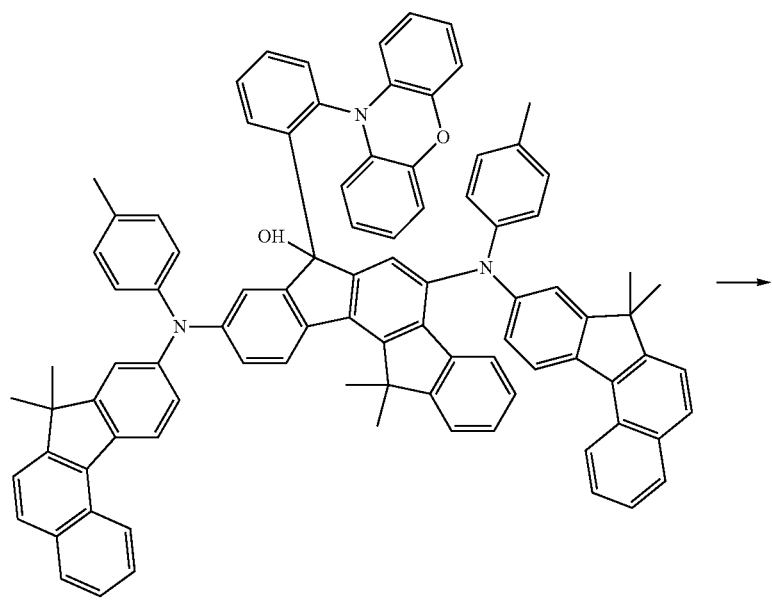
<Intermediate 10-6>

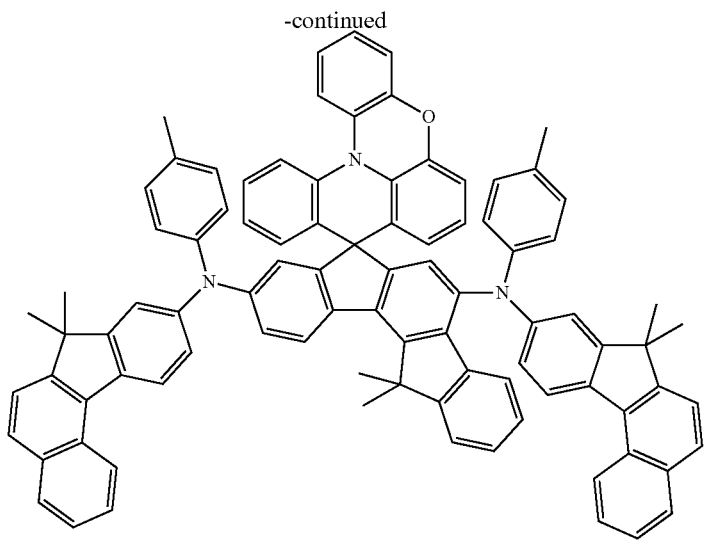

<Compound 86>

Compound 86 was synthesized in the same experimental manner as in Preparation Example 1 using <Intermediate 10-6>.
Mass [M+1]=1232

EXAMPLE

Example 1

A glass substrate on which indium tin oxide (ITO) was coated as a thin film to a thickness of 1,300 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner.

In addition, the substrate was cleaned for 5 minutes using oxygen plasma, and then transferred to a vacuum depositor.

On the transparent ITO electrode prepared as above, a hole injection layer was formed by vacuum depositing the following Compound [HI-A] to a thickness of 600 Å. A hole transfer layer was formed on the hole injection layer by consecutively vacuum depositing the following Compound [HAT-CN] (50 Å) and the following Compound [HT-B] (600 Å).

Subsequently, in forming a light emitting layer on the hole transfer layer, [BH-A] was vacuum deposited to a film thickness of 200 Å with [Compound 3] of the present disclosure being doped in 2.5 wt %. In forming an electron transfer layer on the light emitting layer formed as above, [ET-A] was deposited to 50 Å, and then [ET-B] and Liq were vacuum deposited to 300 Å in a ratio of 1:1. On the electron transfer layer, a cathode was formed by depositing lithium fluoride (LiF) to a thickness of 10 Å and aluminum to a thickness of 1,000 Å in consecutive order to complete the manufacture.

An organic light emitting device was manufactured by maintaining, in the above-mentioned processes, the deposition rates of the organic materials at 0.4 Å/sec to 0.9 Å/sec, the deposition rates of the lithium fluoride and the aluminum of the cathode at 0.3 Å/sec and 2 Å/sec, respectively, and the degree of vacuum during the deposition at $1 \times 10^{-7}$ torr to $5 \times 10^{-8}$ torr.

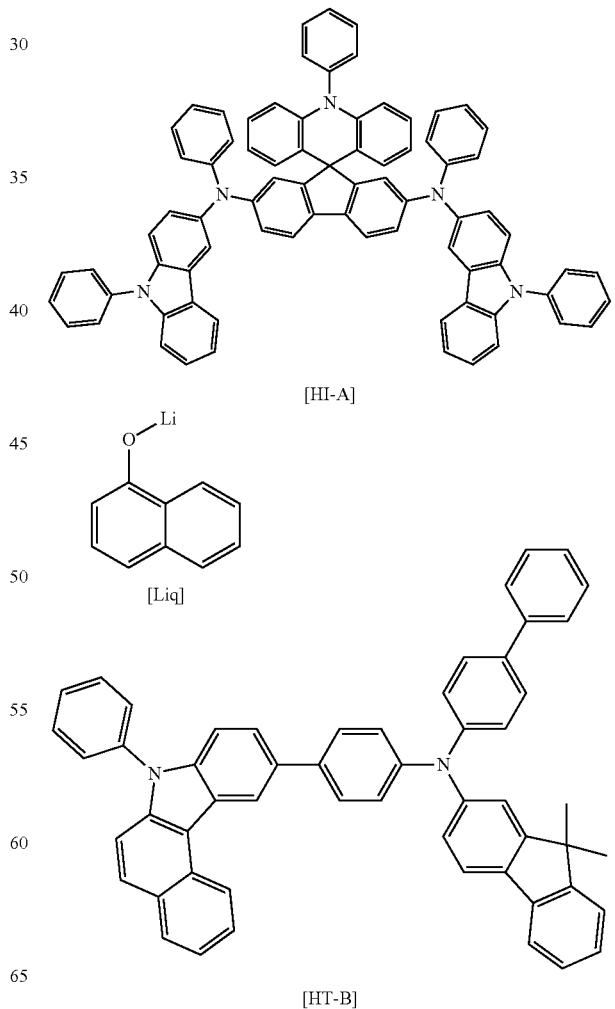

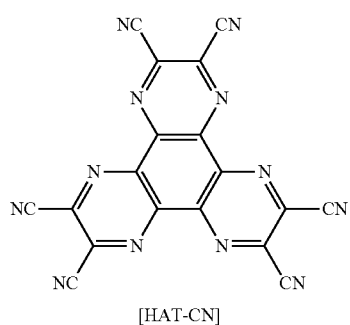
[HAT-CN]
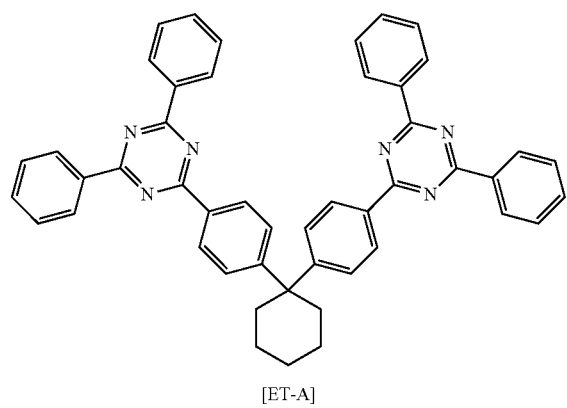
[ET-A]
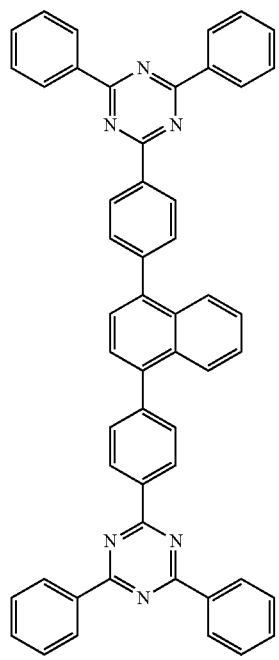
[ET-B]
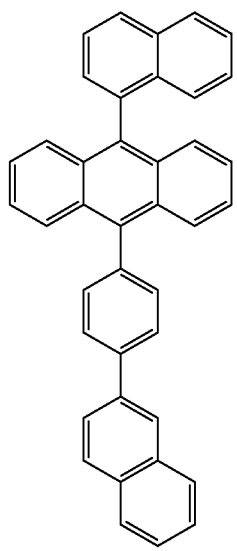
[BH-A]
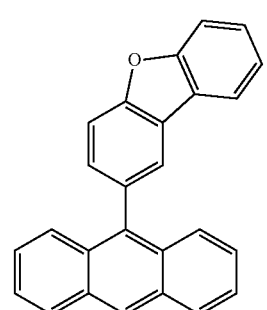
[BH-B]
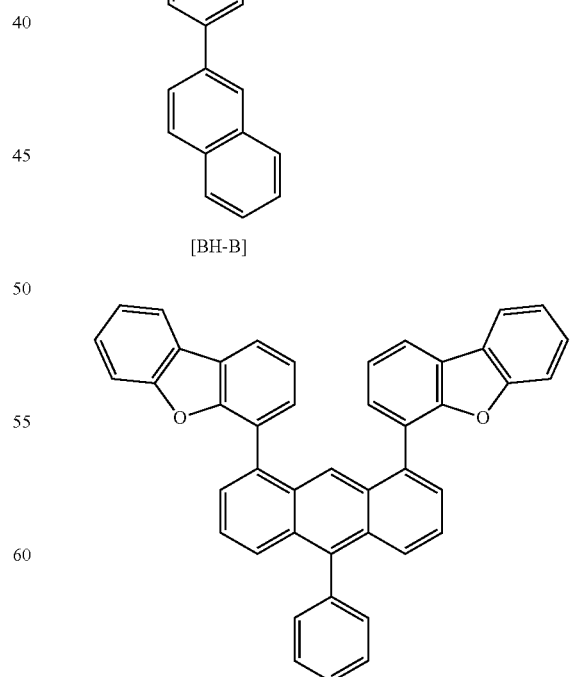
[BH-C]

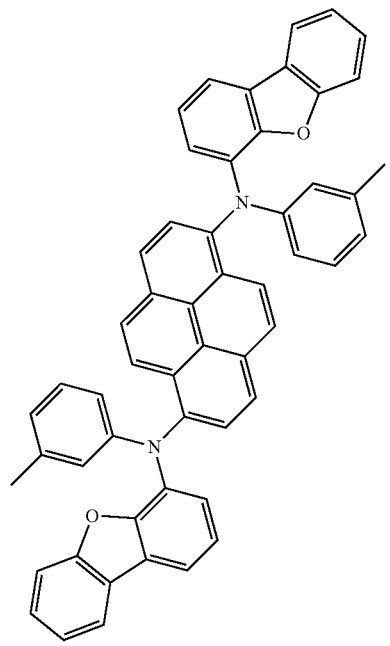

[BD-A]

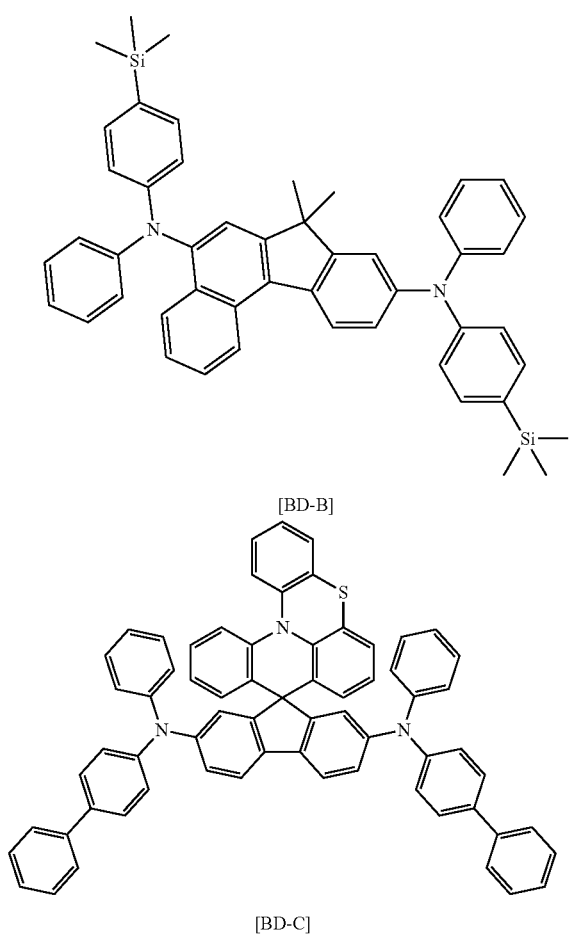

[BD-B]

[BD-C]

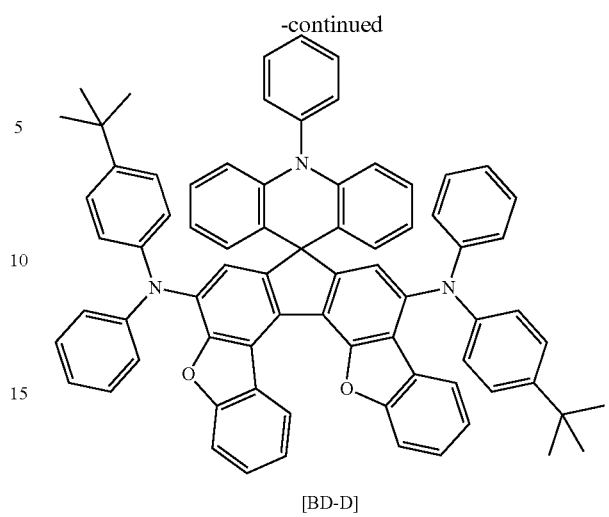

[BD-D]

Example 2

An organic light emitting device was manufactured in the same manner as in Example 1 except that Compound 7 was used instead of Compound 3 in Example 1.

Example 3

An organic light emitting device was manufactured in the same manner as in Example 1 except that Compound 8 was used instead of Compound 3 in Example 1.

Example 4

An organic light emitting device was manufactured in the same manner as in Example 1 except that Compound 19 was used instead of Compound 3 in Example 1.

Example 5

An organic light emitting device was manufactured in the same manner as in Example 1 except that Compound 24 was used instead of Compound 3 in Example 1.

Example 6

An organic light emitting device was manufactured in the same manner as in Example 1 except that Compound 51 was used instead of Compound 3 in Example 1.

Example 7

An organic light emitting device was manufactured in the same manner as in Example 1 except that Compound 65 was used instead of Compound 3 in Example 1.

Example 8

An organic light emitting device was manufactured in the same manner as in Example 1 except that Compound 71 was used instead of Compound 3 in Example 1.

Example 9

An organic light emitting device was manufactured in the same manner as in Example 1 except that Compound 77 was used instead of Compound 3 in Example 1.

Example 10

An organic light emitting device was manufactured in the same manner as in Example 1 except that Compound 86 was used instead of Compound 3 in Example 1.

Example 11

An organic light emitting device was manufactured in the same manner as in Example 1 except that Compound [BH-B] was used instead of Compound [BH-A] in Example 1.

Example 12

An organic light emitting device was manufactured in the same manner as in Example 1 except that Compound [BH-C] was used instead of Compound [BH-A] in Example 1.

Example 13

An organic light emitting device was manufactured in the same manner as in Example 1 except that Compound [BH-B] was used instead of Compound [BH-A] in Example 3.

Example 14

An organic light emitting device was manufactured in the same manner as in Example 1 except that Compound [BH-C] was used instead of Compound [BH-A] in Example 3.

Example 15

An organic light emitting device was manufactured in the same manner as in Example 1 except that Compound [BH-B] was used instead of Compound [BH-A] in Example 4.

Example 16

An organic light emitting device was manufactured in the same manner as in Example 1 except that Compound [BH-C] was used instead of Compound [BH-A] in Example 4.

Example 17

An organic light emitting device was manufactured in the same manner as in Example 1 except that Compound [BH-B] was used instead of Compound [BH-A] in Example 7.

Example 18

An organic light emitting device was manufactured in the same manner as in Example 1 except that Compound [BH-C] was used instead of Compound [BH-A] in Example 7.

Example 19

An organic light emitting device was manufactured in the same manner as in Example 1 except that Compound [BH-B] was used instead of Compound [BH-A] in Example 10.

Example 20

An organic light emitting device was manufactured in the same manner as in Example 1 except that Compound [BH-C] was used instead of Compound [BH-A] in Example 10.

Example 21

An organic light emitting device was manufactured in the same manner as in Example 1 except that the doping ratio of Compound 3 was 1.0% wt. in Example 1.

Example 22

An organic light emitting device was manufactured in the same manner as in Example 1 except that the doping ratio of Compound 3 was 5.0% wt. in Example 1.

Example 23

An organic light emitting device was manufactured in the same manner as in Example 1 except that the doping ratio of Compound 3 was 7.0% wt. in Example 1.

Example 24

An organic light emitting device was manufactured in the same manner as in Example 1 except that the doping ratio of Compound 8 was 1.0% wt. in Example 3.

Example 25

An organic light emitting device was manufactured in the same manner as in Example 1 except that the doping ratio of Compound 8 was 5.0% wt. in Example 3.

Example 26

An organic light emitting device was manufactured in the same manner as in Example 1 except that the doping ratio of Compound 8 was 7.0% wt. in Example 3.

Example 27

An organic light emitting device was manufactured in the same manner as in Example 1 except that the doping ratio of Compound 19 was 1.0% wt. in Example 4.

Example 28

An organic light emitting device was manufactured in the same manner as in Example 1 except that the doping ratio of Compound 19 was 5.0% wt. in Example 4.

Example 29

An organic light emitting device was manufactured in the same manner as in Example 1 except that the doping ratio of Compound 19 was 7.0% wt. in Example 4.

Comparative Example 1

An organic light emitting device was manufactured in the same manner as in Example 1 except that [BD-A] was used instead of Compound 3 in Example 1.

Comparative Example 2

An organic light emitting device was manufactured in the same manner as in Example 1 except that [BD-B] was used instead of Compound 3 in Example 1.

Comparative Example 3

An organic light emitting device was manufactured in the same manner as in Example 1 except that [BD-A] was used instead of Compound 3 in Example 11.

Comparative Example 4

An organic light emitting device was manufactured in the same manner as in Example 7 except that [BD-B] was used instead of Compound 3 in Example 11.

Comparative Example 5

An organic light emitting device was manufactured in the same manner as in Example 7 except that [BD-A] was used instead of Compound 3 in Example 12.

Comparative Example 6

An organic light emitting device was manufactured in the same manner as in Example 7 except that [BD-D] was used instead of Compound 3 in Example 12.

Comparative Example 7

An organic light emitting device was manufactured in the same manner as in Example 1 except that the doping ratio of Compound [BD-A] was 1.0% wt. in Comparative Example 1.

Comparative Example 8

An organic light emitting device was manufactured in the same manner as in Example 1 except that the doping ratio of Compound [BD-A] was 5.0% wt. in Comparative Example 1.

Comparative Example 9

An organic light emitting device was manufactured in the same manner as in Example 1 except that the doping ratio of Compound [BD-A] was 7.0% wt. in Comparative Example 1.

Comparative Example 10

An organic light emitting device was manufactured in the same manner as in Example 1 except that the doping ratio of Compound [BD-B] was 1.0% wt. in Comparative Example 2.

Comparative Example 11

An organic light emitting device was manufactured in the same manner as in Example 1 except that the doping ratio of Compound [BD-B] was 5.0% wt. in Comparative Example 2.

Comparative Example 12

An organic light emitting device was manufactured in the same manner as in Example 1 except that the doping ratio of Compound [BD-B] was 7.0% wt. in Comparative Example 2.

For the organic light emitting devices manufactured using the method described above, driving voltage and light emission efficiency were measured at current density of 10 mA/cm$^2$, and time ($T_{90}$) taken for the luminance becoming 90% from its initial luminance was measured at current density of 20 mA/cm$^2$. The results are shown in the following Table 1.

TABLE 1

| | | | @ 10 mA/cm$^2$ | | | @ 20 mA/cm$^2$ |
| --- | --- | --- | --- | --- | --- | --- |
| Example | Host | Dopant | Voltage (V) | Efficiency (cd/A) | CIE (x, y) | Lifetime ($T_{90}$, hr) |
| Example 1 | [BH-A] | Compound 3 | 3.9 | 8.9 | (0.133, 0.139) | 185 |
| Example 2 | [BH-A] | Compound 7 | 3.8 | 8.6 | (0.133, 0.140) | 170 |
| Example 3 | [BH-A] | Compound 8 | 3.9 | 8.5 | (0.134, 0.142) | 170 |
| Example 4 | [BH-A] | Compound 19 | 3.7 | 9.2 | (0.133, 0.142) | 150 |
| Example 5 | [BH-A] | Compound 24 | 4.2 | 8.7 | (0.133, 0.141) | 165 |
| Example 6 | [BH-A] | Compound 51 | 4.1 | 8.5 | (0.133, 0.139) | 155 |
| Example 7 | [BH-A] | Compound 65 | 3.7 | 9.0 | (0.133, 0.138) | 150 |
| Example 8 | [BH-A] | Compound 71 | 3.8 | 9.1 | (0.134, 0.142) | 180 |
| Example 9 | [BH-A] | Compound 77 | 4.2 | 8.4 | (0.133, 0.137) | 185 |
| Example 10 | [BH-A] | Compound 86 | 3.9 | 8.9 | (0.133, 0.139) | 170 |
| Example 11 | [BH-B] | Compound 3 | 3.7 | 9.1 | (0.133, 0.139) | 160 |
| Example 12 | [BH-C] | Compound 3 | 4.1 | 7.6 | (0.133, 0.138) | 190 |
| Example 13 | [BH-B] | Compound 8 | 3.6 | 9.2 | (0.133, 0.139) | 150 |
| Example 14 | [BH-C] | Compound 8 | 4.2 | 7.5 | (0.133, 0.138) | 200 |
| Example 15 | [BH-B] | Compound 19 | 3.8 | 8.9 | (0.133, 0.139) | 170 |
| Example 16 | [BH-C] | Compound 19 | 4.0 | 7.6 | (0.133, 0.138) | 185 |
| Example 17 | [BH-B] | Compound 65 | 3.6 | 9.2 | (0.133, 0.139) | 140 |
| Example 18 | [BH-C] | Compound 65 | 4.1 | 7.4 | (0.133, 0.139) | 190 |
| Example 19 | [BH-B] | Compound 86 | 3.8 | 8.9 | (0.133, 0.139) | 150 |
| Example 20 | [BH-C] | Compound 86 | 4.0 | 7.3 | (0.133, 0.138) | 160 |

TABLE 1-continued

| Example | Host | Dopant | @ 10 mA/cm² | | | @ 20 mA/cm² |
|---|---|---|---|---|---|---|
| | | | Voltage (V) | Efficiency (cd/A) | CIE (x, y) | Lifetime (T₉₀, hr) |
| Comparative Example 1 | [BH-A] | [BD-A] | 3.9 | 7.1 | (0.133, 0.138) | 80 |
| Comparative Example 2 | [BH-A] | [BD-B] | 3.6 | 6.5 | (0.133, 0.137) | 75 |
| Comparative Example 3 | [BH-B] | [BD-A] | 3.9 | 5.12 | (0.132, 0.138) | 65 |
| Comparative Example 4 | [BH-B] | [BD-B] | 3.7 | 5.03 | (0.132, 0.137) | 60 |
| Comparative Example 5 | [BH-C] | [BD-A] | 4.0 | 8.0 | (0.133, 0.135) | 130 |
| Comparative Example 6 | [BH-C] | [BD-D] | 3.9 | 8.2 | (0.133, 0135) | 120 |
| Comparative Example 7 | [BH-A] | [BD-A] | 4.1 | 4.98 | (0.144, 0.045) | 80 |
| Comparative Example 8 | [BH-A] | [BD-A] | 4.2 | 3.66 | (0.141, 0.044) | 60 |
| Comparative Example 9 | [BH-A] | [BD-A] | 4.2 | 5.12 | (0.142, 0.046) | 90 |

From the results of Table 1, the heterocyclic compound represented by Chemical Formula 1 according to the present disclosure may be used as a fluorescent dopant in an organic light emitting device. The organic light emitting device using the same exhibits high efficiency and long lifetime properties.

Compounds used as a fluorescent dopant in general organic light emitting devices are capable of increasing the light efficiency using a method of doping between host molecules and dopant molecules, and efficiency decreases again when the doping concentration reaches a certain limit. This is caused by generated excitons being in a lull due to closer intermolecular distances between dopant molecules, and this is referred as a potent concentration.

The fluorescent dopant compounds represented by Chemical Formula 1 of the present disclosure are spiro-arylamine-based compounds comprising acridine derivatives, and have a shape closer to a spherical shape in three dimensions with the arylamine and the acridine—comprising spiro part staggering to each other in a cross-shaped form. As a result, an organic light emitting device comprising the compound is considered to exhibit excellent performance by preventing fluorescence decay due to favorable film properties obtained when forming a layer by vacuum deposition with host molecules. Unlike dopants other than those seen in the comparative example table, it was seen that maximum efficiency was obtained in a higher doping concentration.

For the organic light emitting devices manufactured in Examples 21 to 29 and Comparative Examples 7 to 12, driving voltage and light emission efficiency were measured at current density of 10 mA/cm², and time (T₉₀) taken for the luminance becoming 90% from its initial luminance was measured at current density of 20 mA/cm². The results are shown in the following Table 2.

TABLE 2

| Example | Doping Concentration (% wt.) | Dopant | @ 10 mA/cm² | | | @ 20 mA/cm² |
|---|---|---|---|---|---|---|
| | | | Voltage (V) | Efficiency (cd/A) | CIE (x, y) | Lifetime (T₉₀, hr) |
| Example 21 | 1.0 | Compound 3 | 3.9 | 6.8 | (0.133, 0.139) | 200 |
| Example 22 | 5.0 | Compound 3 | 3.9 | 9.1 | (0.133, 0.139) | 190 |
| Example 23 | 7.0 | Compound 3 | 4.0 | 9.1 | (0.134, 0.142) | 170 |
| Example 24 | 1.0 | Compound 8 | 4.1 | 6.0 | (0.134, 0.142) | 190 |
| Example 25 | 5.0 | Compound 8 | 4.2 | 8.6 | (0.134, 0.142) | 180 |
| Example 26 | 7.0 | Compound 8 | 4.2 | 8.7 | (0.134, 0.141) | 130 |
| Example 27 | 1.0 | Compound 19 | 3.5 | 6.1 | (0.133, 0.142) | 170 |
| Example 28 | 5.0 | Compound 19 | 3.7 | 9.4 | (0.133, 0.142) | 160 |
| Example 29 | 7.0 | Compound 19 | 3.8 | 9.4 | (0.133, 0.141) | 120 |
| Comparative Example 7 | 1.0 | [BD-A] | 3.5 | 5.2 | (0.133, 0.138) | 100 |
| Comparative Example 8 | 5.0 | [BD-A] | 3.9 | 6.7 | (0.133, 0.138) | 80 |
| Comparative Example 9 | 7.0 | [BD-A] | 3.9 | 6.4 | (0.133, 0.137) | 60 |
| Comparative Example 10 | 1.0 | [BD-A] | 3.4 | 5.6 | (0.133, 0.137) | 85 |
| Comparative Example 11 | 5.0 | [BD-A] | 3.6 | 6.5 | (0.133, 0.137) | 75 |
| Comparative Example 12 | 7.0 | [BD-A] | 4.2 | 5.9 | (0.132, 0.137) | 55 |

From Table 2, the acridine part in the upper part of the compound of the present disclosure exhibited a result of longer lifetime as the molecular degree of freedom increased, and it was proved that the compound of the present disclosure was suited as a long lifetime blue fluorescent dopant.

In addition, a maximum light emission wavelength of a fluorescent spectrum of a blue fluorescent dopant is preferably from 430 nm to 470 nm, however, as in Chemical Formula BD-C, conjugation of the compound of Chemical Formula 1 of the present disclosure in which A1 and A2 are benzene rings may not be formed to be long compared to Chemical Formula 1 of the present disclosure, and therefore, the wavelength is not able to reach the maximum light emission wavelength.

FIG. 3 shows a fluorescent light emission spectrum of Compound 3 and FIG. 4 shows a fluorescent light emission spectrum of BD-C. From FIGS. 3 and 4, it was identified that Compound 3 was suited as a fluorescent dopant material reproducing blue color with the maximum light emission wavelength of 450 nm, however, the compound of BD-C was not suited as a fluorescent dopant material with the maximum light emission wavelength being just 410 nm. In FIGS. 3 and 4, the horizontal axis represents a wavelength, and the vertical axis represents intensity.

RB28 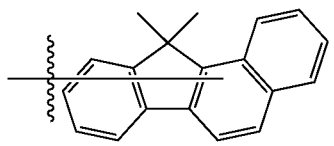
RB29 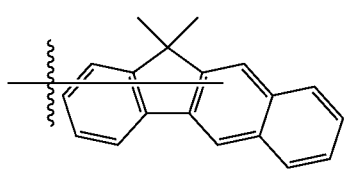
RB30 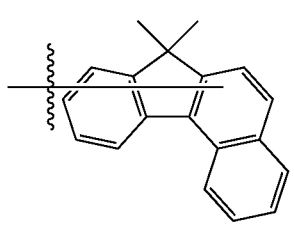
RB31 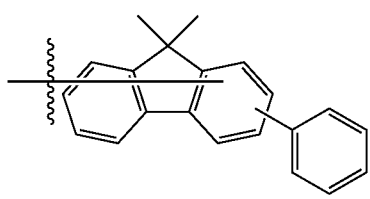
RB32 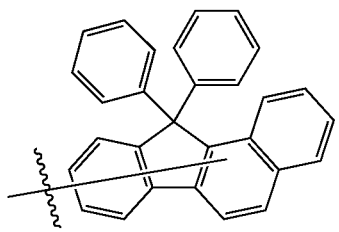
RB33 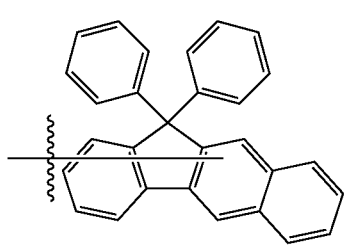
RB34 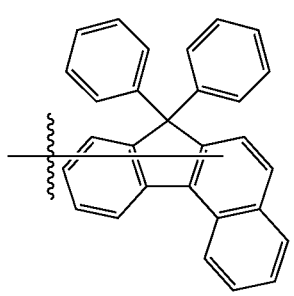
RB35 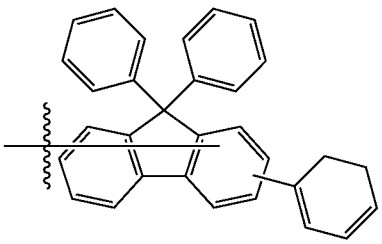
RB36 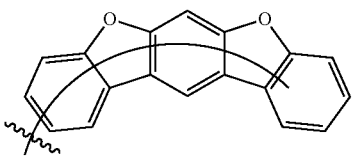
RB37 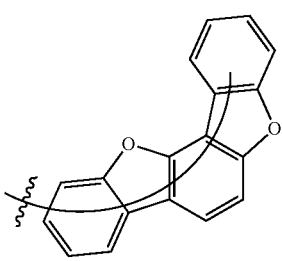
RB38 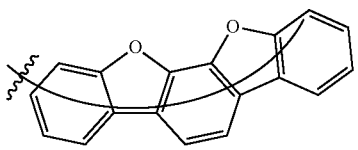
RB39 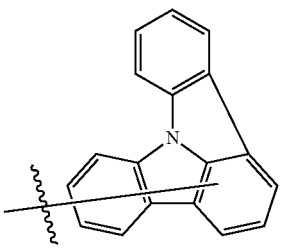
RB40 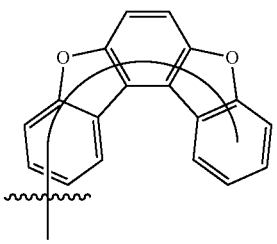
RB41 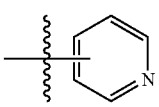
RB42 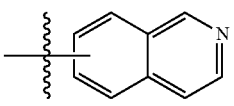

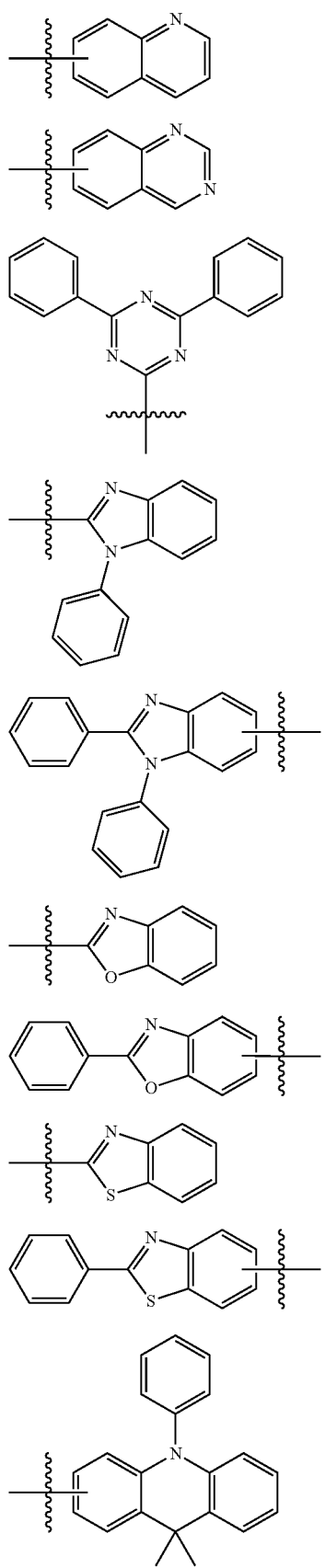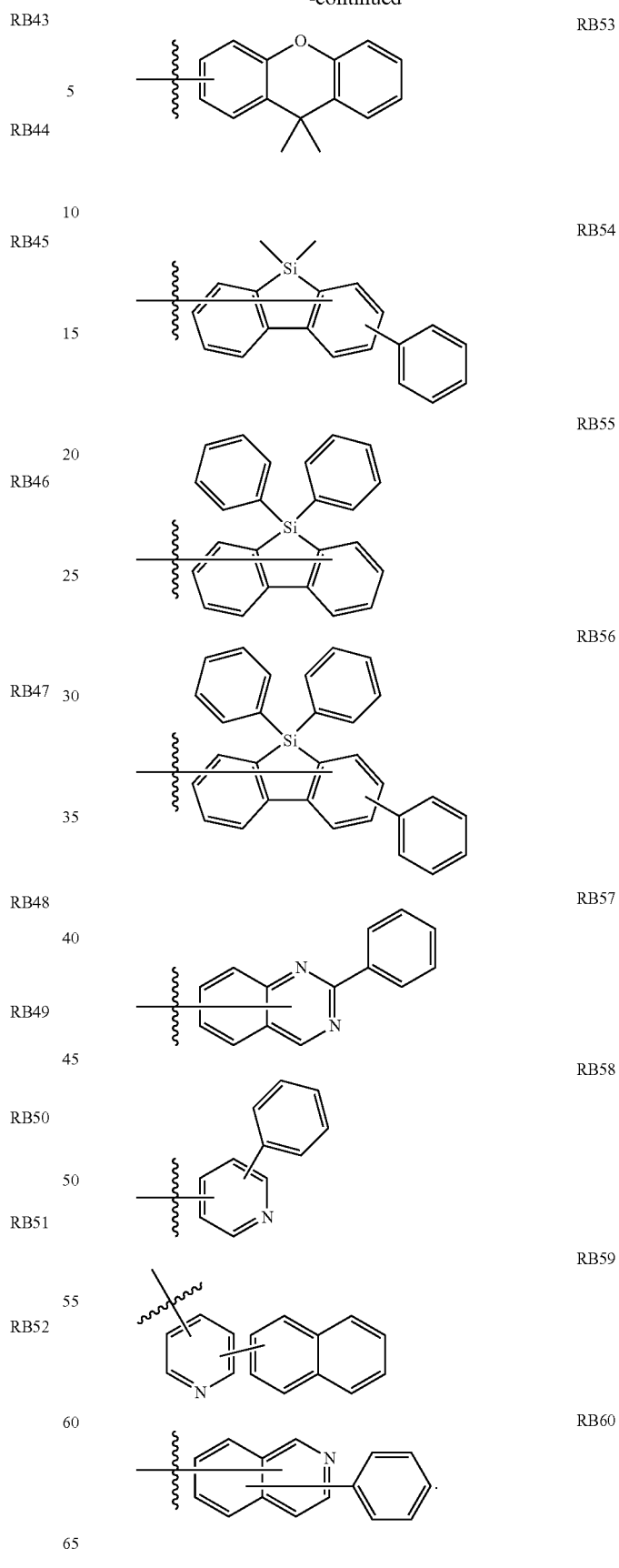

The invention claimed is:

1. A heterocyclic compound represented by the following Chemical Formula 1:

[Chemical Formula 1]

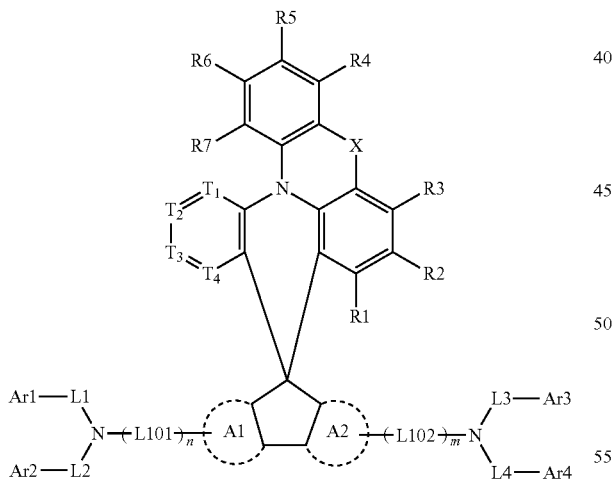

in Chemical Formula 1,

Ar1 to Ar4 are independently selected from hydrogen; deuterium; a halogen group; a nitrile group; a nitro group; a silyl group; a boron group; a substituted or unsubstituted amine group; a substituted or unsubstituted alkyl group; a substituted or unsubstituted cycloalkyl group; a substituted or unsubstituted aryl group; or a substituted or unsubstituted heteroaryl group, L1 to L4, L101 and L102 are independently selected from a direct bond; a substituted or unsubstituted arylene group; or a substituted or unsubstituted heteroarylene group, A1 and A2 are independently selected from a substituted or unsubstituted aromatic hydrocarbon ring; or a substituted or unsubstituted heteroring, provided that when one of A1 and A2 is benzene, the other one of A1 and A2 is a substituted or unsubstituted polycyclic aromatic hydrocarbon ring; or a substituted or unsubstituted heteroring, X is NR, CR'R", O or S, $T_1$ to $T_4$ are independently selected from CRa or N;

R, R', R", R1 to R7 and Ra are independently selected from hydrogen; deuterium; a halogen group; a nitrile group; a nitro group; a silyl group; a boron group; a substituted or unsubstituted amine group; a substituted or unsubstituted alkyl group; a substituted or unsubstituted cycloalkyl group; a substituted or unsubstituted aryl group; or a substituted or unsubstituted heteroaryl group, m and n are each 1 or 2, and provided that m or n is 2, substituents in the parentheses are the same as or different from each other.

2. The heterocyclic compound of claim 1, wherein A1 and A2 are independently selected from a substituted or unsubstituted aromatic hydrocarbon ring having 6 to 30 carbon atoms; or a substituted or unsubstituted heteroring having 2 to 30 carbon atoms, provided that when one of A1 and A2 is benzene, the other one of A1 and A2 is a substituted or unsubstituted polycyclic aromatic hydrocarbon ring; or a substituted or unsubstituted heteroring.

3. The heterocyclic compound of claim 1, wherein A1 and A2 are independently selected from one of the following structures:

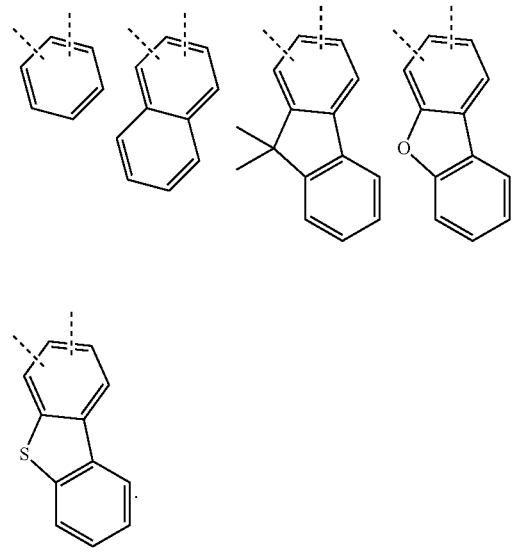

4. The heterocyclic compound of claim 1, wherein Chemical Formula 1 is represented by any one of the following Chemical Formulae 2 to 5:

[Chemical Formula 2]

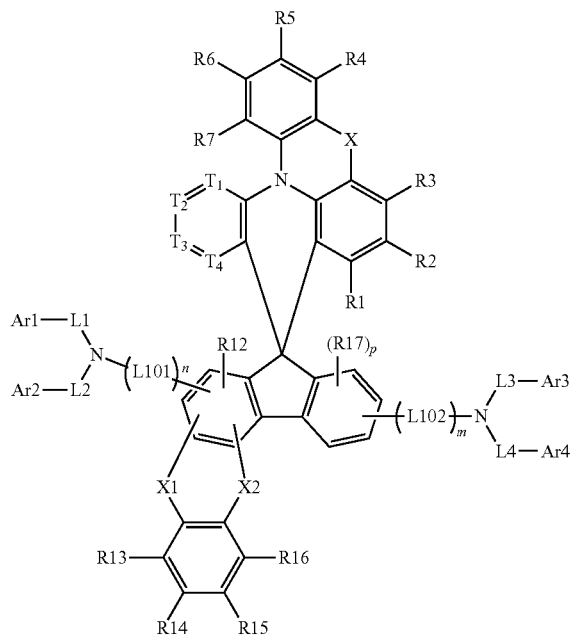

[Chemical Formula 3]

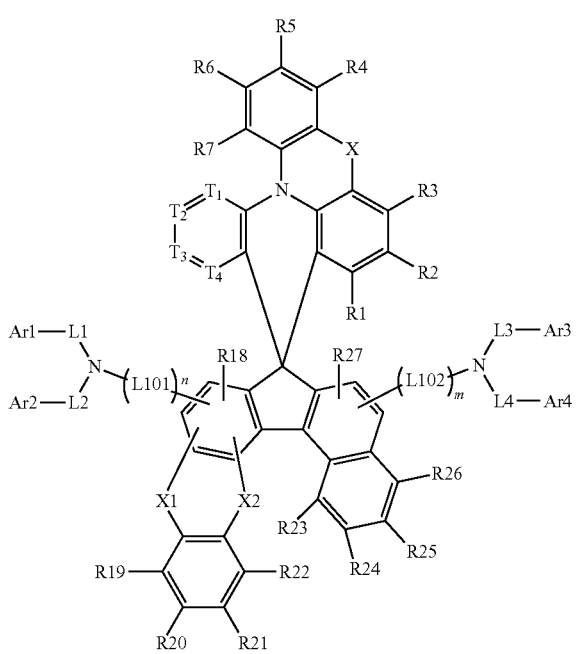

[Chemical Formula 4]

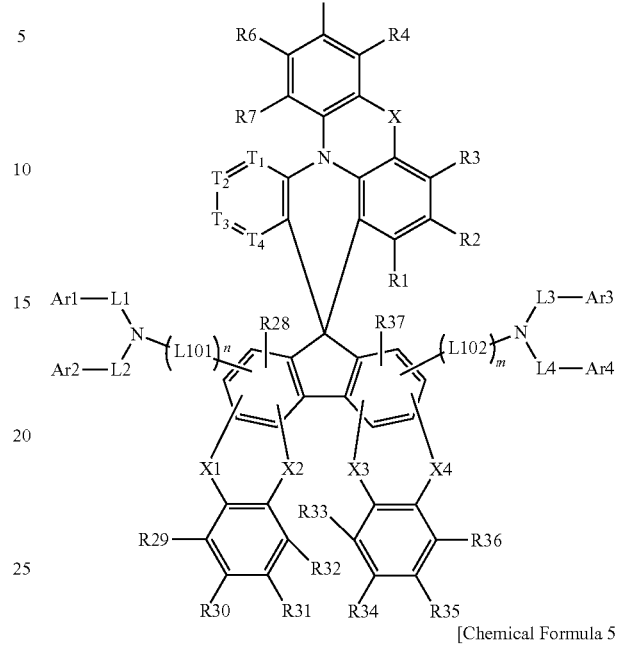

[Chemical Formula 5]

in Chemical Formulae 2 to 5,

L101, L102, L1 to L4, Ar1 to Ar4, R1 to R7, X, T1 to T4, m and n have the same definitions as in Chemical Formula 1, one of X1 and X2 is a direct bond, and the other one of X1 and X2 is selected from O, S or CY1Y2, one of X3 and X4 is a direct bond, and the other one of X3 and X4 is selected from O, S or CY3Y4, Y1 to Y4 and R12 to R43 are independently selected from hydrogen deuterium; a halogen group; a nitrile group; a nitro group; a silyl group; a boron group; a substituted or unsubstituted amine group; a substituted or unsubstituted alkyl group; a substituted or unsubstituted cycloalkyl group; a substituted or unsubstituted aryl group; or a substituted or unsubstituted heteroaryl group, p and q are each an integer of 0 to 3, and when p and q are each 2 or greater, substituents in the parentheses are the same as or different from each other.
5. The heterocyclic compound of claim 1, wherein L101, L102, and L1 to L4 are selected from among a direct bond; or the following structures:
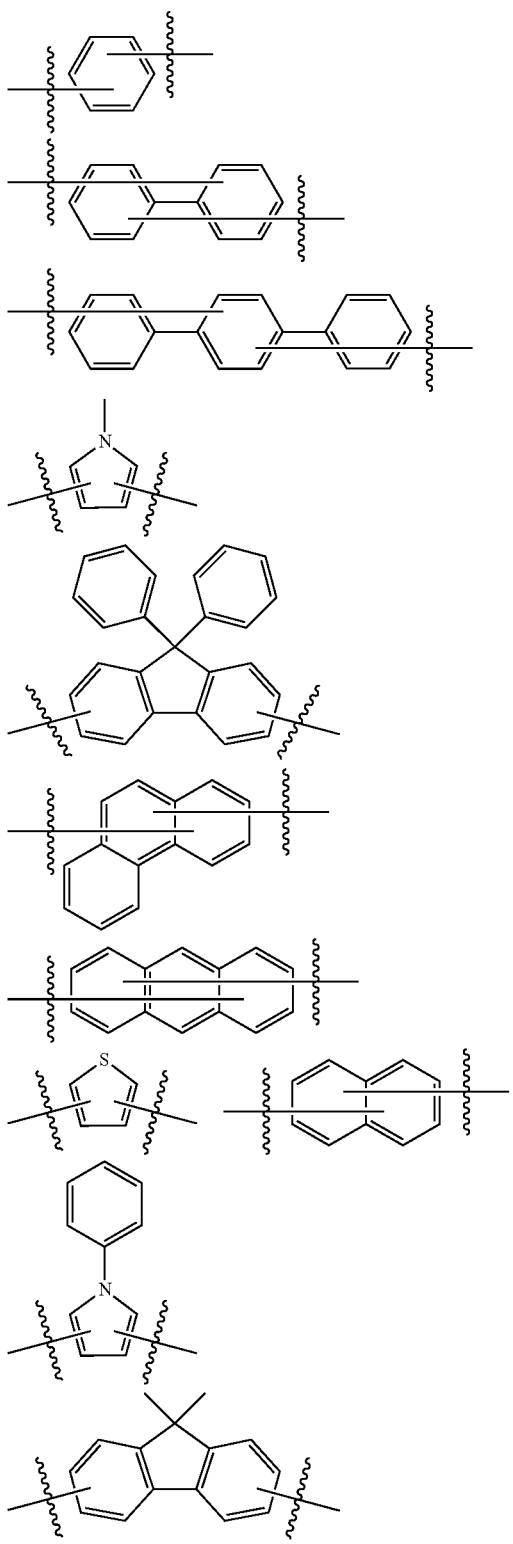
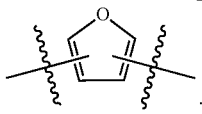
6. The heterocyclic compound of claim 1, wherein Ar1 to Ar4 are any one selected from among the following structures:
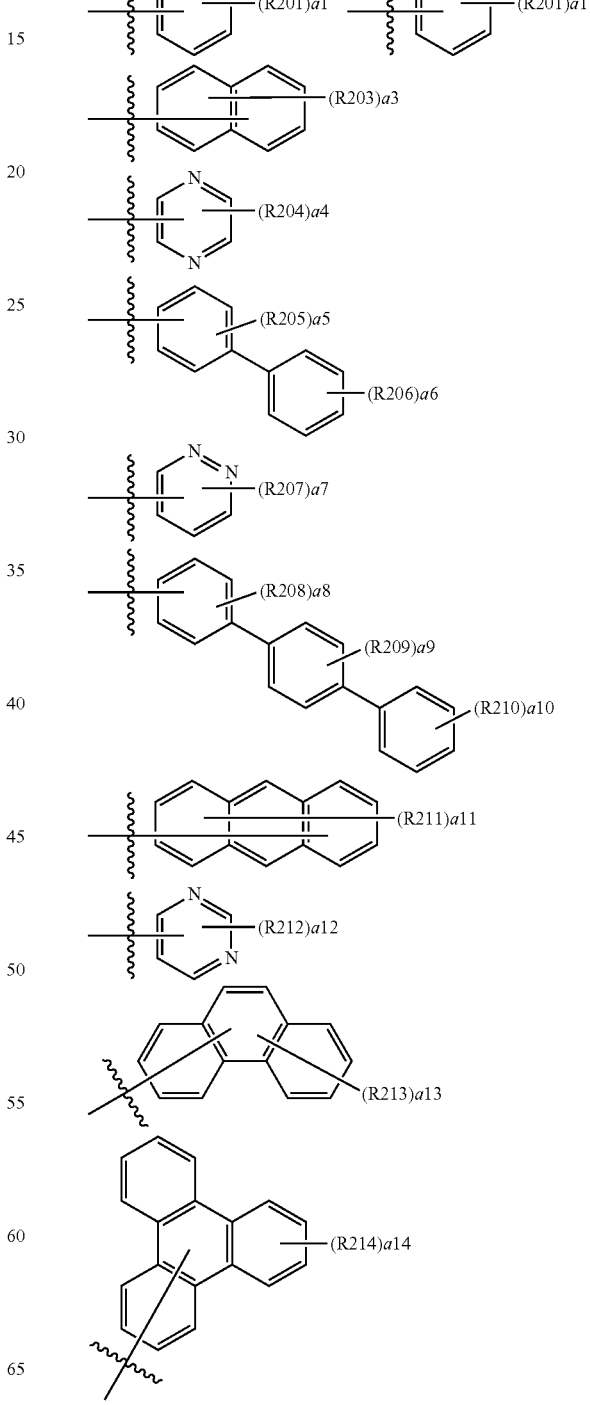

-continued
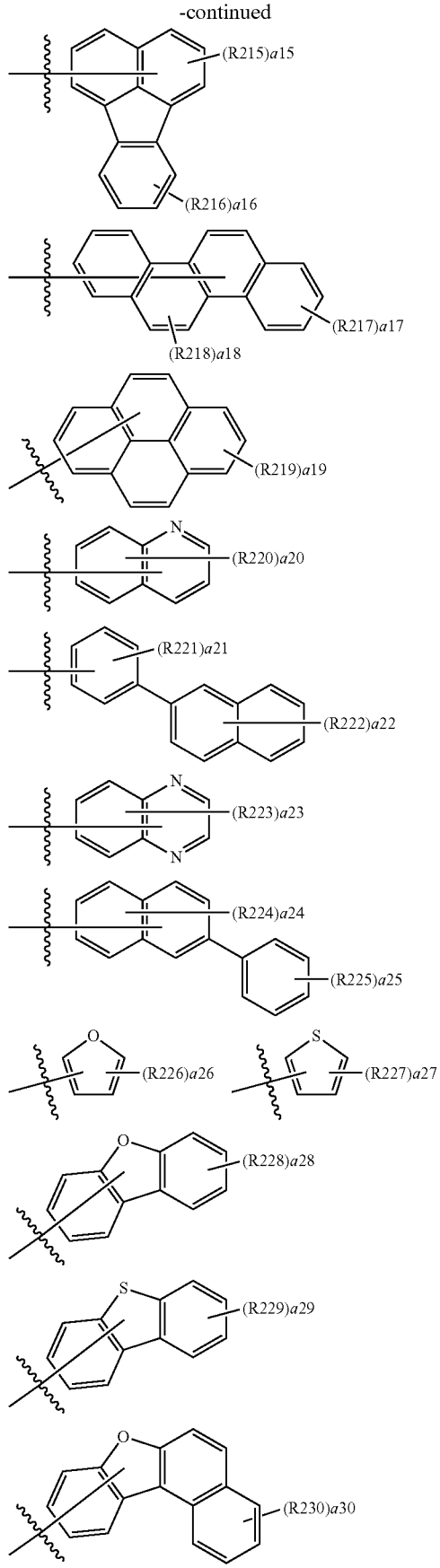
-continued
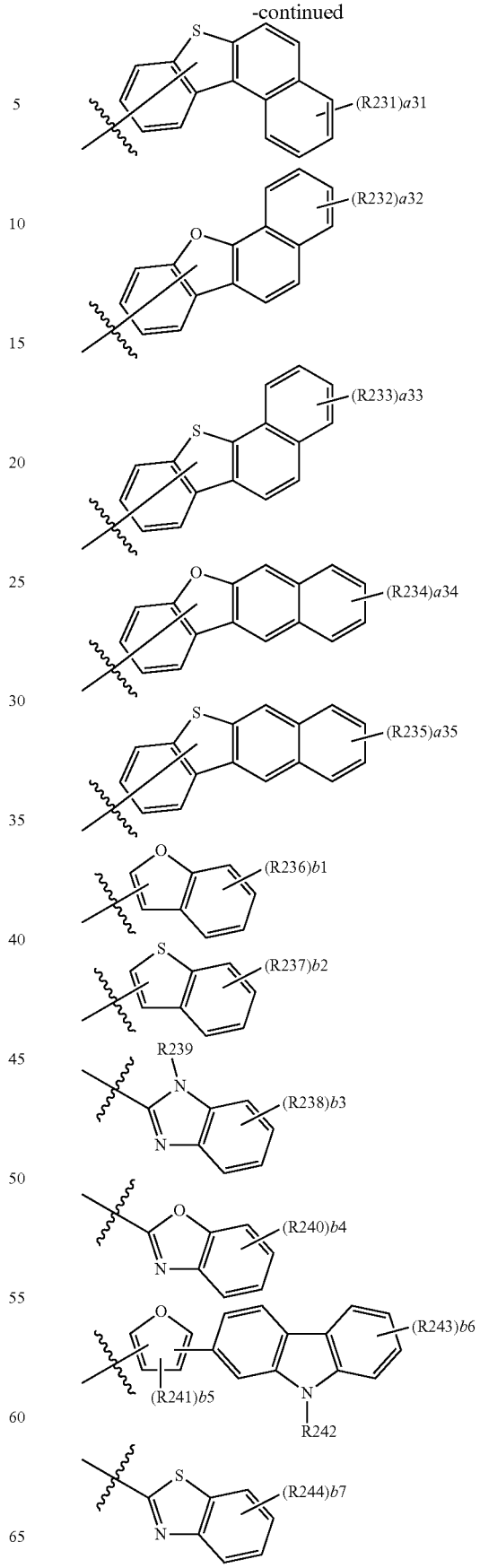

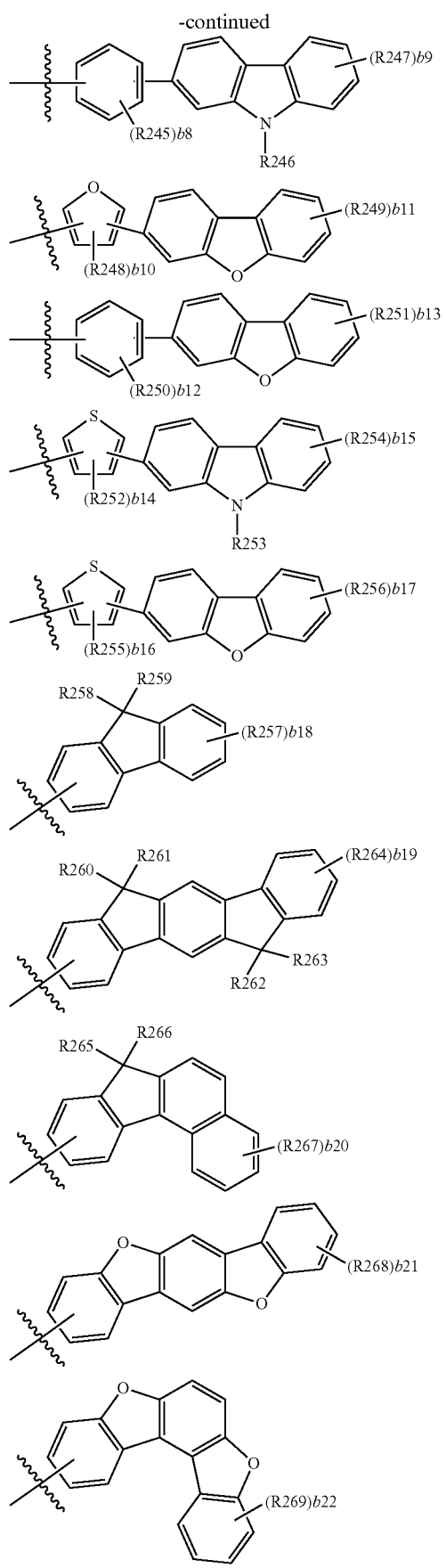
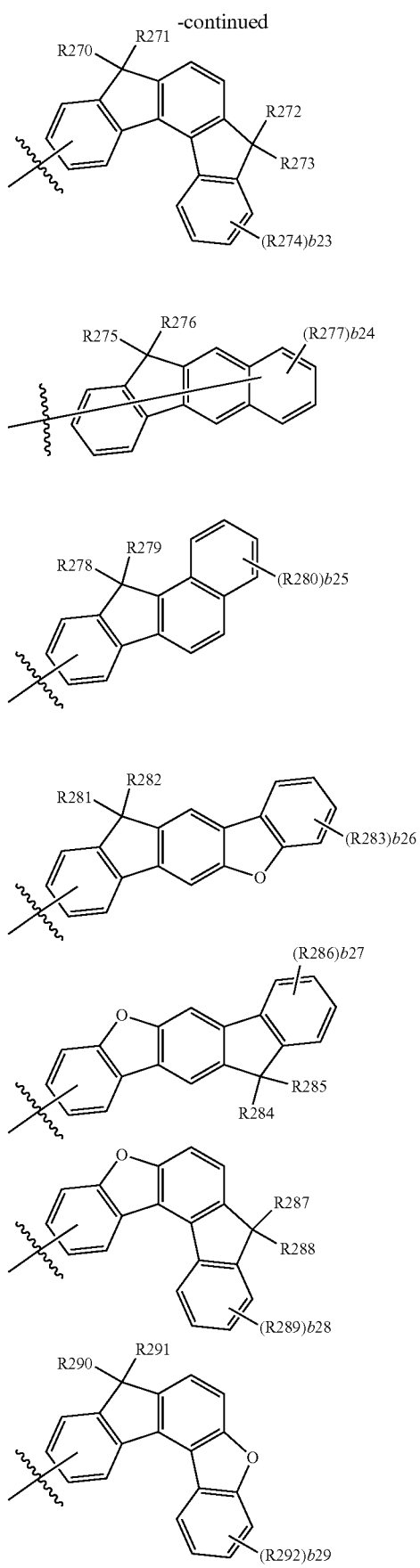

-continued

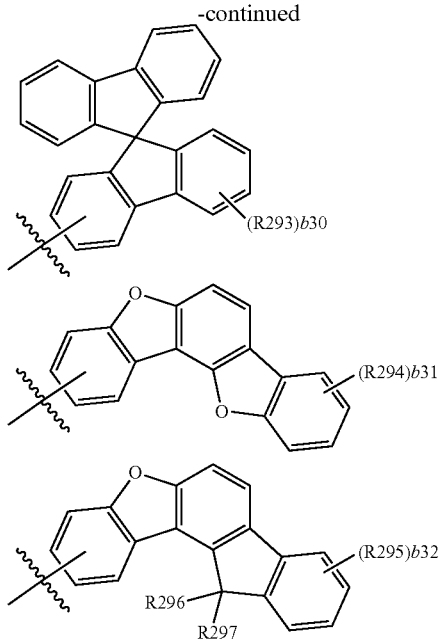

in the structures,
R201 to R297 are the same as or different from each other, and each independently hydrogen; deuterium; a halogen group; a nitrile group; a nitro group; a silyl group; a boron group; a substituted or unsubstituted amine group; a substituted or unsubstituted alkyl group; a substituted or unsubstituted cycloalkyl group; a substituted or unsubstituted aryl group; or a substituted or unsubstituted heteroaryl group, a1, a6, a10, a23 and a25 are each an integer of 0 to 5,
a2, a5, a8, a9, a14, a16, a17, a21, a28 to a35, b1 to b4, b6 to b9, b11 to b13, b15 and b17 to b32 are each an integer of 0 to 4,
a3 and a22 are each an integer of 0 to 7,
a4, a7, a12, a15, a19 a26 and a27 are each an integer of 0 to 3,
a11 is an integer of 0 to 9,
a13, a20 and a24 are each an integer of 0 to 6,
a18, b5, b10, b14 and b16 are each an integer of 0 to 2,
provided that when a18, b5, b10, b14 and b16 are 2, substituents in the parentheses are different from each other, and
provided that when a1, a6, a10, a23, a25, a2, a5, a8, a9, a14, a16, a17, a21, a28 to a35, b1 to b4, b6 to b9, b11 to b13, b15, b17 to b32, a3, a22, a4, a7, a12, a15, a19, a26, a27, a11, a13, a20 and a24 are each 2 or greater, substituents in the parentheses are different from each other.

7. The heterocyclic compound of claim 1, wherein Chemical Formula 1 is any one selected from among the following compounds:

Compound 1

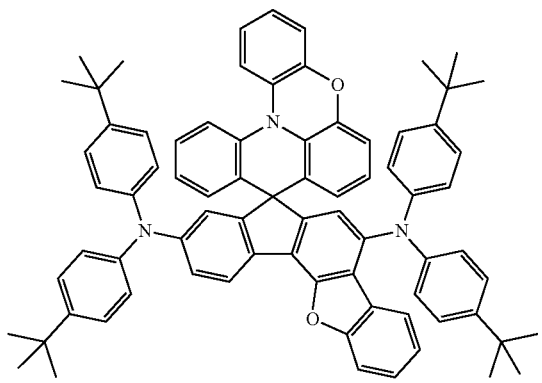

Compound 2

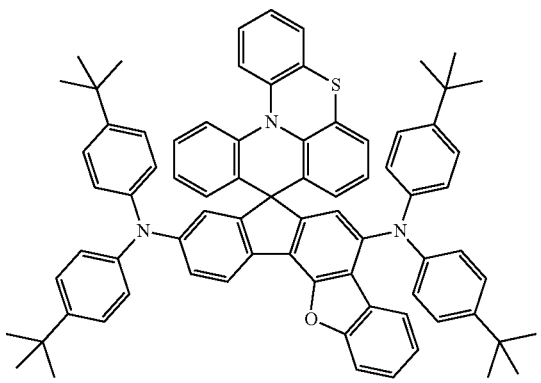

Compound 3

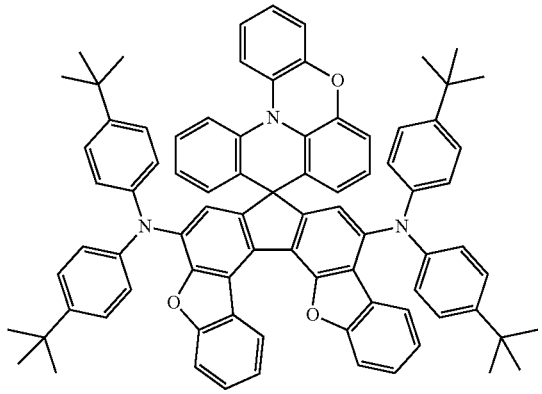

Compound 4

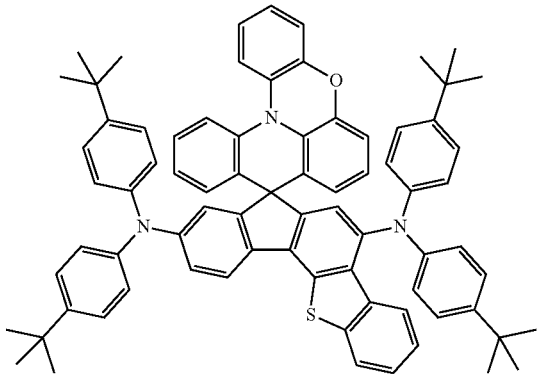

Compound 5
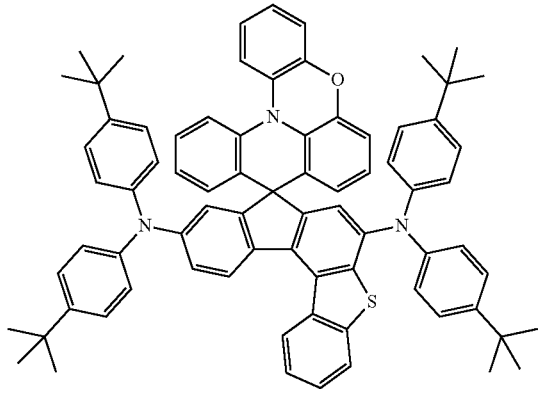
Compound 6
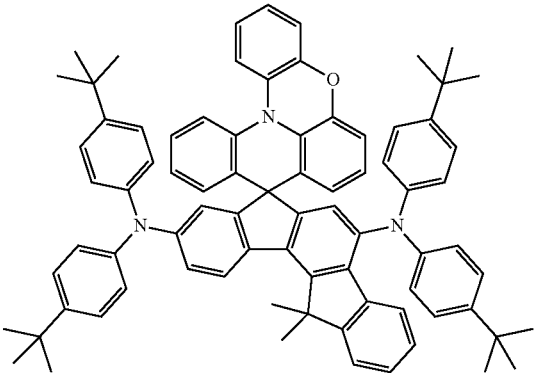
Compound 7
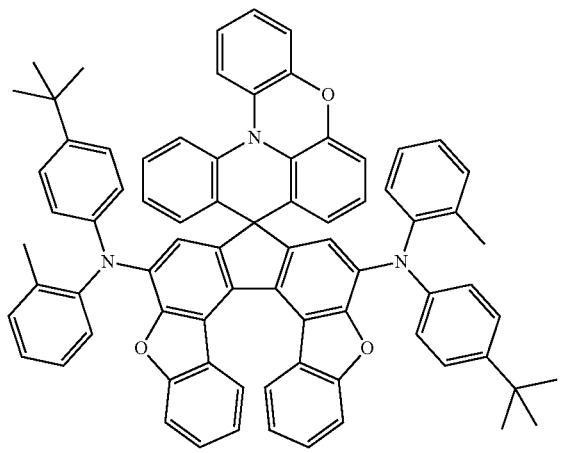
Compound 8
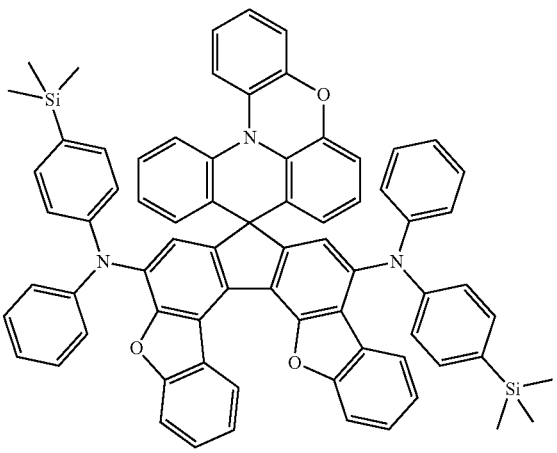
Compound 9
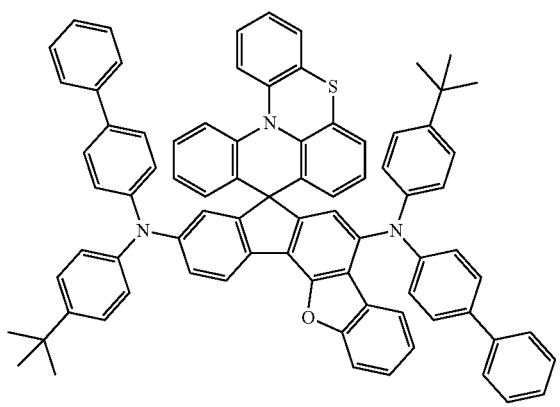
Compound 10
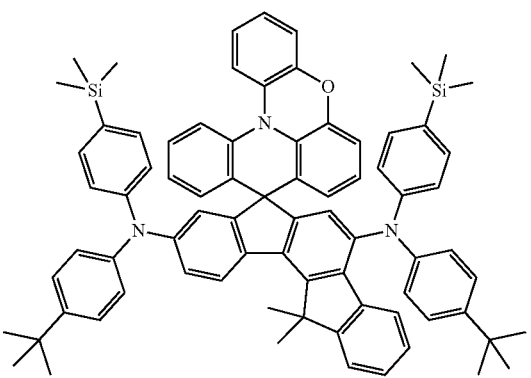

-continued
Compound 11
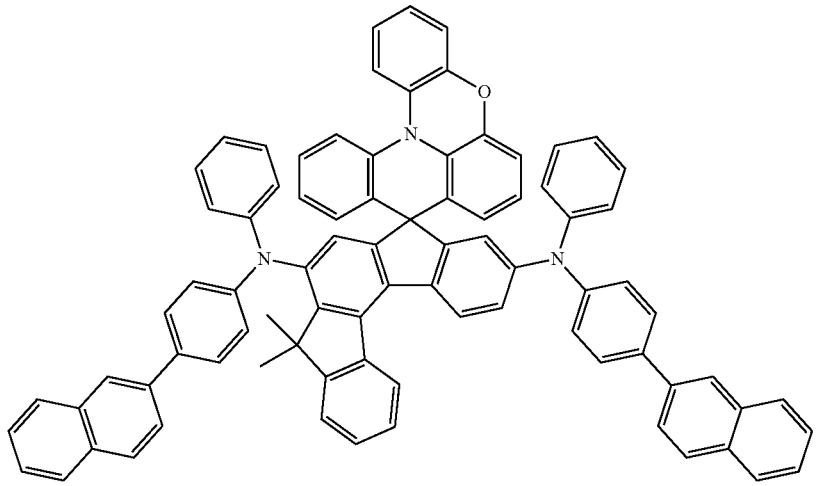
Compound 12
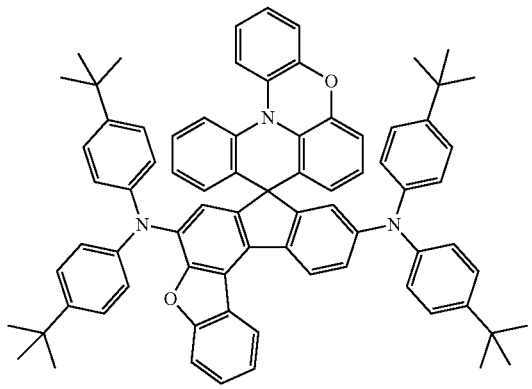
Compound 13
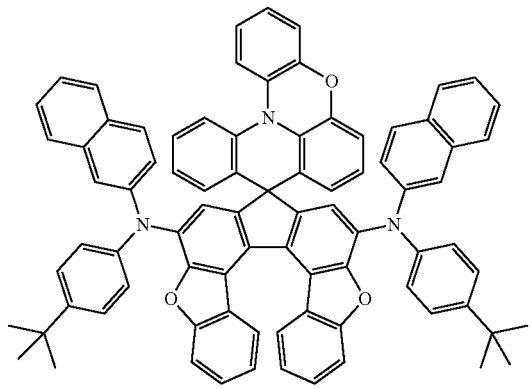
Compound 14
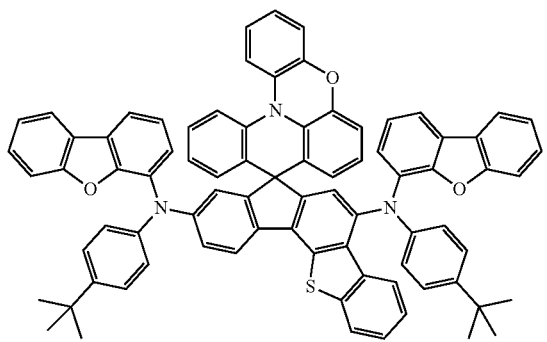
Compound 15
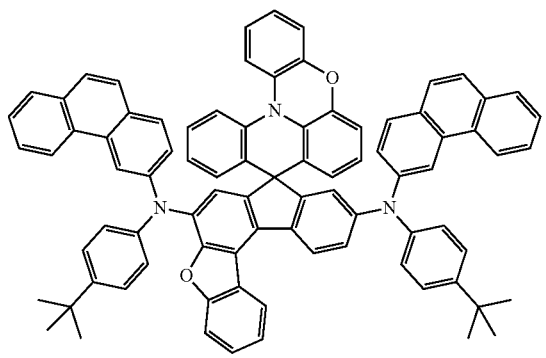

-continued
Compound 16
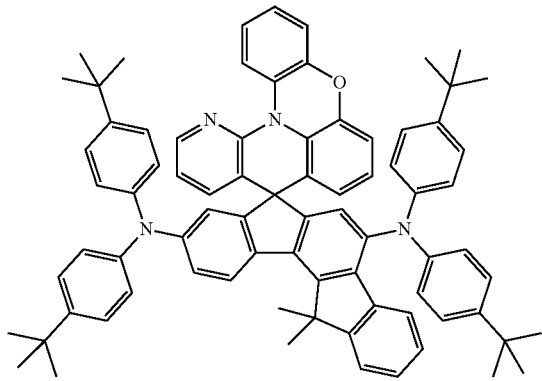
Compound 17
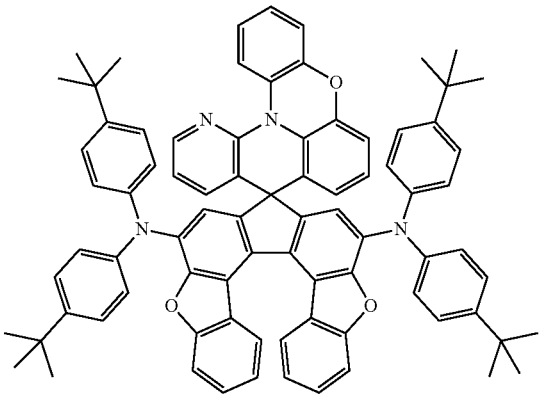
Compound 18
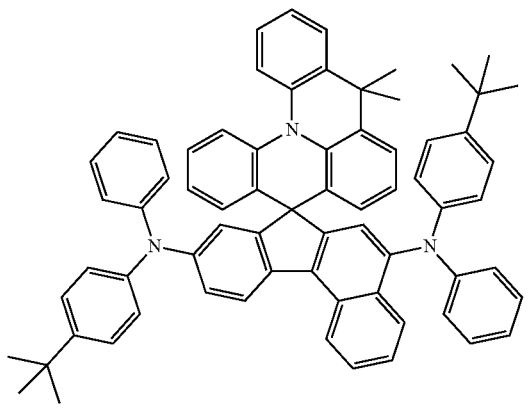
Compound 19
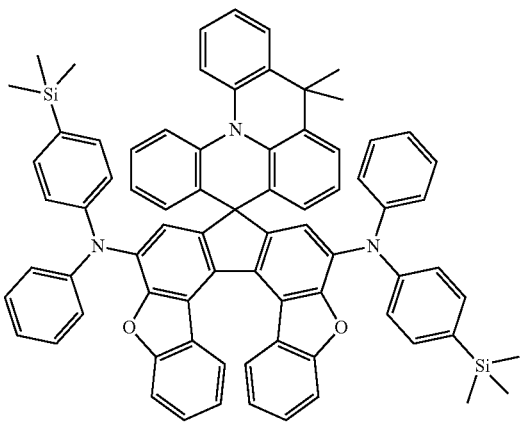
Compound 20
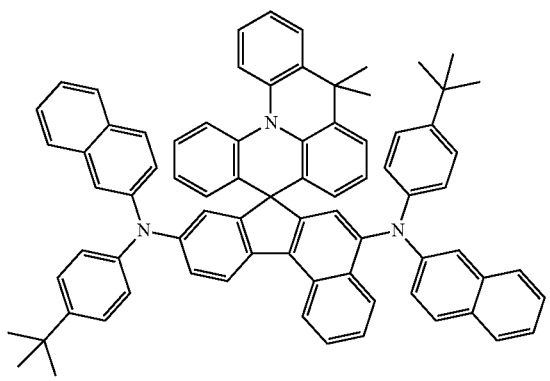
Compound 21
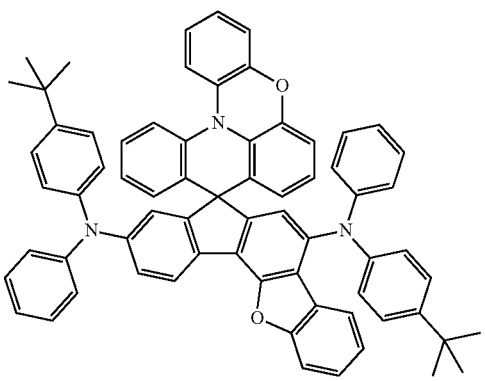

-continued
Compound 22
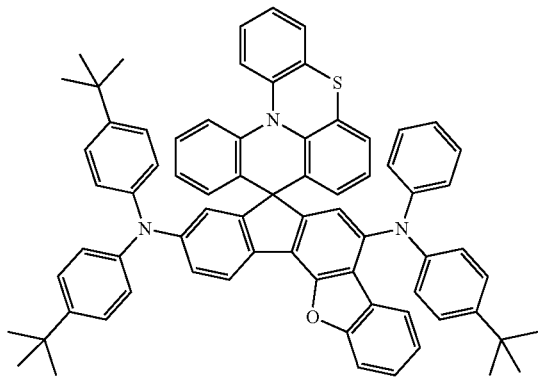
Compound 23
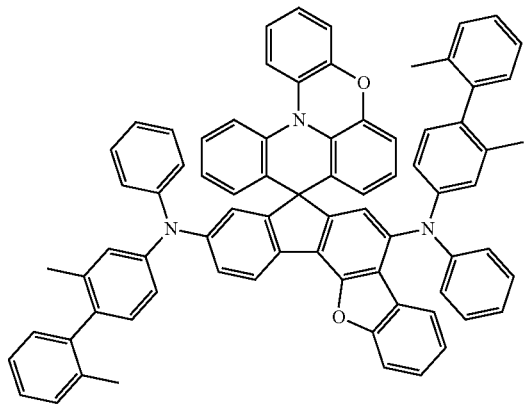
Compound 24
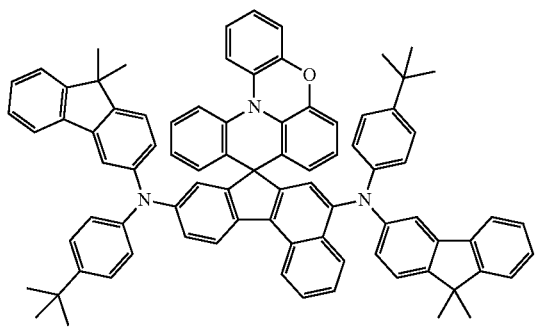
Compound 25
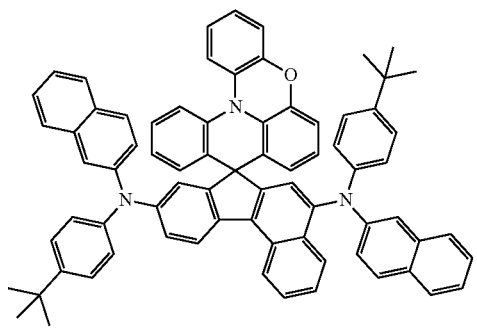
Compound 26
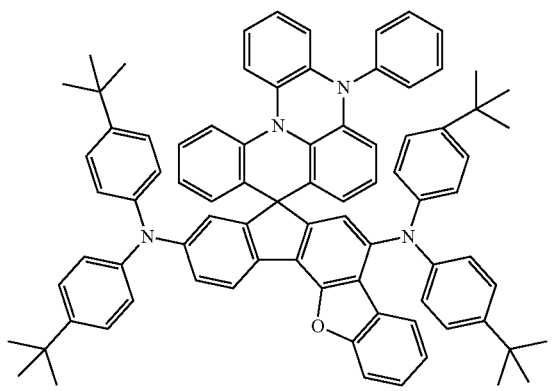
Compound 27
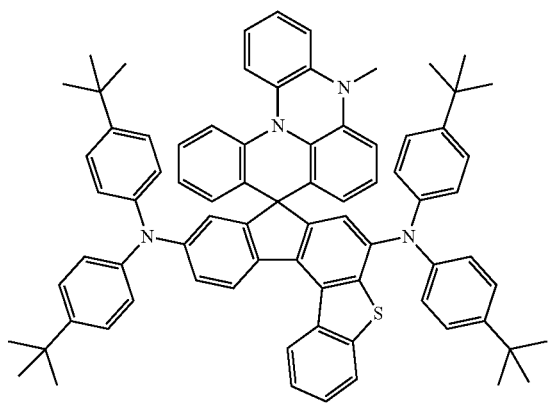
Compound 28
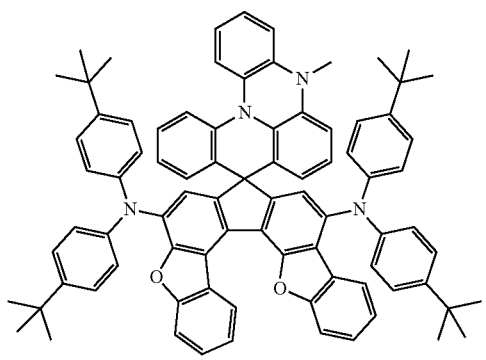
Compound 29
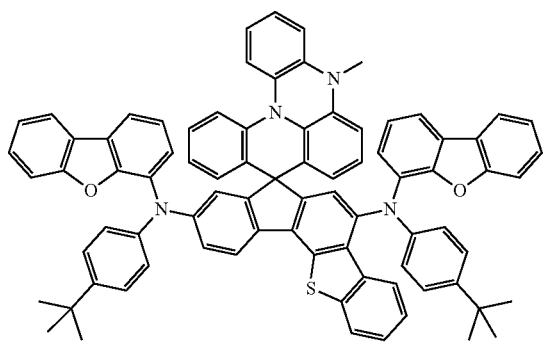

-continued
Compound 30
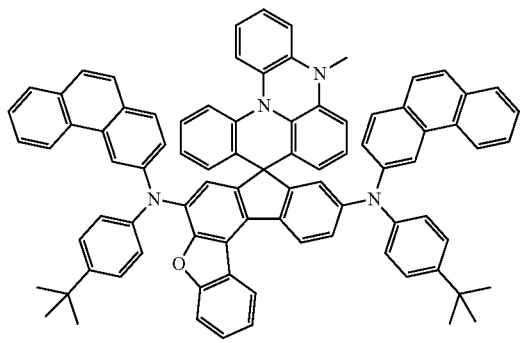
Compound 31
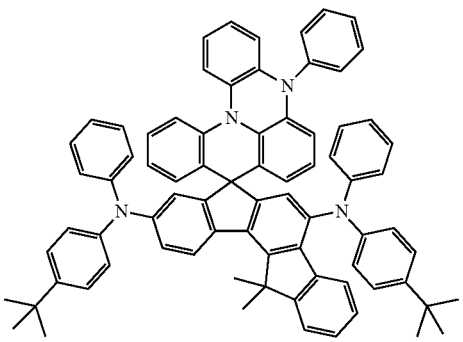
Compound 32
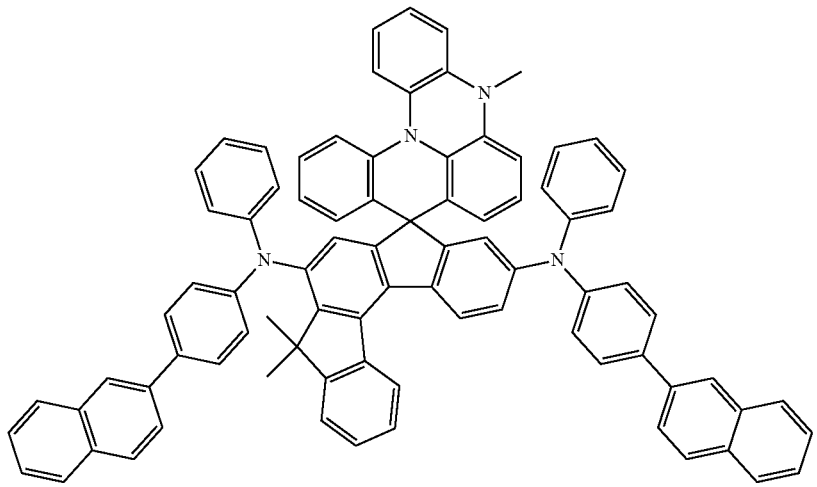
Compound 33
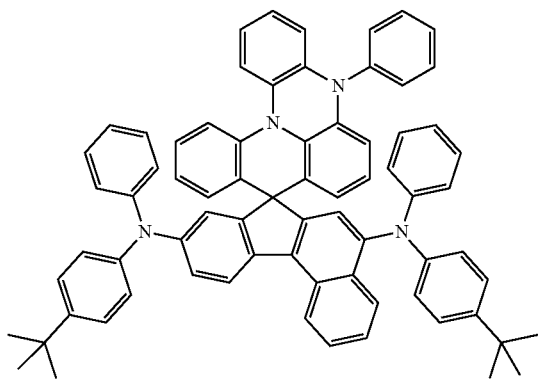
Compound 34
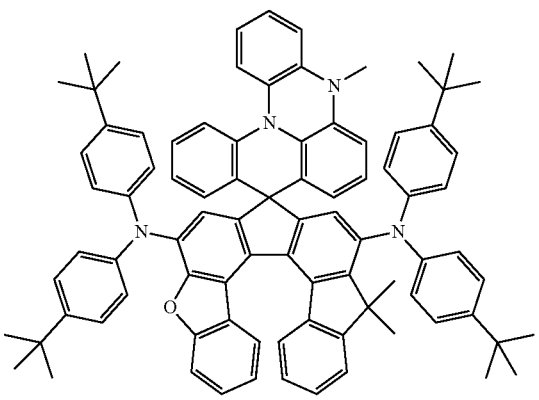
Compound 35
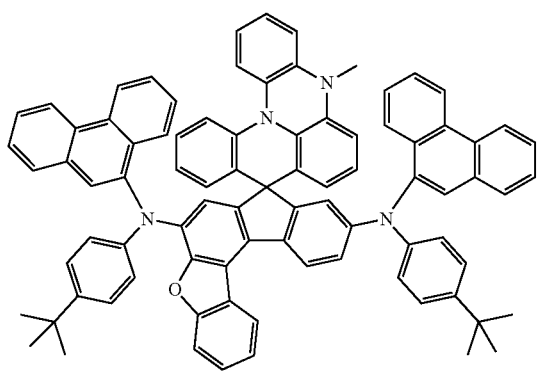
Compound 36
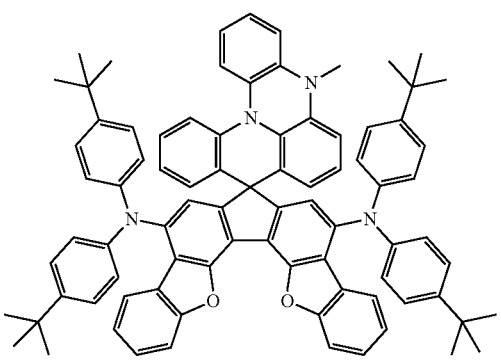

-continued
Compound 37
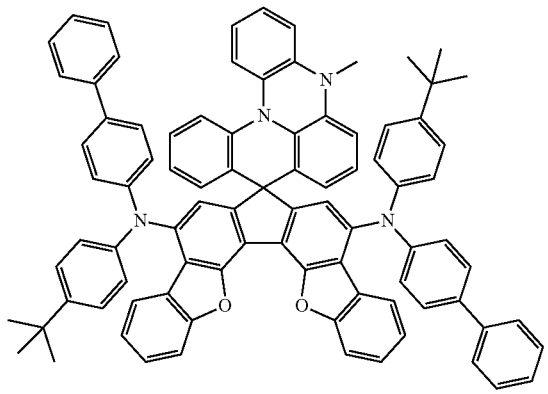
Compound 38
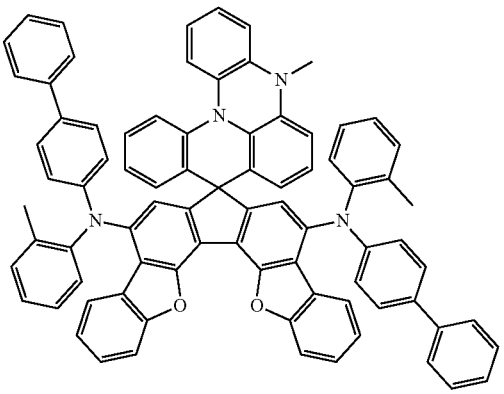
Compound 39
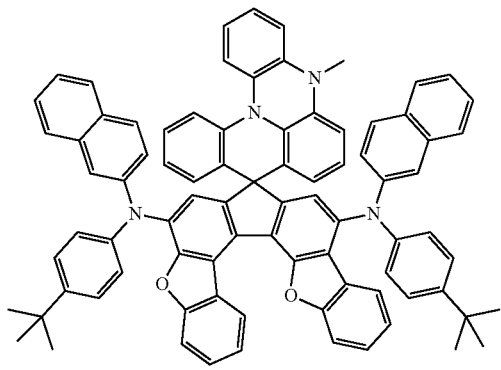
Compound 40
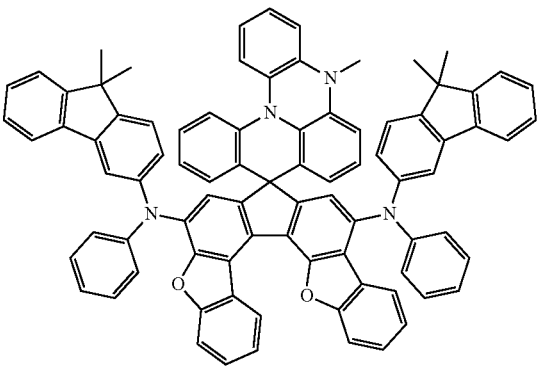
Compound 41
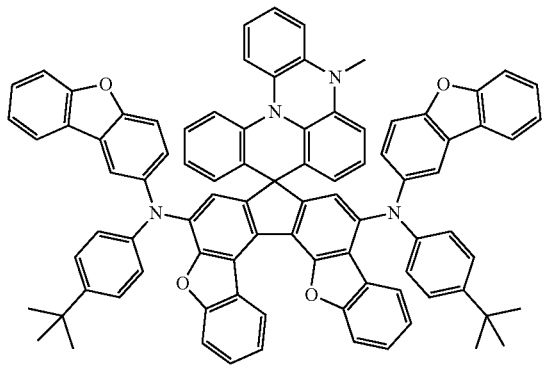
Compound 42
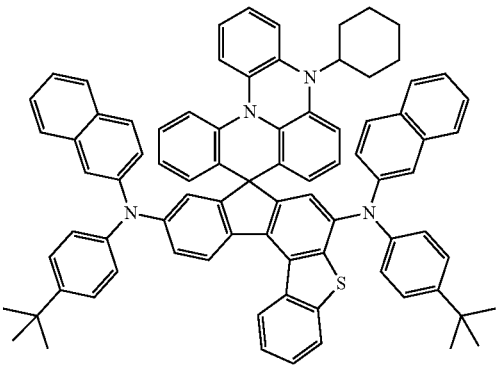
Compound 43
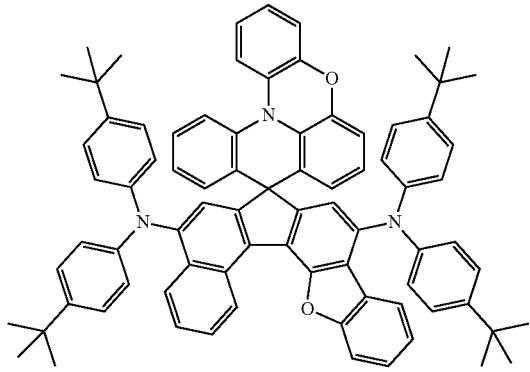
Compound 44
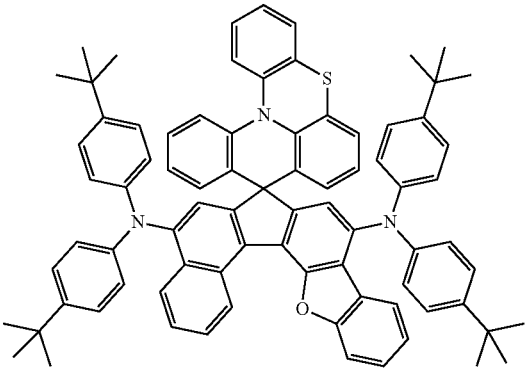

Compound 45
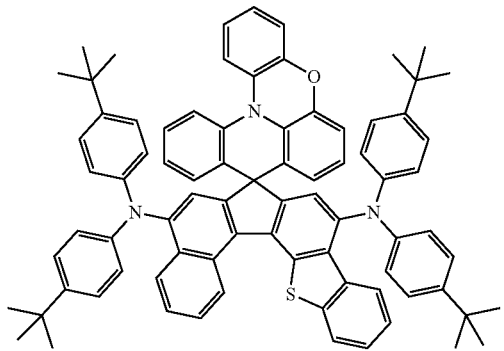
Compound 46
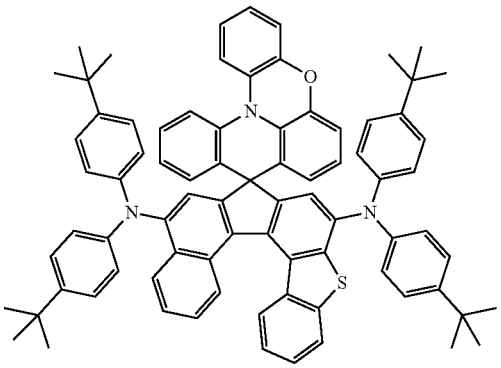
Compound 47
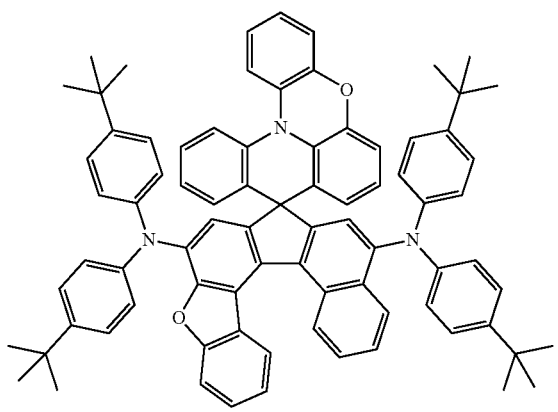
Compound 48
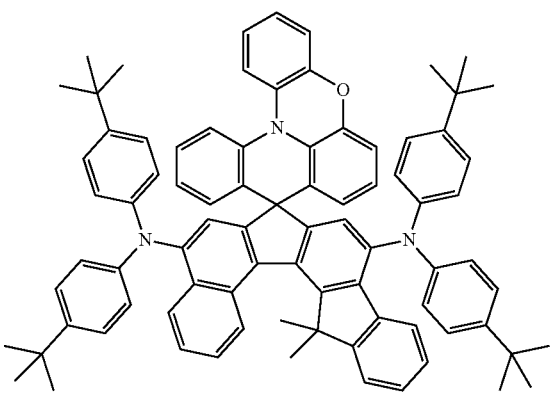
Compound 49
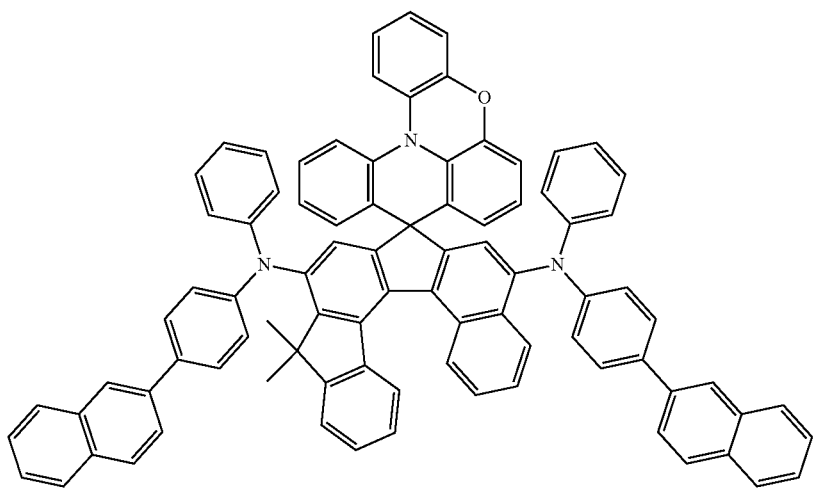

-continued
Compound 50
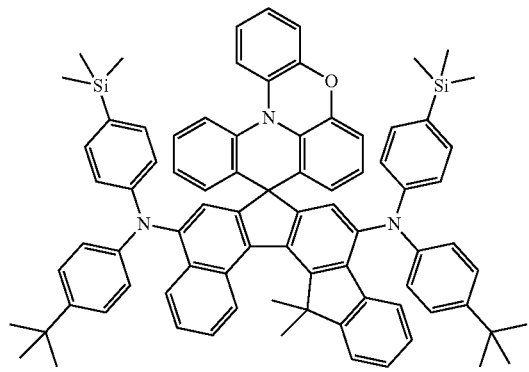
Compound 51
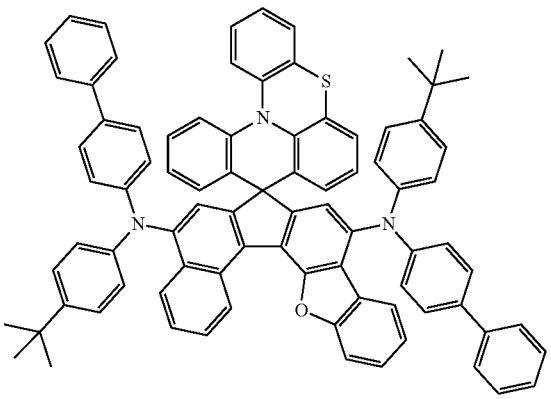
Compound 52
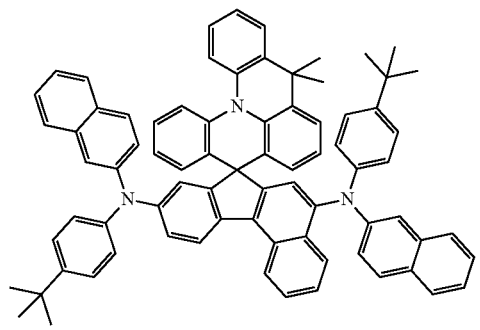
Compound 53
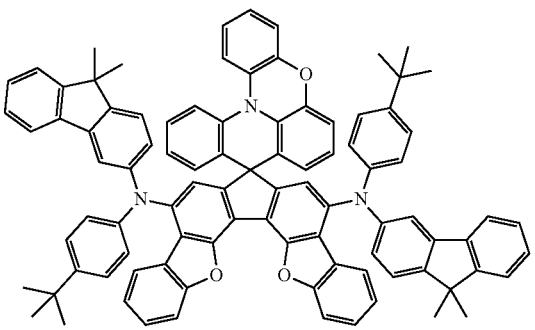
Compound 54
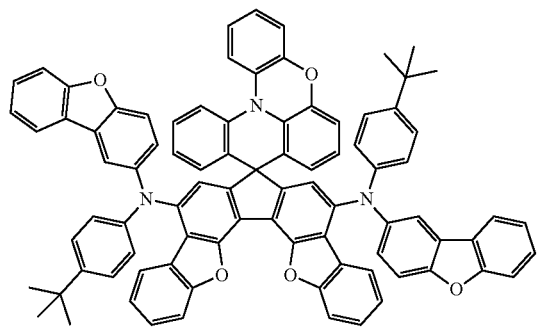
Compound 55
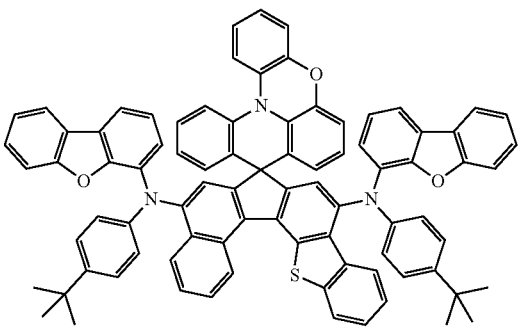
Compound 56
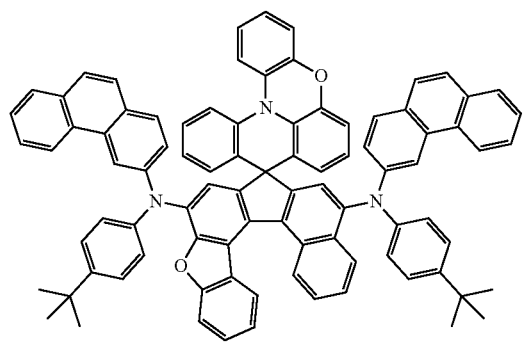
Compound 57
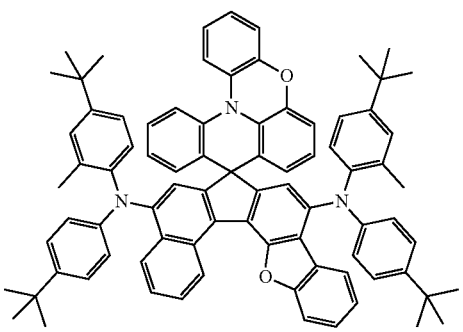

Compound 59
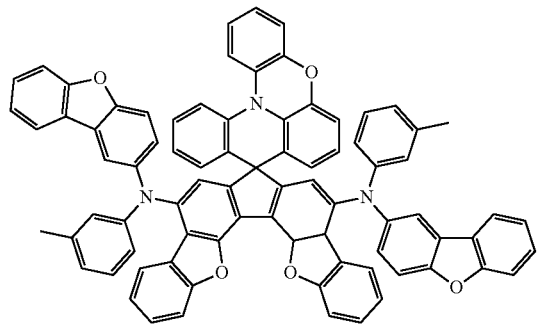
Compound 60
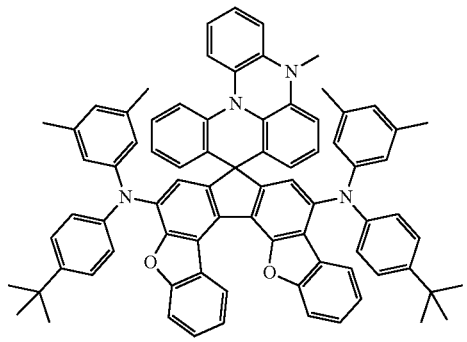
Compound 61
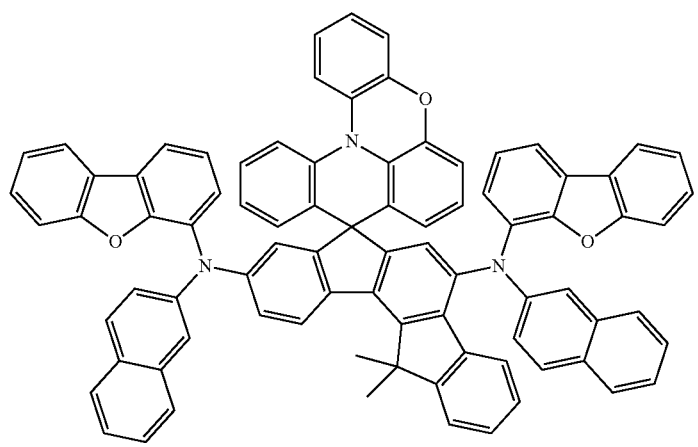
Compound 62
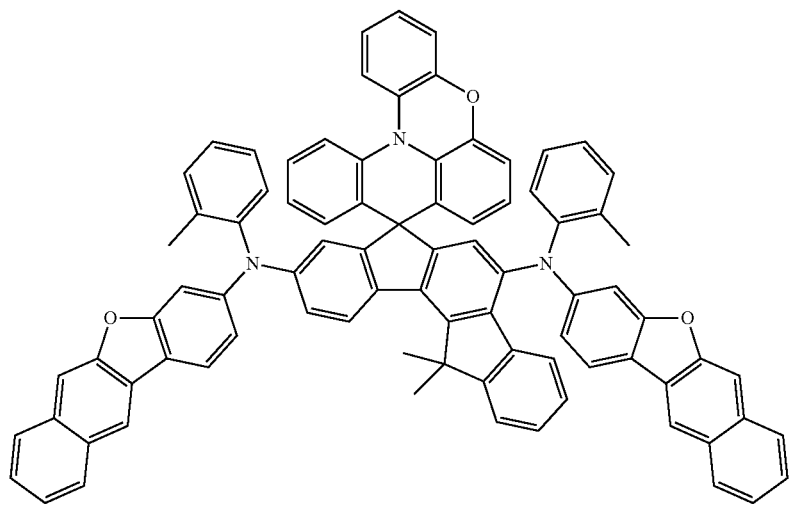

Compound 63
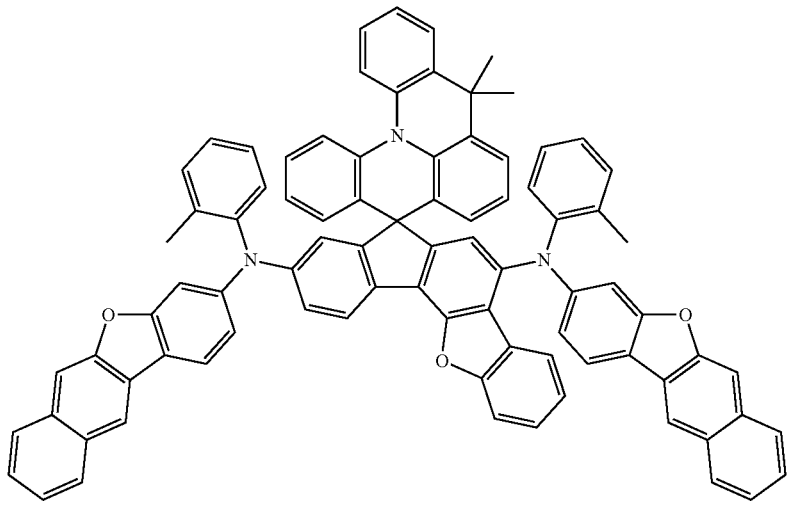
Compound 64
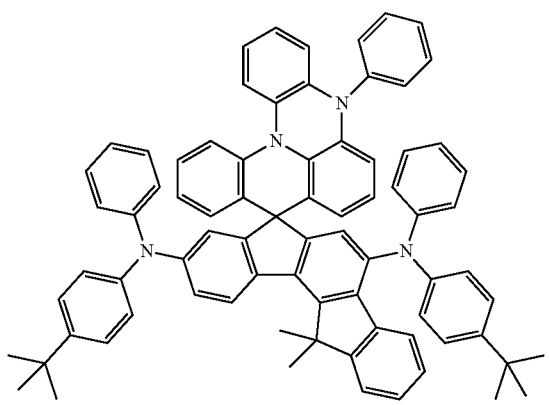
Compound 65
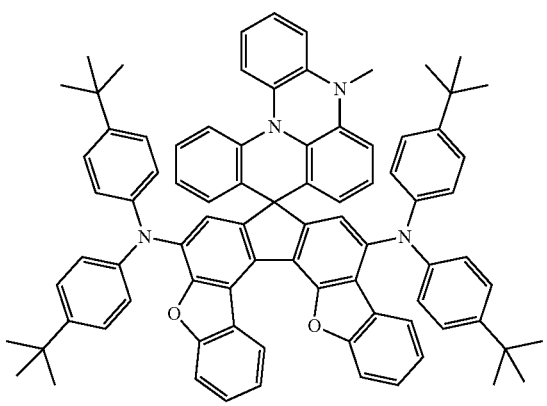
Compound 66
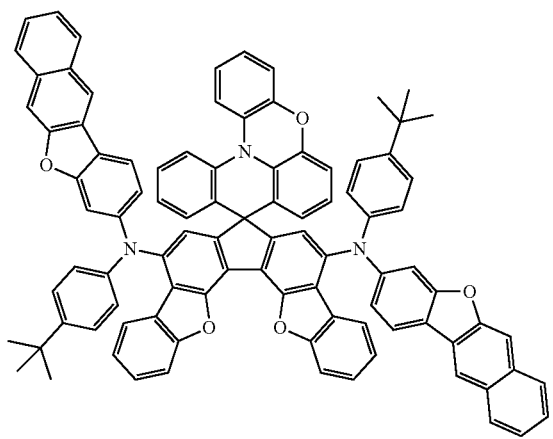
Compound 67
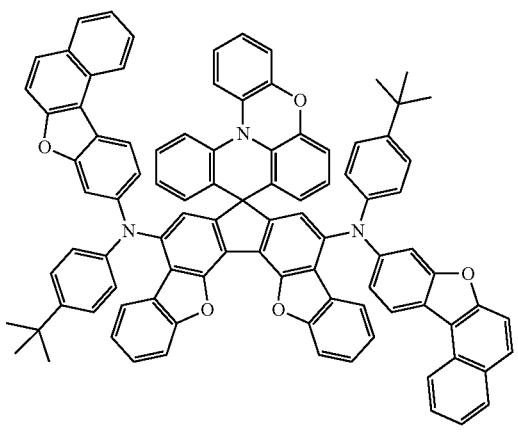

-continued
Compound 68
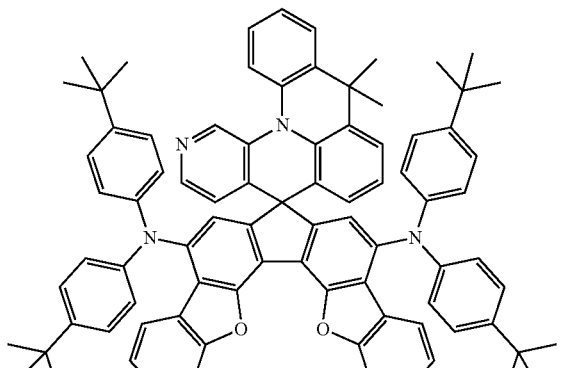
Compound 69
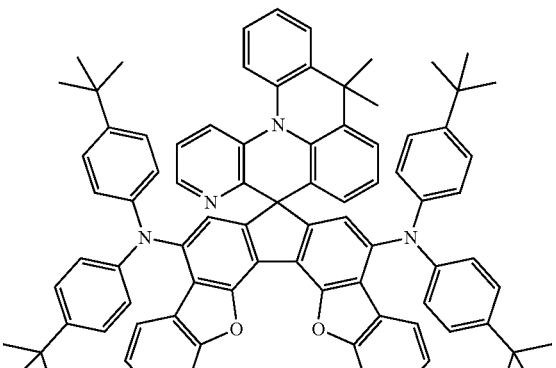
Compound 70
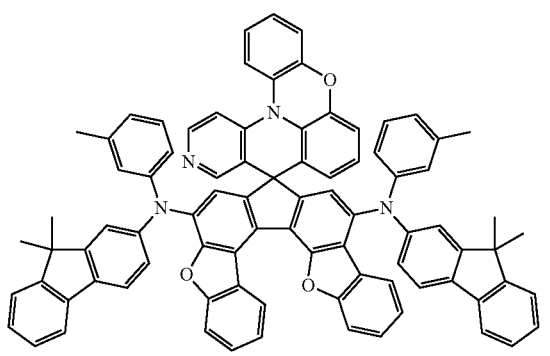
Compound 71
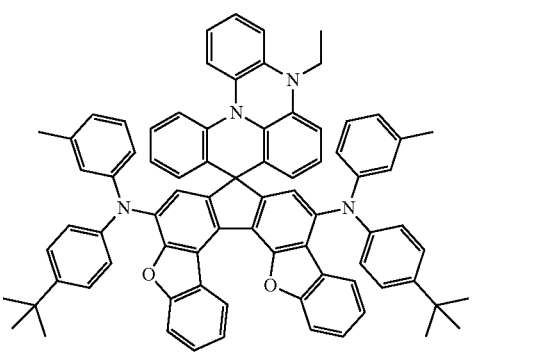
Compound 72
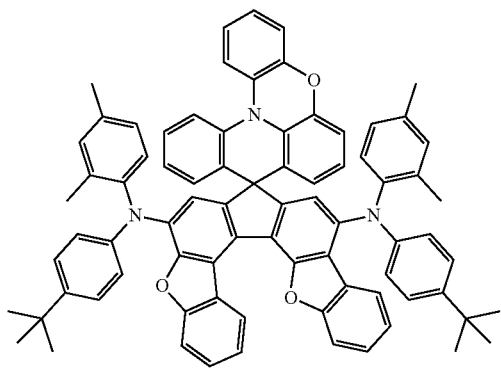
Compound 73
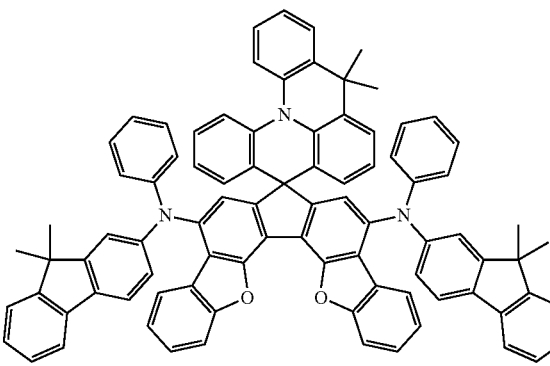
Compound 74
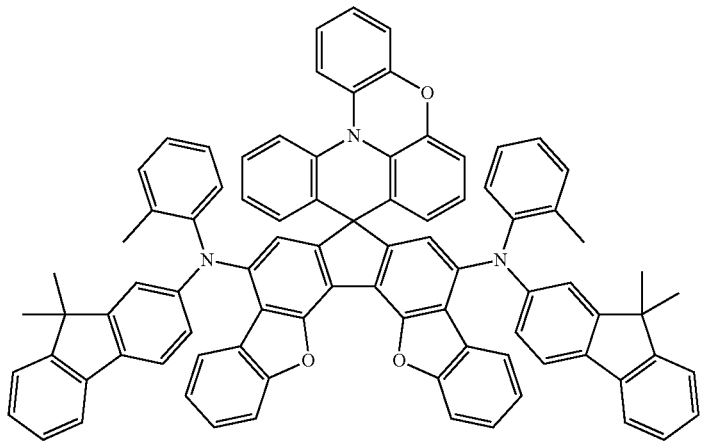

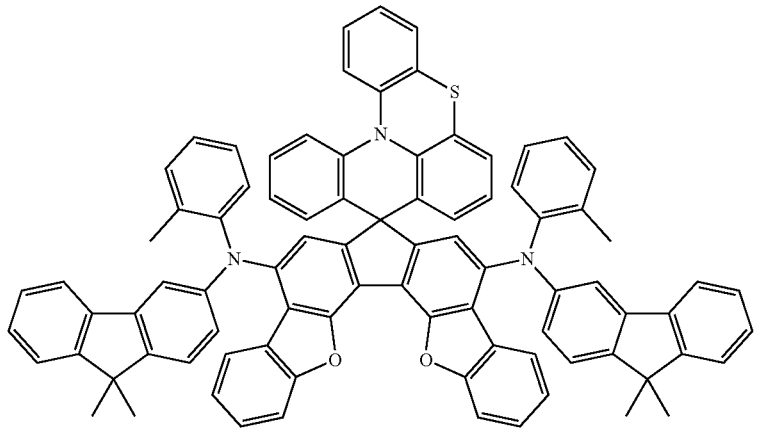
Compound 75
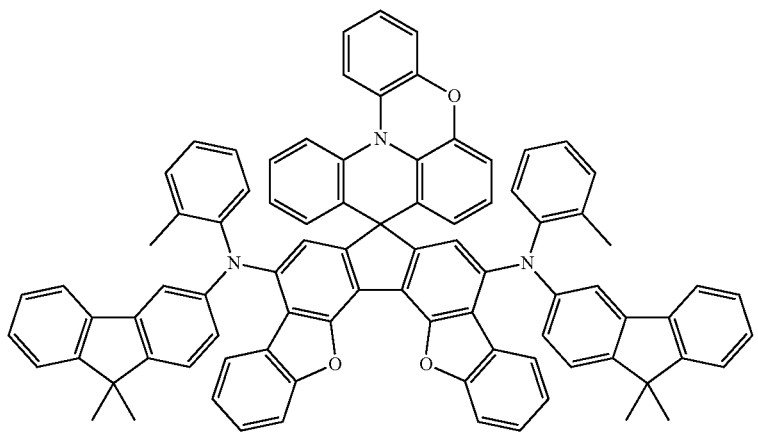
Compound 76
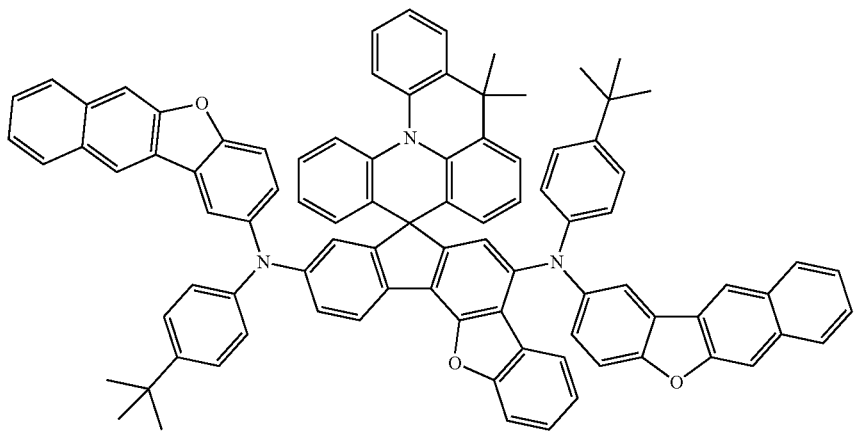
Compound 77

Compound 78
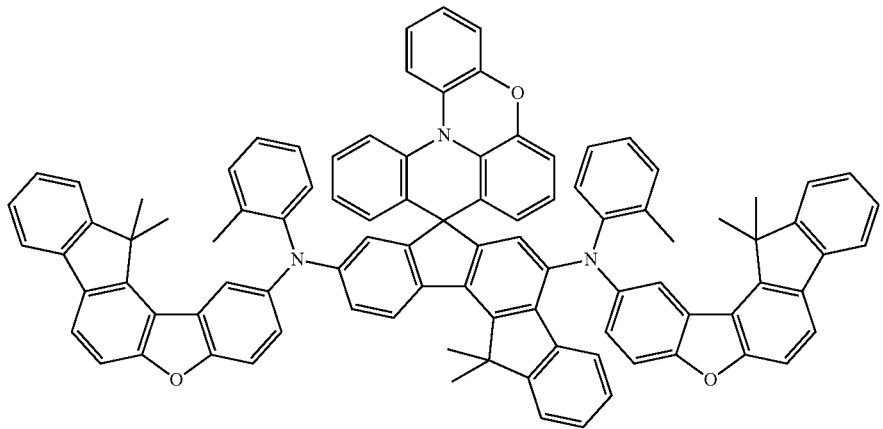
Compound 79
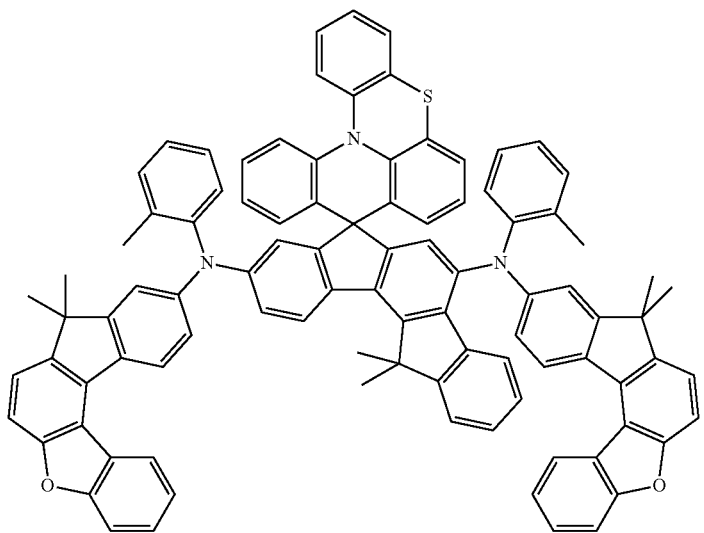
Compound 80
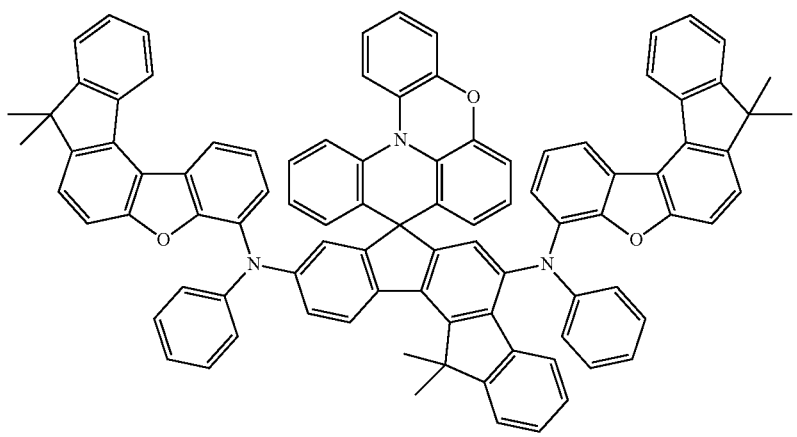

-continued
Compound 81
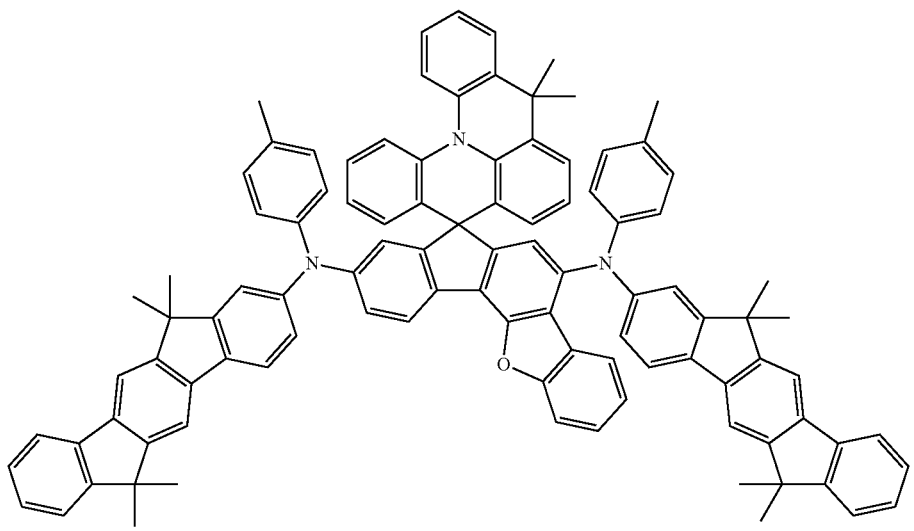
Compound 82
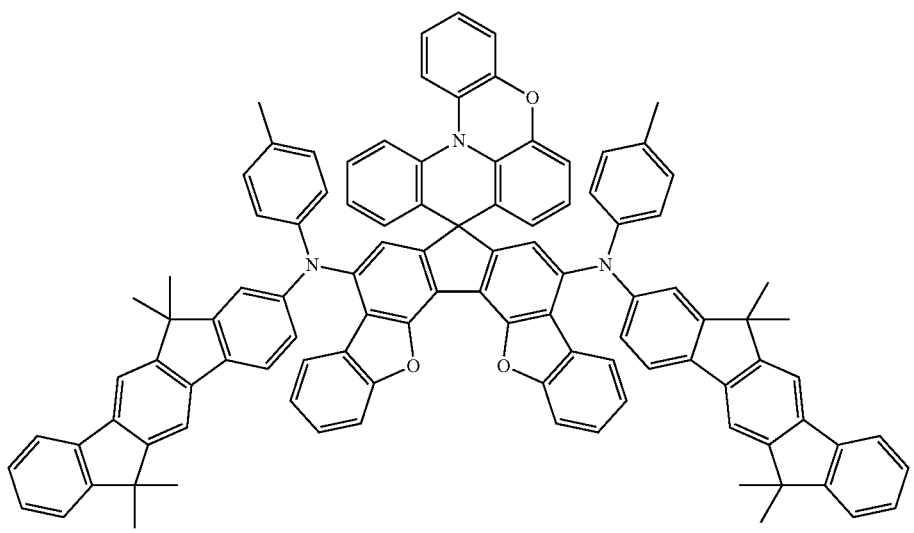
Compound 83
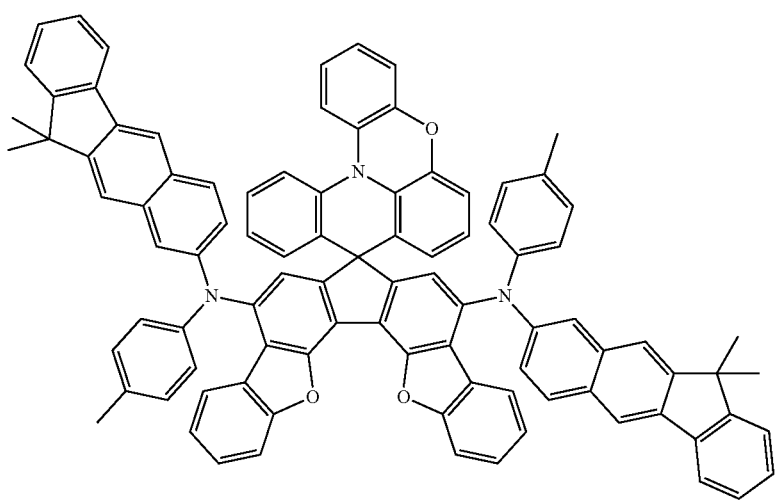

Compound 84
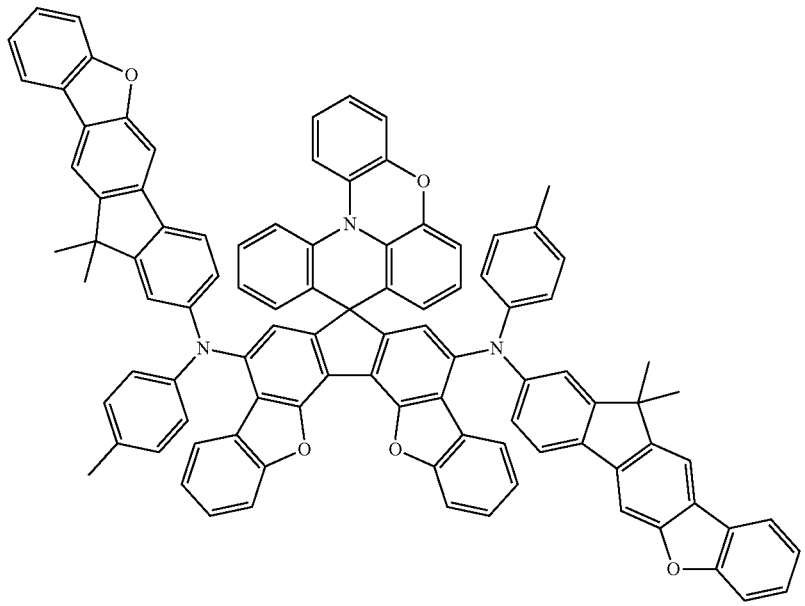
Compound 85
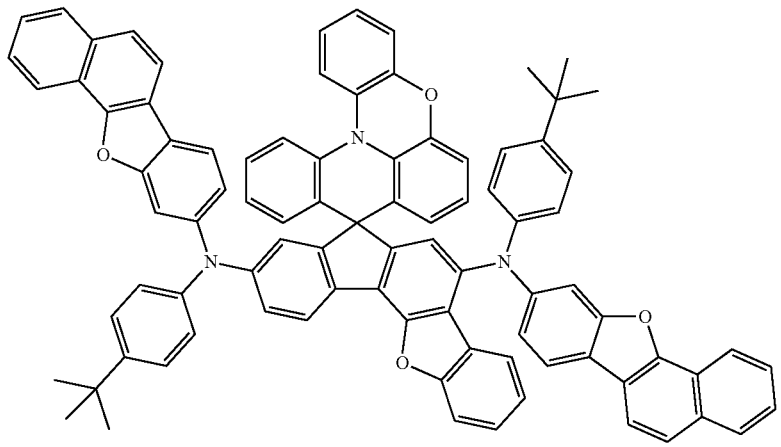
Compound 86
Compound 87
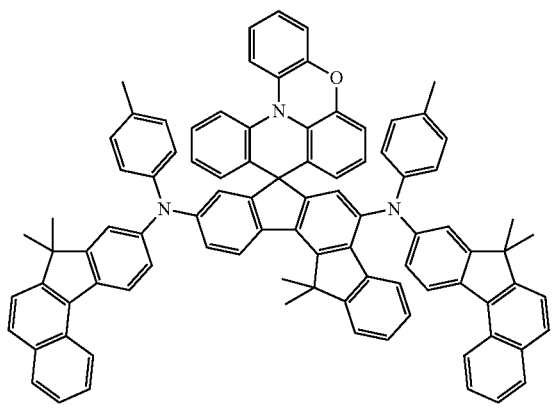
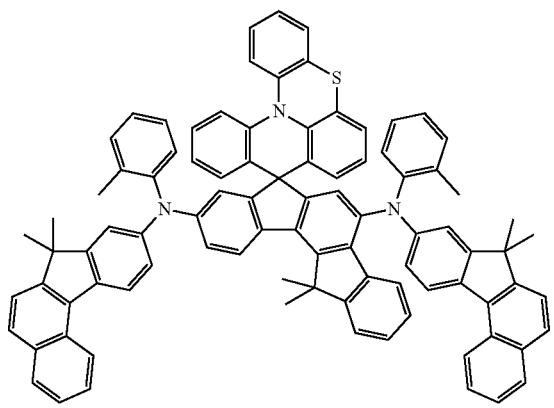

Compound 88

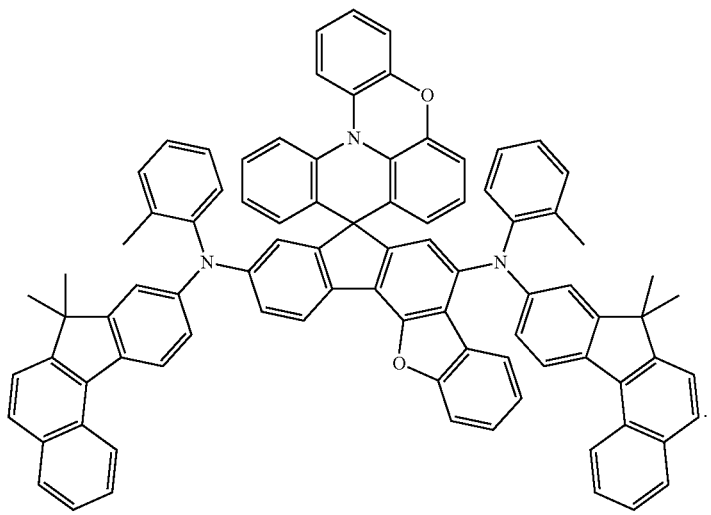

8. An organic light emitting device comprising:
an anode;
a cathode; and
one or more organic material layers disposed between the anode and the cathode,
wherein one or more layers of the organic material layers comprise the heterocyclic compound of claim 1.

9. The organic light emitting device of claim 8, wherein the organic material layers comprise a hole injection layer or a hole transfer layer, and the hole injection layer or the hole transfer layer comprises the heterocyclic compound.

10. The organic light emitting device of claim 8, wherein the organic material layers comprise an electron transfer layer or an electron injection layer, and the electron transfer layer or the electron injection layer comprises the heterocyclic compound.

11. The organic light emitting device of claim 8, wherein the organic material layers comprise a light emitting layer, and the light emitting layer comprises the heterocyclic compound.

12. The organic light emitting device of claim 8, wherein the organic material layers comprise a light emitting layer, and the light emitting layer comprises a compound represented by the following Chemical Formula 1A:

[Chemical Formula 1A]

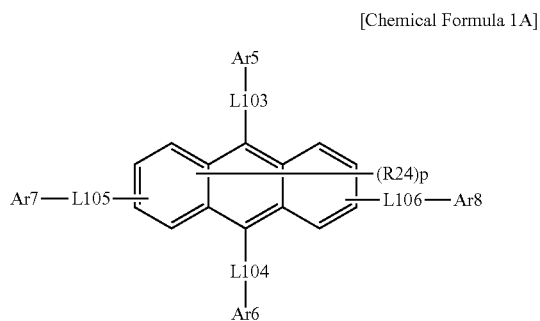

in Chemical Formula 1A,
L103 to L106 are independently selected from a direct bond; a substituted or unsubstituted arylene group; or a substituted or unsubstituted heteroarylene group, Ar5 to Ar8 are independently selected from hydrogen; a substituted or unsubstituted aryl group; or a substituted or unsubstituted heteroaryl group, each R24 is independently selected from hydrogen; deuterium; a halogen group; a nitrile group; a nitro group; a substituted or unsubstituted alkyl group; a substituted or unsubstituted cycloalkyl group; a substituted or unsubstituted silyl group; a substituted or unsubstituted phosphine oxide group; a substituted or unsubstituted aryl group; or a substituted or unsubstituted heteroaryl group, p is an integer of 0 to 6, and provided that when p is 2 or greater, each R24 is the same as or different from each other.

13. The organic light emitting device of claim 12, wherein L103 to L106 are independently selected from a direct bond; or the following structures:

LB1

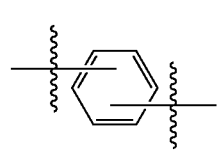

LB2

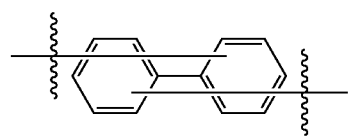

LB3

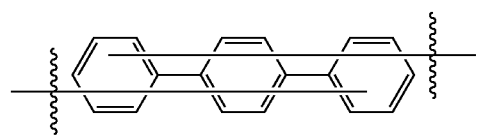

LB4

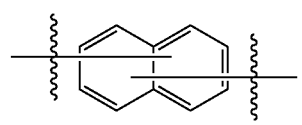

LB5 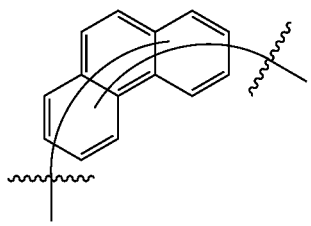
LB6 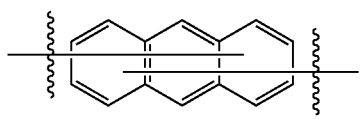
LB7 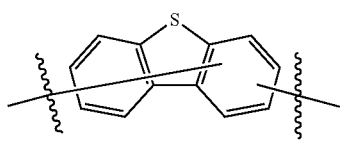
LB8 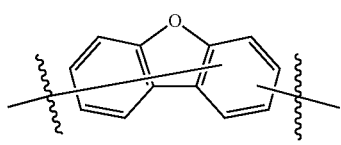
LB9 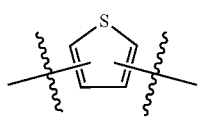
LB10 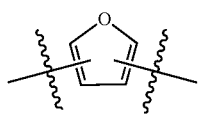
LB11 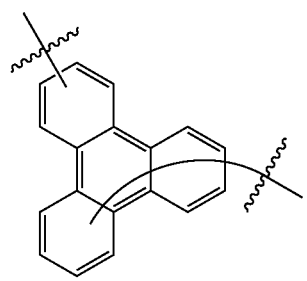
LB12 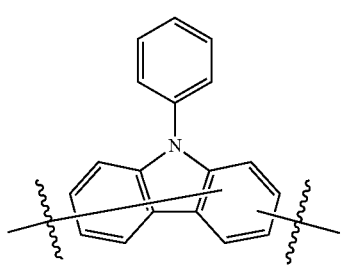
LB13 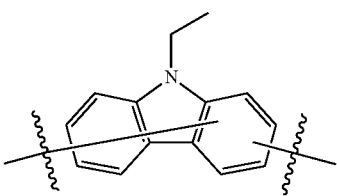
LB14 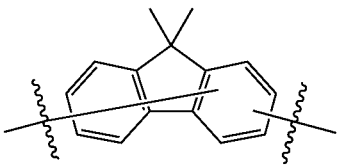
LB15 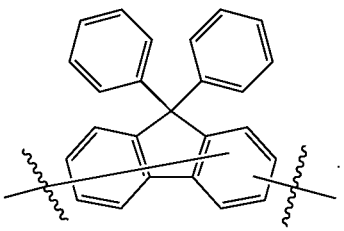
14. The organic light emitting device of claim 12, wherein Ar5 to Ar8 are independently selected from hydrogen; or the following structures:
RA1 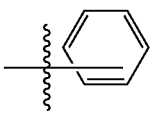
RA2 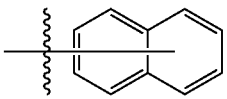
RA3 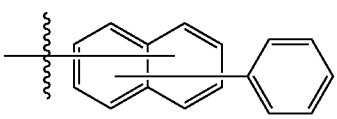
RA4 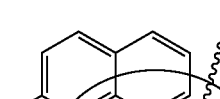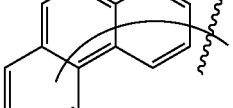
RA5 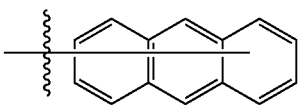

191
-continued
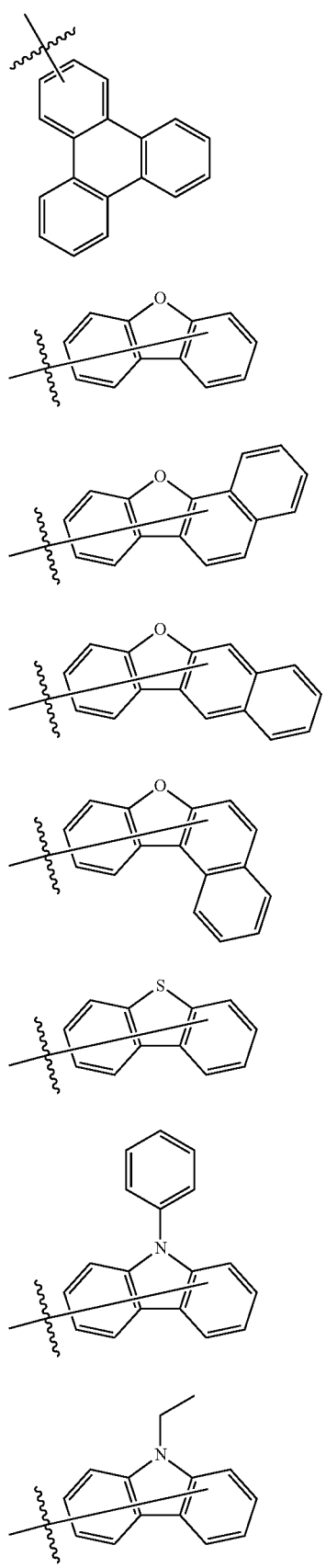
192
-continued
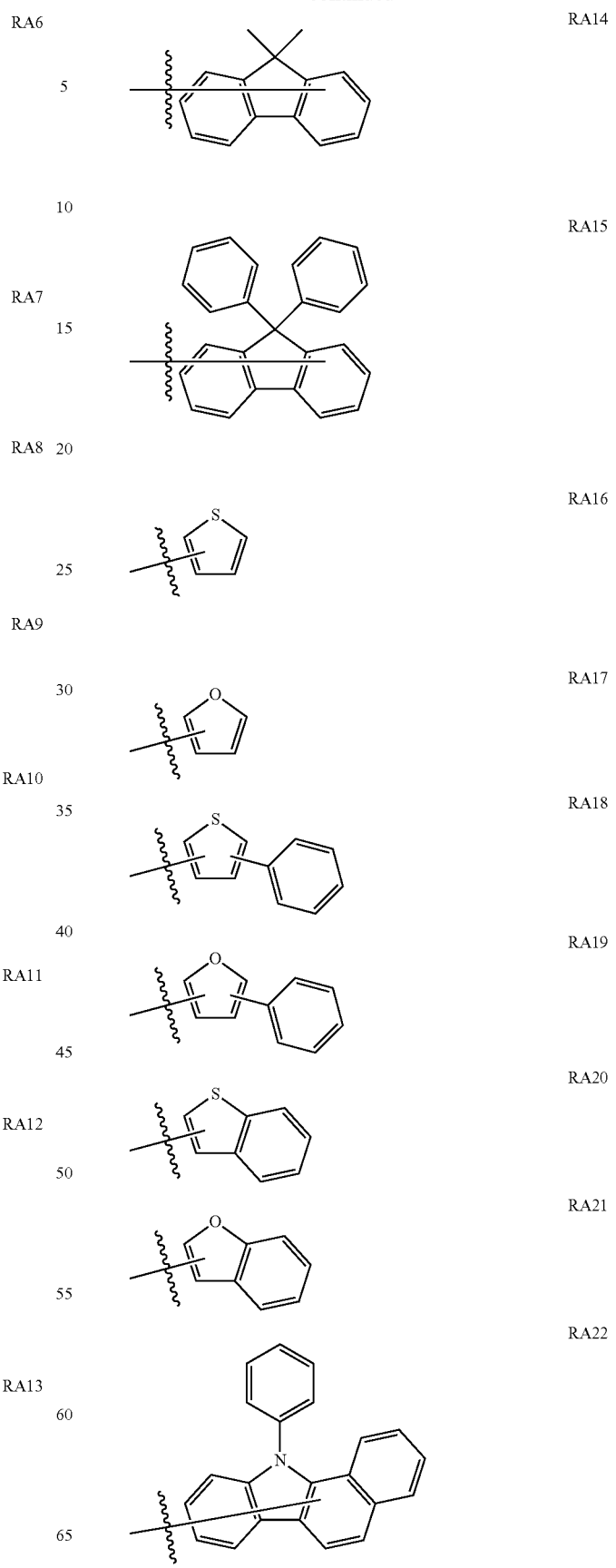

RA23 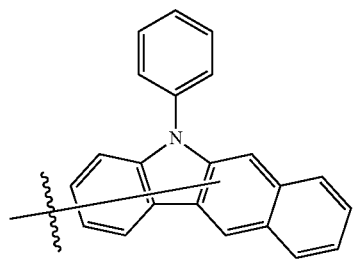
RA24 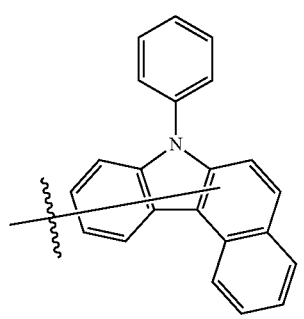
RA25 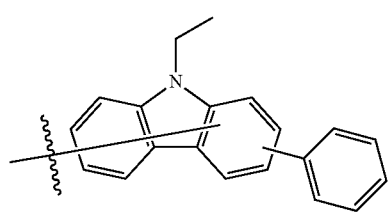
RA26 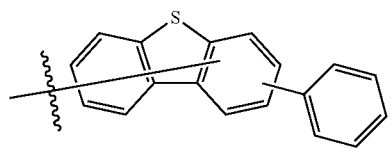
RA27 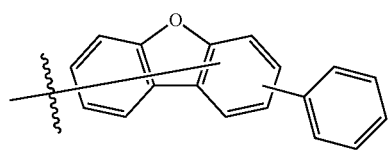
RA28 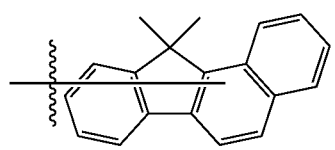
RA29 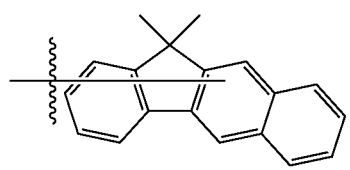
RA30 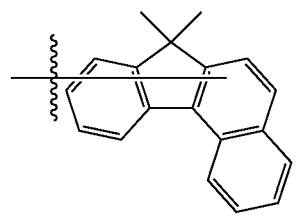
RA31 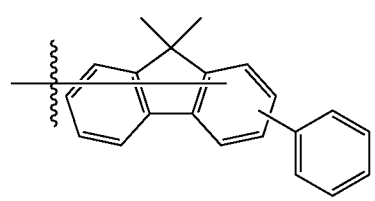
RA32 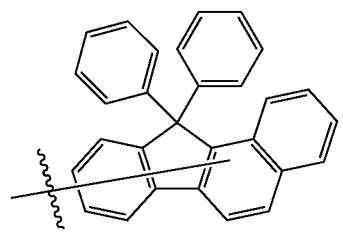
RA33 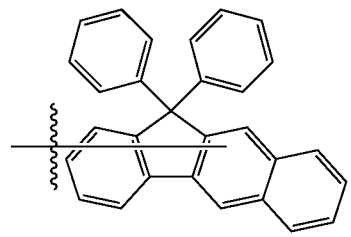
RA34 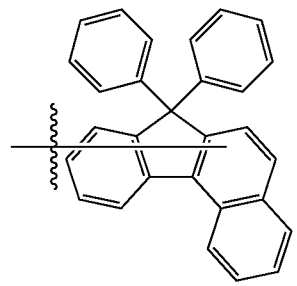
RA35 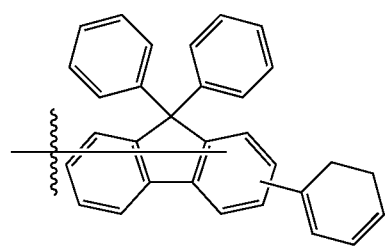
RA36 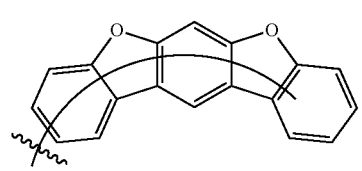

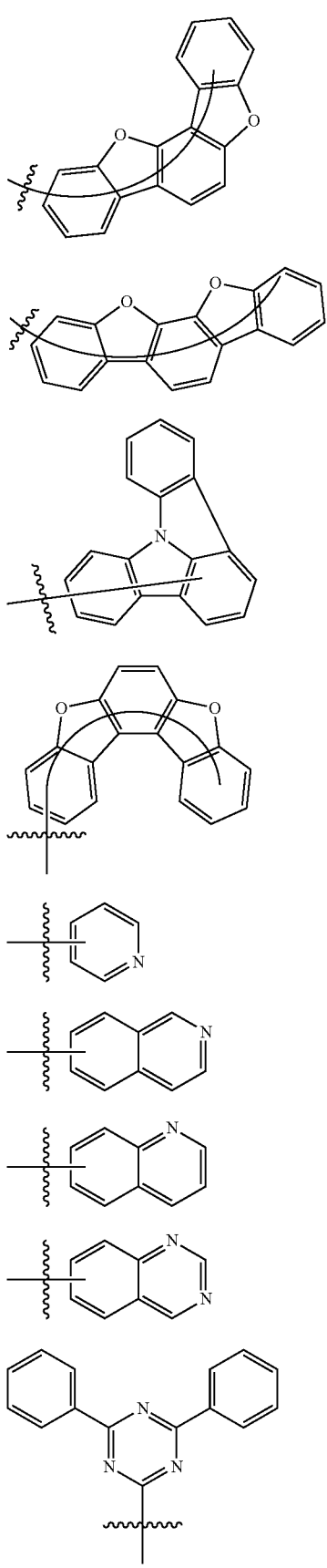

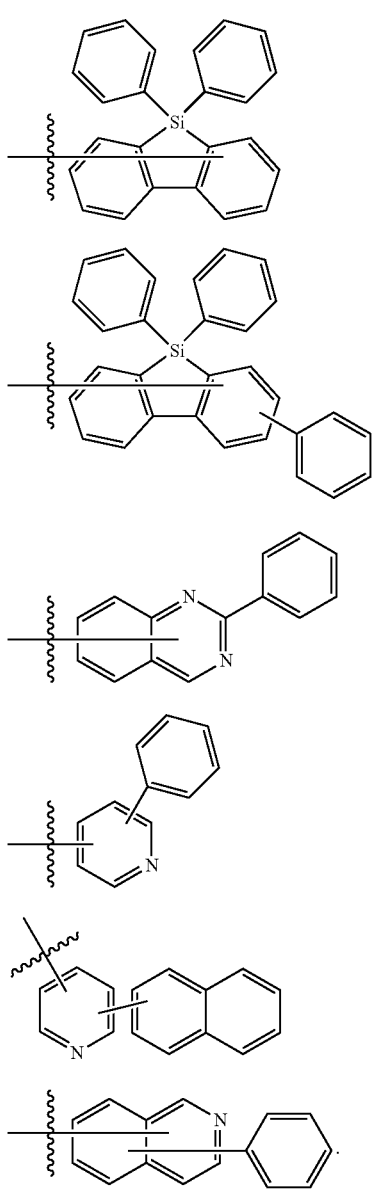

RA55

RA56

RA57

RA58

RA59

RA60

15. The organic light emitting device of claim 8, wherein the organic material layers comprise a light emitting layer, and the light emitting layer comprises a compound represented by the following Chemical Formula 1B:

[Chemical Formula 1B]

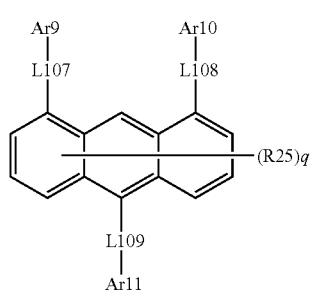

in Chemical Formula 1B,

L107 to L109 are independently selected from a direct bond; a substituted or unsubstituted arylene group; or a substituted or unsubstituted heteroarylene group, Ar9 to Ar11 are independently selected from hydrogen; a substituted or unsubstituted aryl group; or a substituted or unsubstituted heteroaryl group, each R25 is independently selected from hydrogen; deuterium; a halogen group; a nitrile group; a nitro group; a substituted or unsubstituted alkyl group; a substituted or unsubstituted cycloalkyl group; a substituted or unsubstituted silyl group; a substituted or unsubstituted phosphine oxide group; a substituted or unsubstituted aryl group; or a substituted or unsubstituted heteroaryl group, q is an integer of 0 to 7, and provided that when q is 2 or greater, each R25 is the same as or different from each other.

16. The organic light emitting device of claim 15, wherein L107 to L109 are independently selected from a direct bond; or the following structures:

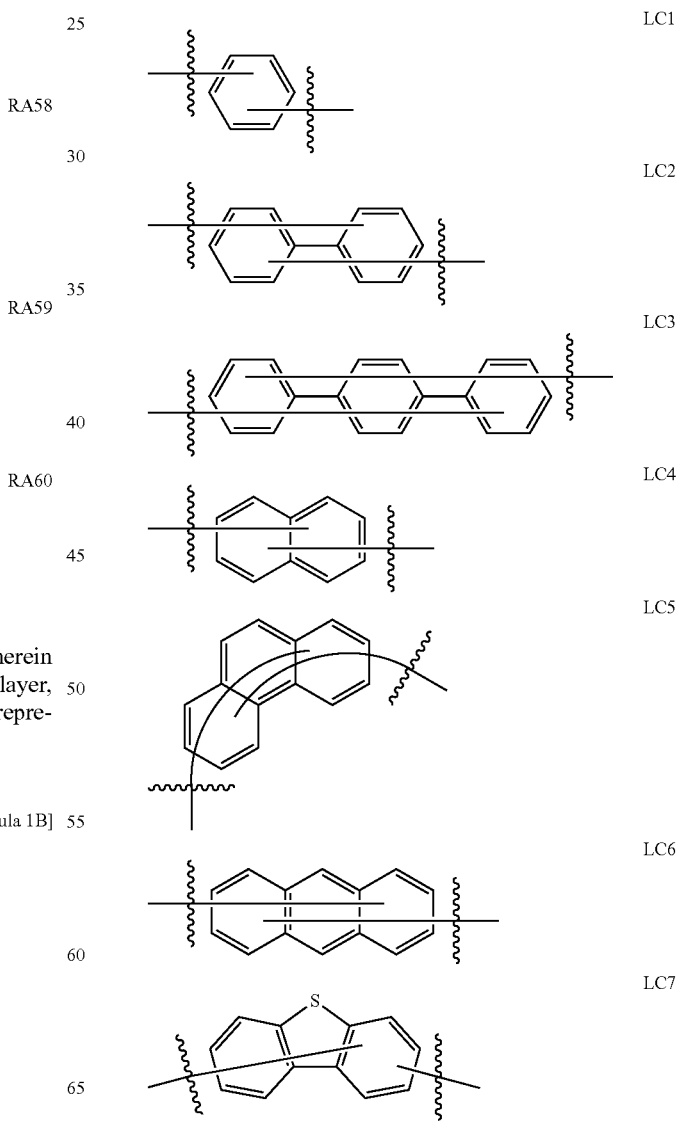

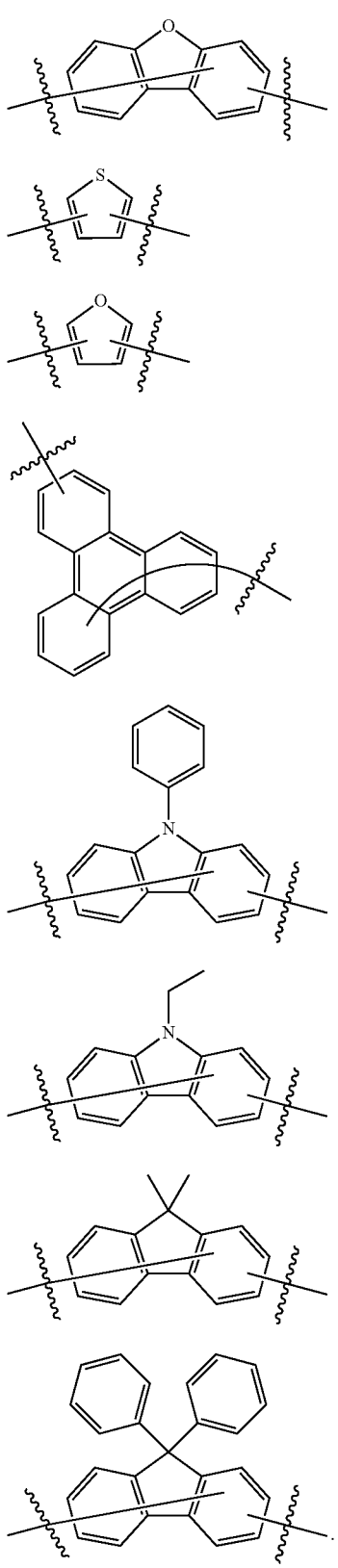
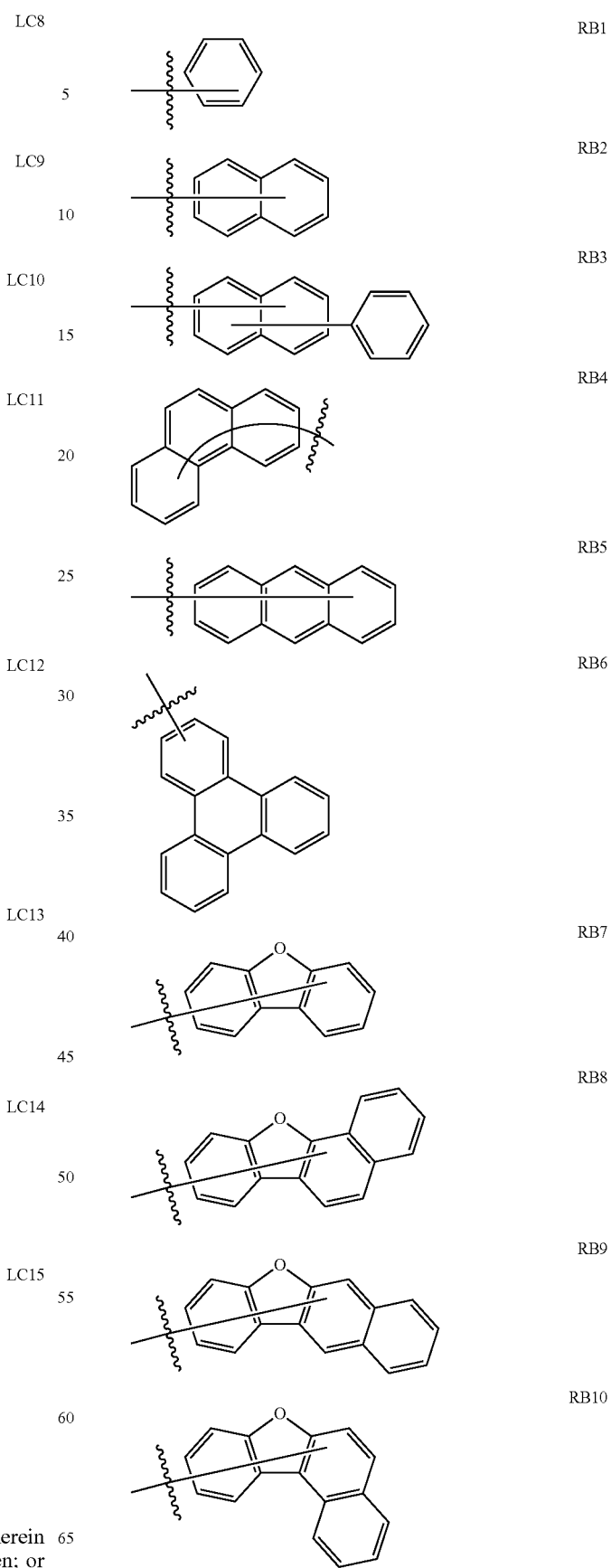
17. The organic light emitting device of claim 15, wherein Ar9 to Ar11 are independently selected from hydrogen; or the following structures:

-continued
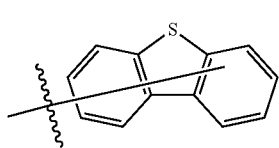
RB11
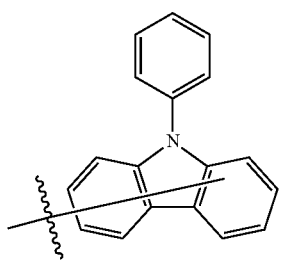
RB12
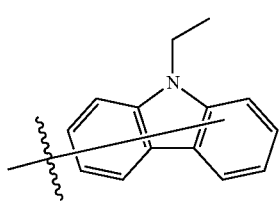
RB13
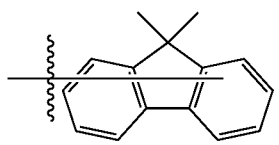
RB14
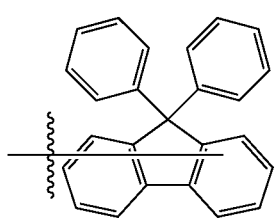
RB15
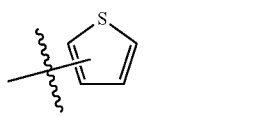
RB16
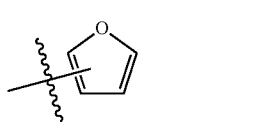
RB17
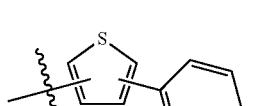
RB18
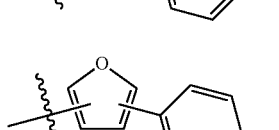
RB19
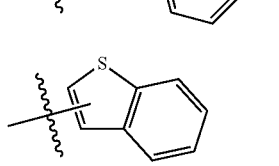
RB20
-continued
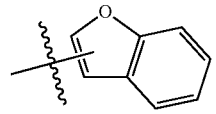
RB21
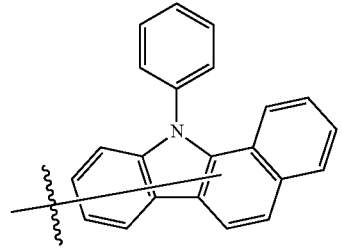
RB22
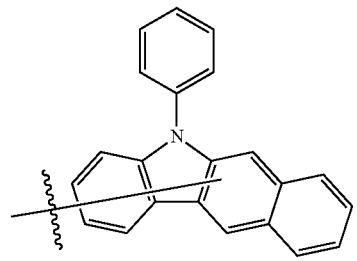
RB23
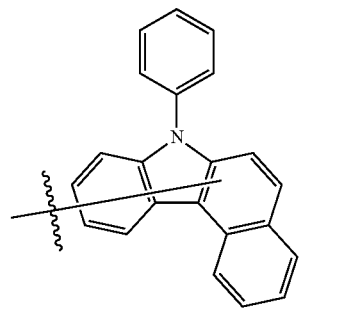
RB24
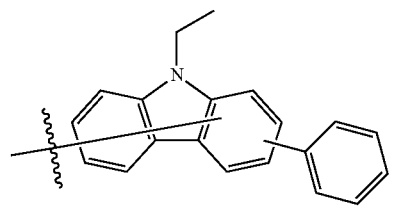
RB25
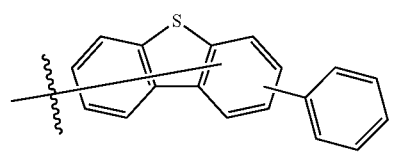
RB26
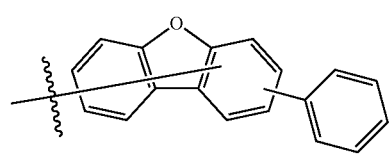
RB27